(12) United States Patent
Gude et al.

(10) Patent No.: US 8,889,676 B2
(45) Date of Patent: Nov. 18, 2014

(54) 3-UREIDOISOQUINOLIN-8-YL DERIVATIVES

(75) Inventors: Markus Gude, Allschwil (CH); Christian Hubschwerlen, Allschwil (CH); Philippe Panchaud, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/009,093

(22) PCT Filed: Mar. 28, 2012

(86) PCT No.: PCT/IB2012/051473
§ 371 (c)(1),
(2), (4) Date: Sep. 30, 2013

(87) PCT Pub. No.: WO2012/131588
PCT Pub. Date: Oct. 4, 2012

(65) Prior Publication Data
US 2014/0038961 A1   Feb. 6, 2014

(30) Foreign Application Priority Data

Mar. 29, 2011   (WO) .................. PCT/IB2011/051320
Sep. 16, 2011   (WO) .................. PCT/IB2012/054063

(51) Int. Cl.
| | | |
|---|---|---|
| C07D 217/22 | (2006.01) | |
| C07D 401/04 | (2006.01) | |
| A61K 31/472 | (2006.01) | |
| C07D 401/12 | (2006.01) | |
| C07D 401/14 | (2006.01) | |

(52) U.S. Cl.
CPC ............ *C07D 217/22* (2013.01); *C07D 401/12* (2013.01); *C07D 401/14* (2013.01); *C07D 401/04* (2013.01)
USPC .............. 514/235.2; 514/252.04; 514/253.05; 514/256; 514/310; 544/128; 544/238; 544/333; 544/363; 546/143

(58) Field of Classification Search
None
See application file for complete search history.

(56) References Cited

U.S. PATENT DOCUMENTS

| | | |
|---|---|---|
| 2004/0009931 A1 | 1/2004 | Clark et al. |
| 2010/0063069 A1 | 3/2010 | Charifson et al. |
| 2013/0096119 A1 | 4/2013 | Bur et al. |

FOREIGN PATENT DOCUMENTS

| | | |
|---|---|---|
| WO | WO 02/060879 | 8/2002 |
| WO | WO 03/080578 | 10/2003 |
| WO | WO 03/105846 | 12/2003 |
| WO | WO 2005/089763 | 9/2005 |
| WO | WO 2006/038116 | 4/2006 |
| WO | WO 2007/051408 | 5/2007 |
| WO | WO 2007/056330 | 5/2007 |
| WO | WO 2007/125405 | 11/2007 |
| WO | WO 2007/146230 | 12/2007 |
| WO | WO 2007/148093 | 12/2007 |
| WO | WO 2008/068470 | 6/2008 |
| WO | WO 2008/082487 | 7/2008 |
| WO | WO 2008/141010 | 11/2008 |
| WO | WO 2009/027732 | 3/2009 |
| WO | WO 2009/074810 | 6/2009 |
| WO | WO 2009/074812 | 6/2009 |
| WO | WO 2009/089083 | 7/2009 |
| WO | WO 2009/106885 | 9/2009 |
| WO | WO 2009/147431 | 12/2009 |
| WO | WO 2009/147433 | 12/2009 |
| WO | WO 2009/147440 | 12/2009 |
| WO | WO 2009/155121 | 12/2009 |
| WO | WO 2009/156966 | 12/2009 |
| WO | WO 2010/136817 | 12/2010 |
| WO | WO 2010/142978 | 12/2010 |
| WO | WO 2011/024004 | 3/2011 |
| WO | WO 2011/121555 | 10/2011 |

OTHER PUBLICATIONS

Bellina, Fabio et al., "Palladium Catalysts for the Suzuki Cross-Coupling Reaction: An Overview of Recent Advances," Synthesis (2004), No. 15, pp. 2419-2440.

(Continued)

*Primary Examiner* — Zinna Northington Davis
(74) *Attorney, Agent, or Firm* — Hunton & Williams LLP

(57) ABSTRACT

The invention relates to 3-ureidoisoquinolin-8-yl derivatives of formula I

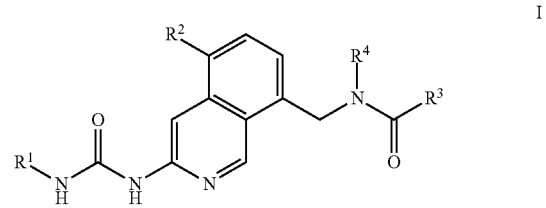

wherein
$R^1$ is alkyl, haloalkyl or cyclopropyl;
$R^2$ is H, halogen, pyridazin-4-yl, pyrimidin-5-yl or an optionally substituted pyridin-3-yl, pyridin-4-yl or phenyl group;
$R^3$ is alkyl, alkynyl, aminoalkyl, carbamoylalkyl, methylcarbamoylalkyl, alkoxy, haloalkoxy, alkynyloxy, (4-hydroxybut-2-yn-1-yl)oxy, (4-aminobut-2-yn-1-yl)oxy, dimethylaminoalkoxy, carbamoylalkoxy, alkylamino, cycloalkyl, cycloalkylalkyl, cycloalkylalkoxy, hydroxyalkyl, hydroxyalkoxy, alkoxyalkyl, alkoxyalkoxy, carboxyalkyl, carboxyalkoxy, alkoxycarbonylalkoxy, aryl, heteroaryl, benzyl, benzyloxy, 2-cyanoethoxy, 2,3-dihydroxypropoxy, 3,4-dihydroxybutoxy, —$CH_2R^a$, —$CH_2CH_2R^b$, —$(CH_2)_n$—$C(O)O$—$R^d$, —$(CH_2)_n$—$N(R^c)C(O)O$—$R^d$, —$O$—$(CH_2)_n$—$N(R^c)C(O)O$—$R^d$, —$(CH_2)_n$—$R^e$ or —$O$—$(CH_2)_n$—$R^e$; $R^a$ is cyano, acetylamino or N,N-dimethylamino; $R^b$ is cyano or carbamoyl; $R^c$ is H or methyl; $R^d$ is alkyl; $R^e$ is pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl or heteroaryl;
$R^4$ is H or methyl;
and to the salts of such compounds.
These compounds are useful for the prevention or the treatment of bacterial infections.

16 Claims, No Drawings

(56) References Cited

OTHER PUBLICATIONS

Benz, Günter, "Synthesis of Amides and Related Compounds," in Comprehensive Organic Synthesis, (1991), vol. 6, pp. 381-417.

Chang, Linda L. et al., "Triazolinones as Nonpeptide Angiotensin II Antagonists. 1. Synthesis and Evaluation of Potent 2,4,5-Trisubstituted Triazolinones," J. Med. Chem. (1993), vol. 36, pp. 2558-2568.

Larock, R. C., "Halogenation of Alcohol," in Comprehensive Organic Transformations, A Guide to Functional Group Preparations, (2nd Edition 1999), pp. 689-703.

Larock, R. C., "Interconversion of Nitriles, Carboxylic Acids and Derivatives," in Comprehensive Organic Transformations, A Guide to Functional Group Preparations, (2nd Edition 1999), pp. 1941-1949.

Frohn, M. et al., "An Efficient Synthesis of 1,6- and 1,7-dibromo-3-aminoisoquinolines: Versatile Templates for the Preparation of Functionalized Isoquinolines," Tetrahedron Letters, vol. 48, (2007), pp. 487-489.

Fu, Gregory C., "The Development of Versatile Methods for Palladium-Catalyzed Coupling Reactions of Aryl Electrophiles through the Use of P(t-Bu)$_3$ and PCy$_3$ as Ligands," Accounts of Chemical Research (2008), vol. 41, No. 11, pp. 1555-1564.

Gould, Philip, "Salt selection for basic drugs," International Journal of Pharmaceuticals (1986), vol. 33, pp. 201-217.

Greene, T. W. et al., "Protection for the Amino Group," in Protecting Groups in Organic Synthesis, (3rd Edition 1999). pp. 494-653.

Greene, T. W. et al., "Protection for the Hydroxyl Group, Including 1,2- and 1,3-Diols," in Protecting Groups in Organic Synthesis, (3rd Edition 1999), pp. 23-147.

Greene, T. W. et al., "Protection for the Carboxyl Group," in Protecting Groups in Organic Synthesis, (3rd Edition 1999). pp. 406-408.

Kantchev, E. A. B. et al, "Pd-N-Heterocyclic Carbene (NHC) Catalysts for Cross-Coupling Reactions," Aldrichimica ACTA (2006), vol. 39, No. 4, pp. 97-111.

Klinkenberg, J. L. et al., "Catalytic Organometallic Reactions of Ammonia," Angew. Chem. Int. Ed. (2011), vol. 50, pp. 86-95.

Kotecki, Brian J. et al, "A General Method for the Synthesis of Unsymmetrically Substituted Ureas via Palladium-Catalyzed Amidation," Organic Letters (2009), vol. 11, No. 4, pp. 947-950.

Larock, R. C., "From Alkyl and Aryl Halides or Sulfonates," in Comprehensive Organic Transformations, a guide to Functional Group Preparations, (2nd Edition 1999), p. 779.

Larock R. C., "From Alcohols and Phenols," in Comprehensive Organic Transformations (2nd Edition 1999), pp. 1114-1120.

Martinelli, Joseph R. et al., "Palladium-Catalyzed Aminocarbonylation of Aryl Chlorides at Atmospheric Pressure: The Dual Role of Sodium Phenoxide," Angew. Chem. Int. Ed. (2007), vol. 46, pp. 8460-8463.

Martinelli, Joseph R. et al., "Palladium-Catalyzed Carbonylation Reactions of Aryl Bromides at Atmospheric Pressure: A General System Based on Xantphos," J. Org. Chem. (2008), vol. 73, pp. 7102-7107.

Mauger, Christelle C. et al, "Synthetic Applications of Buchwald's Phosphines in Palladium-Catalyzed Aromatic-Bond-Forming Reactions," Aldrichimica ACTA (2006), vol. 39, No. 1, pp. 17-24.

Mitsunobu, Oyo, "The Use of Diethyl Azodicarboxylate and Triphenylphosphine in Synthesis and Transformation of Natural Products," Synthesis (1981), pp. 1-28.

Miyaura, Norio & Akira Suzuki, "Palladium-Catalyzed Cross-Coupling Reactions of Organoboron Compounds," Chem. Rev. (1995), vol. 95, pp. 2457-2483.

"Remington: The Science and Practice of Pharmacy," (21st Edition 2005), Lippincott, Williams and Wilkins Publishing.

Shang, Rui et al., J. "Synthesis of Aromatic Esters via Pd-Catalyzed Decarboxylative Coupling of Potassium Oxalate Monoesters with Aryl Bromides and Chlorides," Am. Chem. Soc. (2009), vol. 131, pp. 5738-5739.

Thompson, Andrew S. et al., "Direct Conversion of Activated Alcohols to Azides Using Diphenyl Phosphorazidate. A Practical Alternative to Mitsunobu Conditions," J. Org. Chem. (1993), vol. 58, pp. 5886-5888.

Watson, Donald A. et al., "Carbonylation of Aryl Chlorides with Oxygen Nucleophiles at Atmospheric Pressure. Preparation of Phenyl Esters as Acyl Transfer Agents and the Direct Preparation of Alkyl Esters and Carboxylic Acids," J. Org. Chem. (2008), vol. 73, pp. 7096-7101.

3-UREIDOISOQUINOLIN-8-YL DERIVATIVES

CROSS REFERENCE TO RELATED APPLICATIONS

This application is the U.S. National Phase of International Patent Application No. PCT/IB2012/051473, filed Mar. 28, 2012, which claims priority to PCT/IB2011/051320, filed Mar. 29, 2011, and to PCT/IB2011/054063, filed Sep. 16, 2011, the contents of each are hereby incorporated by reference in their entireties.

The present invention concerns novel 3-ureidoisoquinolin-8-yl derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

The intensive use of antibiotics has exerted a selective evolutionary pressure on microorganisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immune-compromised patients.

An increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccoci* are quinolone and vancomycin resistant and β-lactam antibiotics are inefficacious against these strains;
- *Enterobacteriacea* are cephalosporin and quinolone resistant;
- *P. aeruginosa* are β-lactam and quinolone resistant.

There is also an increasing number of cases of resistance in upper respiratory tract infections caused by fastidious Gram negative pathogens such as *H. influenzae* and *M. catarrhalis*. Further resistant strains of *S. aureus* have spread out of the clinical settings into the community.

Therefore, there is a high medical need for new antibacterial agents harbouring a novel mechanism of action and/or containing new pharmacophoric groups and covering these pathogenic strains.

In addition, microorganisms that are causing persistent infections are increasingly being recognized as causative agents or cofactors of severe chronic diseases like peptic ulcers or heart diseases.

WO 02/060879, WO 2003/105846, WO 2005/089763, WO 2006/038116, WO 2007/056330, WO 2007/148093, WO 2009/074810, WO 2009/074812, WO 2009/147431, WO 2009/156966 and US 2010/0063069 disclose antibacterial benzimidazole and benzothiazole derivatives and their corresponding azaisosteres wherein the alkyl urea is attached to the 5-membered heteroaromatic ring.

WO 2009/027732 and WO 2009/027733 disclose antibacterial benzimidazole derivatives and their corresponding azaisosteres wherein the alkyl urea is attached to the 6-membered heteroaromatic ring.

WO 2008/068470, WO 2009/106885, WO 2009/147433, WO 2009/147440 WO 2010/136817, WO 2010/142978 and WO 2011/024004 disclose pyridine, pyrimidine and thiazole urea derivatives as antibacterial compounds.

1-(isoquinolin-3-yl)-3-(aryl)urea or 1-(isoquinolin-3-yl)-3-(heteroaryl)urea derivatives have been disclosed for example in WO 01/07411, WO 02/062763, WO 2004/078747, WO 2006/049941, US 2006/0025415 or WO 2007/004749.

Moreover, 1-(isoquinolin-3-yl)-3-(alkyl)urea derivatives have been disclosed generically (among many other types of compounds) in US 2004/009931, WO 2007/051408, WO 2007/125405, WO 2008/082487 or WO 2009/155121. Nevertheless, there is no concrete example of any 1-(isoquinolin-3-yl)-3-(alkyl)urea in these documents.

More recently, the Applicants have described certain 3-ureidoisoquinolin-8-yl antibiotic derivatives in WO 2011/121555, published after the priority dates of the present application but before the filing date thereof.

The Applicants have now found particular 3-ureidoisoquinolin-8-yl antibiotic derivatives corresponding to the formula I described hereafter.

Various embodiments of the invention are presented hereafter:

1) The invention firstly relates to compounds of formula I

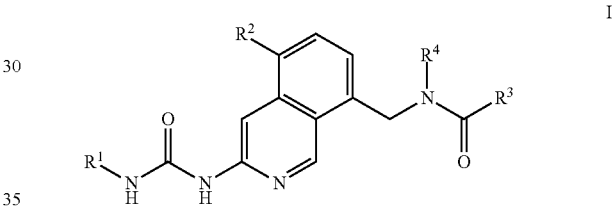

wherein
$R^1$ is $(C_1-C_3)$alkyl, $(C_2-C_3)$haloalkyl or cyclopropyl;
$R^2$ is H, halogen, pyridazin-4-yl, pyrimidin-5-yl or a group having the formula (A1), (A2) or (A3) shown hereafter

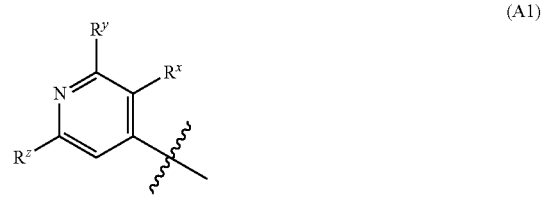

wherein $R^x$ is H and each of $R^y$ and $R^z$ is independently H or methyl, or each of $R^x$ and $R^z$ is H and $R^y$ is halogen, cyano, $(C_2-C_4)$alkyl, $(C_1-C_4)$alkoxy, amino, hydroxy, hydroxy-$(C_1-$ $C_3$)alkyl, trifluoromethyl, carbamoyl, carbamoyl-($C_1$-$C_2$) alkyl, (methylcarbamoyl)-($C_1$-$C_2$)alkyl, (dimethylcarbamoyl)-($C_1$-$C_2$)alkyl, tert-butoxycarbonylmethyl, cyclopropyl, pyrrolidin-1-yl, piperidin-1-yl, morpholin-1-yl or 1-morpholinomethyl, or $R^x$ is H and each of $R^y$ and $R^z$ is independently halogen, or $R^x$ is methyl, $R^y$ is methyl or halogen and $R^z$ is H, or $R^x$ is methyl or halogen, $R^y$ is H and $R^z$ is methyl or halogen, or $R^x$ is methyl or halogen and each of $R^y$ and $R^z$ is H; $R^{x2}$ is H, amino or hydroxymethyl;

$R^{x3}$ is hydroxy, carboxy, carbamoyl, hydroxymethyl or aminomethyl, $R^{y3}$ is H and $R^{z3}$ is H or each of $R^{x3}$ and $R^{z3}$ is H and $R^{y3}$ is hydroxy, acetamidomethyl, (dimethylamino)methyl, carboxymethyl, carbamoyl or aminomethyl, or each of $R^{x3}$ and $R^{y3}$ is H and $R^{z3}$ is hydroxy;

$R^3$ is ($C_1$-$C_4$)alkyl, ($C_2$-$C_4$)alkynyl, amino-($C_1$-$C_3$)alkyl, carbamoyl-($C_1$-$C_3$)alkyl, (methylcarbamoyl)-($C_1$-$C_3$)alkyl, ($C_1$-$C_4$)alkoxy, ($C_1$-$C_4$)haloalkoxy, ($C_3$-$C_4$)alkynyloxy, (4-hydroxybut-2-yn-1-yl)oxy, (4-aminobut-2-yn-1-yl) oxy, dimethylamino-($C_2$-$C_3$)alkoxy, carbamoyl-($C_1$-$C_3$) alkoxy, ($C_1$-$C_3$)alkylamino, ($C_3$-$C_6$)cycloalkyl, ($C_3$-$C_6$) cycloalkyl-($C_1$-$C_4$)alkyl, ($C_3$-$C_6$)cycloalkyl-($C_1$-$C_4$) alkoxy, hydroxy-($C_1$-$C_3$)alkyl, hydroxy-($C_2$-$C_3$)alkoxy, ($C_1$-$C_3$)alkoxy-($C_1$-$C_3$)alkyl, ($C_1$-$C_3$)alkoxy-($C_1$-$C_3$) alkoxy, carboxy-($C_1$-$C_3$)alkyl, carboxy-($C_1$-$C_3$)alkoxy, ($C_1$-$C_2$)alkoxycarbonyl-($C_1$-$C_3$)alkoxy, aryl, ($C_5$-$C_6$)hetero aryl, benzyl, benzyloxy, 2-cyano ethoxy, 2,3-dihydroxypropoxy, 3,4-dihydroxybutoxy, —$CH_2R^a$, —$CH_2CH_2R^b$, —$(CH_2)_n$—C(O)O—$R^d$, —$(CH_2)_n$—N($R^c$)C(O)O—$R^d$, —O—$(CH_2)_n$—N($R^c$)C(O)O—$R^d$, —$(CH_2)_n$—$R^e$ or —O—$(CH_2)$—$R^e$;

n is 1, 2 or 3;

$R^a$ is cyano, acetylamino, N,N-dimethylamino; and $R^b$ is cyano;

$R^c$ is H or methyl;

$R^d$ is ($C_1$-$C_4$)alkyl;

$R^e$ is pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl or ($C_5$-$C_6$)heteroaryl;

$R^4$ is H or methyl;

and to salts (in particular pharmaceutically acceptable salts) of compounds of formula I.

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group containing from one to four carbon atoms. The term "($C_x$-$C_y$) alkyl" (x and y each being an integer) refers to an alkyl group as defined before containing x to y carbon atoms. Representative examples of alkyl groups include methyl, ethyl, propyl, iso-propyl, n-butyl, iso-butyl, sec-butyl and tert-butyl. Representative examples of ($C_1$-$C_3$) alkyl groups include methyl, ethyl, propyl and iso-propyl.

The term "alkynyl" refers to a straight or branched hydrocarbon chain containing two to four carbon atoms with one carbon-carbon triple bond. The term "($C_x$-$C_y$)alkynyl" (x and y each being an integer) refers to an alkynyl group as defined before containing x to y carbon atoms. Representative examples of alkynyl and ($C_2$-$C_4$)alkynyl groups include, but are not limited to, ethynyl, prop-2-yn-1-yl and but-3-yn-1-yl.

The term "alkoxy", used alone or in combination, refers to a straight or branched chain alkoxy group containing from one to four carbon atoms. The term "($C_x$-$C_y$) alkoxy" (x and y each being an integer) refers to an alkoxy group as defined before containing x to y carbon atoms. For example, a ($C_1$-$C_3$)alkoxy group contains from one to three carbon atoms. Representative examples of alkoxy and ($C_1$-$C_3$)alkoxy groups include, but are not limited to, methoxy, ethoxy, n-propoxy and iso-propoxy. Preferred are methoxy and ethoxy.

The term "halogen" refers to fluorine, chlorine, bromine or iodine, preferably to fluorine or chlorine.

The term "haloalkyl", used alone or in combination, refers to a saturated straight or branched chain alkyl group containing from one to four carbon atoms wherein at least one hydrogen atom has been replaced by a halogen atom. The term "($C_x$-$C_y$)haloalkyl" (x and y each being an integer) refers to a haloalkyl group as defined before containing x to y carbon atoms. Representative examples of haloalkyl groups include trifluoromethyl and 2-fluoro-ethyl.

The term "haloalkoxy" refers to an alkoxy group as defined above wherein one or more (and possibly all) of the hydrogen atoms have been replaced by halogen atoms. The term "($C_x$-$C_y$)haloalkoxy" (x and y each being an integer) refers to a haloalkoxy group as defined before containing x to y carbon atoms. Representative examples of haloalkoxy groups include, but are not limited to, trifluoromethoxy and 2-fluoro-ethoxy.

The term "amino-($C_1$-$C_3$)alkyl" refers to a ($C_1$-$C_3$)alkyl group as defined above wherein one of the hydrogen atoms has been replaced by an amino group. Representative examples of amino-($C_1$-$C_3$)alkyl groups include, but are not limited to, aminomethyl, 2-aminoethyl and 3-aminopropyl.

The term "carbamoyl-($C_1$-$C_y$)alkyl", wherein y is an integer, refers to a ($C_1$-$C_y$)alkyl group as defined above wherein one of the hydrogen atoms has been replaced by a carbamoyl group. Thus, the term "carbamoyl-($C_1$-$C_3$) alkyl" refers to a ($C_1$-$C_3$)alkyl group as defined above wherein one of the hydrogen atoms has been replaced by a carbamoyl group. Representative examples of carbamoyl-($C_1$-$C_3$)alkyl groups include, but are not limited to, carbamoylmethyl, 2-carbamoylethyl and 3-carbamoylpropyl. Besides, the term "carbamoyl-($C_1$-$C_2$)alkyl" refers to a methyl or ethyl group wherein one of the hydrogen atoms has been replaced by a carbamoyl group. Representative examples of carbamoyl-($C_1$-$C_2$) alkyl groups therefore include, but are not limited to, carbamoylmethyl and 2-carbamoylethyl.

The term "(methylcarbamoyl)-($C_1$-$C_3$)alkyl" refers to a ($C_1$-$C_3$)alkyl group as defined above wherein one of the hydrogen atoms has been replaced by a methylcarbamoyl group. Representative examples of (methylcarbamoyl)-($C_1$-$C_3$)alkyl groups include, but are not limited to, (methylcarbamoyl)methyl, 2-(methylcarbamoyl)ethyl and 3-(methylcarbamoyl)propyl.

The term "(dimethylcarbamoyl)-($C_1$-$C_2$)alkyl" refers to a ($C_1$-$C_2$)alkyl group as defined above wherein one of the hydrogen atoms has been replaced by a dimethylcarbamoyl group. Representative examples of (dimethylcarbamoyl)-($C_1$-$C_2$)alkyl groups include, but are not limited to, (dimethylcarbamoyl)methyl and 2-(dimethylcarbamoyl)ethyl.

The term "hydroxy-($C_1$-$C_3$)alkyl" refers to a ($C_1$-$C_3$)alkyl group as defined above wherein one of the hydrogen atoms has been replaced by a hydroxy group. Representative examples of hydroxy-$(C_1-C_3)$alkyl groups include, but are not limited to, hydroxymethyl, 2-hydroxyethyl and 3-hydroxypropyl.

The term "$(C_1-C_3)$alkoxy-$(C_1-C_3)$alkyl" refers to a $(C_1-C_3)$alkyl group as defined above wherein one of the hydrogen atoms has been replaced by a $(C_1-C_3)$alkoxy group as defined above. Representative examples of $(C_1-C_3)$alkoxy-$(C_1-C_3)$alkyl groups include, but are not limited to, 2-methoxyethyl, 2-ethoxyethyl and 3-methoxypropyl.

The term "carboxy-$(C_1-C_3)$alkyl" refers to a $(C_1-C_3)$alkyl group as defined above wherein one of the hydrogen atoms has been replaced by a carboxy group. Representative examples of carboxy-$(C_1-C_3)$alkyl groups include, but are not limited to, 2-carboxyethyl and 3-carboxypropyl.

The term "dimethylamino-$(C_2-C_3)$alkoxy" refers to a $(C_2-C_3)$alkoxy group as defined above wherein one of the hydrogen atoms has been replaced by a dimethylamino group. Representative examples of dimethylamino-$(C_2-C_3)$alkoxy groups include, but are not limited to, 2-(dimethylamino)ethoxy and 3-(dimethylamino)propoxy.

The term "hydroxy-$(C_2-C_3)$alkoxy" refers to a $(C_2-C_3)$alkoxy group as defined above wherein one of the hydrogen atoms has been replaced by a hydroxy group. Representative examples of hydroxy-$(C_2-C_3)$alkoxy groups include, but are not limited to, 2-hydroxyethoxy and 3-hydroxypropoxy.

The term "carbamoyl-$(C_1-C_3)$alkoxy" refers to a $(C_1-C_3)$alkoxy group as defined above wherein one of the hydrogen atoms has been replaced by a carbamoyl group. Representative examples of carbamoyl-$(C_1-C_3)$alkoxy groups include, but are not limited to, carbamoylmethoxy, 2-carbamoylethoxy and 3-carbamoylpropoxy.

The term "$(C_1-C_3)$alkoxy-$(C_1-C_3)$alkoxy" refers to a $(C_1-C_3)$alkyl group as defined above wherein one of the hydrogen atoms has been replaced by a $(C_1-C_3)$alkoxy group as defined above. Representative examples of $(C_1-C_3)$alkoxy-$(C_1-C_3)$alkoxy groups include, but are not limited to, 2-methoxyethoxy, 2-ethoxyethoxy and 3-methoxypropoxy.

The term "carboxy-$(C_1-C_3)$alkoxy" refers to a $(C_1-C_3)$alkoxy group as defined above wherein one of the hydrogen atoms has been replaced by a carboxy group. Representative examples of carboxy-$(C_1-C_3)$alkoxy groups include, but are not limited to, 2-carboxyethoxy and 3-carboxypropoxy.

The term "$(C_1-C_2)$alkoxycarbonyl-$(C_1-C_3)$alkoxy" refers to a $(C_1-C_3)$alkoxy group as defined above wherein one of the hydrogen atoms has been replaced by a $(C_1-C_2)$alkoxycarbonyl group wherein the $(C_1-C_2)$alkoxy group is as defined above. Representative examples of $(C_1-C_2)$alkoxycarbonyl-$(C_1-C_3)$alkoxy groups include, but are not limited to, 2-(methoxycarbonyl)ethoxy and 2-(ethoxycarbonyl)ethoxy.

The term "$(C_3-C_4)$alkynyloxy" refers to a prop-2-yn-1-yloxy, but-2-yn-1-yloxy, but-3-yn-1-yloxy or but-3-yn-2-yloxy group.

The expression "linear $(C_3-C_4)$alkynyloxy" refer to a prop-2-yn-1-yloxy, but-2-yn-1-yloxy or but-3-yn-1-yloxy group.

The term "alkylamino" refers to an alkylamino group wherein the alkyl group is as defined above. The term "$(C_x-C_y)$alkylamino" (x and y each being an integer) refers to a alkylamino group as defined before containing x to y carbon atoms. Representative examples of alkylamino groups (and in particular of $(C_1-C_3)$alkylamino groups) include, but are not limited to, methylamino and ethylamino The term "cycloalkyl", used alone or in combination, refers to a saturated cyclic hydrocarbon moiety containing 3 to 6 carbon atoms. The term "$(C_x-C_y)$cycloalkyl" (x and y each being an integer) refers to a cycloalkyl group as defined before containing x to y carbon atoms. Representative examples of cycloalkyl groups include, but are not limited to, cyclopropyl and cyclohexyl.

The term "$(C_3-C_6)$cycloalkyl-$(C_1-C_4)$alkyl" refers to a $(C_1-C_4)$alkyl group as defined before wherein a hydrogen has been replaced by a $(C_3-C_6)$cycloalkyl alkyl group as defined before. Representative examples of $(C_3-C_6)$cycloalkyl-$(C_1-C_4)$alkyl groups include, but are not limited to, cyclopropylmethyl and cyclopentylmethyl.

The term "$(C_3-C_6)$cycloalkyl-$(C_1-C_4)$alkoxy" refers to a $(C_1-C_4)$alkoxy group as defined before wherein a hydrogen has been replaced by a $(C_3-C_6)$cycloalkyl group as defined before. Representative examples of $(C_3-C_6)$cycloalkyl-$(C_1-C_4)$alkoxy groups include, but are not limited to, cyclopropylmethoxy and cyclopentylmethoxy.

The term "aryl" refers to a phenyl or a naphthyl group, and in particular to a phenyl group. Any aryl group as defined herein may be substituted with up to three substituents each independently selected from the group consisting of halogen, $(C_1-C_4)$alkyl, $(C_1-C_4)$alkoxy, trifluoromethyl and trifluoromethoxy. Specific examples of aryl are phenyl, 4-fluoro-phenyl, 4-chloro-phenyl, 4-methoxy-phenyl, 4-methyl-phenyl, 4-trifluoromethyl-phenyl, 4-trifluoromethoxy-phenyl, 2,4-difluoro-phenyl, 2,4-dichloro-phenyl, 2,4-dimethoxy-phenyl, 2,4-dimethyl-phenyl, 2,4-ditrifluoromethyl-phenyl and 2,4-ditrifluoromethoxy-phenyl.

The term "$(C_5-C_6)$heteroaryl", used alone or in combination, refers to a five- or six-membered aromatic ring containing from one to three ring heteroatoms, each of which is independently selected from nitrogen, oxygen and sulphur. Any $(C_5-C_6)$heteroaryl group as defined herein may be substituted with one or two substituents each independently selected from halogen, methyl and methoxy. Representative examples of $(C_5-C_6)$heteroaryl groups include, but are not limited to, pyridin-2-yl, pyridin-3-yl, pyridin-4-yl, pyrimidin-4-yl, pyrimidin-5-yl, 2H-1,2,3-triazol-4-yl, 1H-pyrazol-1-yl, 1H-pyrazol-3-yl, 1-methyl-1H-pyrazol-3-yl, 1H-pyrazol-4-yl, 1H-imidazol-2-yl, 1-methyl-1H-imidazol-2-yl, 1H-imidazol-4-yl, 1H-imidazol-5-yl, 1-methyl-1H-imidazol-5-yl (and in particular pyridin-2-yl, pyridin -3-yl, pyridin-4-yl, 2H-1,2,3-triazol-4-yl, 1H-imidazol-2-yl and 1-methyl-1H-imidazol -5-yl).

The term "($(C_5-C_6)$heteroaryl)methyl" refers to a methyl group wherein one of the hydrogen atoms has been replaced by a $(C_5-C_6)$heteroaryl group as defined above. Representative examples of (($(C_5-C_6)$heteroaryl)methyl groups include, but are not limited to, 1H-imidazol-4-ylmethyl or 1H-pyrazol-1-ylmethyl.

The term "($(C_5-C_6)$heteroaryl)methoxy" refers to a methoxy group wherein one of the hydrogen atoms has been replaced by a $(C_5-C_6)$heteroaryl group as defined above. Representative examples of (($(C_5-C_6)$heteroaryl)methoxy groups include, but are not limited to, (1-methyl-1H-pyrazol-3-yl)methoxy, (1H-pyrazol-4-yl)methoxy, (1-methyl -1H-imidazol-2-yl)methoxy, (1-methyl-1H-imidazol-5-yl)methoxy, pyridin -2-ylmethoxy, pyridin-3-ylmethoxy, pyridin-4-ylmethoxy, pyrimidin-4-ylmethoxy or pyrimidin-5-ylmethoxy (and in particular 1-methyl-1H-pyrazol-3-yl)methoxy, (1H-pyrazol-4-yl)methoxy, (1-methyl-1H-imidazol-5-yl)methoxy, pyridin-2-ylmethoxy, pyridin-3-ylmethoxy, pyridin-4-ylmethoxy, pyrimidin-4-ylmethoxy or pyrimidin-5-ylmethoxy).

In this text, a bond interrupted by a wavy line shows the point of attachment of the radical drawn. For example, the radical drawn below

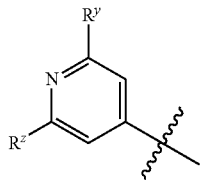

wherein each of $R^y$ and $R^z$ represents hydrogen is the pyridin-4-yl radical.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, the term "room temperature" as used herein refers to a temperature of 20 to 30° C., and preferably 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

2) The invention also relates to compounds of formula I as defined in embodiment 1) that are also compounds of formula $I_{P2}$

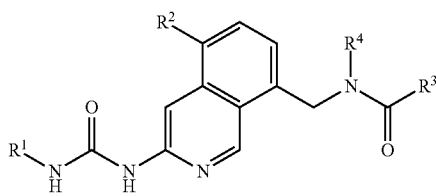

wherein
$R^1$ is $(C_1-C_3)$alkyl, $(C_2-C_3)$haloalkyl or cyclopropyl;
$R^2$ is H, halogen, pyridazin-4-yl, pyrimidin-5-yl or a group having the formula (A1), (A2) or (A3) shown hereafter

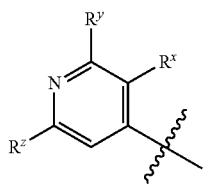

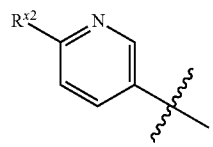

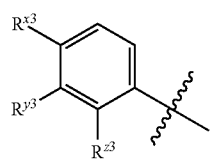

wherein $R^x$ is H and either each of $R^y$ and $R^z$ is independently H or methyl, or $R^z$ is H and $R^y$ is halogen, cyano, methoxy, amino, hydroxymethyl or 1-morpholinomethyl, or $R^x$ is methyl and each of $R^y$ and $R^z$ is H;

$R^{x2}$ is H, amino or hydroxymethyl;

$R^{x3}$ is hydroxy, carboxy, carbamoyl, hydroxymethyl or aminomethyl, $R^{y3}$ is H and $R^{z3}$ is H or each of $R^{x3}$ and $R^{z3}$ is H and $R^{y3}$ is hydroxy, acetamidomethyl, (dimethylamino)methyl, carboxymethyl, carbamoyl or aminomethyl, or each of $R^{x3}$ and $R^{y3}$ is H and $R^{z3}$ is hydroxy;

$R^3$ is $(C_1-C_4)$alkyl, $(C_2-C_4)$alkynyl, amino-$(C_1-C_3)$alkyl, carbamoyl-$(C_1-C_3)$alkyl, (methylcarbamoyl)-$(C_1-C_3)$alkyl, $(C_1-C_4)$alkoxy, $(C_1-C_4)$haloalkoxy, $(C_3-C_4)$alkynyloxy, (4-hydroxybut-2-yn-1-yl)oxy, (4-aminobut-2-yn-1-yl)oxy, dimethylamino-$(C_2-C_3)$alkoxy, carbamoyl-$(C_1-C_3)$alkoxy, $(C_1-C_3)$alkylamino, $(C_3-C_6)$cycloalkyl, $(C_3-C_6)$cycloalkyl-$(C_1-C_4)$alkyl, $(C_3-C_6)$cycloalkyl-$(C_1-C_4)$alkoxy, hydroxy-$(C_1-C_3)$alkyl, hydroxy-$(C_2-C_3)$alkoxy, $(C_1-C_3)$alkoxy-$(C_1-C_3)$alkyl, $(C_1-C_3)$alkoxy-$(C_1-C_3)$alkoxy, carboxy-$(C_1-C_3)$alkyl, carboxy-$(C_1-C_3)$alkoxy, $(C_1-C_2)$alkoxycarbonyl-$(C_1-C_3)$alkoxy, aryl, $(C_5-C_6)$hetero aryl, benzyl, benzyloxy, 2-cyanoethoxy, 2,3-dihydroxypropoxy, 3,4-dihydroxybutoxy, —CH$_2$R$^a$, —CH$_2$CH$_2$R$^b$, —(CH$_2$)$_n$—C(O)O—R$^d$, —(CH$_2$)$_n$—N(R$^c$)C(O)O—R$^d$, —O—(CH$_2$)$_n$—N(R$^c$)C(O)O—R$^d$, —(CH$_2$)$_n$—R$^e$ or —O—(CH$_2$)$_n$—R$^e$;

n is 1, 2 or 3;

$R^a$ is cyano, acetylamino, N,N-dimethylamino; and $R^b$ is cyano;

$R^c$ is H or methyl;

$R^d$ is $(C_1-C_4)$alkyl;

$R^e$ is pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl or $(C_5-C_6)$heteroaryl;

$R^4$ is H or methyl;

and to salts (in particular pharmaceutically acceptable salts) of compounds of formula I.

3) The invention furthermore relates to compounds of formula I as defined in embodiment 1) that are also compounds of formula $I_{P1}$

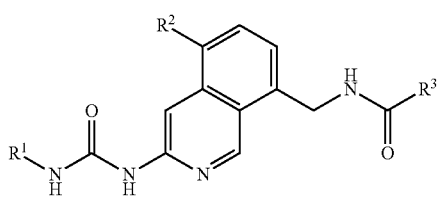

wherein
R¹ represents (C₁-C₃)alkyl, (C₂-C₃)haloalkyl or cyclopropyl;
R² represents H or a group of formula (A1')

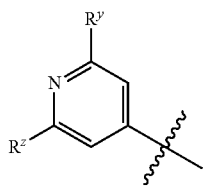

(A1')

wherein either each of $R^y$ and $R^z$ represents independently hydrogen or methyl, or $R^z$ represents hydrogen and $R^y$ represents halogen, methoxy or amino;
R³ represents (C₁-C₄)alkyl, (C₂-C₄)alkynyl, (C₁-C₄)alkoxy, (C₁-C₄)haloalkoxy, linear (C₃-C₄)alkynyloxy, (C₁-C₃)alkylamino, (C₃-C₆)cycloalkyl, (C₃-C₆)cycloalkyl-(C₁-C₄)alkyl, (C₃-C₆)cycloalkyl-(C₁-C₄)alkoxy, aryl, (C₅-C₆)hetero aryl, ((C₅-C₆)heteroaryl)methoxy, benzyl, benzyloxy, methoxymethyl, 2-methoxyethoxy, 2-cyanoethoxy, —CH₂Rᵃ or —CH₂CH₂Rᵇ;
$R^a$ is cyano, acetylamino or N,N-dimethylamino; and
$R^b$ is cyano or carbamoyl;

and to salts (in particular pharmaceutically acceptable salts) of compounds of formula $I_{P1}$.

4) The invention in particular relates to compounds of formula I according to embodiment 1) that are also compounds of formula $I_{CE}$

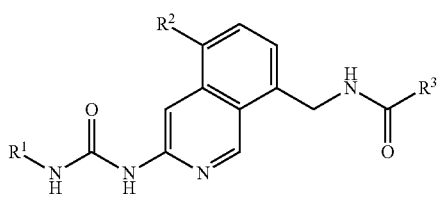

$I_{CE}$ wherein
R¹ is (C₁-C₃)alkyl;
R² is H, halogen, pyridazin-4-yl, pyrimidin-5-yl or a group having the formula (A1), (A2) or (A3) shown hereafter

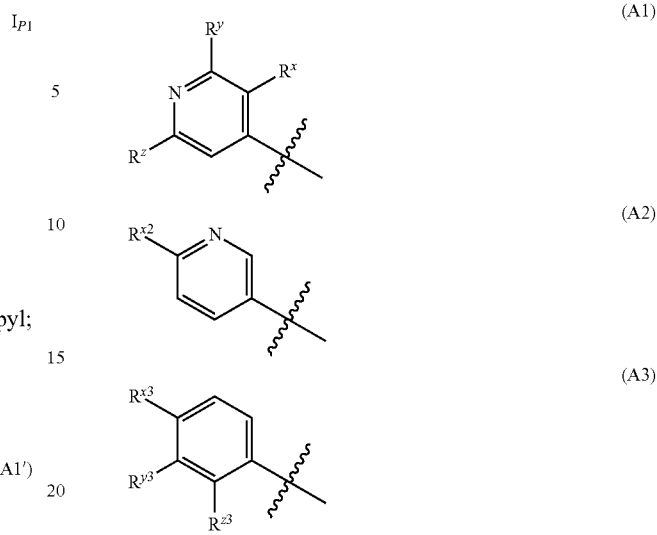

wherein $R^x$ is H and either each of $R^y$ and $R^z$ is independently H or methyl, or $R^z$ represents H and $R^y$ is halogen, cyano, (C₂-C₄)alkyl, (C₁-C₄)alkoxy, amino, hydroxy, hydroxy-(C₁-C₃)alkyl, trifluoromethyl, carbamoyl, carbamoyl-(C₁-C₂)alkyl, (methylcarbamoyl)-(C₁-C₂)alkyl, (dimethylcarbamoyl)-(C₁-C₂)alkyl, tert-butoxycarbonylmethyl, cyclopropyl, pyrrolidin-1-yl, piperidin-1-yl, morpholin-1-yl or 1-morpholinomethyl, or $R^x$ is methyl, $R^y$ is methyl or halogen and $R^z$ is H, or $R^x$ is methyl or halogen, $R^y$ is H and $R^z$ is methyl or halogen, or $R^x$ is H and each of $R^y$ and $R^z$ is independently halogen, or $R^x$ is methyl or halogen and each of $R^y$ and $R^z$ is H;
$R^{x2}$ is H, amino or hydroxymethyl;
$R^{x3}$ is hydroxy, carboxy, carbamoyl, hydroxymethyl or aminomethyl, $R^{y3}$ is H and $R^{z3}$ is H or each of $R^{x3}$ and $R^{z3}$ is H and $R^{y3}$ is hydroxy, acetamidomethyl, (dimethylamino)methyl, carboxymethyl, carbamoyl or aminomethyl, or each of $R^{x3}$ and $R^{y3}$ is H and $R^{z3}$ is hydroxy;
R³ is (C₁-C₄)alkyl, (C₂-C₄)alkynyl, amino-(C₁-C₃)alkyl, carbamoyl-(C₁-C₃)alkyl, (methylcarbamoyl)-(C₁-C₃)alkyl, (C₁-C₄)alkoxy, (C₁-C₄)haloalkoxy, (C₃-C₄)alkynyloxy, (4-hydroxybut-2-yn-1-yl)oxy, (4-aminobut-2-yn-1-yl)oxy, dimethylamino-(C₂-C₃)alkoxy, carbamoyl-(C₁-C₃)alkoxy, (C₁-C₃)alkylamino, (C₃-C₆)cycloalkyl, (C₃-C₆)cycloalkylmethyl, (C₃-C₆)cycloalkylmethoxy, hydroxy-(C₁-C₃)alkyl, hydroxy-(C₁-C₃)alkoxy, (C₁-C₃)alkoxy-(C₁-C₃)alkyl, (C₁-C₃)alkoxy-(C₁-C₃)alkoxy, carboxy-(C₁-C₃)alkyl, carboxy-(C₁-C₃)alkoxy, (C₁-C₂)alkoxycarbonyl-(C₁-C₃)alkoxy, phenyl, benzyl, benzyloxy, 2-cyanoethoxy, 2,3-dihydroxypropoxy, 3,4-dihydroxybutoxy, —CH₂Rᵃ, —(CH₂)ₙ—C(O)O—Rᵈ, —(CH₂)ₙ—N(Rᶜ)C(O)O—Rᵈ, —O—(CH₂)ₙ—N(Rᶜ)C(O)O—Rᵈ, —(CH₂)ₙ—Rᵉ or —O—(CH₂)ₙ—Rᵉ, or R³ is a five- or six-membered heteroaryl group which has one to three ring heteroatoms, each of which is nitrogen, whereby said heteroaryl group can be substituted once with methyl, or also R³ is a (heteroaryl)methoxy group wherein the heteroaryl is a five- or six-membered heteroaryl group which has one to three ring heteroatoms, each of which is nitrogen, whereby said heteroaryl group can be substituted once with methyl; and
n is 1, 2 or 3;
$R^a$ is cyano, acetylamino or N,N-dimethylamino;
$R^c$ is H or methyl;

$R^d$ is ($C_1$-$C_4$)alkyl;

$R^e$ is pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl, or $R^e$ is a five- or six-membered heteroaryl group which has one to three ring heteroatoms, each of which is nitrogen, whereby said heteroaryl group can be substituted once with methyl;

$R^4$ is H or methyl;

and to salts (in particular pharmaceutically acceptable salts) of compounds of formula $I_{CE}$.

5) The invention furthermore relates to compounds of formula I according to embodiment 2) that are also compounds of formula $I_{CEP2}$

$I_{CEP2}$ wherein $R^1$ is ($C_1$-$C_3$)alkyl;

$R^2$ is H, halogen, pyridazin-4-yl, pyrimidin-5-yl or a group having the formula (A1), (A2) or (A3) shown hereafter

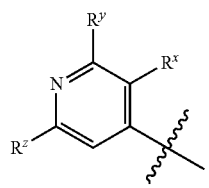

(A1)

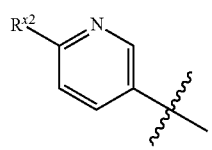

(A2)

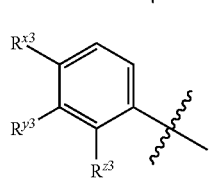

(A3)

wherein $R^x$ is H and either each of $R^y$ and $R^z$ is independently H or methyl, or $R^z$ represents H and $R^y$ is halogen, cyano, methoxy, amino, hydroxymethyl or 1-morpholinomethyl, or $R^x$ is methyl and each of $R^y$ and $R^z$ is H;

$R^{x2}$ is H, amino or hydroxymethyl;

$R^{x3}$ is hydroxy, carboxy, carbamoyl, hydroxymethyl or aminomethyl, $R^{y3}$ is H and $R^{z3}$ is H or each of $R^{x3}$ and $R^{z3}$ is H and $R^{y3}$ is hydroxy, acetamidomethyl, (dimethylamino)methyl, carboxymethyl, carbamoyl or aminomethyl, or each of $R^{x3}$ and $R^{y3}$ is H and $R^{z3}$ is hydroxy;

$R^3$ is ($C_1$-$C_4$)alkyl, ($C_2$-$C_4$)alkynyl, amino-($C_1$-$C_3$)alkyl, carbamoyl-($C_1$-$C_3$)alkyl, (methylcarbamoyl)-($C_1$-$C_3$)alkyl, ($C_1$-$C_4$)alkoxy, ($C_1$-$C_4$)haloalkoxy, ($C_3$-$C_4$)alkynyloxy, (4-hydroxybut-2-yn-1-yl)oxy, (4-aminobut-2-yn-1-yl)oxy, dimethylamino-($C_2$-$C_3$)alkoxy, carbamoyl-($C_1$-$C_3$)alkoxy, ($C_1$-$C_3$)alkylamino, ($C_3$-$C_6$)cycloalkyl, ($C_3$-$C_6$)cycloalkylmethyl, ($C_3$-$C_6$)cycloalkylmethoxy, hydroxy-($C_1$-$C_3$)alkyl, hydroxy-($C_1$-$C_3$)alkoxy, ($C_1$-$C_3$)alkoxy-($C_1$-$C_3$)alkyl, ($C_1$-$C_3$)alkoxy-($C_1$-$C_3$)alkoxy, carboxy-($C_1$-$C_3$)alkyl, carboxy-($C_1$-$C_3$)alkoxy, ($C_1$-$C_2$)alkoxycarbonyl-($C_1$-$C_3$)alkoxy, phenyl, benzyl, benzyloxy, 2-cyanoethoxy, 2,3-dihydroxypropoxy, 3,4-dihydroxybutoxy, —$CH_2R^a$, —$(CH_2)_n$—C(O)O—$R^d$, —$(CH_2)_n$—N($R^c$)C(O)O—$R^d$, —O—$(CH_2)_n$—N($R^c$)C(O)O—$R^d$, —$(CH_2)_n$—$R^e$ or —O—$(CH_2)_n$—$R^e$, or $R^3$ is a five- or six-membered heteroaryl group which has one to three ring heteroatoms, each of which is nitrogen, whereby said heteroaryl group can be substituted once with methyl, or also $R^3$ is a (heteroaryl)methoxy group wherein the heteroaryl is a five- or six-membered heteroaryl group which has one to three ring heteroatoms, each of which is nitrogen, whereby said heteroaryl group can be substituted once with methyl; and n is 1, 2 or 3;

$R^a$ is cyano, acetylamino or N,N-dimethylamino;

$R^c$ is H or methyl;

$R^d$ is ($C_1$-$C_4$)alkyl;

$R^e$ is pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl, or $R^e$ is a five- or six-membered heteroaryl group which has one to three ring heteroatoms, each of which is nitrogen, whereby said heteroaryl group can be substituted once with methyl;

$R^4$ is H or methyl;

and to salts (in particular pharmaceutically acceptable salts) of compounds of formula $I_{CEP2}$.

6) The invention also relates to compounds of formula $I_{P1}$ according to embodiment 3) that are also compounds of formula $I_{CEP1}$

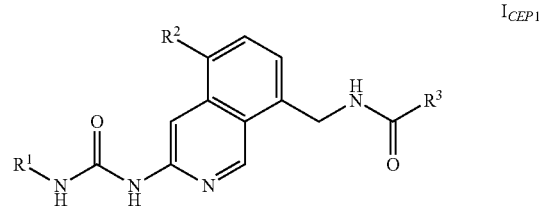

$I_{CEP1}$ wherein $R^1$ represents ($C_1$-$C_3$)alkyl;

$R^2$ represents H or pyridin-4-yl;

$R^3$ represents ($C_1$-$C_4$)alkyl, ($C_2$-$C_4$)alkynyl, ($C_1$-$C_4$)alkoxy, ($C_1$-$C_4$)haloalkoxy, linear ($C_3$-$C_4$)alkynyloxy, ($C_1$-$C_3$)alkylamino, ($C_3$-$C_6$)cycloalkyl, ($C_3$-$C_6$)cycloalkylmethyl, ($C_3$-$C_6$)cycloalkylmethoxy, phenyl, benzyl, benzyloxy, methoxymethyl, 2-methoxyethoxy, 2-cyanoethoxy, —$CH_2R^a$ or 2-carbamoyl-ethyl, or $R^3$ represents a five- or six-membered heteroaryl group which has one to three ring heteroatoms, each of which is nitrogen, whereby said heteroaryl group can be substituted once with methyl, or also $R^3$ represents a (heteroaryl)methoxy group wherein the heteroaryl is a five- or six-membered heteroaryl group which has one to three ring heteroatoms, each of which is nitrogen, whereby said heteroaryl group can be substituted once with methyl; and $R^a$ is cyano, acetylamino or N,N-dimethylamino;

and to salts (in particular pharmaceutically acceptable salts) of compounds of formula $I_{CEP1}$.

7) According to one embodiment of the invention, the compounds of formula I as defined in one of embodiments 1) to 6) will be such that $R^1$ represents $(C_1-C_3)$alkyl.

8) Preferably, the compounds of formula I as defined in embodiment 7) will be such that $R^1$ represents ethyl.

9) According to another embodiment of the invention, the compounds of formula I as defined in one of embodiments 1) to 3) will be such that $R^1$ represents $(C_1-C_3)$haloalkyl (notably $(C_1-C_2)$haloalkyl and in particular 2-fluoroethyl).

10) According to yet another embodiment of the invention, the compounds of formula I as defined in one of embodiments 1) to 3) will be such that $R^1$ represents cyclopropyl.

11) According to a main variant of the invention, the compounds of formula I as defined in one of embodiments 1) to 10) will be such that $R^2$ represents H.

12) According to a sub-variant of embodiment 11), the compounds of formula I as defined in embodiment 11) will be such that $R^3$ represents $(C_1-C_4)$alkyl, $(C_2-C_4)$alkynyl, amino -$(C_1-C_3)$alkyl, carbamoyl-$(C_1-C_3)$alkyl, (methylcarbamoyl)-$(C_1-C_3)$alkyl, $(C_1-C_3)$alkoxy-$(C_1-C_3)$alkyl or carboxy-$(C_1-C_3)$alkyl (and notably such that $R^3$ represents $(C_1-C_4)$alkyl, methoxymethyl or $(C_2-C_4)$alkynyl).

13) According to another sub-variant of embodiment 11), the compounds of formula I as defined in embodiment 11) will be such that $R^3$ represents $(C_1-C_4)$alkoxy, $(C_1-C_4)$haloalkoxy, $(C_3-C_4)$alkynyloxy, (4-hydroxybut-2-yn-1-yl)oxy, (4-aminobut-2-yn -1-yl)oxy, dimethylamino-$(C_2-C_3)$alkoxy, carbamoyl-$(C_1-C_3)$alkoxy, hydroxy-$(C_2-C_3)$alkoxy, $(C_1-C_3)$alkoxy-$(C_1-C_3)$alkoxy, carboxy-$(C_1-C_3)$alkoxy, $(C_1-C_2)$alkoxycarbonyl-$(C_1-C_3)$alkoxy, 2-cyanoethoxy, 2,3-dihydroxypropoxy or 3,4-dihydroxybutoxy (in particular such that $R^3$ represents $(C_1-C_4)$alkoxy, $(C_1-C_4)$haloalkoxy, linear $(C_3-C_4)$alkynyloxy, 2-methoxyethoxy or 2-cyanoethoxy, and notably such that $R^3$ represents $(C_1-C_4)$alkoxy, $(C_1-C_4)$haloalkoxy or linear $(C_3-C_4)$alkynyloxy).

14) According to yet another sub-variant of embodiment 11), the compounds of formula I as defined in embodiment 11) will be such that $R^3$ represents $(C_1-C_3)$alkylamino.

15) According to yet another sub-variant of embodiment 11), the compounds of formula I as defined in embodiment 11) will be such that $R^3$ represents $(C_3-C_6)$cycloalkyl.

16) According to yet another sub-variant of embodiment 11), the compounds of formula I as defined in embodiment 11) will be such that $R^3$ represents $(C_3-C_6)$cycloalkyl-$(C_1-C_4)$alkyl (and in particular $(C_3-C_6)$cycloalkylmethyl).

17) According to yet another sub-variant of embodiment 11), the compounds of formula I as defined in embodiment 11) will be such that $R^3$ represents $(C_3-C_6)$cycloalkyl-$(C_1-C_4)$alkoxy (and in particular $(C_3-C_6)$cycloalkylmethoxy).

18) According to yet another sub-variant of embodiment 11), the compounds of formula I as defined in embodiment 11) will be such that $R^3$ represents phenyl.

19) According to yet another sub-variant of embodiment 11), the compounds of formula I as defined in embodiment 11) will be such that $R^3$ represents benzyl.

20) According to yet another sub-variant of embodiment 11), the compounds of formula I as defined in embodiment 11) will be such that $R^3$ represents benzyloxy.

21) According to yet another sub-variant of embodiment 11), the compounds of formula I as defined in embodiment 11) will be such that $R^3$ represents —$CH_2R^a$.

22) According to yet another sub-variant of embodiment 11), the compounds of formula I as defined in embodiment 11) will be such that $R^3$ represents —$CH_2CH_2R^b$.

23) According to yet another sub-variant of embodiment 11), the compounds of formula I as defined in embodiment 11) will be such that $R^3$ represents a five- or six-membered heteroaryl group which has one to three ring heteroatoms, each of which is nitrogen, and said heteroaryl group can be substituted once with methyl.

24) According to yet another sub-variant of embodiment 11), the compounds of formula I as defined in embodiment 11) will be such that $R^3$ represents a (heteroaryl)methoxy group wherein the heteroaryl is a five- or six-membered heteroaryl group which has one to three ring heteroatoms, each of which is nitrogen, and said heteroaryl group can be substituted once with methyl.

25) According to yet another sub-variant of embodiment 11), the compounds of formula I as defined in embodiment 11) will be such that $R^3$ represents —$(CH_2)_n$—C(O)O—$R^d$.

26) According to yet another sub-variant of embodiment 11), the compounds of formula I as defined in embodiment 11) will be such that $R^3$ represents —$(CH_2)_n$—N($R^c$)C(O)O—$R^d$.

27) According to yet another sub-variant of embodiment 11), the compounds of formula I as defined in embodiment 11) will be such that $R^3$ represents —O—$(CH_2)_n$—N($R^c$)C(O)O—$R^d$.

28) According to yet another sub-variant of embodiment 11), the compounds of formula I as defined in embodiment 11) will be such that $R^3$ represents —$(CH_2)_n$—$R^e$.

29) According to a particular sub-embodiment of embodiment 28), $R^e$ will represent pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl.

30) According to another particular sub-embodiment of embodiment 28), $R^e$ will represent $(C_5-C_6)$heteroaryl.

31) According to yet another sub-variant of embodiment 11), the compounds of formula I as defined in embodiment 11) will be such that $R^3$ represents —O—$(CH_2)_n$—$R^e$ (and notably such that $R^3$ represents —O—$(CH_2)_n$—$R^e$ wherein n is 1).

32) According to a particular sub-embodiment of embodiment 31), the compounds of formula I will be such that $R^e$ represents pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl.

33) According to another particular sub-embodiment of embodiment 31), the compounds of formula I will be such that $R^e$ represents $(C_5-C_6)$heteroaryl.

34) According to another main variant of the invention, the compounds of formula I as defined in one of embodiments 1), 2), 4) and 5), or as defined in one of embodiments 1), 2), 4) or 5) taken together with the additional features of one of embodiments 7) to 10), will be such that $R^2$ is halogen (in particular Cl or F and notably Cl); this embodiment will notably relate to compounds of formula I as defined in embodiment 2) or 5), or as defined in embodiment 2) or 5) taken together with the additional features of one of embodiments 7) to 10), wherein $R^2$ is halogen (in particular Cl or F and notably Cl).

35) According to a sub-variant of embodiment 34), the compounds of formula I as defined in embodiment 34) will be such that $R^3$ represents $(C_1-C_4)$alkyl, $(C_2-C_4)$alkynyl, amino-$(C_1-C_3)$alkyl, carbamoyl-$(C_1-C_3)$alkyl, (methylcarbamoyl)-$(C_1-C_3)$alkyl, $(C_1-C_3)$alkoxy-$(C_1-C_3)$alkyl or carboxy-$(C_1-C_3)$alkyl.

36) According to another sub-variant of embodiment 34), the compounds of formula I as defined in embodiment 34) will be such that $R^3$ represents $(C_1-C_4)$alkoxy, $(C_1-C_4)$haloalkoxy, $(C_3-C_4)$alkynyloxy, (4-hydroxybut-2-yn-1-yl)oxy, (4-aminobut-2-yn-1-yl)oxy, dimethylamino-$(C_2-C_3)$alkoxy, carbamoyl-$(C_1-C_3)$alkoxy, hydroxyl -$(C_2-C_3)$alkoxy, $(C_1-C_3)$alkoxy-$(C_1-C_3)$alkoxy, carboxy-$(C_1-C_3)$alkoxy, $(C_1-C_2)$alkoxycarbonyl-$(C_1-C_3)$alkoxy, 2-cyanoethoxy, 2,3-dihydroxypropoxy or 3,4-dihydroxybutoxy.

37) According to yet another sub-variant of embodiment 34), the compounds of formula I as defined in embodiment 34) will be such that $R^3$ represents $(C_1-C_3)$alkylamino.

38) According to yet another sub-variant of embodiment 34), the compounds of formula I as defined in embodiment 34) will be such that $R^3$ represents $(C_3-C_6)$cycloalkyl.

39) According to yet another sub-variant of embodiment 34), the compounds of formula I as defined in embodiment 34) will be such that $R^3$ represents $(C_3-C_6)$cycloalkyl-$(C_1-C_4)$alkyl (and in particular $(C_3-C_6)$cycloalkylmethyl).

40) According to yet another sub-variant of embodiment 34), the compounds of formula I as defined in embodiment 34) will be such that $R^3$ represents $(C_3-C_6)$cycloalkyl-$(C_1-C_4)$alkoxy (and in particular $(C_3-C_6)$cycloalkylmethoxy).

41) According to yet another sub-variant of embodiment 34), the compounds of formula I as defined in embodiment 34) will be such that $R^3$ represents phenyl.

42) According to yet another sub-variant of embodiment 34), the compounds of formula I as defined in embodiment 34) will be such that $R^3$ represents benzyl.

43) According to yet another sub-variant of embodiment 34), the compounds of formula I as defined in embodiment 34) will be such that $R^3$ represents benzyloxy.

44) According to yet another sub-variant of embodiment 34), the compounds of formula I as defined in embodiment 34) will be such that $R^3$ represents —$CH_2R^a$.

45) According to yet another sub-variant of embodiment 34), the compounds of formula I as defined in embodiment 34) will be such that $R^3$ represents —$CH_2CH_2R^b$.

46) According to yet another sub-variant of embodiment 34), the compounds of formula I as defined in embodiment 34) will be such that $R^3$ represents a five- or six-membered heteroaryl group which has one to three ring heteroatoms, each of which is nitrogen, and said heteroaryl group can be substituted once with methyl.

47) According to yet another sub-variant of embodiment 34), the compounds of formula I as defined in embodiment 34) will be such that $R^3$ represents a (heteroaryl)methoxy group wherein the heteroaryl is a five- or six-membered heteroaryl group which has one to three ring heteroatoms, each of which is nitrogen, and said heteroaryl group can be substituted once with methyl.

48) According to yet another sub-variant of embodiment 34), the compounds of formula I as defined in embodiment 34) will be such that $R^3$ represents —$(CH_2)_n$—C(O)O—$R^d$.

49) According to yet another sub-variant of embodiment 34), the compounds of formula I as defined in embodiment 34) will be such that $R^3$ represents —$(CH_2)_n$—N($R^c$)C(O)O—$R^d$.

50) According to yet another sub-variant of embodiment 34), the compounds of formula I as defined in embodiment 34) will be such that $R^3$ represents —O—$(CH_2)_n$—N($R^c$)C(O)O—$R^d$.

51) According to yet another sub-variant of embodiment 34), the compounds of formula I as defined in embodiment 34) will be such that $R^3$ represents —$(CH_2)_n$—$R^e$.

52) According to a particular sub-embodiment of embodiment 51), $R^e$ will represent pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl.

53) According to another particular sub-embodiment of embodiment 51), $R^e$ will represent $(C_5-C_6)$heteroaryl.

54) According to yet another sub-variant of embodiment 34), the compounds of formula I as defined in embodiment 34) will be such that $R^3$ represents —O—$(CH_2)_n$—$R^e$ (and notably such that $R^3$ represents —O—$(CH_2)_n$—$R^e$ wherein n is 1).

55) According to a particular sub-embodiment of embodiment 54), the compounds of formula I will be such that $R^e$ represents pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl) cyclohexyl.

56) According to another particular sub-embodiment of embodiment 54), the compounds of formula I will be such that $R^e$ represents $(C_5-C_6)$heteroaryl.

57) According to yet another main variant of the invention, the compounds of formula I as defined in one of embodiments 1) to 10) will be such that $R^2$ represents a group of formula (A1) for embodiments related to embodiment 1), 2), 4) or 5), or such that $R^2$ represents a group of formula (A1') for embodiments related to embodiment 3) or 6) (and notably such that $R^2$ represents pyridin-4-yl).

58) Preferably, the compounds of formula I as defined in embodiment 57) will be such that the compounds of formula I are as defined in embodiment 1), 2), 4) or 5), or as defined in embodiment 1), 2) 4) or 5) taken together with the additional features of one of embodiments 7) to 10), and $R^2$ represents a group of formula (A1) wherein $R^x$ is H and either each of $R^y$ and $R^z$ is independently H or methyl, or $R^z$ is H and $R^y$ is halogen, cyano or methoxy; this embodiment will notably relate to compounds of formula I as defined in embodiment 2) or 5), or as defined in embodiment 2) or 5) taken together with the additional features of one of embodiments 7) to 10), wherein $R^2$ represents a group of formula (A1) wherein $R^x$ is H and either each of $R^y$ and $R^z$ is independently H or methyl, or $R^z$ is H and $R^y$ is halogen, cyano or methoxy.

59) According to a sub-variant of embodiment 57) or 58), the compounds of formula I as defined in embodiment 57) or 58) will be such that $R^3$ represents —O—$(CH_2)_n$—$R^e$ (and notably such that $R^3$ represents a (heteroaryl)methoxy group wherein the heteroaryl is an unsubstituted five- or six-membered heteroaryl group which has one to three ring heteroatoms, each of which is nitrogen).

60) According to another sub-variant of embodiment 57) or 58), the compounds of formula I as defined in embodiment 57) or 58) will be such that $R^3$ represents $(C_3-C_4)$alkynyloxy (and notably linear $(C_3-C_4)$alkynyloxy).

61) According to yet another sub-variant of embodiment 57) or 58), the compounds of formula I as defined in embodiment 57) or 58) will be such that a $R^3$ represents a five- or six-membered heteroaryl group which has one to three ring heteroatoms, each of which is nitrogen, whereby said heteroaryl group can be substituted once with methyl.

62) According to yet another main variant of the invention, the compounds of formula I according to this invention will be as defined in embodiment 1), 2), 4) or 5) or as defined in embodiment 1), 2), 4) or 5) taken together with the additional features of one of embodiments 7) to 10) and such that $R^2$ represents a group of formula (A1); this embodiment will notably relate to compounds of formula I as defined in embodiment 2) or 5), or as defined in embodiment 2) or 5) taken together with the additional features of one of embodiments 7) to 10), wherein $R^2$ represents a group of formula (A1).

63) According to a sub-variant of embodiment 62), the compounds of formula I as defined in embodiment 62) will be such that $R^3$ represents $(C_1\text{-}C_4)$alkyl, $(C_2\text{-}C_4)$alkynyl, amino-$(C_1\text{-}C_3)$alkyl, carbamoyl-$(C_1\text{-}C_3)$alkyl, (methylcarbamoyl)-$(C_1\text{-}C_3)$alkyl, $(C_1\text{-}C_3)$alkoxy-$(C_1\text{-}C_3)$alkyl or carboxy-$(C_1\text{-}C_3)$alkyl.

64) According to another sub-variant of embodiment 62), the compounds of formula I as defined in embodiment 62) will be such that $R^3$ represents $(C_1\text{-}C_4)$alkoxy, $(C_1\text{-}C_4)$haloalkoxy, $(C_3\text{-}C_4)$alkynyloxy, (4-hydroxybut-2-yn-1-yl)oxy, (4-aminobut-2-yn-1-yl)oxy, dimethylamino-$(C_2\text{-}C_3)$alkoxy, carbamoyl-$(C_1\text{-}C_3)$alkoxy, hydroxy-$(C_2\text{-}C_3)$alkoxy, $(C_1\text{-}C_3)$alkoxy-$(C_1\text{-}C_3)$alkoxy, carboxy-$(C_1\text{-}C_3)$alkoxy, $(C_1\text{-}C_2)$alkoxycarbonyl-$(C_1\text{-}C_3)$alkoxy, 2-cyanoethoxy, 2,3-dihydroxypropoxy or 3,4-dihydroxybutoxy.

65) According to yet another sub-variant of embodiment 62), the compounds of formula I as defined in embodiment 62) will be such that $R^3$ represents $(C_1\text{-}C_3)$alkylamino.

66) According to yet another sub-variant of embodiment 62), the compounds of formula I as defined in embodiment 62) will be such that $R^3$ represents $(C_3\text{-}C_6)$cycloalkyl.

67) According to yet another sub-variant of embodiment 62), the compounds of formula I as defined in embodiment 62) will be such that $R^3$ represents $(C_3\text{-}C_6)$cycloalkyl-$(C_1\text{-}C_4)$alkyl (and in particular $(C_3\text{-}C_6)$cycloalkylmethyl).

68) According to yet another sub-variant of embodiment 62), the compounds of formula I as defined in embodiment 62) will be such that $R^3$ represents $(C_3\text{-}C_6)$cycloalkyl-$(C_1\text{-}C_4)$alkoxy (and in particular $(C_3\text{-}C_6)$cycloalkylmethoxy).

69) According to yet another sub-variant of embodiment 62), the compounds of formula I as defined in embodiment 62) will be such that $R^3$ represents phenyl or benzyl.

70) According to yet another sub-variant of embodiment 62), the compounds of formula I as defined in embodiment 62) will be such that $R^3$ represents benzyloxy.

71) According to yet another sub-variant of embodiment 62), the compounds of formula I as defined in embodiment 62) will be such that $R^3$ represents $-CH_2R^a$.

72) According to yet another sub-variant of embodiment 62), the compounds of formula I as defined in embodiment 62) will be such that $R^3$ represents $-CH_2CH_2R^b$.

73) According to yet another sub-variant of embodiment 62), the compounds of formula I as defined in embodiment 62) will be such that $R^3$ represents a five- or six-membered heteroaryl group which has one to three ring heteroatoms, each of which is nitrogen, and said heteroaryl group can be substituted once with methyl.

74) According to yet another sub-variant of embodiment 62), the compounds of formula I as defined in embodiment 62) will be such that $R^3$ represents a (heteroaryl)methoxy group wherein the heteroaryl is a five- or six-membered heteroaryl group which has one to three ring heteroatoms, each of which is nitrogen, and said heteroaryl group can be substituted once with methyl.

75) According to yet another sub-variant of embodiment 62), the compounds of formula I as defined in embodiment 62) will be such that $R^3$ represents $-(CH_2)_n-C(O)O-R^d$.

76) According to yet another sub-variant of embodiment 62), the compounds of formula I as defined in embodiment 62) will be such that $R^3$ represents $-(CH_2)_n-N(R^c)C(O)O-R^d$.

77) According to yet another sub-variant of embodiment 62), the compounds of formula I as defined in embodiment 62) will be such that $R^3$ represents $-O-(CH_2)_n-N(R^c)C(O)O-R^d$.

78) According to yet another sub-variant of embodiment 62), the compounds of formula I as defined in embodiment 62) will be such that $R^3$ represents $-(CH_2)_n-R^e$.

79) According to a particular sub-embodiment of embodiment 78), $R^e$ will represent pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl or 4-(aminomethyl)cyclohexyl.

80) According to another particular sub-embodiment of embodiment 78), $R^e$ will represent $(C_5\text{-}C_6)$heteroaryl.

81) According to yet another sub-variant of embodiment 62), the compounds of formula I as defined in embodiment 62) will be such that $R^3$ represents $-O-(CH_2)_n-R^e$ (and notably such that $R^3$ represents $-O-(CH_2)_n-R^e$ wherein n is 1).

82) According to a particular sub-embodiment of embodiment 81), the compounds of formula I will be such that $R^e$ represents pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl or 4-(aminomethyl)cyclohexyl.

83) According to another particular sub-embodiment of embodiment 81), the compounds of formula I will be such that $R^e$ represents $(C_5\text{-}C_6)$heteroaryl.

84) According to yet another main variant of the invention, the compounds of formula I as defined in embodiment 1), 2) 4) or 5), or as defined in embodiment 1), 2), 4) or 5) taken together with the additional features of one of embodiments 7) to 10), will be such that $R^2$ represents a group of formula (A2); this embodiment will notably relate to compounds of formula I as defined in embodiment 2) or 5), or as defined in embodiment 2) or 5) taken together with the additional features of one of embodiments 7) to 10), wherein $R^2$ represents a group of formula (A2).

85) According to a sub-variant of embodiment 84), the compounds of formula I as defined in embodiment 84) will be such that $R^3$ represents $(C_1\text{-}C_4)$alkyl, $(C_2\text{-}C_4)$alkynyl, amino-$(C_1\text{-}C_3)$alkyl, carbamoyl-$(C_1\text{-}C_3)$alkyl, (methylcarbamoyl)-$(C_1\text{-}C_3)$alkyl, $(C_3\text{-}C_6)$cycloalkyl, $(C_3\text{-}C_6)$cycloalkyl-$(C_1\text{-}C_4)$alkyl, $(C_1\text{-}C_3)$alkoxy-$(C_1\text{-}C_3)$alkyl or carboxy-$(C_1\text{-}C_3)$alkyl.

86) According to another sub-variant of embodiment 84), the compounds of formula I as defined in embodiment 84) will be such that $R^3$ represents $(C_1\text{-}C_4)$alkoxy, $(C_1\text{-}C_4)$haloalkoxy, $(C_3\text{-}C_4)$alkynyloxy, (4-hydroxybut-2-yn-1-yl)oxy, (4-aminobut-2-yn-1-yl)oxy, dimethylamino-$(C_2\text{-}C_3)$alkoxy, carbamoyl-$(C_1\text{-}C_3)$alkoxy, $(C_3\text{-}C_6)$cycloalkyl-$(C_1\text{-}C_4)$alkoxy, hydroxy-$(C_2\text{-}C_3)$alkoxy, $(C_1\text{-}C_3)$alkoxy-$(C_1\text{-}C_3)$alkoxy, carboxy-$(C_1\text{-}C_3)$alkoxy, $(C_1\text{-}C_2)$alkoxycarbonyl-$(C_1\text{-}C_3)$alkoxy, 2-cyanoethoxy, 2,3-dihydroxypropoxy or 3,4-dihydroxybutoxy.

87) According to yet another sub-variant of embodiment 84), the compounds of formula I as defined in embodiment 84) will be such that $R^3$ represents $(C_1-C_3)$alkylamino.
88) According to yet another sub-variant of embodiment 84), the compounds of formula I as defined in embodiment 84) will be such that $R^3$ represents phenyl or benzyl.
89) According to yet another sub-variant of embodiment 84), the compounds of formula I as defined in embodiment 84) will be such that $R^3$ represents benzyloxy.
90) According to yet another sub-variant of embodiment 84), the compounds of formula I as defined in embodiment 84) will be such that $R^3$ represents —$CH_2R^a$ or —$CH_2CH_2R^b$.
91) According to yet another sub-variant of embodiment 84), the compounds of formula I as defined in embodiment 84) will be such that $R^3$ represents a five- or six-membered heteroaryl group which has one to three ring heteroatoms, each of which is nitrogen, and said heteroaryl group can be substituted once with methyl.
92) According to yet another sub-variant of embodiment 84), the compounds of formula I as defined in embodiment 84) will be such that $R^3$ represents a (heteroaryl)methoxy group wherein the heteroaryl is a five- or six-membered heteroaryl group which has one to three ring heteroatoms, each of which is nitrogen, and said heteroaryl group can be substituted once with methyl.
93) According to yet another sub-variant of embodiment 84), the compounds of formula I as defined in embodiment 84) will be such that $R^3$ represents —$(CH_2)_n$—$C(O)O$—$R^d$.
94) According to yet another sub-variant of embodiment 84), the compounds of formula I as defined in embodiment 84) will be such that $R^3$ represents —$(CH_2)_n$—$N(R^c)C(O)O$—$R^d$.
95) According to yet another sub-variant of embodiment 84), the compounds of formula I as defined in embodiment 84) will be such that $R^3$ represents —O—$(CH_2)_n$—$N(R^c)C(O)O$—$R^d$.
96) According to yet another sub-variant of embodiment 84), the compounds of formula I as defined in embodiment 84) will be such that $R^3$ represents —$(CH_2)_n$—$R^e$.
97) According to yet another sub-variant of embodiment 84), the compounds of formula I as defined in embodiment 84) will be such that $R^3$ represents —O—$(CH_2)$—$R^e$ (and notably such that $R^3$ represents —O—$(CH_2)_n$—$R^e$ wherein n is 1).
98) According to yet another main variant of the invention, the compounds of formula I as defined in embodiment 1), 2), 4) or 5), or as defined in embodiment 1), 2), 4) or 5) taken together defined in embodiment 1), 2), 4) or 5), or as defined in embodiment 1), 2), 4) or 5) taken with the additional features of one of embodiments 7) to 10), will be such that $R^2$ represents a group of formula (A3) (and notably such that $R^2$ represents a group of formula (A3) wherein $R^{x3}$ is hydroxy, carboxy or carbamoyl, $R^{y3}$ is H and $R^{z3}$ is H); this embodiment will notably relate to compounds of formula I as defined in embodiment 2) or 5), or as defined in embodiment 2) or 5) taken together with the additional features of one of embodiments 7) to 10), wherein $R^2$ represents a group of formula (A3) (and notably wherein $R^2$ represents a group of formula (A3) wherein $R^{x3}$ is hydroxy, carboxy or carbamoyl, $R^{y3}$ is H and $R^{z3}$ is H).
99) According to a sub-variant of embodiment 98), the compounds of formula I as defined in embodiment 98) will be such that $R^3$ represents $(C_1-C_4)$alkyl, $(C_2-C_4)$alkynyl, amino -$(C_1-C_3)$alkyl, carbamoyl-$(C_1-C_3)$alkyl, (methyl-carbamoyl)-$(C_1-C_3)$alkyl, $(C_3-C_6)$cycloalkyl, $(C_3-C_6)$cycloalkyl-$(C_1-C_4)$alkyl, $(C_1-C_3)$alkoxy-$(C_1-C_3)$alkyl or carboxy-$(C_1-C_3)$alkyl.
100) According to another sub-variant of embodiment 98), the compounds of formula I as defined in embodiment 98) will be such that $R^3$ represents $(C_1-C_4)$alkoxy, $(C_1-C_4)$haloalkoxy, $(C_3-C_4)$alkynyloxy, (4-hydroxybut-2-yn-1-yl)oxy, (4-aminobut-2-yn-1-yl)oxy, dimethylamino-$(C_2-C_3)$alkoxy, carbamoyl-$(C_1-C_3)$alkoxy, $(C_3-C_6)$cycloalkyl-$(C_1-C_4)$alkoxy, hydroxy-$(C_2-C_3)$alkoxy, $(C_1-C_3)$alkoxy-$(C_1-C_3)$alkoxy, carboxy-$(C_1-C_3)$alkoxy, $(C_1-C_2)$alkoxycarbonyl-$(C_1-C_3)$alkoxy, 2-cyanoethoxy, 2,3-dihydroxypropoxy or 3,4-dihydroxybutoxy.
101) According to yet another sub-variant of embodiment 98), the compounds of formula I as defined in embodiment 98) will be such that $R^3$ represents $(C_1-C_3)$alkylamino.
102) According to yet another sub-variant of embodiment 98), the compounds of formula I as defined in embodiment 98) will be such that $R^3$ represents phenyl or benzyl.
103) According to yet another sub-variant of embodiment 98), the compounds of formula I as defined in embodiment 98) will be such that $R^3$ represents benzyloxy.
104) According to yet another sub-variant of embodiment 98), the compounds of formula I as defined in embodiment 98) will be such that $R^3$ represents —$CH_2R^a$ or —$CH_2CH_2R^b$.
105) According to yet another sub-variant of embodiment 98), the compounds of formula I as defined in embodiment 98) will be such that $R^3$ represents a five- or six-membered heteroaryl group which has one to three ring heteroatoms, each of which is nitrogen, and said heteroaryl group can be substituted once with methyl.
106) According to yet another sub-variant of embodiment 98), the compounds of formula I as defined in embodiment 98) will be such that $R^3$ represents a (heteroaryl)methoxy group wherein the heteroaryl is a five- or six-membered heteroaryl group which has one to three ring heteroatoms, each of which is nitrogen, and said heteroaryl group can be substituted once with methyl.
107) According to yet another sub-variant of embodiment 98), the compounds of formula I as defined in embodiment 98) will be such that $R^3$ represents —$(CH_2)_n$—$C(O)O$—$R^d$.
108) According to yet another sub-variant of embodiment 98), the compounds of formula I as defined in embodiment 98) will be such that $R^3$ represents —$(CH_2)_n$—$N(R^c)C(O)O$—$R^d$.
109) According to yet another sub-variant of embodiment 98), the compounds of formula I as defined in embodiment 98) will be such that $R^3$ represents —O—$(CH_2)_n$—$N(R^c)C(O)O$—$R^d$.
110) According to yet another sub-variant of embodiment 98), the compounds of formula I as defined in embodiment 98) will be such that $R^3$ represents —$(CH_2)_n$—$R^e$.
111) According to yet another sub-variant of embodiment 98), the compounds of formula I as defined in embodiment 98) will be such that $R^3$ represents —O—$(CH_2)_n$—$R^e$ (and notably such that $R^3$ represents —O—$(CH_2)_n$—$R^e$ wherein n is 1).
112) According to yet another main variant of the invention, the compounds of formula I as defined in embodiment 1), 2), 4) or 5), or as defined in embodiment 1), 2), 4) or 5) taken together with the additional features of one of embodiments 7) to 10), will be such that $R^2$ represents pyridazin-4-yl or pyrimidin-5-yl; this embodiment will notably relate to compounds of formula I as defined in embodiment 2) or 5), or as defined in embodiment 2) or 5)

taken together with the additional features of one of embodiments 7) to 10), wherein $R^2$ represents pyridazin-4-yl or pyrimidin-5-yl.

113) According to one variant of embodiment 112), the compounds of formula I as defined in embodiment 112) will be such that $R^2$ represents pyridazin-4-yl.

114) According to the other variant of embodiment 112), the compounds of formula I as defined in embodiment 112) will be such that $R^2$ represents pyrimidin-5-yl.

115) According to a sub-variant of embodiments 112) to 114), the compounds of formula I as defined in embodiments 112) to 114) will be such that $R^3$ represents $(C_1-C_4)$alkyl, $(C_2-C_4)$alkynyl, amino-$(C_1-C_3)$alkyl, carbamoyl-$(C_1-C_3)$alkyl, (methylcarbamoyl)-$(C_1-C_3)$alkyl, $(C_3-C_6)$cycloalkyl, $(C_3-C_6)$cycloalkyl-$(C_1-C_4)$alkyl, $(C_1-C_3)$alkoxy-$(C_1-C_3)$alkyl or carboxy-$(C_1-C_3)$alkyl.

116) According to another sub-variant of embodiments 112) to 114), the compounds of formula I as defined in embodiments 112) to 114) will be such that $R^3$ represents $(C_1-C_4)$alkoxy, $(C_1-C_4)$haloalkoxy, $(C_3-C_4)$alkynyloxy, (4-hydroxybut-2-yn-1-yl)oxy, (4-aminobut-2-yn-1-yl)oxy, dimethylamino-$(C_2-C_3)$alkoxy, carbamoyl-$(C_1-C_3)$alkoxy, $(C_3-C_6)$cycloalkyl-$(C_1-C_4)$alkoxy, hydroxy-$(C_2-C_3)$alkoxy, $(C_1-C_3)$alkoxy-$(C_1-C_3)$alkoxy, carboxy-$(C_1-C_3)$alkoxy, $(C_1-C_2)$alkoxycarbonyl-$(C_1-C_3)$alkoxy, 2-cyanoethoxy, 2,3-dihydroxypropoxy or 3,4-dihydroxybutoxy.

117) According to yet another sub-variant of embodiments 112) to 114), the compounds of formula I as defined in embodiments 112) to 114) will be such that $R^3$ represents $(C_1-C_3)$alkylamino.

118) According to yet another sub-variant of embodiments 112) to 114), the compounds of formula I as defined in embodiments 112) to 114) will be such that $R^3$ represents phenyl or benzyl.

119) According to yet another sub-variant of embodiments 112) to 114), the compounds of formula I as defined in embodiments 112) to 114) will be such that $R^3$ represents benzyloxy.

120) According to yet another sub-variant of embodiments 112) to 114), the compounds of formula I as defined in embodiments 112) to 114) will be such that $R^3$ represents —$CH_2R^a$ or —$CH_2CH_2R^b$.

121) According to yet another sub-variant of embodiments 112) to 114), the compounds of formula I as defined in embodiments 112) to 114) will be such that $R^3$ represents a five- or six-membered heteroaryl group which has one to three ring heteroatoms, each of which is nitrogen, and said heteroaryl group can be substituted once with methyl.

122) According to yet another sub-variant of embodiments 112) to 114), the compounds of formula I as defined in embodiments 112) to 114) will be such that $R^3$ represents a (heteroaryl)methoxy group wherein the heteroaryl is a five- or six-membered heteroaryl group which has one to three ring heteroatoms, each of which is nitrogen, and said heteroaryl group can be substituted once with methyl.

123) According to yet another sub-variant of embodiments 112) to 114), the compounds of formula I as defined in embodiments 112) to 114) will be such that $R^3$ represents —$(CH_2)_n$—C(O)O—$R^d$.

124) According to yet another sub-variant of embodiments 112) to 114), the compounds of formula I as defined in embodiments 112) to 114) will be such that $R^3$ represents —$(CH_2)_n$—N($R^c$)C(O)O—$R^d$.

125) According to yet another sub-variant of embodiments 112) to 114), the compounds of formula I as defined in embodiments 112) to 114) will be such that $R^3$ represents —O—$(CH_2)_n$—N($R^c$)C(O)O—$R^d$.

126) According to yet another sub-variant of embodiments 112) to 114), the compounds of formula I as defined in embodiments 112) to 114) will be such that $R^3$ represents —$(CH_2)_n$—$R^e$.

127) According to yet another sub-variant of embodiments 112) to 114), the compounds of formula I as defined in embodiments 112) to 114) will be such that $R^3$ represents —O—$(CH_2)_n$—$R^e$ (and notably such that $R^3$ represents —O—$(CH_2)_n$—$R^e$ wherein n is 1).

128) The compounds of formula I as defined in embodiment 1) or 2) can notably be such that:
$R^1$ represents $(C_1-C_3)$alkyl (and in particular ethyl);
$R^2$ represents H, F, Cl or pyridazin-4-yl, or $R^2$ represents a group of formula (A1) wherein $R^x$ is H and either each of $R^y$ and $R^z$ is independently H or methyl, or $R^z$ is H and $R^y$ is halogen, cyano or methoxy, or also $R^2$ represents a group of formula (A3) wherein $R^{x3}$ is hydroxy, carboxy or carbamoyl, $R^{y3}$ is H and $R^{z3}$ is H;
$R^3$ is $(C_1-C_4)$alkyl, $(C_2-C_4)$alkynyl, $(C_1-C_4)$alkoxy, $(C_3-C_4)$alkynyloxy, (4-hydroxybut-2-yn-1-yl)oxy, $(C_3-C_6)$cycloalkyl, $(C_3-C_6)$cycloalkyl-$(C_1-C_4)$alkyl, $(C_3-C_6)$cycloalkyl-$(C_1-C_4)$alkoxy, hydroxy-$(C_1-C_3)$alkyl, hydroxy-$(C_2-C_3)$alkoxy, $(C_1-C_3)$alkoxy-$(C_1-C_3)$alkyl, $(C_1-C_3)$alkoxy-$(C_1-C_3)$alkoxy, $(C_5-C_6)$heteroaryl, —$(CH_2)_n$—N($R^c$)C(O)O—$R^d$, —O—$(CH_2)_n$—N($R^c$)C(O)O—$R^d$, —$(CH_2)_n$—$R^e$ or —O—$(CH_2)$—$R^e$;
n is 1, 2 or 3;
$R^c$ is H or methyl;
$R^d$ is $(C_1-C_4)$alkyl;
$R^e$ is morpholin-1-yl, 2-oxopyrrolidin-1-yl or $(C_5-C_6)$heteroaryl; and
$R^4$ is H.

129) According to a sub-embodiment of embodiment 128), the compounds of formula I as defined in embodiment 128) will be such that $R^3$ is $(C_1-C_4)$alkyl (and notably such that $R^2$ is pyridin-4-yl and $R^3$ is $(C_1-C_4)$alkyl).

130) According to another sub-embodiment of embodiment 128), the compounds of formula I as defined in embodiment 128) will be such that $R^3$ is $(C_1-C_4)$alkoxy (and notably such that $R^2$ is pyridin-4-yl and $R^3$ is $(C_1-C_4)$alkoxy).

131) According to a sub-embodiment of embodiment 128), the compounds of formula I as defined in embodiment 128) will be such that $R^3$ is $(C_2-C_4)$alkynyl (and notably such that $R^2$ is pyridin-4-yl and $R^3$ is $(C_2-C_4)$alkynyl).

132) According to another sub-embodiment of embodiment 128), the compounds of formula I as defined in embodiment 128) will be such that $R^3$ is $(C_3-C_4)$alkynyloxy (and notably such that $R^2$ is pyridin-4-yl or 4-carboxyphenyl and $R^3$ is $(C_3-C_4)$alkynyloxy).

133) According to another sub-embodiment of embodiment 128), the compounds of formula I as defined in embodiment 128) will be such that $R^3$ is $(C_1-C_3)$alkoxy-$(C_1-C_3)$alkoxy (and notably such that $R^2$ is pyridin-4-yl and $R^3$ is $(C_1-C_3)$alkoxy-$(C_1-C_3)$alkoxy).

134) According to another sub-embodiment of embodiment 128), the compounds of formula I as defined in embodiment 128) will be such that $R^3$ is $(C_5-C_6)$heteroaryl (and notably such that $R^2$ is pyridin-4-yl and $R^3$ is $(C_5-C_6)$heteroaryl).

135) According to a sub-embodiment of embodiment 128), the compounds of formula I as defined in embodiment 128) will be such that $R^3$ is —$(CH_2)_n$—N($R^c$)C(O)O—$R^d$ or —O—$(CH_2)_n$—N($R^c$)C(O)O—$R^d$ (and notably such that $R^2$ is pyridin-4-yl and $R^3$ is —$(CH_2)_n$—N($R^c$)C(O)O—$R^d$ or —O—$(CH_2)$—N($R^c$)C(O)O—$R^d$).

136) According to another sub-embodiment of embodiment 128), the compounds of formula I as defined in embodiment 128) will be such that $R^3$ is —$(CH_2)_n$—$R^e$ or —O—$(CH_2)_n$—$R^e$ (and notably such that $R^2$ is pyridin-4-yl and $R^3$ is —$(CH_2)_n$—$R^e$ or —O—$(CH_2)_n$—$R^e$).

137) The compounds of formula I as defined in one of embodiments 1) to 3) can notably be such that:
$R^1$ represents $(C_1-C_3)$alkyl (and in particular ethyl);
$R^2$ represents H; and
$R^3$ represents $(C_2-C_4)$alkynyl, linear $(C_3-C_4)$alkynyloxy, $(C_3-C_6)$cycloalkyl, $(C_3-C_6)$cycloalkyl-$(C_1-C_4)$alkyl, aryl, $(C_5-C_6)$heteroaryl, $((C_5-C_6)$heteroaryl)methoxy or benzyl.

138) In particular, the compounds of formula I as defined in embodiment 137) can be such that:
$R^1$ represents ethyl;
$R^2$ represents H; and
$R^3$ represents ethynyl, prop-2-yn-1-yl, prop-2-yn-1-yloxy, cyclopropyl, cyclopropylmethyl, phenyl, 2H-1,2,3-triazol-4-yl, pyridin-2-yl, pyridin-4-yl, (1H-pyrazol-4-yl)methoxy, pyridin-4-ylmethoxy or benzyl.

139) The compounds of formula I as defined in one of embodiments 1) to 3) can also notably be such that:
$R^1$ represents $(C_1-C_3)$alkyl (and in particular ethyl);
$R^2$ represents pyridin-4-yl; and
$R^3$ represents $(C_2-C_4)$alkynyl, linear $(C_3-C_4)$alkynyloxy, $(C_3-C_6)$cycloalkyl, $(C_3-C_6)$cycloalkyl-$(C_1-C_4)$alkyl, aryl, $(C_5-C_6)$heteroaryl, $((C_5-C_6)$heteroaryl)methoxy or benzyl.

140) In particular, the compounds of formula I as defined in embodiment 139) can be such that:
$R^1$ represents $(C_1-C_3)$alkyl (and in particular ethyl);
$R^2$ represents pyridin-4-yl; and
$R^3$ represents linear $(C_3-C_4)$alkynyloxy, $(C_5-C_6)$heteroaryl or $((C_5-C_6)$heteroaryl)methoxy.

141) More particularly, the compounds of formula I as defined in embodiment 139) can be such that:
$R^1$ represents ethyl;
$R^2$ represents pyridin-4-yl; and
$R^3$ represents prop-2-yn-1-yloxy, pyridin-3-yl or pyridin-3-ylmethoxy.

142) According to another main variant of the invention, the compounds of formula I as defined in one of embodiments 1) to 3) will be such that $R^2$ represents the group

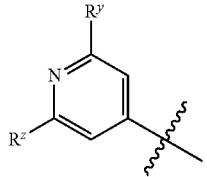

wherein either each of $R^y$ and $R^z$ represents independently hydrogen or methyl, or $R^z$ represents hydrogen and $R^y$ represents halogen, methoxy or amino (and notably wherein $R^y$ represents hydrogen and $R^z$ represents methyl).

143) According to one sub-variant of embodiment 142), the compounds of formula I as defined in embodiment 142) will be such that $R^1$ represents $(C_1-C_3)$alkyl.

144) Preferably, the compounds of formula I as defined in embodiment 143) will be such that $R^1$ represents ethyl.

145) According to another sub-variant of embodiment 142), the compounds of formula I as defined in embodiment 142) will be such that $R^1$ represents $(C_1-C_3)$haloalkyl (notably $(C_1-C_2)$haloalkyl and in particular 2-fluoroethyl).

146) According to yet another sub-variant of embodiment 142), the compounds of formula I as defined in embodiment 142) will be such that $R^1$ represents cyclopropyl.

147) Preferably, the compounds of formula I as defined in one of embodiments 142) to 146) will be such that $R^z$ represents hydrogen and $R^y$ represents hydrogen, halogen, methyl, methoxy or amino.

148) The compounds of formula I as defined in one of embodiments 142) to 147) will notably be such that $R^3$ represents ethynyl, prop-2-yn-1-yl, prop-2-yn-1-yloxy, cyclopropyl, cyclopropylmethyl, phenyl, 2H-1,2,3-triazol-4-yl, pyridin-2-yl, pyridin-3-yl, pyridin-4-yl, (1H-pyrazol-4-yl)methoxy, pyridin-3-ylmethoxy, pyridin-4-ylmethoxy or benzyl.

149) In particular, the compounds of formula I as defined in embodiment 142) can be such that:
$R^1$ represents $(C_1-C_3)$alkyl (and in particular ethyl);
$R^2$ represents the group

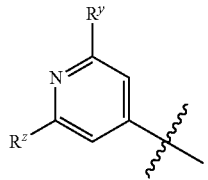

wherein either each of $R^y$ and $R^z$ represents independently hydrogen or methyl, or $R^z$ represents hydrogen and $R^y$ represents halogen, methoxy or amino; and
$R^3$ represents linear $(C_3-C_4)$alkynyloxy, $(C_5-C_6)$heteroaryl or $((C_5-C_6)$heteroaryl)methoxy.

150) More particularly, the compounds of formula I as defined in embodiment 142) can be such that:
$R^1$ represents ethyl;
$R^2$ represents the group pyridin-4-yl, 2-fluoropyridin-4-yl, 2-chloropyridin-4-yl, 2-bromopyridin-4-yl, 2-methylpyridin-4-yl or 2-methoxypyridin-4-yl; and
$R^3$ represents prop-2-yn-1-yloxy, pyridin-3-yl or pyridin-3-ylmethoxy.

151) According to yet another main variant of the invention, the compounds of formula I as defined in one of embodiments 1) to 6) will be such that $R^2$ represents hydrogen or pyridin-4-yl.

152) According to one sub-variant of embodiment 151), the compounds of formula I as defined in embodiment 151) will be such that $R^1$ represents $(C_1-C_3)$alkyl.

153) Preferably, the compounds of formula I as defined in embodiment 152) will be such that $R^1$ represents ethyl.

154) According to another sub-variant of embodiment 151), the compounds of formula I as defined in embodiment 151) will be such that $R^1$ represents $(C_1-C_3)$haloalkyl (notably $(C_1-C_2)$haloalkyl and in particular 2-fluoroethyl).

155) According to yet another sub-variant of embodiment 151), the compounds of formula I as defined in embodiment 151) will be such that $R^1$ represents cyclopropyl.

156) In particular, the compounds of formula I as defined in one of embodiments 151) to 155) will be such that $R^3$ represents ethynyl, prop-2-yn-1-yl, prop-2-yn-1-yloxy, cyclopropyl, cyclopropylmethyl, phenyl, 2H-1,2,3-triazol-4-yl, pyridin-2-yl, pyridin-3-yl, pyridin-4-yl, (1H-pyrazol-4-yl)methoxy, pyridin-3-ylmethoxy, pyridin-4-ylmethoxy or benzyl.

157) According to another main variant of the invention, the compounds of formula I as defined in embodiment 1) or 2) will be such that:
$R^1$ is $(C_1-C_3)$alkyl (and in particular ethyl);
$R^2$ is the group (A1) wherein $R^x$ is H and each of $R^y$ and $R^z$ is independently H or methyl, or each of $R^x$ and $R^z$ is H and $R^y$ is halogen, $(C_2-C_4)$alkyl or cyclopropyl;
$R^3$ is $(C_1-C_4)$alkyl, $(C_2-C_4)$alkynyl, $(C_1-C_4)$alkoxy, $(C_3-C_4)$alkynyloxy, $(C_3-C_6)$cycloalkyl, $(C_3-C_6)$cycloalkyl-$(C_1-C_4)$alkyl, $(C_3-C_6)$cycloalkyl-$(C_1-C_4)$alkoxy, $(C_1-C_3)$alkoxy-$(C_1-C_3)$alkyl or $(C_1-C_3)$alkoxy-$(C_1-C_3)$alkoxy; and
$R^4$ is H.
158) In particular, the compounds of formula I as defined in embodiment 157) will be such that:
$R^1$ is ethyl;
$R^2$ is the group (A1) wherein each of $R^x$ and $R^z$ is H and $R^y$ is halogen, methyl or ethyl;
$R^3$ is $(C_1-C_4)$alkyl or $(C_1-C_4)$alkoxy (and notably methyl or methoxy); and
$R^4$ is H.
159) Yet another embodiment of this invention relates to the compounds of formula I that are also compounds of formula $I_{NP}$

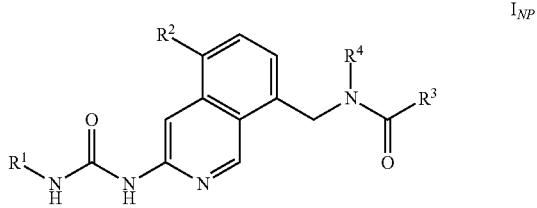

wherein
each of $R^1$, $R^3$ and $R^4$ is as defined in formula I according to embodiment 1); and
$R^2$ is a group having the formula (A1") shown hereafter

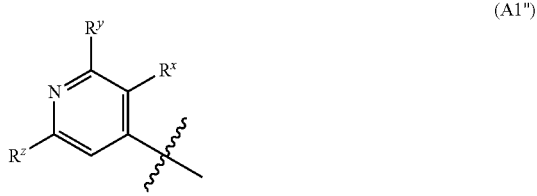

wherein each of $R^x$ and $R^z$ is H and $R^y$ is $(C_2-C_4)$alkyl, $(C_2-C_4)$alkoxy, hydroxy, hydroxyl -$(C_2-C_3)$alkyl, trifluoromethyl, carbamoyl, carbamoyl-$(C_1-C_2)$alkyl, (methylcarbamoyl)-$(C_1-C_2)$alkyl, (dimethylcarbamoyl)-$(C_1-C_2)$alkyl, tert-butoxycarbonylmethyl, cyclopropyl, pyrrolidin-1-yl, piperidin-1-yl or morpholin-1-yl, or $R^x$ is H and each of $R^y$ and $R^z$ is independently halogen, or $R^x$ is methyl, $R^y$ is methyl or halogen and $R^z$ is H, or $R^x$ is methyl or halogen, $R^y$ is H and $R^z$ is methyl or halogen, or le is halogen and each of $R^y$ and $R^z$ is H; and to salts (in particular pharmaceutically acceptable salts) of compounds of formula $I_{NP}$.
160) According to a variant of embodiment 159), the compounds of formula $I_{NP}$ as defined in embodiment 159) will be such that $R^x$ is H.
161) According to one sub-variant of embodiment 160), the compounds of formula $I_{NP}$ as defined in embodiment 160) will be such that $R^z$ is H and $R^y$ is $(C_2-C_4)$alkyl.
162) According to another sub-variant of embodiment 160), the compounds of formula $I_{NP}$ as defined in embodiment 160) will be such that $R^z$ is H and $R^y$ is $(C_2-C_4)$alkoxy.
163) According to a further sub-variant of embodiment 160), the compounds of formula $I_{NP}$ as defined in embodiment 160) will be such that $R^z$ is H and $R^y$ is hydroxy-$(C_2-C_3)$alkyl.
164) According to yet another sub-variant of embodiment 160), the compounds of formula $I_{NP}$ as defined in embodiment 160) will be such that $R^z$ is H and $R^y$ is hydroxy or trifluoromethyl.
165) According to yet another sub-variant of embodiment 160), the compounds of formula $I_{NP}$ as defined in embodiment 160) will be such that $R^z$ is H and $R^y$ is carbamoyl.
166) According to yet another sub-variant of embodiment 160), the compounds of formula $I_{NP}$ as defined in embodiment 160) will be such that $R^z$ is H and $R^y$ is carbamoyl-$(C_1-C_2)$alkyl, (methylcarbamoyl)-$(C_1-C_2)$alkyl or (dimethylcarbamoyl)-$(C_1-C_2)$alkyl.
167) According to yet another sub-variant of embodiment 160), the compounds of formula $I_{NP}$ as defined in embodiment 160) will be such that $R^z$ is H and $R^y$ is tert-butoxycarbonylmethyl.
168) According to yet another sub-variant of embodiment 160), the compounds of formula $I_{NP}$ as defined in embodiment 160) will be such that $R^z$ is H and $R^y$ is cyclopropyl.
169) According to yet another sub-variant of embodiment 160), the compounds of formula $I_{NP}$ as defined in embodiment 160) will be such that $R^z$ is H and $R^y$ is pyrrolidin-1-yl, piperidin-1-yl or morpholin-1-yl.
170) According to yet another sub-variant of embodiment 160), the compounds of formula $I_{NP}$ as defined in embodiment 160) will be such that each of $R^y$ and $R^z$ is independently halogen.
171) According to another variant of embodiment 159), the compounds of formula $I_{NP}$ as defined in embodiment 159) will be such that $R^z$ is H.
172) According to a sub-variant of embodiment 171), the compounds of formula $I_{NP}$ as defined in embodiment 171) will be such that $R^x$ is methyl and $R^y$ is methyl or halogen.
173) According to another sub-variant of embodiment 171), the compounds of formula $I_{NP}$ as defined in embodiment 171) will be such that $R^x$ is halogen and $R^y$ is H.
174) According to yet another variant of embodiment 159), the compounds of formula $I_{NP}$ as defined in embodiment 159) will be such that $R^y$ is H.
175) According to a sub-variant of embodiment 174), the compounds of formula $I_{NP}$ as defined in embodiment 174) will be such that $R^x$ is methyl or halogen and $R^z$ is methyl or halogen.
176) According to another sub-variant of embodiment 174), the compounds of formula $I_{NP}$ as defined in embodiment 174) will be such that $R^x$ is halogen and $R^z$ is H.
177) Another embodiment of this invention relates to compounds of formula I as defined in one of embodiments 1) to 176) as well as to isotopically labelled, especially $^2$H (deuterium) labelled compounds of formula I as defined in one of embodiments 1) to 176), which compounds are identical to the compounds of formula I as defined in one of embodiments 1) to 176) except that one or more atoms has or have each been replaced by an atom having the same atomic number but an atomic mass different from the atomic mass usually found in nature. Isotopically labelled, especially $^2$H (deuterium) labelled compounds of formula I and salts (in particular pharmaceutically acceptable salts) thereof are thus within the scope of the present invention. Substitution of hydrogen with the heavier isotope $^2$H (deuterium)

may lead to greater metabolic stability, resulting e.g. in increased in-vivo half-life or reduced dosage requirements, or may lead to reduced inhibition of cytochrome P450 enzymes, resulting e.g. in an improved safety profile. In one variant of the invention, the compounds of formula I are not isotopically labelled, or they are labelled only with one or more deuterium atoms. Isotopically labelled compounds of formula I may be prepared in analogy to the methods described hereinafter, but using the appropriate isotopic variation of suitable reagents or starting materials.

178) Particularly preferred are the following compounds of formula I as defined in one of embodiments 1) to 6):

but-3-ynoic acid [3-(3-ethyl-ureido)-isoquinolin-8-ylmethyl]-amide;
N-[3-(3-ethyl-ureido)-isoquinolin-8-ylmethyl]-isonicotinamide;
N-[3-(3-ethyl-ureido)-isoquinolin-8-ylmethyl]-acetamide;
N-[3-(3-ethyl-ureido)-isoquinolin-8-ylmethyl]-benzamide;
2-cyano-N-[3-(3-ethyl-ureido)-isoquinolin-8-ylmethyl]-acetamide;
cyclohexanecarboxylic acid [3-(3-ethyl-ureido)-isoquinolin-8-ylmethyl]-amide;
2-cyclopropyl-N-[3-(3-ethyl-ureido)-isoquinolin-8-ylmethyl]-acetamide;
2-acetylamino-N-[3-(3-ethyl-ureido)-isoquinolin-8-ylmethyl]-acetamide;
propynoic acid [3-(3-ethyl-ureido)-isoquinolin-8-ylmethyl]-amide;
N-[3-(3-ethyl-ureido)-isoquinolin-8-ylmethyl]-nicotinamide;
pyridine-2-carboxylic acid [3-(3-ethyl-ureido)-isoquinolin-8-ylmethyl]-amide;
N-[3-(3-ethyl-ureido)-isoquinolin-8-ylmethyl]-2-phenyl-acetamide;
cyclopropanecarboxylic acid [3-(3-ethyl-ureido)-isoquinolin-8-ylmethyl]-amide;
N-[3-(3-ethyl-ureido)-isoquinolin-8-ylmethyl]-2,2-dimethyl-propionamide;
N-[3-(3-ethyl-ureido)-isoquinolin-8-ylmethyl]-2-methoxy-acetamide;
1H-imidazole-2-carboxylic acid [3-(3-ethyl-ureido)-isoquinolin-8-ylmethyl]-amide;
pent-4-ynoic acid [3-(3-ethyl-ureido)-isoquinolin-8-ylmethyl]-amide;
N-[3-(3-ethyl-ureido)-isoquinolin-8-ylmethyl]-isobutyramide;
2-dimethylamino-N-[3-(3-ethyl-ureido)-isoquinolin-8-ylmethyl]-acetamide;
2H-[1,2,3]triazole-4-carboxylic acid [3-(3-ethyl-ureido)-isoquinolin-8-ylmethyl]-amide;
N-[3-(3-ethyl-ureido)-isoquinolin-8-ylmethyl]-succinamide;
3-methyl-3H-imidazole-4-carboxylic acid [3-(3-ethyl-ureido)-isoquinolin-8-ylmethyl]-amide;
N-[3-(3-ethyl-ureido)-5-pyridin-4-yl-isoquinolin-8-ylmethyl]-nicotinamide;
[3-(3-ethyl-ureido)-isoquinolin-8-ylmethyl]-carbamic acid ethyl ester;
[3-(3-ethyl-ureido)-isoquinolin-8-ylmethyl]-carbamic acid pyridin-4-ylmethyl ester;
[3-(3-ethyl-ureido)-isoquinolin-8-ylmethyl]-carbamic acid pyrimidin-5-ylmethyl ester;
[3-(3-ethyl-ureido)-isoquinolin-8-ylmethyl]-carbamic acid 2-fluoro-ethyl ester;
[3-(3-ethyl-ureido)-isoquinolin-8-ylmethyl]-carbamic acid cyclopropylmethyl ester;
[3-(3-ethyl-ureido)-isoquinolin-8-ylmethyl]-carbamic acid pyrimidin-4-ylmethyl ester;
[3-(3-ethyl-ureido)-isoquinolin-8-ylmethyl]-carbamic acid isopropyl ester;
[3-(3-ethyl-ureido)-isoquinolin-8-ylmethyl]-carbamic acid prop-2-ynyl ester;
[3-(3-ethyl-ureido)-isoquinolin-8-ylmethyl]-carbamic acid 2-cyano-ethyl ester;
[3-(3-ethyl-ureido)-isoquinolin-8-ylmethyl]-carbamic acid pyridin-3-ylmethyl ester;
[3-(3-ethyl-ureido)-isoquinolin-8-ylmethyl]-carbamic acid pyridin-2-ylmethyl ester;
[3-(3-ethyl-ureido)-isoquinolin-8-ylmethyl]-carbamic acid (1-methyl-1H-pyrazol-3-yl)methyl ester;
[3-(3-ethyl-ureido)-isoquinolin-8-ylmethyl]-carbamic acid benzyl ester;
[3-(3-ethyl-ureido)-isoquinolin-8-ylmethyl]-carbamic acid 2-methoxy-ethyl ester;
[3-(3-ethyl-ureido)-isoquinolin-8-ylmethyl]-carbamic acid 3-methyl-3H-imidazol-4-ylmethyl ester;
[3-(3-ethyl-ureido)-isoquinolin-8-ylmethyl]-carbamic acid 1H-pyrazol-4-ylmethyl ester;
[3-(3-ethyl-ureido)-isoquinolin-8-ylmethyl]-carbamic acid but-3-ynyl ester;
[3-(3-ethyl-ureido)-5-pyridin-4-yl-isoquinolin-8-ylmethyl]-carbamic acid prop-2-ynyl ester;
[3-(3-ethyl-ureido)-5-pyridin-4-yl-isoquinolin-8-ylmethyl]-carbamic acid pyridin-3-ylmethyl ester;
1-ethyl-3-{8-[(3-ethyl-ureido)-methyl]-isoquinolin-3-yl}-urea;

as well as the salts (in particular the pharmaceutically acceptable salts) thereof 179) Further particularly preferred compounds are the following compounds of formula I as defined in embodiment 1), 2), 4) or 5):

[3-(3-ethyl-ureido)-isoquinolin-8-ylmethyl]-methyl-carbamic acid prop-2-ynyl ester;
N-[3-(3-ethyl-ureido)-5-pyridin-4-yl-isoquinolin-8-ylmethyl]-malonamic acid;
N-[3-(3-ethyl-ureido)-5-pyridin-4-yl-isoquinolin-8-ylmethyl]-succinamic acid tert-butyl ester;
({[3-(3-ethyl-ureido)-5-pyridin-4-yl-isoquinolin-8-ylmethyl]-carbamoyl}-methyl)-carbamic acid tert-butyl ester;
({[3-(3-ethyl-ureido)-5-pyridin-4-yl-isoquinolin-8-ylmethyl]-carbamoyl}-methyl)-methyl-carbamic acid tert-butyl ester;
(2-{[3-(3-ethyl-ureido)-5-pyridin-4-yl-isoquinolin-8-ylmethyl]-carbamoyl}-ethyl)-carbamic acid tert-butyl ester;
2-amino-N-[3-(3-ethyl-ureido)-5-pyridin-4-yl-isoquinolin-8-ylmethyl]-acetamide;
3-amino-N-[3-(3-ethyl-ureido)-5-pyridin-4-yl-isoquinolin-8-ylmethyl]-propionamide;
N-[3-(3-ethyl-ureido)-5-pyridin-4-yl-isoquinolin-8-ylmethyl]-malonamide;
N-[3-(3-ethyl-ureido)-5-pyridin-4-yl-isoquinolin-8-ylmethyl]-N'-methyl-malonamide;
N-[3-(3-ethyl-ureido)-5-pyridin-4-yl-isoquinolin-8-ylmethyl]-succinamide;
N-[3-(3-ethyl-ureido)-5-pyridin-4-yl-isoquinolin-8-ylmethyl]-N'-methyl-succinamide;
(3-{[3-(3-ethyl-ureido)-5-pyridin-4-yl-isoquinolin-8-ylmethyl]-carbamoyl}-propyl)-carbamic acid tert-butyl ester;

2-cyclopropyl-N-[3-(3-ethyl-ureido)-5-pyridin-4-yl-isoquinolin-8-ylmethyl]-acetamide;
(2-{[3-(3-ethyl-ureido)-5-pyridin-4-yl-isoquinolin-8-ylmethyl]-carbamoyl}-ethyl)-methyl-carbamic acid tert-butyl ester;
N-[3-(3-ethyl-ureido)-5-pyridin-4-yl-isoquinolin-8-ylmethyl]-propionamide;
N-[3-(3-ethyl-ureido)-5-pyridin-4-yl-isoquinolin-8-ylmethyl]-2-(1H-imidazol-4-yl)-acetamide;
N-[3-(3-ethyl-ureido)-5-pyridin-4-yl-isoquinolin-8-ylmethyl]-2-hydroxy-acetamide;
(3-{[3-(3-ethyl-ureido)-5-pyridin-4-yl-isoquinolin-8-ylmethyl]-carbamoyl}-propyl)-methyl-carbamic acid tert-butyl ester;
N-[3-(3-ethyl-ureido)-5-pyridin-4-yl-isoquinolin-8-ylmethyl]-3-methoxy-propionamide;
N-[3-(3-ethyl-ureido)-5-pyridin-4-yl-isoquinolin-8-ylmethyl]-acetamide;
cyclopropanecarboxylic acid [3-(3-ethyl-ureido)-5-pyridin-4-yl-isoquinolin-8-ylmethyl]-amide;
N-[3-(3-ethyl-ureido)-5-pyridin-4-yl-isoquinolin-8-ylmethyl]-3-methyl-butyramide;
N-[3-(3-ethyl-ureido)-5-pyridin-4-yl-isoquinolin-8-ylmethyl]-isobutyramide;
N-[3-(3-ethyl-ureido)-5-pyridin-4-yl-isoquinolin-8-ylmethyl]-3-hydroxy-propionamide;
pent-4-ynoic acid [3-(3-ethyl-ureido)-5-pyridin-4-yl-isoquinolin-8-ylmethyl]-amide;
N-[3-(3-ethyl-ureido)-5-pyridin-4-yl-isoquinolin-8-ylmethyl]-2-pyrazol-1-yl-acetamide;
3H-imidazole-4-carboxylic acid [3-(3-ethyl-ureido)-5-pyridin-4-yl-isoquinolin -8-ylmethyl]-amide;
1H-pyrazole-3-carboxylic acid [3-(3-ethyl-ureido)-5-pyridin-4-yl-isoquinolin -8-ylmethyl]-amide;
1H-pyrazole-4-carboxylic acid [3-(3-ethyl-ureido)-5-pyridin-4-yl-isoquinolin -8-ylmethyl]-amide;
1H-imidazole-2-carboxylic acid [3-(3-ethyl-ureido)-5-pyridin-4-yl-isoquinolin -8-ylmethyl]-amide;
propynoic acid [3-(3-ethyl-ureido)-5-pyridin-4-yl-isoquinolin-8-ylmethyl]-amide;
[3-(3-ethyl-ureido)-5-pyridin-4-yl-isoquinolin-8-ylmethyl]-carbamic acid tert-butyl ester;
[3-(3-ethyl-ureido)-5-pyridin-4-yl-isoquinolin-8-ylmethyl]-carbamic acid isopropyl ester;
[3-(3-ethyl-ureido)-5-pyridin-4-yl-isoquinolin-8-ylmethyl]-carbamic acid 2-dimethylamino-ethyl ester;
[3-(3-ethyl-ureido)-5-pyridin-4-yl-isoquinolin-8-ylmethyl]-carbamic acid methyl ester;
[3-(3-ethyl-ureido)-5-pyridin-4-yl-isoquinolin-8-ylmethyl]-carbamic acid 2-pyrrolidin -1-yl-ethyl ester;
[3-(3-ethyl-ureido)-5-pyridin-4-yl-isoquinolin-8-ylmethyl]-carbamic acid 2-tert-butoxycarbonylamino-ethyl ester;
tert-butyl (2-((((3-(3-ethylureido)-5-(pyridin-4-yl)isoquinolin -8-yl)methyl)carbamoyl)oxy)ethyl)(methyl)carbamate;
tert-butyl 4-(2-((((3-(3-ethylureido)-5-(pyridin-4-yl)isoquinolin -8-yl)methyl)carbamoyl)oxy)ethyl)piperazine-1-carboxylate;
[3-(3-ethyl-ureido)-5-pyridin-4-yl-isoquinolin-8-ylmethyl]-carbamic acid cyclopropylmethyl ester;
[3-(3-ethyl-ureido)-5-pyridin-4-yl-isoquinolin-8-ylmethyl]-carbamic acid 3-(2-oxo-pyrrolidin -1-yl)-propyl ester;
(1-methyl-1H-imidazol-2-yl)methyl[(3-(3-ethylureido)-5-(pyridin-4-yl)isoquinolin-8-yl)methyl]carbamate;
(S)-[3-(3-ethyl-ureido)-5-pyridin-4-yl-isoquinolin-8-ylmethyl]-carbamic acid 5-oxo-pyrrolidin -2-ylmethyl ester;
[3-(3-ethyl-ureido)-5-pyridin-4-yl-isoquinolin-8-ylmethyl]-carbamic acid 3-methyl -3H-imidazol-4-ylmethyl ester;
[3-(3-ethyl-ureido)-5-pyridin-4-yl-isoquinolin-8-ylmethyl]-carbamic acid 3-dimethylamino-propyl ester;
N-[3-(3-ethyl-ureido)-5-pyridin-4-yl-isoquinolin-8-ylmethyl]-4-hydroxy-butyramide;
[3-(3-ethyl-ureido)-5-pyridin-4-yl-isoquinolin-8-ylmethyl]-carbamic acid 2-morpholin -4-yl-ethyl ester;
[3-(3-ethyl-ureido)-5-pyridin-4-yl-isoquinolin-8-ylmethyl]-carbamic acid 3-piperidin -1-yl-propyl ester;
[3-(3-ethyl-ureido)-5-pyridin-4-yl-isoquinolin-8-ylmethyl]-carbamic acid 2-(2-oxo-imidazolidin -1-yl)-ethyl ester;
[3-(3-ethyl-ureido)-5-pyridin-4-yl-isoquinolin-8-ylmethyl]-carbamic acid 3-methoxy-propyl ester;
N-[3-(3-ethyl-ureido)-5-pyridin-4-yl-isoquinolin-8-ylmethyl]-4-methoxy-butyramide;
[3-(3-ethyl-ureido)-5-pyridin-4-yl-isoquinolin-8-ylmethyl]-carbamic acid carbamoylmethyl ester;
[3-(3-ethyl-ureido)-5-pyridin-4-yl-isoquinolin-8-ylmethyl]-carbamic acid 2-(2,5-dioxo-pyrrolidin -1-yl)-ethyl ester;
[3-(3-ethyl-ureido)-5-pyridin-4-yl-isoquinolin-8-ylmethyl]-carbamic acid 2-piperidin -1-yl-ethyl ester;
[3-(3-ethyl-ureido)-5-pyridin-4-yl-isoquinolin-8-ylmethyl]-carbamic acid isobutyl ester;
[3-(3-ethyl-ureido)-5-pyridin-4-yl-isoquinolin-8-ylmethyl]-carbamic acid (R)-2-piperidin -3-yl-ethyl ester;
trans-[3-(3-ethyl-ureido)-5-pyridin-4-yl-isoquinolin-8-ylmethyl]-carbamic acid 4-(aminomethyl)-(cyclohexylmethyl)ester;
(R)-[3-(3-ethyl-ureido)-5-pyridin-4-yl-isoquinolin-8-ylmethyl]-carbamic acid 3,4-dihydroxy-butyl ester;
[3-(3-ethyl-ureido)-5-pyridin-4-yl-isoquinolin-8-ylmethyl]-carbamic acid 2,3-dihydroxy-propyl ester;
3-((((3-(3-ethylureido)-5-(pyridin-4-yl)isoquinolin-8-yl)methyl)carbamoyl)oxy)propanoic acid;
methyl 3-((((3-(3-ethylureido)-5-(pyridin-4-yl)isoquinolin -8-yl)methyl)carbamoyl)oxy)propanoate;
[3-(3-ethyl-ureido)-5-pyridin-4-yl-isoquinolin-8-ylmethyl]-carbamic acid 4-hydroxy-but -2-ynyl ester;
[3-(3-ethyl-ureido)-5-pyridin-4-yl-isoquinolin-8-ylmethyl]-carbamic acid 2-hydroxy-ethyl ester;
[3-(3-ethyl-ureido)-5-pyridin-4-yl-isoquinolin-8-ylmethyl]-carbamic acid 1-methyl-prop -2-ynyl ester;
[3-(3-ethyl-ureido)-5-pyridin-4-yl-isoquinolin-8-ylmethyl]-carbamic acid 4-amino-but -2-ynyl ester;
[3-(3-ethyl-ureido)-5-pyridin-4-yl-isoquinolin-8-ylmethyl]-carbamic acid 3-morpholin -4-yl-propyl ester;
[5-chloro-3-(3-ethyl-ureido)-isoquinolin-8-ylmethyl]-carbamic acid 2-methoxy-ethyl ester;
[5-chloro-3-(3-ethyl-ureido)-isoquinolin-8-ylmethyl]-carbamic acid prop-2-ynyl ester;
[5-chloro-3-(3-ethyl-ureido)-isoquinolin-8-ylmethyl]-carbamic acid tert-butyl ester;
[3-(3-ethyl-ureido)-5-pyridin-4-yl-isoquinolin-8-ylmethyl]-carbamic acid 2-methoxy-ethyl ester;
[5-(2-amino-pyridin-4-yl)-3-(3-ethyl-ureido)-isoquinolin-8-ylmethyl]-carbamic acid 2-methoxy-ethyl ester;
[5-(2,6-dimethyl-pyridin-4-yl)-3-(3-ethyl-ureido)-isoquinolin-8-ylmethyl]-carbamic acid 2-methoxy-ethyl ester;

[3-(3-ethyl-ureido)-5-(2-methoxy-pyridin-4-yl)-isoquinolin-8-ylmethyl]-carbamic acid 2-methoxy-ethyl ester;
[3-(3-ethyl-ureido)-5-(2-fluoro-pyridin-4-yl)-isoquinolin-8-ylmethyl]-carbamic acid 2-methoxy-ethyl ester;
[3-(3-ethyl-ureido)-5-(2-methyl-pyridin-4-yl)-isoquinolin-8-ylmethyl]-carbamic acid 2-methoxy-ethyl ester;
[5-(2-cyano-pyridin-4-yl)-3-(3-ethyl-ureido)-isoquinolin-8-ylmethyl]-carbamic acid 2-methoxy-ethyl ester;
[3-(3-ethyl-ureido)-5-(3-methyl-pyridin-4-yl)-isoquinolin-8-ylmethyl]-carbamic acid 2-methoxy-ethyl ester;
[3-(3-ethyl-ureido)-5-(2-hydroxymethyl-pyridin-4-yl)-isoquinolin-8-ylmethyl]-carbamic acid 2-methoxy-ethyl ester;
{3-(3-ethyl-ureido)-5-[(2-morpholin-4-ylmethyl)-pyridin-4-yl]-isoquinolin-8-ylmethyl}-carbamic acid 2-methoxy-ethyl ester;
[3-(3-ethyl-ureido)-5-pyridazin-4-yl-isoquinolin-8-ylmethyl]-carbamic acid tert-butyl ester;
[3-(3-ethyl-ureido)-5-pyridin-3-yl-isoquinolin-8-ylmethyl]-carbamic acid prop-2-ynyl ester;
[3-(3-ethyl-ureido)-5-(3-methyl-pyridin-4-yl)-isoquinolin-8-ylmethyl]-carbamic acid prop-2-ynyl ester;
[3-(3-ethyl-ureido)-5-pyridazin-4-yl-isoquinolin-8-ylmethyl]-carbamic acid prop-2-ynyl ester;
[5-(2-cyano-pyridin-4-yl)-3-(3-ethyl-ureido)-isoquinolin-8-ylmethyl]-carbamic acid prop-2-ynyl ester;
propynoic acid [3-(3-ethyl-ureido)-5-pyridazin-4-yl-isoquinolin-8-ylmethyl]-amide;
3-cyclopropyl-N-[3-(3-ethyl-ureido)-5-pyridin-4-yl-isoquinolin-8-ylmethyl]-propionamide;
[5-(6-amino-pyridin-3-yl)-3-(3-ethyl-ureido)-isoquinolin-8-ylmethyl]-carbamic acid prop-2-ynyl ester;
{5-[3-(acetylamino-methyl)-phenyl]-3-(3-ethyl-ureido)-isoquinolin-8-ylmethyl}-carbamic acid prop-2-ynyl ester;
[3-(3-ethyl-ureido)-5-(3-hydroxy-phenyl)-isoquinolin-8-ylmethyl]-carbamic acid prop-2-ynyl ester;
prop-2-yn-1-yl((5-(3-((dimethylamino)methyl)phenyl)-3-(3-ethylureido)isoquinolin-8-yl)methyl)carbamate;
{3-[3-(3-ethyl-ureido)-8-(prop-2-ynyloxycarbonylamino-methyl)-isoquinolin-5-yl]-phenyl}-acetic acid;
[5-(3-carbamoyl-phenyl)-3-(3-ethyl-ureido)-isoquinolin-8-ylmethyl]-carbamic acid prop-2-ynyl ester;
4-[3-(3-ethyl-ureido)-8-(prop-2-ynyloxycarbonylamino-methyl)-isoquinolin-5-yl]-benzoic acid;
[3-(3-ethyl-ureido)-5-(4-hydroxy-phenyl)-isoquinolin-8-ylmethyl]-carbamic acid prop-2-ynyl ester;
[3-(3-ethyl-ureido)-5-(2-hydroxy-phenyl)-isoquinolin-8-ylmethyl]-carbamic acid prop-2-ynyl ester;
[3-(3-ethyl-ureido)-5-pyrimidin-5-yl-isoquinolin-8-ylmethyl]-carbamic acid prop-2-ynyl ester;
[5-(4-carbamoyl-phenyl)-3-(3-ethyl-ureido)-isoquinolin-8-ylmethyl]-carbamic acid prop-2-ynyl ester;
[3-(3-ethyl-ureido)-5-(6-hydroxymethyl-pyridin-3-yl)-isoquinolin-8-ylmethyl]-carbamic acid prop-2-ynyl ester;
[3-(3-ethyl-ureido)-5-(4-hydroxymethyl-phenyl)-isoquinolin-8-ylmethyl]-carbamic acid prop-2-ynyl ester;
[5-(2-amino-pyridin-4-yl)-3-(3-ethyl-ureido)-isoquinolin-8-ylmethyl]-carbamic acid prop-2-ynyl ester;
prop-2-yn-1-yl((5-(4-(aminomethyl)phenyl)-3-(3-ethylureido)isoquinolin-8-yl)methyl)carbamate;
prop-2-yn-1-yl((5-(3-(aminomethyl)phenyl)-3-(3-ethylureido)isoquinolin-8-yl)methyl)carbamate;
N-[3-(3-ethyl-ureido)-5-pyridin-4-yl-isoquinolin-8-ylmethyl]-4-morpholin-4-yl-butyramide;
[5-chloro-3-(3-ethyl-ureido)-isoquinolin-8-ylmethyl]-carbamic acid 3-morpholin-4-yl-propyl ester;
[3-(3-ethyl-ureido)-5-fluoro-isoquinolin-8-ylmethyl]-carbamic acid 3-morpholin-4-yl-propyl ester;
[3-(3-ethyl-ureido)-5-fluoro-isoquinolin-8-ylmethyl]-carbamic acid prop-2-ynyl ester;
[3-(3-ethyl-ureido)-5-fluoro-isoquinolin-8-ylmethyl]-carbamic acid 2-methoxy-ethyl ester;

as well as the salts (in particular the pharmaceutically acceptable salts) thereof.

180) Yet further particularly preferred compounds are the following compounds of formula I as defined in embodiment 1) or 4):
[3-(3-ethyl-ureido)-5-pyridin-4-yl-isoquinolin-8-ylmethyl]-carbamic acid 2-(3H-[1,2,3]triazol-4-yl)-ethyl ester;
N-[3-(3-ethyl-ureido)-5-(2-methyl-pyridin-4-yl)-isoquinolin-8-ylmethyl]-acetamide;
cyclopropanecarboxylic acid [3-(3-ethyl-ureido)-5-(2-methyl-pyridin-4-yl)-isoquinolin-8-ylmethyl]-amide;
propynoic acid [3-(3-ethyl-ureido)-5-(2-methyl-pyridin-4-yl)-isoquinolin-8-ylmethyl]-amide;
1H-imidazole-2-carboxylic acid [3-(3-ethyl-ureido)-5-(2-methyl-pyridin-4-yl)-isoquinolin-8-ylmethyl]-amide;
N-[3-(3-ethyl-ureido)-5-(2-methyl-pyridin-4-yl)-isoquinolin-8-ylmethyl]-3-methoxy-propionamide;
[3-(3-ethyl-ureido)-5-(2-methyl-pyridin-4-yl)-isoquinolin-8-ylmethyl]-carbamic acid prop-2-ynyl ester;
[5-chloro-3-(3-ethyl-ureido)-isoquinolin-8-ylmethyl]-carbamic acid methyl ester;
[5-(2-cyclopropyl-pyridin-4-yl)-3-(3-ethyl-ureido)-isoquinolin-8-ylmethyl]-carbamic acid methyl ester;
[3-(3-ethyl-ureido)-5-(2-fluoro-pyridin-4-yl)-isoquinolin-8-ylmethyl]-carbamic acid methyl ester;
[3-(3-ethyl-ureido)-5-(2-methoxy-pyridin-4-yl)-isoquinolin-8-ylmethyl]-carbamic acid methyl ester;
[5-(2-amino-pyridin-4-yl)-3-(3-ethyl-ureido)-isoquinolin-8-ylmethyl]-carbamic acid methyl ester;
[5-(2,6-dimethyl-pyridin-4-yl)-3-(3-ethyl-ureido)-isoquinolin-8-ylmethyl]-carbamic acid methyl ester;
[3-(3-ethyl-ureido)-5-(2-trifluoromethyl-pyridin-4-yl)-isoquinolin-8-ylmethyl]-carbamic acid methyl ester;
[5-(2-ethoxy-pyridin-4-yl)-3-(3-ethyl-ureido)-isoquinolin-8-ylmethyl]-carbamic acid methyl ester;
[5-(2-tert-butoxy-pyridin-4-yl)-3-(3-ethyl-ureido)-isoquinolin-8-ylmethyl]-carbamic acid methyl ester;
[3-(3-ethyl-ureido)-5-(2-hydroxy-pyridin-4-yl)-isoquinolin-8-ylmethyl]-carbamic acid methyl ester;
[3-(3-ethyl-ureido)-5-(2-morpholin-4-yl-pyridin-4-yl)-isoquinolin-8-ylmethyl]-carbamic acid methyl ester;
[5-(2-ethyl-pyridin-4-yl)-3-(3-ethyl-ureido)-isoquinolin-8-ylmethyl]-carbamic acid methyl ester;
[3-(3-ethyl-ureido)-5-(2-pyrrolidin-1-yl-pyridin-4-yl)-isoquinolin-8-ylmethyl]-carbamic acid methyl ester;
[5-(2,6-difluoro-pyridin-4-yl)-3-(3-ethyl-ureido)-isoquinolin-8-ylmethyl]-carbamic acid methyl ester;
[3-(3-ethyl-ureido)-5-(2-isopropoxy-pyridin-4-yl)-isoquinolin-8-ylmethyl]-carbamic acid methyl ester;
[3-(3-ethyl-ureido)-5-(3,4,5,6-tetrahydro-2H-[1,2']bipyridinyl-4'-yl)-isoquinolin-8-ylmethyl]-carbamic acid methyl ester;
[3-(3-ethyl-ureido)-5-(2-methyl-pyridin-4-yl)-isoquinolin-8-ylmethyl]-carbamic acid methyl ester;
[3-(3-ethyl-ureido)-5-(2-methyl-pyridin-4-yl)-isoquinolin-8-ylmethyl]-carbamic acid tert-butyl ester;

[5-[2-(2-carbamoyl-ethyl)-pyridin-4-yl]-3-(3-ethyl-ureido)-isoquinolin-8-ylmethyl]-carbamic acid 2-methoxy-ethyl ester;
(4-{3-(3-ethyl-ureido)-8-[(2-methoxy-ethoxycarbonylamino)-methyl]-isoquinolin-5-yl}-pyridin-2-yl)-acetic acid tert-butyl ester;
[5-(2-carbamoyl-pyridin-4-yl)-3-(3-ethyl-ureido)-isoquinolin-8-ylmethyl]-carbamic acid 2-methoxy-ethyl ester;
[3-(3-ethyl-ureido)-5-(2-methyl-pyridin-4-yl)-isoquinolin-8-ylmethyl]-methyl-carbamic acid methyl ester;
[3-(3-ethyl-ureido)-5-(2-methyl-pyridin-4-yl)-isoquinolin-8-ylmethyl]-methyl-carbamic acid 2-methoxy-ethyl ester;
[3-(3-ethyl-ureido)-5-pyridin-4-yl-isoquinolin-8-ylmethyl]-carbamic acid 2-carbamoyl-ethyl ester;
3H-[1,2,3]triazole-4-carboxylic acid [3-(3-ethyl-ureido)-isoquinolin-8-ylmethyl]-amide;
[3-(3-ethyl-ureido)-5-(3-fluoro-pyridin-4-yl)-isoquinolin-8-ylmethyl]-carbamic acid methyl ester;
[3-(3-ethyl-ureido)-5-(3-methyl-pyridin-4-yl)-isoquinolin-8-ylmethyl]-carbamic acid methyl ester;
[3-(3-ethyl-ureido)-5-(2-fluoro-5-methyl-pyridin-4-yl)-isoquinolin-8-ylmethyl]-carbamic acid methyl ester;
[3-(3-ethyl-ureido)-5-(2-fluoro-3-methyl-pyridin-4-yl)-isoquinolin-8-ylmethyl]-carbamic acid methyl ester;
[3-(3-ethyl-ureido)-5-(5-fluoro-2-methyl-pyridin-4-yl)-isoquinolin-8-ylmethyl]-carbamic acid methyl ester;
[5-(2,3-dimethyl-pyridin-4-yl)-3-(3-ethyl-ureido)-isoquinolin-8-ylmethyl]-carbamic acid methyl ester;
[5-(2,5-dimethyl-pyridin-4-yl)-3-(3-ethyl-ureido)-isoquinolin-8-ylmethyl]-carbamic acid methyl ester;
[5-(2,5-difluoro-pyridin-4-yl)-3-(3-ethyl-ureido)-isoquinolin-8-ylmethyl]-carbamic acid methyl ester;
{3-(3-ethyl-ureido)-5-[2-(3-hydroxy-propyl)-pyridin-4-yl]-isoquinolin-8-ylmethyl}-carbamic acid methyl ester;
[3-(3-ethyl-ureido)-5-(2-(methylcarbamoyl-methyl)-pyridin-4-yl)-isoquinolin-8-ylmethyl]-carbamic acid methyl ester;
[5-[2-(dimethylcarbamoyl-methyl)-pyridin-4-yl]-3-(3-ethyl-ureido)-isoquinolin -8-ylmethyl]-carbamic acid methyl ester;
[3-(3-ethyl-ureido)-5-[2-(2-methylcarbamoyl-ethyl)-pyridin-4-yl]-isoquinolin -8-ylmethyl]-carbamic acid methyl ester;
[5-[2-(2-dimethylcarbamoyl-ethyl)-pyridin-4-yl]-3-(3-ethyl-ureido)-isoquinolin -8-ylmethyl]-carbamic acid methyl ester;
[5-(2-cyano-pyridin-4-yl)-3-(3-ethyl-ureido)-isoquinolin-8-ylmethyl]-carbamic acid methyl ester;
as well as the salts (in particular the pharmaceutically acceptable salts) thereof.
181) The invention further relates to each group of compounds of formula I selected from the compounds listed in embodiment 178), the compounds listed in embodiment 179) and the compounds listed in embodiment 180), which group of compounds furthermore corresponds to one of embodiments 2) to 176), as well as to the salts (in particular the pharmaceutically acceptable salts) of such compounds (and notably to each group of compounds of formula I selected from the compounds listed in embodiment 178), which group of compounds furthermore corresponds to one of embodiments 2) to 176), or also to each group of compounds of formula I selected from the compounds listed in embodiment 179), which group of compounds furthermore corresponds to one of embodiments 2) to 176)).

182) The invention moreover relates to any individual compound of formula I selected from the compounds listed in one of embodiments 178) to 180) and to the salts (in particular the pharmaceutically acceptable salts) of such individual compound.

The compounds of formula I according to the present invention, i.e. according to one of embodiments 1) to 182), are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to the invention are particularly active against bacteria and bacteria-like organisms. They are therefore particularly suitable for use in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, Enterococcus faecium, Enterococcus casseliflavus, Staphylococcus epidermidis, Staphylococcus haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *Staphylococcus aureus, Staphylococcus haemolyticus, Enterococcus faecalis, Enterococcus faecium, Enterococcus durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *Staphylococcus epidermidis, Staphylococcus haemolyticus*, etc.), *Streptococcus pyogenes, Streptococcus agalactiae*, Streptococcal groups C-F, viridans streptococci, *Corynebacterium* spp. or *Clostridium* spp., uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *Staphylococcus aureus* (food poisoning and toxic shock syndrome), or Groups A, B and C streptococci; ulcers related to infection by *Helicobacter pylori*; conjunctivitis, keratitis, and dacrocystitis related to infection by *Chlamydia trachomatis, Neisseria gonorrhoeae, Staphylococcus aureus, Streptococcus pneumoniae, Streptococcus pyogenes, Haemophilus influenzae*, or *Listeria* spp.; disseminated *Mycobacterium avium* complex (MAC) disease related to infection by *Mycobacterium avium*, or *Mycobacterium intracellulare*; infections caused by *Mycobacterium* such as *Mycobacterium tuberculosis*; gastroenteritis related to infection by *Campylobacter jejuni*; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to the present invention are further useful for the preparation of a medicament and are suitable for use in the treatment of infections that are mediated by bacteria such as *Clostridium difficile, Corynebacterium* spp., *Propionibacterium acnes* and *Bacteroides* spp. They can be used for example in the treatment of, inter alia, Gram positive infections (notably those caused by *Staphylococcus aureus*, enterococci and streptococci), community acquired pneumonias, skin and skin structure infections, acne vulgaris and infected atopic dermatitis.

The present list of pathogens is to be interpreted merely as examples and in no way as limiting.

The compounds of formula I according to one of embodiments 1) to 182), or the pharmaceutically acceptable salts thereof, may be used for the preparation of a medicament, and are suitable, for use in the prevention or treatment of a bacterial infection.

As well as in humans, bacterial infections can also be treated using compounds of formula I according to one of embodiments 1) to 182) (or pharmaceutically acceptable salts thereof) in other species like pigs, ruminants, horses, dogs, cats and poultry.

Accordingly, the compounds of formula I according to one of embodiments 1) to 182), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, gastrointestinal infections, *Clostridium difficile* infections, sexually transmitted infections, foreign body infections, osteomyelitis, topical infections, opthalmological infections and tuberculosis, and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

In particular, the compounds of formula I according to one of embodiments 1) to 182), or the pharmaceutically acceptable salts thereof, may be used for the preparation of a medicament, and are suitable, for use in the prevention or treatment of a bacterial infection caused by bacteria selected from the group consisting of *Staphylococcus aureus*, enterococci, pneumococci, streptococci, *Haemophilus influenzae, Moraxella catarrhalis* and *Clostridium difficile* (and in particular caused by *Streptococcus pneumoniae* bacteria).

The present invention also relates to pharmacologically acceptable salts and to compositions and formulations of compounds of formula I according to one of embodiments 1) to 182).

Any reference to a compound of formula I in this text (and notably in the embodiments presented above) is to be understood as referring also to the salts (and especially the pharmaceutically acceptable salts) of such compounds, as appropriate and expedient.

A pharmaceutical composition according to the present invention contains at least one compound of formula I according to one of embodiments 1) to 182) (or a pharmaceutically acceptable salt thereof) as the active agent and optionally carriers and/or diluents and/or adjuvants, and may also contain additional known antibiotics.

The compounds of formula I according to one of embodiments 1) to 182) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the prevention or the treatment of a bacterial infection, and in particular a method for the treatment of a bacterial infection caused by *Streptococcus pneumoniae* bacteria, in a patient comprising the administration to said patient of a pharmaceutically active amount of a compound of formula I according to one of embodiments 1) to 182) or a pharmaceutically acceptable salt thereof.

Moreover, the compounds of formula I according to one of embodiments 1) to 182) may also be used for cleaning purposes, e.g. to remove pathogenic microbes and bacteria from surgical instruments or to make a room or an area aseptic. For such purposes, the compounds of formula I could be contained in a solution or in a spray formulation.

The compounds of formula I can be manufactured in accordance with the present invention using the procedures described hereafter.

Preparation of Compounds of Formula I

Abbreviations:

The following abbreviations are used throughout the specification and the examples:

Ac acetyl
anhydr. anhydrous
aq. aqueous
bippyphos 5-(di-tert-butylphosphino)-1',3',5'-triphenyl-1'H-[1,4']bipyrazole
Boc tert-butoxycarbonyl
CC column chromatography over silica gel
CDI 1,1'-carbonyldiimidazole
conc. concentrated
DBU 1,8-diazabicyclo[5.4.0]undec-7-ene
DCC N,N'-dicyclohexylcarbodiimide
DCM dichloromethane
dcpp 1,3-bis(dicyclohexylphosphino)propane
DEAD diethyl azodicarboxylate
DIAD diisopropyl azodicarboxylate
DIBAH diisobutyl aluminium hydride
DIPEA N,N-diisopropylethylamine
DMAP 4-(dimethylamino)pyridine
DME 1,2-dimethoxyethane
DMF N,N-dimethylformamide
DMSO dimethylsulfoxide
DPPA diphenyl phosphoryl azide
dppf 1,1'-bis(diphenylphosphino)ferrocene
DSC N,N'-disuccinimidyl carbonate
EA ethyl acetate
EDC 1-ethyl-3-(3-dimethylaminopropyl)carbodiimide hydrochloride
ESI Electron Spray Ionisation
eq. equivalent
Et ethyl EtOH ethanol
HATU 0-(7-azabenzotriazol-1-yl)-N,N,N',N'-tetramethyluronium hexafluorophosphate
Hex hexane
Hept heptane
HOAT 1-hydroxy-7-aza-benzotriazole
HOBT 1-hydroxybenzotriazole
LC liquid chromatography
Me methyl
MeCN acetonitrile
MeOH methanol
MS Mass Spectroscopy
Ms methanesulfonyl (mesyl)
org. organic
NMP N-methyl-2-pyrrolidone
$PCy_3$ tricyclohexylphosphine
Pd/C palladium on carbon
$Pd_2(dba)_3$ tris[dibenzylideneacetone]dipalladium(0)
$Pd(PPh_3)_4$ tetrakis(triphenylphosphine)palladium(0)
PEPPSI™-IPr [1,3-bis(2,6-diisopropylphenyl)imidazol-2-ylidene](3-chloropyridyl)palladium(II) dichloride
Ph phenyl
prep-HPLC preparative HPLC
Pyr pyridine
Q-phos 1,2,3,4,5-pentaphenyl-1'-(di-tert-butylphosphino) ferrocene
rt room temperature
sat. saturated
S-Phos 2-dicyclohexylphosphino-2',6'-dimethoxybiphenyl
SK-CC01-A 2'-(dimethylamino)-2-biphenylyl-palladium(II) chloride dinorbornylphosphine complex
T3P propylphosphonic anhydride
tBu tert-butyl
tBuDavePhos 2-di-tert-butylphosphino-2'-(N,N-dimethylamino)biphenyl
TEA triethylamine
Tf trifluoromethanesulfonyl
TFA trifluoroacetic acid
THF tetrahydrofuran
TLC thin layer chromatography
$t_R$ retention time
$T_S$ p-toluenesulfonyl
v/v proportion by volume
wt % percent in weight
XantPhos 4,5-bis(diphenylphosphino)-9,9-dimethylxanthene General Reaction Techniques:

General Reaction Technique 1 (Urea Formation):

The amine is reacted with the required isocyanate or carbamic chloride derivative in the presence or absence of a base such as TEA, DIPEA, $K_2CO_3$, $NaHCO_3$ or Pyr between 20 and 120° C. in a solvent such as DCM, THF, dioxane, Pyr, DMF or NMP. Alternatively, the amine is reacted first with an activating agent such as CDI, DSC, phosgene, triphosgene or trichloroacetyl chloride, the resulting intermediate being then reacted with the required amine General Reaction Technique 2 (Suzuki Coupling):

The aromatic halide (typically a bromide, a chloride or an iodide) is reacted with the required boronic acid derivative or its boronate ester equivalent (e.g. pinacol ester) in the presence of a palladium catalyst, a base such as $K_2CO_3$, $Cs_2CO_3$, $K_3PO_4$, tBuONa or tBuOK between 20 and 120° C. in a solvent such as toluene, THF, dioxane, DME or DMF, usually in the presence of water (20 to 50%). Examples of typical palladium catalysts are triarylphosphine palladium complexes such as $Pd(PPh_3)_4$. These catalysts can also be prepared in situ from a common palladium source such as $Pd(OAc)_2$ or $Pd_2(dba)_3$ and a ligand such as trialkylphosphines (e.g. $PCy_3$ or $P(tBu)_3$), dialkylphosphinobiphenyls (e.g. S-Phos) or ferrocenylphosphines (e.g. Q-phos). Alternatively, one can use a commercially available precatalyst based on palladacycle (e.g. SK-CC01-A) or N-heterocyclic carbene complexes (e.g. PEPPSI™-IPr). The reaction can also be performed by using the corresponding aromatic triflate. Further variations of the reaction are described in *Chem. Rev.* (1995), 95, 2457-2483, *Synthesis* (2004), 2419-2440, *Aldrichimica Acta* (2006), 39, 17-24 and 97-111, *Acc. Chem. Res.* (2008), 41, 1555-1564, and references cited therein.

General Reaction Technique 3 (Carbamate Formation with Chloroformate):

The amine is reacted with the required chloroformate derivative in the presence of a base such as TEA, DIPEA, $K_2CO_3$, $NaHCO_3$ or NaOH between 20 and 120° C. in a solvent such as DCM, THF, dioxane, Pyr, MeOH, DMF or NMP.

General Reaction Technique 4 (Carbamate Formation Via Activation of an Alcohol):

The required alcohol derivative is first treated with an activating agent such as CDI, DSC, phosgene or triphosgene in the presence or absence of a base such as DMAP, TEA, DIPEA, $K_2CO_3$ or $NaHCO_3$ between 20 and 80° C. in a solvent such as DCM, THF, dioxane, Pyr, MeOH, DMF or NMP. The activated alcohol is then reacted with the amine between 20 and 120° C.

General Reaction Technique 5 (Carbamate Formation Via Activation of the Amine):

The amine is first reacted with an activating agent such as CDI, DSC, phosgene, triphosgene or trichloroacetyl chloride between 20 and 120° C. in a solvent such as DMF or NMP. The activated amine is then treated with the required alcohol derivative between 20 and 120° C.

General Reaction Technique 6 (Amide Formation):

The amine is reacted with the required carboxylic acid in the presence of an activating agent such as DCC, EDC, T3P, HATU or DSC, optionally in the presence of an additional agent such as HOAT or HOBT, in a dry aprotic solvent such as DCM, MeCN or DMF between −20 and +60° C. (see G. Benz in *Comprehensive Organic Synthesis*, B. M. Trost, I. Fleming, Eds; Pergamon Press: New York (1991), vol. 6, p. 381). Alternatively, the carboxylic acid can be first activated by conversion into its corresponding acid chloride by reaction with oxalyl chloride or thionyl chloride neat or in a solvent such as DCM between −20 and 100° C. Further activating agents can be found in *Comprehensive Organic Transformations. A guide to Functional Group Preparations;* $2^{nd}$ Edition, R. C. Larock, Wiley-VC; New York, Chichester, Weinheim, Brisbane, Singapore, Toronto, 1999; Section nitriles, carboxylic acids and derivatives, p. 1941-1949.

General Reaction Technique 7 (Alcohol Activation);

The alcohol is reacted with a sulfonyl chloride derivative such as MsCl, TfCl or TsCl in presence of a base such as TEA in a dry aprotic solvent such as Pyr, THF or DCM between −30 and +50° C. In the case of the triflate or mesylate, $Tf_2O$ or $Ms_2O$ can also be used. These sulfonates can be reacted with a sodium halide such as NaI or NaBr in MeCN or DMF between 40 and 120° C., delivering the corresponding iodide or bromide derivatives. Alternatively the corresponding chlorides or bromides can also be obtained respectively by reaction of the corresponding alcohol derivatives with $SOCl_2$ or $POCl_3$ either neat or in a solvent such as DCM, MeCN or toluene between 20 and 120° C., or by reaction of the corresponding alcohol derivatives with $PBr_3$ in a solvent such as DCM, THF or toluene between 20 and 120° C. Further variations of this transformation can be found in *Comprehensive*

*Organic Transformations. A guide to Functional Group Preparations;* 2nd Edition, R. C. Larock, Wiley-VC; New York, Chichester, Weinheim, Brisbane, Singapore, Toronto, 1999; Section halides, p. 689-703.

General Reaction Technique 8 (Formation of Azides):

The activated alcohol (activated either as a sulfonate or a iodide derivative) is reacted with sodium azide in the presence of an organic base such as DIPEA or TEA or an inorganic base such as $Na_2CO_3$ in a solvent such as DMSO or DMF between 20 and 100° C. Alternatively, the azide can also be obtained by activation of the alcohol under Mitsunobu conditions in the presence of $PPh_3$ and DEAD or DIAD in a solvent such as THF, DMF, DCM or DME between −20 and +60° C. as reviewed in *Synthesis* (1981), 1-28. Alternatively, the alcohol is directly reacted with DPPA in the presence of a base such as TEA or DBU in a solvent such as THF between −20 and +60° C. as described in *J. Org. Chem.* (1993), 58, 5886-5888.

General Reaction Technique 9 (Formation of Phthalimides):

The activated alcohol (activated either as a sulfonate or a iodide derivative) is reacted with potassium phthalimide in a solvent such as DMSO or DMF between 20 and 100° C.

General Reaction Technique 10 (Formation of Amines):

Azide derivatives are hydrogenated over a noble metal catalyst such as Pd/C in a solvent such as MeOH or EA. In case the molecule is containing an unsaturated double or triple bond, the reduction can be performed using $PPh_3$ in the presence of water as described in *J. Med. Chem.* (1993), 36, 2558-68. Besides, phthalimide derivatives are treated between 50 and 120° C. with a hydrazine derivative such as hydrazine hydrate, methylhydrazine or an amine such as $N^1,N^1$-dimethylpropane-1,3-diamine in a solvent such as MeOH or EtOH. Further general methods have been described in *Protecting Groups in Organic Synthesis*, 3rd Ed (1999), 564-566; T. W. Greene, P. G. M. Wuts (Publisher: John Wiley and Sons, Inc., New York).

General Reaction Technique 11 (Ester Formation from an Aromatic Halide):

The aromatic halide is reacted under a carbon monoxide atmosphere in presence of an alcohol, such as MeOH, a palladium catalyst, a base such as $K_2CO_3$, $Cs_2CO_3$, $K_3PO_4$, tBuONa or tBuOK between 20 and 120° C. in a solvent such as toluene, THF, dioxane, DME, DMSO or DMF. Examples of typical palladium catalysts are phosphine palladium complexes that can be prepared in situ from a common palladium source such as $Pd(OAc)_2$ or $Pd_2(dba)_3$ and a ligand such as bidentate phosphines (e.g. XantPhos, dcpp) or ferrocenylphosphines (e.g. dppf). Alternatively, the reaction can also be performed by forming first the corresponding aromatic phenyl ester in the presence of phenol or sodium phenoxide and then treating it with the desired alcohol. Further variations of the reaction are described in *J. Org. Chem.* (2008), 73, 7102-7107, *J. Org. Chem.* (2008), 73, 7096-7101, *Angew. Chem. Int. Ed.* (2007), 46, 8460-8463, and references cited therein. Besides, one can also perform a Pd-catalyzed decarboxylative coupling using potassium oxalate monoesters as described in *J. Am. Chem. Soc.* (2009), 131, 5738-5739.

General Reaction Technique 12 (Reduction of Esters into Alcohols):

The ester is reduced into its corresponding alcohol using a reducing agent selected among those mentioned in Larock, R. C. in *Comprehensive Organic Transformations A guide to Functional Group Preparations*, 2nd Ed., Wiley, New York, Chichester, Weinheim, Brisbane, Singapore, Toronto (1999), Section Alcohols and phenols; p. 1114 to 1120. Among them $LiAlH_4$ or DIBAH are the most preferred.

General Reaction Technique 13 (Addition of Benzyl Amine on an Imidate Derivative):

The required benzyl amine is reacted with 2,2-diethoxy-ethanimidic acid methyl ester in a solvent such as MeOH between 0 and 70° C. as described in WO 2007/125405. If not commercially available, the imidate is obtained by reacting NaOMe with diethoxyacetonitrile in MeOH between 0 and 70° C.

General Reaction Technique 14 (Isoquinoline Formation by Cyclisation):

The crude intermediate from general reaction technique 13 undergoes a cyclisation reaction in conc. $H_2SO_4$ between 0 and 100° C. as described in WO 2007/125405.

General Reaction Technique 15 (Removal of Amine Protecting Groups):

The benzyl or benzyl carbamate protecting groups are removed by hydrogenolysis over a noble metal catalyst (e.g. Pd/C or $Pd(OH)_2$/C). The Boc group is removed under acidic conditions such as HCl in an organic solvent such as MeOH or dioxane, or TFA neat or diluted in a solvent such as DCM. Further general methods to remove amine protecting groups have been described in *Protecting Groups in Organic Synthesis,* 3rd Ed (1999), 494-653; T. W. Greene, P. G. M. Wuts (Publisher: John Wiley and Sons, Inc., New York).

General Reaction Technique 16 (Removal of Hydroxy Protecting Groups):

The silyl groups are removed either using a fluoride anion source such as TBAF in THF or HF in MeCN or water, or using acidic conditions such as AcOH in aq. THF or HCl in MeOH, between 0° C. and 80° C. Further methods are given in T. W. Greene, P. G. M. Wuts, *Protecting Groups in Organic Synthesis,* 3rd Ed (1999), 133-139 and 142-143 respectively (Publisher: John Wiley and Sons, Inc., New York, N.Y.). Further general methods to remove alcohol protecting groups are described in T. W. Greene, P. G. M. Wuts, *Protecting Groups in Organic Synthesis,* 3rd Ed (1999), 23-147 (Publisher: John Wiley and Sons, Inc., New York, N.Y.).

General Reaction Technique 17 (Ketal and Acetonide Deprotection):

The ketal or acetonide is converted into its corresponding deprotected ketone or diol respectively, by treatment under acidic conditions such as aq. HCl in MeOH or AcOH in aq. THF, between rt and reflux temperature, or by using an acidic resin such as Amberlite IR120H or DOWEX 50W8 in a water-solvent mixture such as MeOH/water, dioxane/water or THF/water.

General Reaction Technique 18 (tBu Ester Hydrolysis):

The tBu ester is treated with TFA neat or diluted in an organic solvent such as DCM, or with a solution of HCl in an organic solvent such as dioxane, between 0° C. and 80° C. Further methods to remove the TBDMS and TBDPS groups are given in T. W. Greene, P. G. M. Wuts, *Protecting Groups in Organic Synthesis,* 3rd Ed (1999), 406-408 (Publisher: John Wiley and Sons, Inc., New York, N.Y.).

General Reaction Technique 19 (Nucleophilic Substitution with an Amine):

The activated alcohol (activated either as a sulfonate or a halide derivative) is reacted with ammonia or the appropriate amine derivative in presence of an inorganic base such as $K_2CO_3$ or an org. base such as TEA in a solvent such as THF, DMF or DMSO between 0° C. and 80° C. Further details can be found in *Comprehensive Organic Transformations. A guide to Functional Group Preparations;* 2nd Edition, R. C. Larock, Wiley-VC; New York, Chichester, Weinheim, Brisbane, Singapore, Toronto, (1999). Section Amines p. 779.

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

If the group $R^2$ or $R^3$ contains a free hydroxy, an amino group, a free diol or a free carboxylic acid which might be incompatible with the assembly illustrated in the procedures and schemes hereafter, each of these functional groups will be protected, prior to the reaction described in the procedures and schemes hereafter, as a silyl ether, a Boc group, an acetonide group or a tBu ester respectively. The use of protecting groups is well known in the art (see for example "*Protective Groups in Organic Synthesis*", T. W. Greene, P. G. M. Wuts, Wiley-Interscience, 1999). The protecting groups can be removed following the reaction described in the procedures and schemes hereafter using general reaction techniques 15, 16, 17 and 18.

The compounds of formula I can be manufactured in accordance with the present invention by a) reacting the compounds of formula II

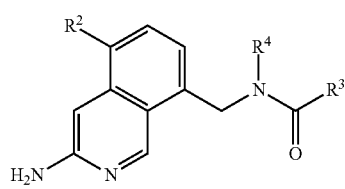

II wherein $R^2$, $R^3$ and $R^4$ are as defined in formula I with the compounds of formula III or IIIa

III $R^1$—N=C=O

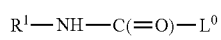

IIIa $R^1$—NH—C(=O)—$L^0$ wherein $R^1$ is as defined in formula I and $L^0$ represents halogen such as chlorine using general reaction technique 1; or b) reacting the compounds of formula II as defined in item a) with the compounds of formula IV

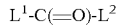

IV $L^1$-C(=O)-$L^2$ wherein $L^1$ represents halogen such as chlorine and $L^2$ represents trichloromethoxy or $L^1$ and $L^2$ both represent trichloromethoxy, N-succinimidyloxy, imidazol-1-yl or halogen such as chlorine, and then reacting the resulting intermediates with the amines of formula V

V $R^1$—$NH_2$ wherein $R^1$ is as defined in formula I using general reaction technique 1; or c) reacting the compounds of formula VI

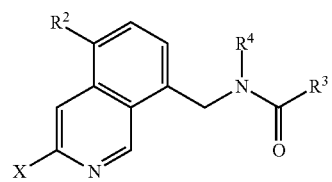

VI wherein $R^2$, $R^3$ and $R^4$ are as defined in formula I and X represents halogen such as chlorine or bromine, with the compounds of formula VII

VII $R^1$—NH—$CONH_2$ wherein $R^1$ is as defined in formula I in the presence of a catalyst such as $Pd_2(dba)_3$, a ligand such as bippyphos and a base such as $K_3PO_4$ in a solvent such as DME between 60 and 100° C. (e.g. as described in *Org. Lett.* (2009), 11, 947-950); or d) reacting the compounds of formula VIII

VIII wherein $R^1$, $R^3$ and $R^4$ are as defined in formula I, either with the compounds of formula IX

IX $L^3$-$B(OH)_2$ wherein $L^3$ represents one of the aromatic and heteroaromatic groups mentioned in the possible meanings for $R^2$ in formula I, or with the corresponding boronate esters (e.g. pinacol ester) using general reaction technique 2; or e) reacting the compounds of formula Xa

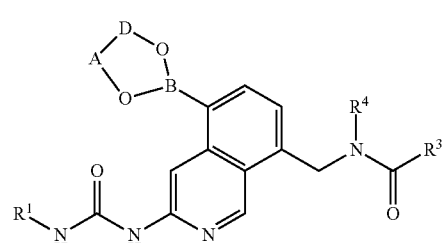

Xa or the compounds of formula Xb

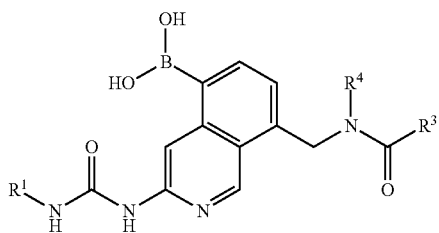

wherein $R^1$, $R^3$ and $R^4$ are as defined in formula I and -A-D- represents —C(Me)$_2$C(Me)$_2$- or —CH$_2$C(Me)$_2$CH$_2$— with the compounds of formula XI L$^4$-X$^a$      XI wherein $L^4$ represents one of the aromatic and heteroaromatic groups mentioned in the possible meanings for $R^2$ in formula I and $X^a$ represents halogen (such as chlorine, bromine or iodine) using general reaction technique 2; or f) reacting the compounds of formula XII

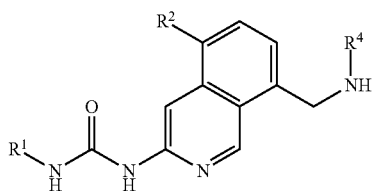

wherein $R^1$, $R^2$ and $R^4$ are as defined in formula I with the compounds of formula XIII L$^5$-C(=O)—X$^a$      XIII wherein $L^5$ represents (C$_1$-C$_4$)alkoxy, (C$_1$-C$_4$)haloalkoxy, alkynyloxy, (4-hydroxybut -2-yn-1-yl)oxy, dimethylamino-(C$_2$-C$_3$)alkoxy, carbamoyl-(C$_1$-C$_3$)alkoxy, (C$_3$-C$_6$)cycloalkyl-(C$_1$-C$_4$)alkoxy, hydroxy-(C$_2$-C$_3$)alkoxy, (C$_1$-C$_3$)alkoxy-(C$_1$-C$_3$)alkoxy, carboxy-(C$_1$-C$_3$)alkoxy, benzyloxy, 2-cyanoethoxy, the group —O—(CH$_2$)$_n$—N(R$^c$)C(O)O—R$^d$ or the group —O—(CH$_2$)$_n$—R$^e$ wherein n, R$^c$, R$^d$ and R$^e$ are as defined in formula I and X$^a$ represents halogen such as chlorine or a group such as imidazol-1-yl or N-succinimidyloxy, using general reaction technique 3 or 4; or g) reacting the compounds of formula XII as defined in item f) with the compounds of formula XIV L$^{1a}$-C(=O)-L$^{2a}$      XIV wherein $L^{1a}$ and $L^{2a}$ both represent trichloromethoxy, N-succinimidyloxy, imidazol -1-yl or halogen such as chlorine (and preferably both represent imidazol-1-yl), and then reacting the resulting intermediates with the alcohols of formula XV

L$^6$-OH      XV wherein $L^6$ represents (C$_1$-C$_4$)alkyl, (C$_1$-C$_4$)haloalkyl, prop-2-yn-1-yl, but-2-yn-1-yl, but-3-yn-1-yl, but-3-yn-2-yl, (C$_3$-C$_6$)cycloalkyl-(C$_1$-C$_4$)alkyl, (C$_1$-C$_3$)alkoxy-(C$_1$-C$_3$)alkyl, benzyl, 2-cyanoethyl or the group —(CH$_2$)$_n$—R$^e$ wherein R$^e$ is as defined in formula I using general reaction technique 5; or h) reacting the compounds of formula XII as defined in item f) with the acids of formula XVI

L$^7$-COOH      XVI wherein $L^7$ represents (C$_1$-C$_4$)alkyl, (C$_2$-C$_4$)alkynyl, amino-(C$_1$-C$_3$)alkyl, (C$_3$-C$_6$)cycloalkyl, (C$_3$-C$_6$)cycloalkyl-(C$_1$-C$_4$)alkyl, hydroxy-(C$_1$-C$_3$)alkyl, (C$_1$-C$_3$)alkoxy-(C$_1$-C$_3$)alkyl, carboxy-(C$_1$-C$_3$)alkyl, aryl, (C$_5$-C$_6$)heteroaryl, benzyl, the group —CH$_2$R$^a$, the group —CH$_2$CH$_2$R$^b$, the group —(CH$_2$)$_n$—C(O)O—R$^d$, the group —(CH$_2$)$_n$—N(R$^c$)C(O)O—R$^d$ or the group —(CH$_2$)$_n$—R$^e$ wherein n, R$^a$, R$^b$, R$^c$, R$^d$ and R$^e$ are as defined in formula I using general reaction technique 6; or i) reacting the compounds of formula XII as defined in item f) with the isocyanates of formula XVII

L$^8$-N=C=O      XVII wherein $L^8$ represents (C$_1$-C$_3$)alkyl using general reaction technique 1;

j) reacting the compounds of formula XVIII

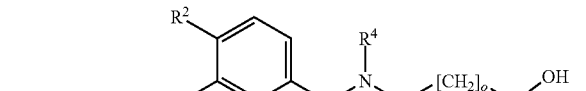

wherein $R^1$, $R^2$ and $R^4$ are as defined in formula I and o represents 1, 2 or 3 with ammonia or methylamine, using general reaction technique 6; or k) reacting the compounds of formula XIX

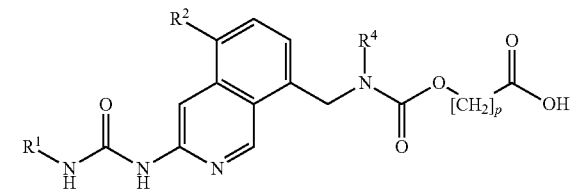

wherein $R^1$, $R^2$ and $R^4$ are as defined in formula I and p represents 1, 2 or 3, with MeOH or EtOH under acidic conditions such as TFA or catalytic sulfuric acid in a solvent such as MeOH, EtOH or DCM between 0° C. and 80° C.; or l) reacting the compounds of formula XX

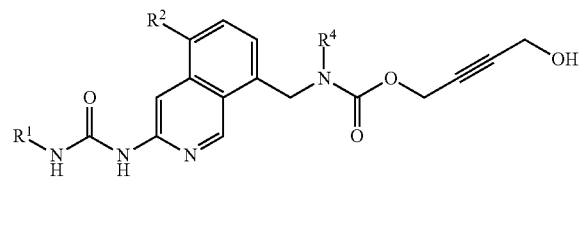

wherein $R^1$, $R^2$ and $R^4$ are as defined in formula I, with DPPA using general reaction technique 8, and transforming in situ the intermediate obtained into the corresponding amine using general reaction technique 10; or m) reacting the compounds of formula XIX as defined in item k) with ammonia using general reaction technique 6.

The compounds of formula I thus obtained may, if desired, be converted into their salts, and notably into their pharmaceutically acceptable salts.

Besides, whenever the compounds of formula I are obtained in the form of mixtures of diastereomers, the diastereomers can be separated using methods known to one skilled in the art, e.g. by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as TEA or diethylamine) and eluent B (Hex), at a flow rate of 0.8 to 150 mL/min. The mixtures of diastereomers may also be separated by an appropriate combination of silica gel chromatography, HPLC and crystallization techniques.

Preparation of the Intermediates Used in the Preparation of the Compounds of Formula I:

The compounds of formula III, IIIa, IV, V, VII, IX, XI, XIII, XIV, XV, XVI or XVII are commercially available or can be obtained by methods known to someone skilled in the art. The other intermediates can be prepared (for example) as described hereafter.

Compounds of Formula II:

The compounds of formula II can be prepared as summarised in Scheme 1 hereafter.

In Scheme 1, $R^2$, $R^3$ and $R^4$ are as defined in formula I and X represents halogen such as chlorine or bromine.

The compounds of formula I-1 can be reacted (Scheme 1) with the corresponding boronic acid derivatives of formula IX using general reaction technique 2, affording the compounds of formula II wherein $R^2$ is an aromatic or heteroaromatic group. The corresponding derivatives of formula II wherein $R^2$ is H can be obtained by reducing the compounds of formula I-1 by hydrogenation over a noble metal catalyst such as Pd/C.

Besides, the compounds of formula I-2 can be hydrogenated (Scheme 1) over a noble metal catalyst such as Pd/C to yield the compounds of formula II.

According to another method for preparing the compounds of formula II, the compounds of formula I-3 can be reacted (Scheme 1) with the compounds of formula XIII, XVI or XVII using general reaction technique 1, 3, 4 or 6. Alternatively, the compounds of formula I-3 can be reacted with the compounds of formula XIV, the resulting intermediates being further reacted with the compounds of formula XV using general reaction technique 5.

Moreover, the compounds of formula II can also be obtained (Scheme 1) by reaction of the compounds of formula VI with ammonia in the presence of a palladium catalyst such as $Pd_2(dba)_3$, a ligand such as tBuDavePhos and a base such as tBuONa in a solvent such as dioxane between 60 and 100° C. (further variations of this reaction are described in Angew. Chem. Int. Ed. (2011), 50, 86-95).

Compounds of Formula VI:

The compounds of formula VI can be prepared as summarised in Scheme 2 hereafter.

Scheme 1

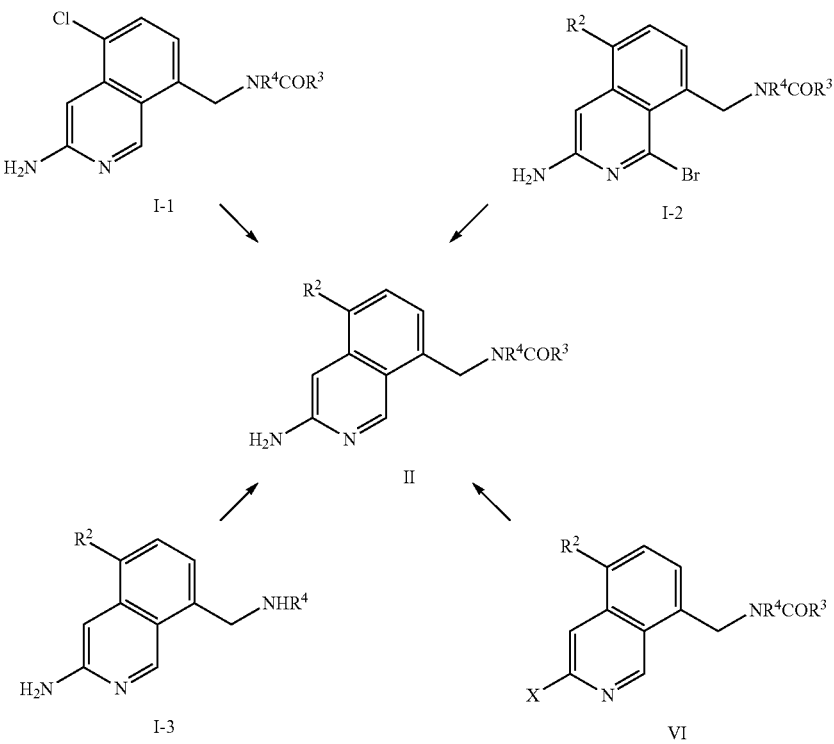

Scheme 2

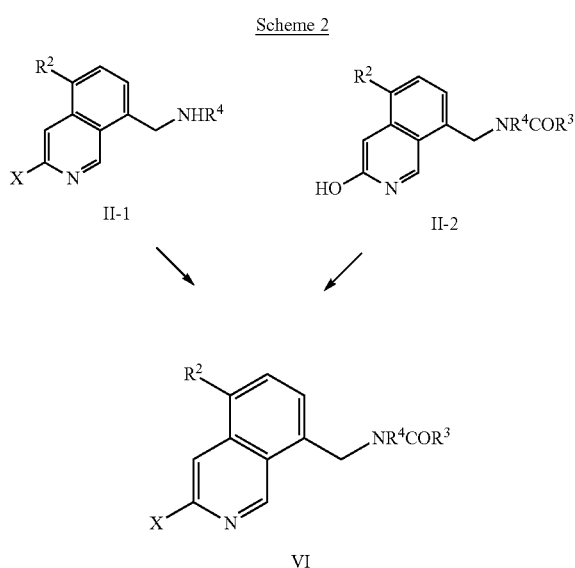

In Scheme 2, $R^2$, $R^3$ and $R^4$ are as defined in formula I, X represents halogen such as chlorine or bromine.

The compounds of formula II-1 can be reacted (Scheme 2) with the compounds of formula XIII, XVI or XVII using general reaction technique 1, 3, 4 or 6. Alternatively, the compounds of formula II-1 can also be reacted with the compounds of formula XIV, the resulting intermediates being further reacted with the compounds of formula XV using general reaction technique 5. Besides, the compounds of formula II-2 can be reacted with $POCl_3$ or $PBr_3$ using general reaction technique 7 to yield the compounds of formula VI.

Compounds of Formula VIII:

The compounds of formula VIII can be prepared as summarised in Scheme 3 hereafter.

Scheme 3

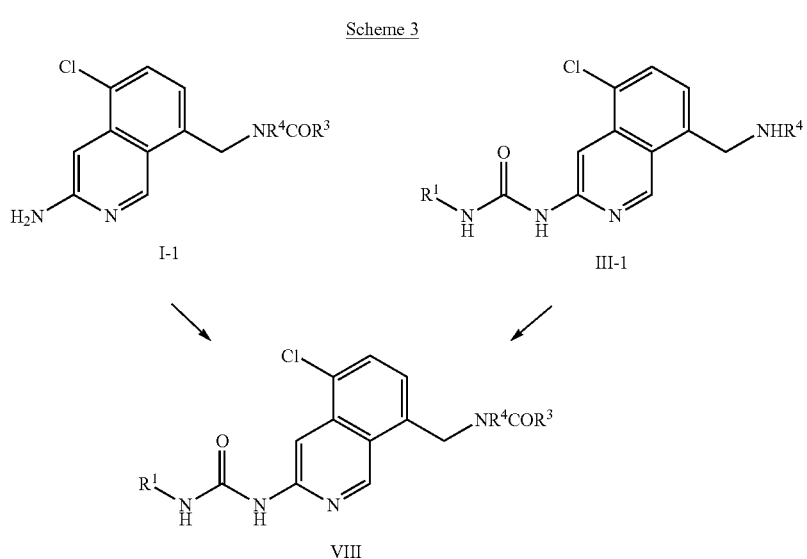

In Scheme 3, $R^1$, $R^3$ and $R^4$ are as defined in formula I.

The compounds of formula I-1 can be reacted (Scheme 3) with the compounds of formula III or IIIa using general reaction technique 1 to yield the compounds of formula VIII. Alternatively, the compounds of formula I-1 can be reacted with the compounds of formula IV, the resulting intermediates being then reacted with the compounds of formula V (see general reaction technique 1), thus affording the compounds of formula VIII. Besides, the compounds of formula III-1 can be reacted with the compounds of formula XIII, XVI or XVII using general reaction technique 1, 3, 4 or 6. Alternatively, the compounds of formula III-1 can also be reacted with the compounds of formula XIV, the resulting intermediates being further reacted with the compounds of formula XV using general reaction technique 5.

Compounds of Formulae Xa and Xb:

The compounds of formulae Xa and Xb can be prepared as summarised in Scheme 4 hereafter.

Scheme 4

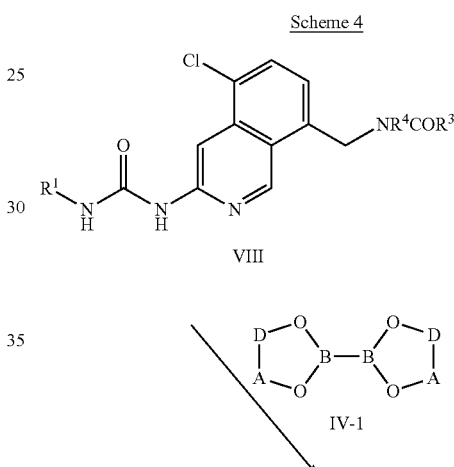

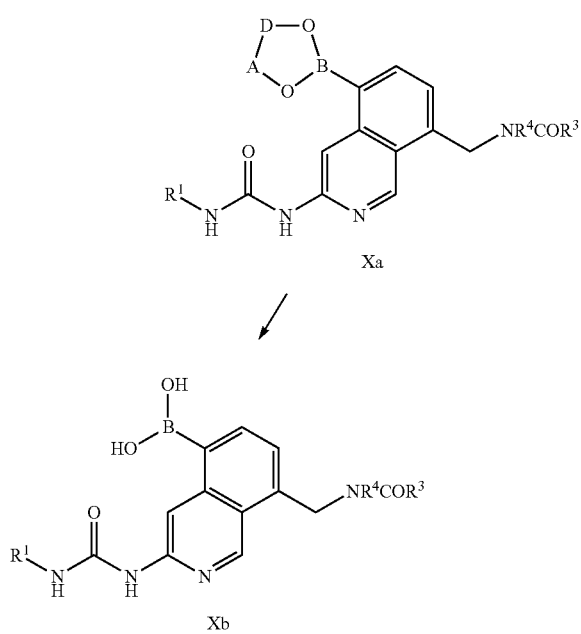

In Scheme 4, $R^1$, $R^3$ and $R^4$ are as defined in formula I and -A-D- represents —C(Me)$_2$C(Me)$_2$- or —CH$_2$C(Me)$_2$CH$_2$—.

The compounds of formula VIII can be reacted (Scheme 4) with the boronate ester derivatives of formula IV-1 (commercially available) wherein -A-D- represents —C(Me)$_2$C(Me)$_2$- or —CH$_2$C(Me)$_2$CH$_2$— using general reaction technique 2. The resulting derivatives of formula Xa can be directly hydrolysed in acidic medium, affording the derivatives of formula Xb.

Compounds of Formula XII:

The compounds of formula XII can be prepared as summarised in Scheme 5 hereafter.

In Scheme 5, $R^1$, $R^2$ and $R^4$ are as defined in formula I.

The compounds of formula III-1 can be reacted (Scheme 5) with the corresponding boronic acid derivatives of formula IX using general reaction technique 2, affording the compounds of formula XII wherein $R^2$ is an aromatic or heteroaromatic group. The corresponding derivatives of formula XII wherein $R^2$ is H can be obtained by reducing the compounds of formula III-1 by hydrogenation over a noble metal catalyst such as Pd/C. Besides, the compounds of formula V-1 can be sequentially reacted with alkyl or arylsulfonyl chlorides using general reaction technique 7, followed either by reaction with sodium azide using general reaction technique 8 or by reaction with potassium phthalimide using general reaction technique 9, and subsequently deprotected using general reaction technique 10. Alternatively, the compounds of formula V-1 can be directly reacted with DPPA using general reaction technique 8 and the resulting azides can be transformed in situ into the corresponding amines of formula XII wherein $R^4$ is H using general reaction technique 10. The corresponding derivatives of formula XII wherein $R^4$ is Me can be obtained by reacting the compounds of formula V-1 with SOCl$_2$ using general reaction technique 7 followed by treatment with methylamine using general reaction technique 19.

Compounds of Formula XVIII:

The compounds of formula XVIII can be obtained by reacting the compounds of formula XII with the compounds of formula XVI wherein $L^7$ represents —(CH$_2$)$_n$—COOtBu (as described in item h) of the above section relating to the preparation of the compounds of formula I), followed by removal of the tBu ester using general reaction technique 18.

Compounds of Formula XIX:

The compounds of formula XIX can be obtained by reacting the compounds of formula XII with the compounds of formula $L^5$-C(=O)—X$^a$ wherein $L^5$ represents —O(CH$_2$)$_p$—COOtBu, p represents 1, 2 or 3 and X$^a$ represents a group such as imidazol-1-yl or N-succinimidyloxy, followed by removal of the tBu ester using general reaction technique 18.

Compounds of Formula XX:

The compound of formula XX can be obtained by reacting the compound of formula XII with the compounds of formula Scheme 5

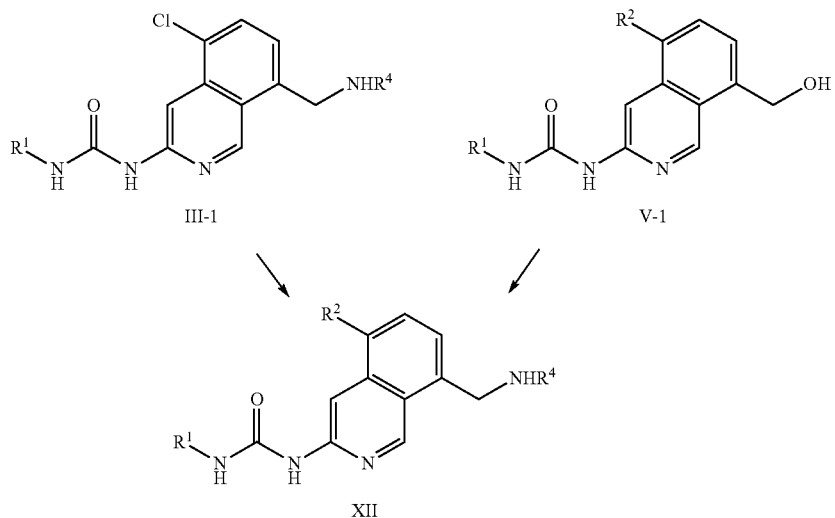

XIII wherein $L^5$ represents (4-hydroxybut-2-yn-1-yl)oxy using general reaction technique 4.

Compounds of Formula I-1:

The compounds of formula I-1 can be prepared as summarised in Scheme 6 hereafter.

Scheme 6

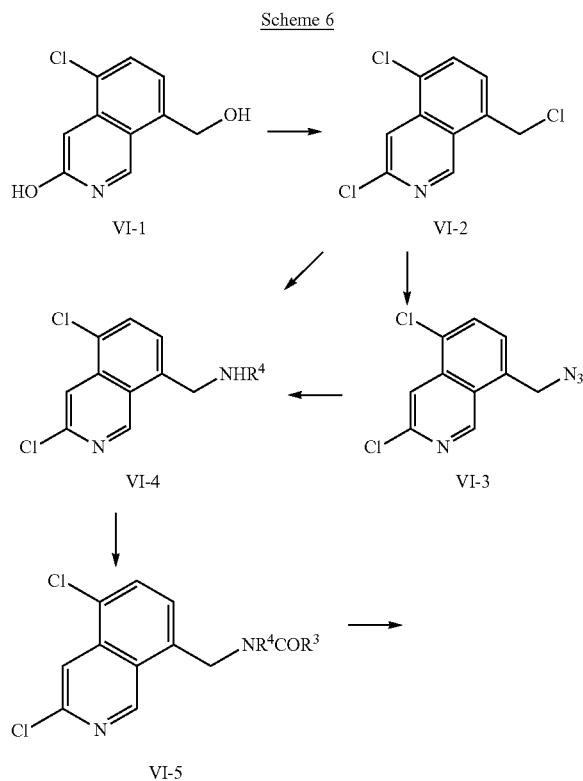

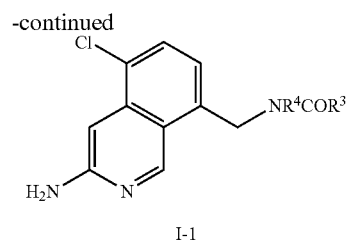

In Scheme 6, $R^3$ and $R^4$ are as defined in formula I.

The compound of formula VI-1 can be reacted (Scheme 6) with $POCl_3$ using general reaction technique 7, affording the trichloro derivative of formula VI-2 which can be further reacted with sodium azide using general reaction technique 8 and transformed into the corresponding amine of formula VI-4 wherein $R^4$ is H after reaction with $PPh_3$ in the presence of water using general reaction technique 10. The corresponding derivatives of formula VI-4 wherein $R^4$ is Me can be obtained by reacting the compound of formula VI-2 with methylamine using general reaction technique 19. The compounds of formula VI-4 can be further transformed into the derivatives of formula VI-5 after reaction with the compounds of formula XIII, XVI or XVII using general reaction technique 1, 3, 4 or 6. Alternatively, the amine of formula VI-4 can also be reacted with the compounds of formula XIV, the resulting intermediates being further reacted with the compounds of formula XV using general reaction technique 5. The compounds of formula I-1 can then be obtained by reaction of the derivatives of formula VI-5 with ammonia in the presence of a palladium catalyst such as $Pd_2(dba)_3$, a ligand such as tBuDavePhos and a base such as tBuONa in a solvent such as dioxane between 60 and 100° C. (further variations of this reaction are described in *Angew. Chem. Int. Ed.* (2011), 50, 86-95).

Compounds of Formula I-2:

The compounds of formula I-2 can be prepared as summarised in Scheme 7 hereafter.

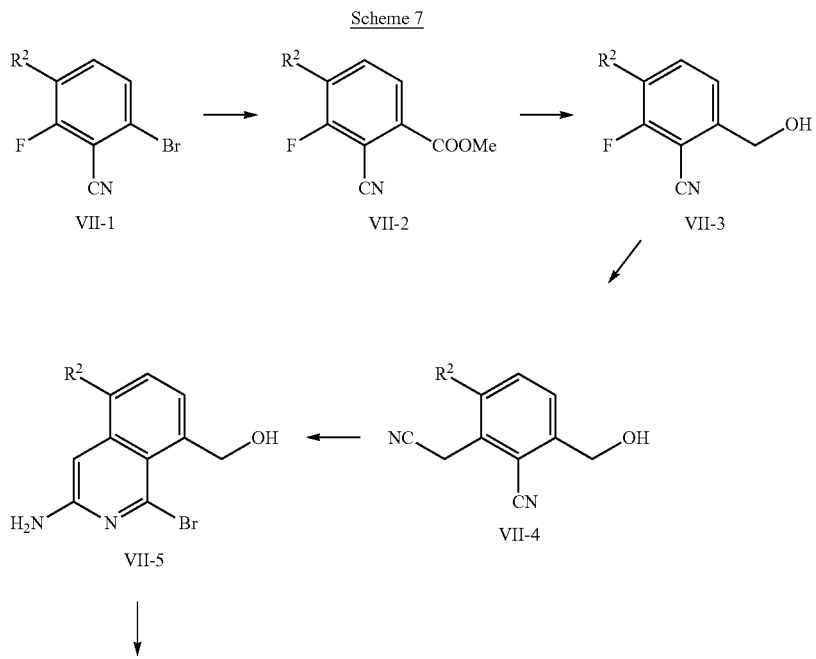

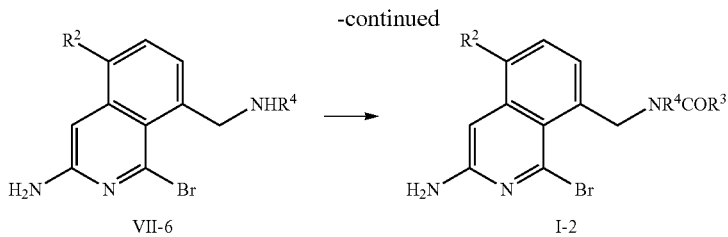

In Scheme 7, $R^2$, $R^3$ and $R^4$ are as defined in formula I.

The compounds of formula VII-1 can be reacted (Scheme 7) with MeOH using general reaction technique 11, affording the esters of formula VII-2 which can be reduced into the alcohol derivatives of formula VII-3 using general reaction technique 12. These derivatives can then be transformed into the di-cyano derivatives of formula VII-4 by reaction with methyl or ethyl cyanomalonate followed by decarboxylation, and cyclised into the isoquinoline derivatives of formula VII-5 by reaction with HBr in $Cl_2CHCOOH$ as described in *Tetrahedron Lett.* (2007), 48, 487-489. The isoquinoline derivatives of formula VII-5 can be sequentially reacted with alkyl or arylsulfonyl chlorides using general reaction technique 7, followed either by reaction with sodium azide using general reaction technique 8 or by reaction with potassium phthalimide using general reaction technique 9, and subsequently deprotected using general reaction technique 10. Alternatively the compounds of formula VII-5 can be directly reacted with DPPA using general reaction technique 8 and the corresponding azides can be transformed in situ into the amines of formula VII-6 wherein $R^4$ is H using general reaction technique 10. The corresponding derivatives of formula VII-6 wherein $R^4$ is Me can be obtained by reacting the compounds of formula VII-5 with $SOCl_2$ using general reaction technique 7 followed by treatment with methylamine using general reaction technique 19. The amines of formula VII-6 can be further transformed into the derivatives of formula I-2 after reaction with the compounds of formula XIII, XVI or XVII using general reaction techniques 1, 3, 4 or 6. Alternatively, the amines of formula VII-6 can be reacted with the compounds of formula XIV, the resulting intermediates being further reacted with the compounds of formula XV using general reaction technique 5.

Compounds of Formula I-3:

The compounds of formula I-3 can be prepared as summarised in Scheme 8 hereafter.

Scheme 8

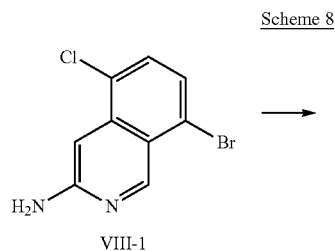

In Scheme 8, $R^2$ and $R^4$ are as defined in formula I.

The compound of formula VIII-1 can be reacted (Scheme 8) with MeOH using general reaction technique 11, affording the ester of formula VIII-2 which can be reduced using general reaction technique 12. The resulting alcohol of formula VIII-3 can be reacted with the corresponding boronic acid derivatives of formula IX using general reaction technique 2, affording the compounds of formula VIII-4 wherein $R^2$ is an aromatic or heteroaromatic group. The corresponding derivatives of formula VIII-4 wherein $R^2$ is H can be obtained by reducing the compound of formula VIII-3 by hydrogenation over a noble metal catalyst such as Pd/C. The alcohol derivatives of formula VIII-4 can be sequentially reacted with alkyl or arylsulfonyl chlorides using general reaction technique 7, followed either by reaction with sodium azide using general reaction technique 8 or by reaction with potassium phthalimide using general reaction technique 9, and subsequently deprotected using general reaction technique 10. Alternatively, the compounds of formula VIII-4 can be directly reacted with DPPA using general reaction technique 8 and the corresponding azides can be transformed in situ into the amines of formula I-3 wherein $R^4$ is H using general reaction technique 10. The corresponding derivatives of formula I-3 wherein $R^4$ is Me can be obtained by reacting the compounds of formula VIII-4 with $SOCl_2$ using general reaction technique 7 followed by treatment with methylamine using general reaction technique 19. The corresponding derivatives of formula I-3 wherein $R^2$ is Cl can be obtained by applying the same reaction sequences to the compound of formula VIII-3.

Besides, the compounds of formula VIII-4 can also be obtained as described in Scheme 9 hereafter.

Scheme 9

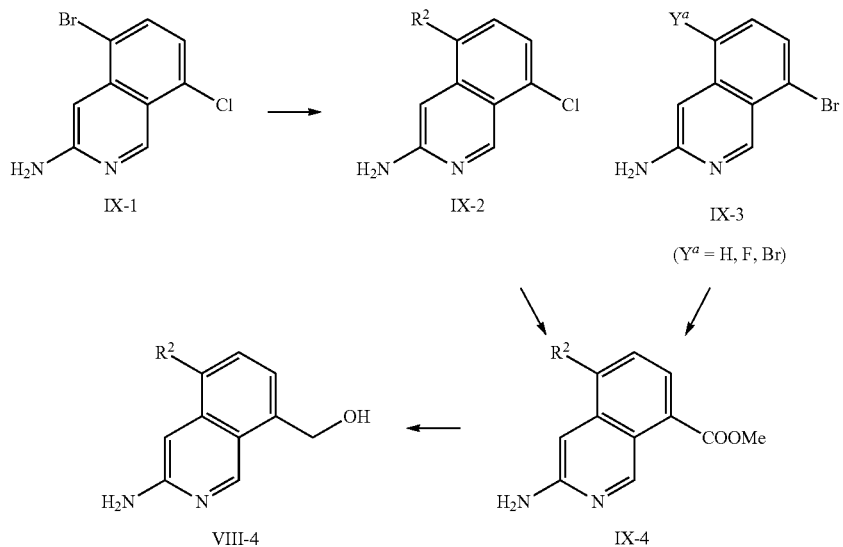

In Scheme 9, R² is as defined in formula I.

The compound of formula IX-1 can be reacted (Scheme 9) with the corresponding boronic acid derivatives of formula IX using general reaction technique 2, affording the compounds of formula IX-2 wherein R² is an aromatic or heteroaromatic group, which can be reacted with MeOH using general reaction technique 11, affording the esters of formula IX-4. The corresponding derivatives of formula IX-4 wherein R² is H, F or Br can be obtained by reacting the compound of formula IX-3 with MeOH using general reaction technique 11. Finally, the ester derivatives of formula IX-4 can be reduced into the compounds of formula VIII-4 using general reaction technique 12.

Compounds of Formula II-1:

The compounds of formula II-1 can be prepared as summarised in Scheme 10 hereafter.

mula IX using general reaction technique 2, affording the compounds of formula X-1 wherein R² is an aromatic or heteroaromatic group. The corresponding derivatives of formula X-1 wherein R² is H can be obtained by reducing the compounds of formula VI-1 by hydrogenation over a noble metal catalyst such as Pd/C. The resulting derivatives of formula X-1 can be transformed into the dihalo derivatives of formula X-2 using general reaction technique 7. Finally, the latter are transformed into the derivatives of formula II-1 wherein R⁴ is H by reaction with sodium azide using general reaction technique 8 and subsequent reaction with PPh₃ in presence of water using general reaction technique 10. The corresponding derivatives of formula II-1 wherein R⁴ is Me can be obtained by reacting the compound of formula X-2 with methylamine using general reaction technique 19.

Compounds of Formula II-2:

The compounds of formula II-2 can be prepared as summarised in Scheme 11 hereafter.

Scheme 10

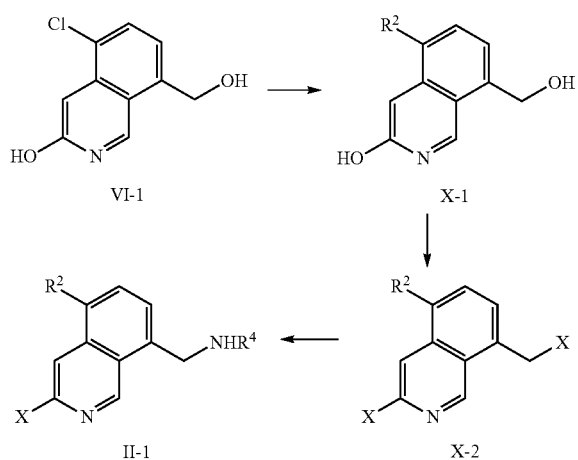

Scheme 11

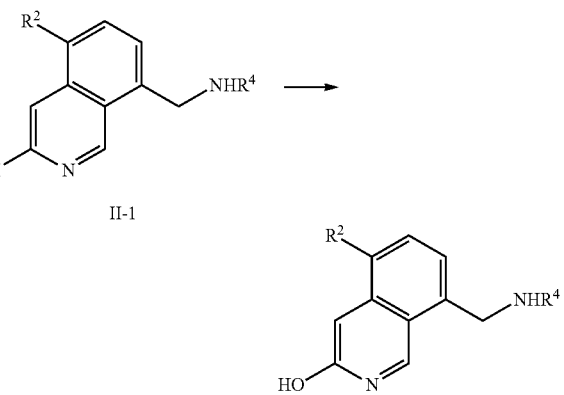

In Scheme 10, R² and R⁴ are as defined in formula I and X represents halogen such as chlorine or bromine.

The compound of formula VI-1 can be reacted (Scheme 10) with the corresponding boronic acid derivatives of for-

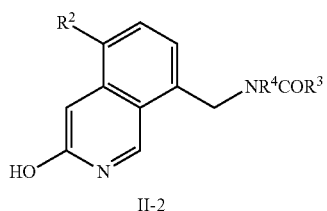

II-2

In Scheme 11, $R^2$, $R^3$ and $R^4$ are as defined in formula I and X represents halogen such as chlorine or bromine.

The compounds of formula II-1 can be converted (Scheme 11), in the presence of a base such as aq. NaOH, into the derivatives of formula XI-1. The amines of formula XI-1 can be further transformed into the corresponding derivatives of formula II-2 after reaction with the compounds of formula XIII, XVI or XVII using general reaction technique 1, 3, 4 or 6. Alternatively, the amines of formula XI-1 can be reacted with the compounds of formula XIV, the resulting intermediates being further reacted with the compounds of formula XV using general reaction technique 5.

Compounds of Formula III-1:

The compounds of formula III-1 can be prepared as summarised in Scheme 12 hereafter.

In Scheme 12, $R^1$ and $R^4$ are as defined in formula I.

The compound of formula VIII-1 can be reacted (Scheme 12) with the compounds of formula III or IIIa using general reaction technique 1 to yield the compounds of formula XII-1. Alternatively, the compounds of formula VIII-1 can be reacted with the compounds of formula IV, the resulting intermediates being then reacted with the compounds of formula V (see general reaction technique 1), thus affording the compounds of formula XII-1. The latter can be transformed into the corresponding ester derivatives of formula XII-2 using general reaction technique 11. The ester derivatives of formula XII-2 can then be reduced into the alcohol derivatives of formula XII-3 using general reaction technique 12. Alternatively, the sequence of reactions used to obtain the compounds of formula XII-3 can be inverted in such a way that the urea can be formed after the carbonylation-reduction sequence. Finally, the compounds of formula XII-3 can be sequentially reacted with alkyl or arylsulfonyl chlorides using general reaction technique 7, followed either by reaction with sodium azide using general reaction technique 8 or by reaction with potassium phthalimide using general reaction technique 9, and subsequently deprotected using general reaction technique 10. Alternatively, the compounds of formula XII-3 can be directly reacted with DPPA using general reaction technique 8 and the corresponding azides can be transformed in situ into the amines of formula III-1 wherein $R^4$ is H using general reaction technique 10. The corresponding derivatives of formula III-1 wherein $R^4$ is Me can be Scheme 12

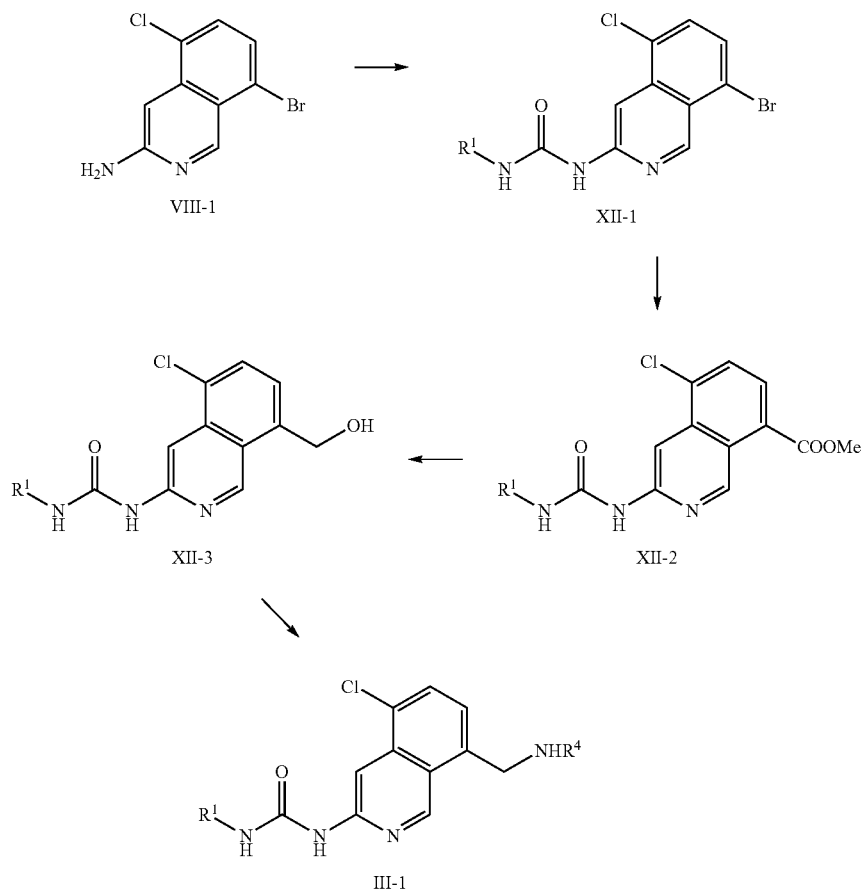

obtained by reacting the compounds of formula XII-3 with SOCl₂ using general reaction technique 7 followed by treatment with methylamine using general reaction technique 19.

Compounds of Formula V-1:

The compounds of formula V-1 can be prepared as summarised in Scheme 13 hereafter.

mula IX-4 can be reacted with the compounds of formula III or IIIa using general reaction technique 1 to yield the compounds of formula XIII-1. Alternatively, the compounds of formula IX-4 can be reacted with the compounds of formula IV, the resulting intermediates being then reacted with the compounds of formula V (see general reaction technique 1),

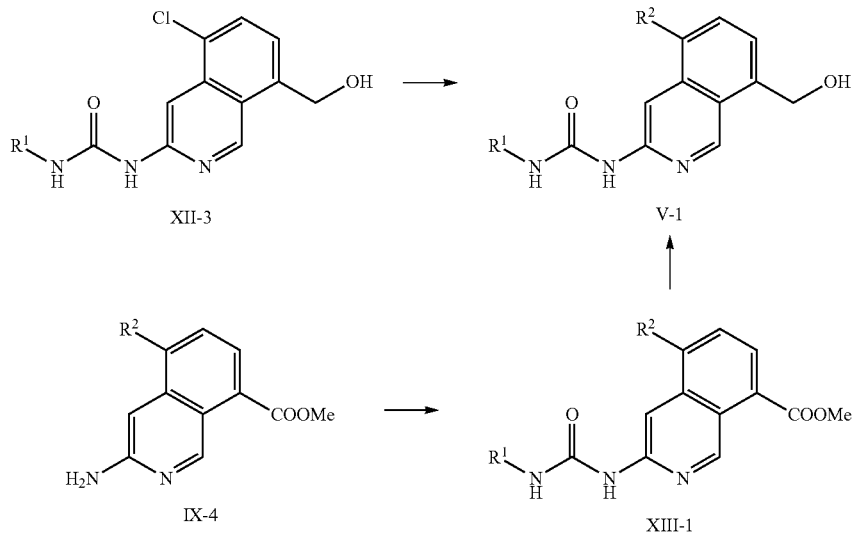

Scheme 13

In Scheme 13, $R^1$ and $R^2$ are as defined in formula I.

The compounds of formula XII-3 can be reacted (Scheme 13) with the corresponding boronic acid derivatives of formula IX using general reaction technique 2, affording the compounds of formula V-1 wherein $R^2$ is an aromatic or heteroaromatic group. The corresponding derivatives of formula V-1 wherein $R^2$ is H can be obtained by reducing the compounds of formula XII-3 by hydrogenation over a noble metal catalyst such as Pd/C. Besides, the compounds of for-thus affording the compounds of formula XIII-1. The ester derivatives of formula XIII-1 can finally be reduced into the alcohol derivatives of formula V-1 using general reaction technique 12.

Compound of Formula VI-1:

The compound of formula VI-1 can be prepared as summarised in Scheme 14 hereafter.

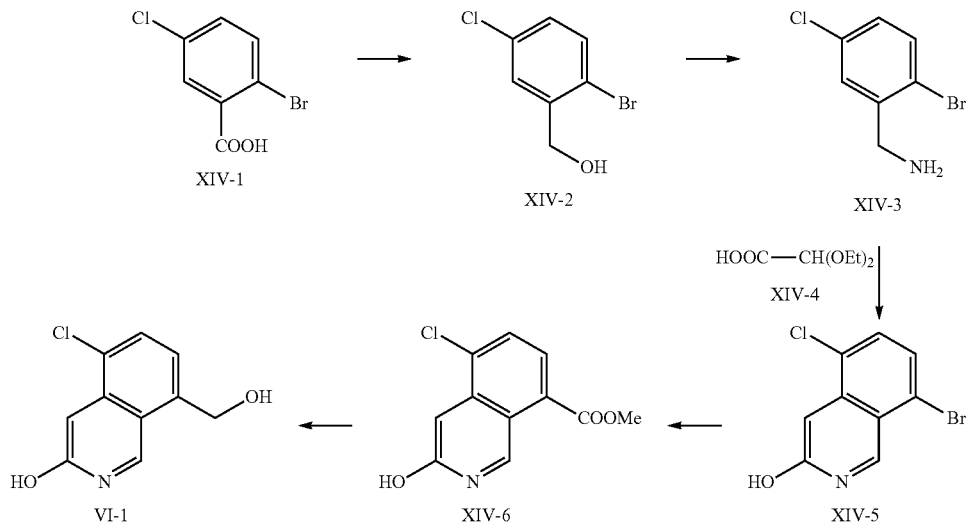

Scheme 14

The compound of formula XIV-1 (commercially available) can be reduced (Scheme 14) using BH$_3$ in a solvent such as THF between 0 and 60° C. The resulting benzylic alcohol of formula XIV-2 can be sequentially reacted with alkyl or arylsulfonyl chlorides using general reaction technique 7, followed either by reaction with sodium azide using general reaction technique 8 or by reaction with potassium phthalimide using general reaction technique 9, and subsequently deprotected using general reaction technique 10. Alternatively, the compound of formula XIV-2 can be directly reacted with DPPA using general reaction technique 8 and the corresponding azide can be transformed in situ into the amine of formula XIV-3 using general reaction technique 10. The latter amine can be converted into the isoquinoline derivative of formula XIV-5 by reaction with diethoxyacetic acid (XIV-4; commercially available or prepared according to WO 03/080578) followed by ring closure in the presence of conc. sulfuric acid as described in WO 03/080578. The compound of formula XIV-5 can be transformed into the ester derivative of formula XIV-6 using general reaction technique 11, which can finally be reduced into the alcohol derivative of formula VI-1 using general reaction technique 12.

Compounds of Formula VII-1:

The compounds of formula VII-1 can be prepared as summarised in Scheme 15 hereafter.

acid derivatives of formula IX using general reaction technique 2, affording the compounds of formula XV-2 wherein R$^2$ is an aromatic or heteroaromatic group. The corresponding derivatives of formula XV-2 wherein R$^2$ is H or Br are commercially available. The aniline derivatives of formula XV-2 can then be treated with a nitrite reagent such as isoamyl nitrite in the presence of CuBr$_2$, affording the derivatives of formula VII-1. The corresponding derivative of formula VII-1 wherein R$^2$ is Cl can be obtained by applying the same reaction to the aniline derivative of formula XV-1.

Compound of Formula VIII-1:

The compound of formula VIII-1 can be prepared as summarised in Scheme 16 hereafter.

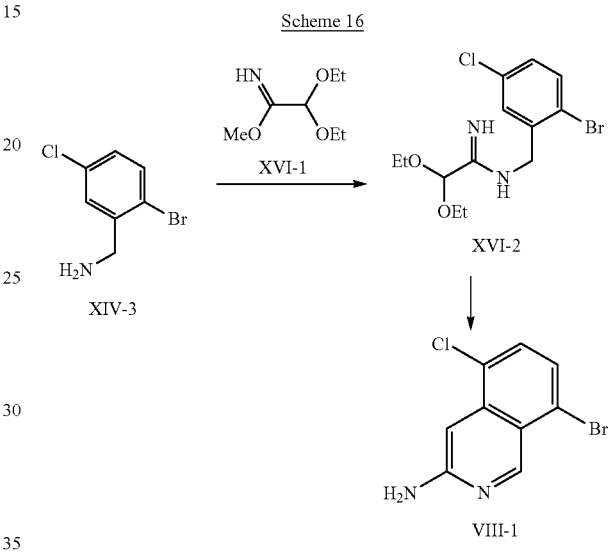

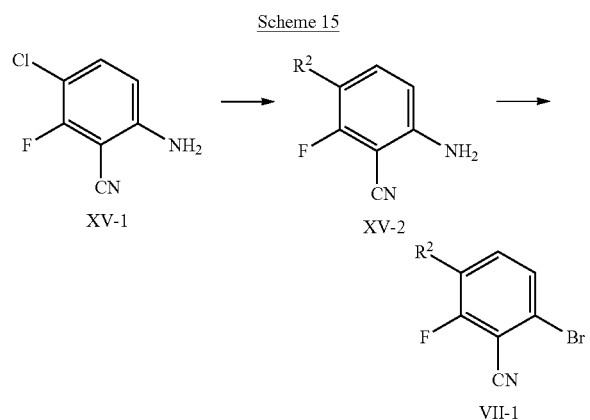

In Scheme 15, R$^2$ is as defined in formula I.

The compound of formula XV-1 (commercially available) can be reacted (Scheme 15) with the corresponding boronic The compound of formula XIV-3 can be reacted (Scheme 16) with 2,2-diethoxy-ethanimidic acid methyl ester (XVI-1; commercially available or prepared according to WO 2007/125405) according to general reaction technique 13, affording the intermediate of formula XVI-2. The latter can then be ring closed in conc. sulfuric acid using general reaction technique 14 to give the isoquinoline derivative of formula VIII-1.

Compounds of Formulae IX-1 and IX-3:

The compounds of formulae IX-1 and IX-3 can be prepared as summarised in Scheme 17 hereafter.

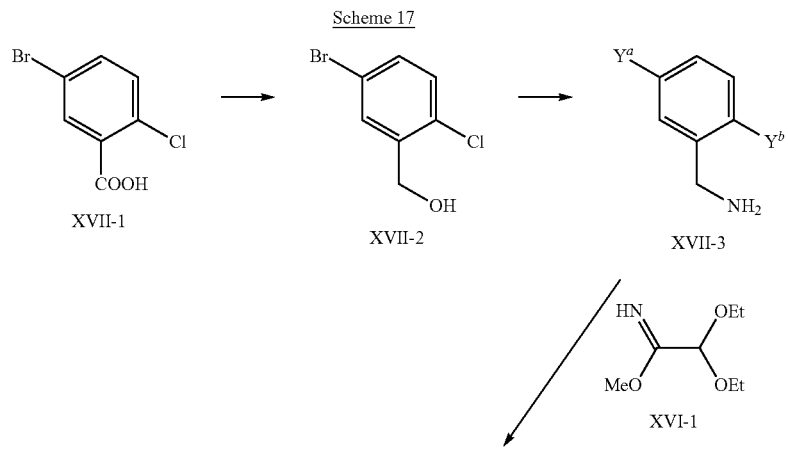

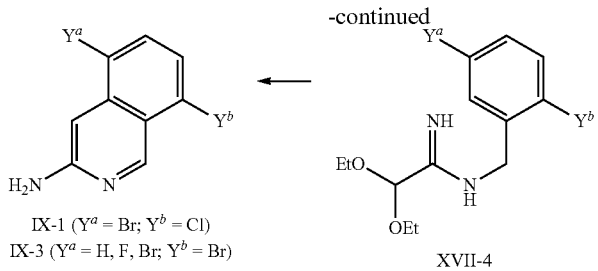

IX-1 (Y$^a$ = Br; Y$^b$ = Cl)
IX-3 (Y$^a$ = H, F, Br; Y$^b$ = Br)

XVII-4

The compound of formula XVII-1 (commercially available) can be reduced (Scheme 17) using BH$_3$ in a solvent such as THF between 0 and 60° C. The resulting benzylic alcohol of formula XVII-2 can be sequentially reacted with alkyl or arylsulfonyl chlorides using general reaction technique 7, followed either by reaction with sodium azide using general reaction technique 8 or by reaction with potassium phthalimide using general reaction technique 9, and subsequently deprotected using general reaction technique 10, affording the amine of formula XVII-3 wherein Y$^a$ is Br and Y$^b$ is Cl. Alternatively, the compound of formula XVII-2 can be directly reacted with DPPA using general reaction technique 8 and the corresponding azide can be transformed in situ into the amine of formula XVII-3 wherein Y$^a$ is Br and Y$^b$ is Cl using general reaction technique 10. The amines of formula XVII-3 wherein Y$^a$ is H, F or Br and Y$^b$ is Br are commercially available. The benzyl amine derivatives of formula XVII-3 can be reacted with 2,2-diethoxy-ethanimidic acid methyl ester (XVI-1; commercially available or prepared according to WO 2007/125405) using general reaction technique 13, affording the intermediates of formula XVII-4, which can finally be ring closed in conc. sulfuric acid using general reaction technique 14 to give the isoquinoline derivatives of formulae IX-1 and IX-3.

Particular embodiments of the invention are described in the following Examples, which serve to illustrate the invention in more detail without limiting its scope in any way.

EXAMPLES

All temperatures are stated in ° C. Unless otherwise indicated, the reactions take place at rt.

Analytical TLC characterisations were performed with 0.2 mm plates: Merck, Silica gel 60 F$_{254}$. Elution was performed with EA, Hept, DCM, MeOH or mixtures thereof. Detection was done with UV or with a solution of KMnO$_4$ (3 g), K$_2$CO$_3$ (20 g), 5% NaOH (3 mL) and H$_2$O (300 mL) with subsequent heating.

CCs were performed using Brunschwig 60A silica gel (0.032-0.63 mm), SNAP KP-Sil™ cartridges from Biotage or EasyVarioFlash® cartridges from Merck; elution was performed with EA, Hept, DCM, MeOH or mixtures thereof. In the cases of compounds containing a basic function (e.g. amine), 1% of NH$_4$OH (25% aq.) was added to the eluent(s).

Prep-HPLCs were performed on XBridge Prep C18 columns from Waters. The following conditions were used:
Eluents: A: H$_2$O+0.1% acidic or basic additive; B: MeCN +0.1% acidic or basic additive;
Gradient: 5% B→95% B over 5 min.
Detection: UV/Vis and/or MS and/or ELSD.
Prep-HPLC (acidic conditions): additive in A and B is 0.1% HCO$_2$H.
Prep-HPLC (basic conditions): additive in A and B is 0.1% NH$_4$OH.

The LC-MS data following the identifier "LC-MS(01)" or "LC-MS(02)" have been performed using the following respective conditions:
Conditions for LC-M (01) data:
Pump: Waters Acquity Binary, Solvent Manager; MS: Waters SQ Detector; DAD: Acquity UPLC PDA Detector; ELSD: Acquity UPLC ELSD.
Column: Acquity UPLC CSH C18 1.7 μm, 2.1×50 mm from Waters, thermostated in the Acquity UPLC Column Manager at 60° C.
Eluents: A: H$_2$O+0.02% TFA; B: MeCN +0.02% TFA. Gradient: 2% B→98% B over 2.0 min. Flow: 1.2 mL/min.
Detection: UV 214 nm, ELSD and MS; the retention time t$_R$ is given in min.
Conditions for LC-MS(02) data:
Pump: Waters Acquity Binary, Solvent Manager; MS: Waters SQ Detector; DAD: Acquity UPLC PDA Detector; ELSD: Acquity UPLC ELSD.
Column: Acquity UPLC CSH C18 1.7 μm, 2.1×50 mm from Waters, thermostated in the Acquity UPLC Column Manager at 60° C.
Eluents: A: H$_2$O+0.05% formic acid; B: MeCN +0.045% formic acid. Gradient: 2% B→98% B over 2.0 min. Flow: 1.2 mL/min.
Detection: UV 214 nm, ELSD and MS; the retention time t$_R$ is given in min.

The other LC-MS data were obtained on Sciex API 2000 with Agilent 1100 Binary Pump with DAD and ELSD; or Agilent quadrupole MS 6140 with Agilent 1200 Binary Pump, DAD and ELSD; or Thermo Finnigan MSQ Surveyor MS with Agilent 1100 Binary Pump, DAD and ELSD; or Thermo MSQ Plus with Dionex GHP 3200 Binary Pump, DAD and ELSD. The number of decimals given for the corresponding [M+H$^+$] peak(s) of each tested compound depends upon the accuracy of the LC-MS device actually used.

NMR spectra were recorded on a Varian Mercury 300 (300 MHz) spectrometer unless indicated otherwise ("400 MHz" being used to mean a Bruker Avance 400 (400 MHz) spectrometer). Chemical shifts are given in ppm relative to the solvent used; multiplicities: s=singlet, d=doublet, t=triplet, q=quadruplet, p=pentuplet, hex=hextet, hept=heptet, m=multiplet; br.=broad; coupling constants are given in Hz.

Detailed Synthetic Procedures

Procedure A (Addition of Benzyl Amine on Imidate Derivatives):

To the required benzyl amine derivative (10.0 mmol, 1.0 eq.), under inert atmosphere (N$_2$), are added dry MeOH (25.0 mL) and a solution of 2,2-diethoxy-ethanimidic acid methyl ester (1.2 eq.; prepared as described in WO 2007/125405) in dry MeOH (25.0 mL). The reaction mixture is stirred at rt and monitored by LC-MS. Upon reaction completion, the reaction mixture is concentrated under reduced pressure. The residue is dissolved in DCM and the org. layer is washed with water and brine, dried over Na$_2$SO$_4$, filtered and concentrated under reduced pressure. The crude product is used without further purification in the next step.

Procedure B (Isoquinoline Formation by Cyclisation):

To the crude product of Procedure A, at 0° C. under inert atmosphere (N$_2$), is added conc. H$_2$SO$_4$ (45 eq). The reaction mixture is stirred at 80° C. and monitored by LC-MS. Upon reaction completion, the reaction mixture is slowly poured into water at 0° C. The resulting acidic aq. solution is then treated with a 12N aq. NaOH solution at 0° C. until a pH of 12 is obtained. The resulting suspension is filtered and the cake washed with warm water, collected and dried. Purification of the residue gives the desired product.

Procedure C (Urea Formation in Dioxane):

To the required aminoisoquinoline derivative (1.0 mmol, 1.0 eq.), under inert atmosphere (N$_2$), are added dry dioxane (5.0 mL) and ethyl isocyanate (2.5 eq.). The reaction mixture is stirred at 50° C. and monitored by LC-MS. Upon reaction completion, the reaction mixture is cooled to 10° C. The precipitate is filtered, washed with a minimum amount of dioxane and dried to give the desired product.

Procedure D (Pd-Catalysed Ester Formation):

To the aromatic halide (1 mmol; 1.0 eq.), sodium acetate (1.2 eq.) and [1,1'-bis(diphenylphosphino)ferrocene]dichloropalladium(II) complex with DCM (0.05 eq.) in an autoclave is added MeOH (5 mL). The reaction mixture is stirred under a CO atmosphere (3 atm) at 60° C. and monitored by LC-MS. Upon reaction completion, MeOH is removed under reduced pressure, the residue is dissolved in EA (10 mL) and washed with water and brine, dried over Na$_2$SO$_4$ and concentrated under reduced pressure. Purification of the residue gives the desired product.

Procedure E (Ester Reduction with LiAlH$_4$):

A solution of the ester (1.0 mmol, 1.0 eq.) in anhydr. THF (25 mL) at 0° C. in a round-bottomed flask, under inert atmosphere (N$_2$), is treated with a 1M solution of LiAlH$_4$ (3.0 eq.) in THF at 0° C. Alternatively, the ester solution can be added dropwise to a suspension of LiAlH$_4$ (3.0 eq.) in THF at 0° C. The reaction mixture is stirred at 0° C. and monitored by LC-MS. Upon reaction completion, it is treated with a sat. aq. NH$_4$Cl solution and extracted with EA (3×). The combined org. layers are washed with brine, dried over MgSO$_4$, filtered and concentrated under reduced pressure. Purification of the residue gives the desired product.

Procedure F (One-Pot Conversion of Alcohol into Amine):

A suspension of the alcohol (1.0 mmol, 1.0 eq.) in anhydr. THF (5 mL) in a round-bottomed flask under inert atmosphere (N$_2$) at rt is treated with DPPA (1.2 eq.) and DBU (1.2 eq.). The reaction mixture is stirred at rt and monitored by LC-MS. Upon reaction completion, the reaction mixture is treated with water (0.5 mL) and PPh$_3$ (1.25 eq.) and heated to 60° C. It is stirred at 60° C. and monitored by LC-MS. Upon reaction completion, it cooled down to rt and concentrated under reduced pressure. Purification of the residue gives the desired product.

Procedure G (Amide Formation Using HATU):

To a solution of the amine (0.1 mmol, 1.0 eq.) in DMF (1.0 mL) in a round-bottomed flask, under inert atmosphere (N$_2$), are added DIPEA (2.0 eq.) and the required acid (1.25 eq.). The mixture is stirred at rt for 10 min and HATU (1.05 eq.) is added at once. The reaction mixture is stirred at rt and monitored by LC-MS. Upon reaction completion, the reaction mixture is concentrated under reduced pressure and the residue dissolved in DCM. The org. layer is washed with a sat. aq. NH$_4$Cl solution and brine, dried over MgSO$_4$, filtered and concentrated under reduced pressure. Purification of the residue gives the desired product.

Procedure H (Amide Formation Using HATU):

To a solution of the amine (0.1 mmol, 1.0 eq.) in DMF (1.0 mL) in a round-bottomed flask, under inert atmosphere (N$_2$), are added DIPEA (2.7 eq.) and the required acid (2.5 eq.). The mixture is stirred at rt for 10 min and HATU (1.05 eq.) is added at once. The reaction mixture is stirred at rt and monitored by LC-MS. Upon reaction completion, the reaction mixture is treated with PL-HCO$_3$ (214 mg; Polymer Laboratories; loading: 2.06 mmol/g; particle size: 150-300 µm; pore diameter: 100 Å). It is shaken 2 h at rt, filtered and concentrated under reduced pressure. Purification of the residue gives the desired product.

Procedure I (Reduction of Carboxylic Acid):

A solution of the acid (1.0 mmol; 1.0 eq.) in dry THF (4 mL), under inert atmosphere (N$_2$), is treated with a solution of borane-THF complex (1M in THF; 1.5 eq.) at 0° C. The reaction mixture is stirred at rt and monitored by LC-MS. Upon reaction completion, the reaction mixture is poured into an aq. 2N HCl solution at 0° C. It is further stirred at 0° C. for 1 h and THF is removed under reduced pressure. The obtained aq. layer is extracted with EA (3×) and the combined org. layers are washed with 1N NaOH, water and brine, dried over Na$_2$SO$_4$, filtered and concentrated under reduced pressure. Purification of the residue gives the desired product.

Procedure J (Mesylation):

A solution of the alcohol (1.0 mmol; 1.0 eq.) in dry THF (4 mL), under inert atmosphere (N$_2$), is treated with TEA (1.5 eq.) and a solution of methanesulfonic anhydride (1.5 eq.) in dry THF (1 mL) at 0° C. The reaction mixture is stirred at rt and monitored by LC-MS. Upon reaction completion, the reaction mixture is concentrated under reduced pressure and diluted with EA and water. The layers are separated and the aq. layer is extracted with EA. The combined org. layers are washed with water and brine, dried over Na$_2$SO$_4$, filtered and concentrated under reduced pressure. Purification of the residue gives the desired product.

Procedure K (Nucleophilic Substitution of Mesylate with Phthalimide):

A solution of the mesylate (1.0 mmol; 1.0 eq.) in dry DMF (5 mL), under inert atmosphere (N$_2$), is treated with phthalimide potassium salt (1.2 eq.) at rt. The reaction mixture is stirred at rt and monitored by LC-MS. Upon reaction completion, the reaction mixture is concentrated under reduced pressure and diluted with DCM and water. The layers are separated and the aq. layer is extracted with DCM. The combined org. layers are washed with water and brine, dried over Na$_2$SO$_4$, filtered and concentrated under reduced pressure. Purification of the residue gives the desired product.

Procedure L (Phthalimide Hydrolysis):

A solution of the phthalimide derivative (1.0 mmol; 1.0 eq.) in dry MeOH (5 mL) in a round-bottomed flask, under inert atmosphere (N$_2$), is treated with hydrazine monohydrate (2.0 eq.) at rt. The reaction mixture is stirred at 65° C. and monitored by LC-MS. Upon reaction completion, the reaction mixture is cooled to rt and treated with water. Then most of the MeOH is removed under reduced pressure. The resulting aq. suspension is acidified with 2N HCl, stirred at rt for 1 h and filtered. The aq. filtrate is washed twice with DCM, treated with 2N NaOH until pH 12 and extracted with DCM (3×). The combined org. layers are dried over Na$_2$SO$_4$, filtered and concentrated under reduced pressure. Purification of the residue gives the desired product.

Procedure M (Urea Formation in Pyridine):

To the required aminoisoquinoline derivative (1.0 mmol, 1.0 eq.), under inert atmosphere ($N_2$), are added dry pyridine (6.0 mL) and ethyl isocyanate (2.5 eq.). The reaction mixture is stirred at 50° C. and monitored by LC-MS. Upon reaction completion, pyridine is removed under reduced pressure and dioxane (6.0 mL) is added to the residue. The suspension is stirred at rt for 1 h and cooled to 10° C. The precipitate is filtered, washed with a minimum amount of dioxane and dried to give the desired product.

Procedure N (Suzuki Coupling with Tricyclohexylphosphine and SCX Treatment):

To the aromatic halide (1.0 mmol; 1.0 eq.), the required boronic acid (1.2 eq.), $Pd_2(dba)_3$ (0.1 eq.) and $PCy_3$ (0.2 eq.) in a glass vial, under inert atmosphere ($N_2$), are added dioxane (8.0 mL) and an aq. 1N $K_2CO_3$ solution (2.0 mL; 2.0 eq.). The reaction mixture is purged with $N_2$ for 5 min, stirred at 100° C. and monitored by LC-MS. Upon reaction completion, the reaction mixture is either treated with silica gel-supported sulfonic acid (5.0 eq.; Silicycle SiliaBond® Tosic Acid; SCX; R60530B; 0.8 mmol/g), shaken 1 h at rt and filtered, or loaded on a corresponding cartridge. In both cases, the resin is washed with DCM, 1:1 DCM/MeOH and MeOH, and the product is eventually released from the resin with a 7M ammonia solution in MeOH. The solution of crude product is concentrated under reduced pressure and purification of the residue gives the desired product.

Procedure O (Carbamate Formation Via Amine CDI-Activation):

A solution of the amine (0.1 mmol; 1.0 eq.) in dry NMP (0.5 mL), under inert atmosphere ($N_2$), is treated with CDI (1.05 eq.) at rt. The reaction mixture is stirred at rt overnight and treated with the required alcohol (2.0 eq.). The reaction mixture is stirred at 80° C. and monitored by LC-MS. Upon reaction completion, the reaction mixture is concentrated under reduced pressure. Purification of the residue gives the desired product.

Procedure P (Carbamate Formation Using Chloroformate):

A solution of the amine (0.1 mmol; 1.0 eq.) in dry DCM (1.0 mL), under inert atmosphere ($N_2$), is treated with TEA (1.2 eq.) and the required chloroformate (1.2 eq.) at 0° C. The reaction mixture is stirred at rt and monitored by LC-MS. Upon reaction completion, the reaction mixture is diluted with DCM and water. The layers are separated and the aq. layer is extracted with 9:1 DCM/MeOH (3×). The combined org. layers are washed with water and brine, dried over $MgSO_4$, filtered and concentrated under reduced pressure. Purification of the residue gives the desired product.

Procedure Q (Suzuki Coupling with Tricyclohexylphosphine and Scavenger Treatment):

To the aromatic halide (0.1 mmol; 1.0 eq.), the required boronic acid (1.2 eq.), $Pd_2(dba)_3$ (0.1 eq.) and $PCy_3$ (0.2 eq.) in a glass vial, under inert atmosphere ($N_2$), are added dioxane (0.8 mL) and an aq. 1N $K_2CO_3$ solution (0.2 mL; 2.0 eq.). The reaction mixture is purged with $N_2$ for 5 min, stirred at 100° C. and monitored by LC-MS. Upon reaction completion, the reaction mixture is diluted with DCM and a sat. aq. $NaHCO_3$ solution. The layers are separated and the aq. layer is extracted with 9:1 DCM/MeOH (3×). The combined org. layers are washed with a sat. aq. $NaHCO_3$ solution, water and brine, dried over $MgSO_4$, filtered and concentrated under reduced pressure. The residue is dissolved in 9:1 DCM/MeOH (2.0 mL) and treated with a 1:1 mixture (40 mg) of triamine ethyl sulfide amide silica (PhosphonicS STA3; loading: 0.8 mmol/g; particle size: 60-200 μm; pore diameter: 60 Å) and methyl thiourea ethylsulfide ethyl silica (PhosphonicS MTCf; loading: 0.6 mmol/g; particle size: 60-200 μm; pore diameter: 90 Å). The mixture is shaken at rt overnight and filtered. The scavengers are washed with 9:1 DCM/MeOH and the filtrate is concentrated under reduced pressure. Purification of the residue gives the desired product.

Procedure R (Chloride Formation Using Thionyl Chloride Neat):

To the alcohol (10 mmol; 1.0 eq.) is added thionyl chloride (25 mL; 35 eq.) at rt under inert atmosphere ($N_2$). The reaction mixture is stirred at rt and monitored by LC-MS. Upon reaction completion, the reaction mixture is concentrated under reduced pressure. Purification of the residue gives the desired product.

Procedure S (Nucleophilic Substitution of Chloride with an Amine):

To a solution of the chloride (0.1 mmol; 1.0 eq.) in dry DMF (1.0 mL), at rt under inert atmosphere ($N_2$), is a solution of added the required amine in THF (2.0 eq.). The reaction mixture is stirred at rt and monitored by LC-MS. Upon reaction completion, the reaction mixture is concentrated under reduced pressure. Purification of the residue gives the desired product.

Procedure T (Amide Formation Using HOAT):

To a solution of the amine (0.1 mmol; 1.0 eq.), the required acid (1.5 eq.) and HOAT (0.5 eq.) in dry 1:1 DMF/DCM (0.6 mL), under inert atmosphere ($N_2$), is added Si-DCC (2.0 eq.; SiliCycle; loading: 1.10 mmol/g). The reaction mixture is shaken at rt and monitored by LC-MS. Upon reaction completion, the reaction mixture is treated with $PL-HCO_3$ (107 mg; Polymer Laboratories; loading: 1.87 mmol/g; particle size: 150-300 μm; pore diameter: 100 Å) and PL-DETA (77 mg; Polymer Laboratories; loading: 2.6 mmol/g). It is shaken 4 h at rt, filtered, the resins are washed with DCM and MeOH and the mother liquor is concentrated under reduced pressure. Purification of the residue gives the desired product.

Procedure U (Amide Formation Using HATU):

To a solution of the acid (0.05 mmol; 1.0 eq.) and DIPEA (3.0 eq.) in DMF (0.5 mL), under inert atmosphere ($N_2$), are added the required amine (4.0 eq.) and HATU (1.05 eq.). The reaction mixture is stirred at rt and monitored by LC-MS. Upon reaction completion, the reaction mixture is concentrated under reduced pressure. Purification of the residue gives the desired product.

Procedure V (Tert-Butyl Ester Deprotection Using TFA):

To a solution of the ester (0.1 mmol; 1.0 eq.) in dry DCM (0.5 mL), under inert atmosphere ($N_2$), is added TFA (0.5 mL, 50 eq.). The reaction mixture is stirred at rt and monitored by LC-MS. Upon reaction completion, the reaction mixture is concentrated under reduced pressure. Purification of the residue gives the desired product.

Procedure W (Amide Formation Using T3P and SCX Treatment):

To a solution of the amine (0.1 mmol; 1.0 eq.), the required acid (1.25 eq.) and DIPEA (3.0 eq.) in dry DMF (1.0 mL), under inert atmosphere ($N_2$), is added dropwise a 50 wt % solution of T3P in EA (1.2 eq.). The reaction mixture is stirred at rt and monitored by LC-MS. Upon reaction completion, MeOH (1.3 mL) and acetic acid (2.6 mL) are added and the reaction mixture is either treated with silica gel-supported sulfonic acid (5.0 eq.; Silicycle SiliaBond® Tosic Acid; SCX; R60530B; 0.8 mmol/g), shaken 1 h at rt and filtered, or loaded on a corresponding cartridge. In both cases, the resin is washed with DCM, 1:1 DCM/MeOH and MeOH, and the product is eventually released from the resin with a 7M ammonia solution in MeOH. The solution of crude product is concentrated under reduced pressure and purification of the residue gives the desired product.

Procedure X (Boc Deprotection Using HCl in Dioxane):

To a solution of the protected amine (0.1 mmol, 1.0 eq.) in dry MeOH (1.0 mL), under inert atmosphere (N$_2$), is added dropwise a 4M solution of HCl in dioxane (20 eq.). The reaction mixture is stirred at rt and monitored by LC-MS. Upon reaction completion, the reaction mixture is concentrated under reduced pressure and purification of the residue gives the desired product.

Procedure Y (Carbamate Formation Via Alcohol CDI-Activation):

To a solution of CDI (2.0 eq.) in dry DCM (0.5 mL), under inert atmosphere (N$_2$), are added DIPEA (2.0 eq.) and the required alcohol (2.0 eq.). The reaction mixture is stirred at rt for 3 h and a solution of the amine (0.1 mmol; 1.0 eq.) and DIPEA (1.0 eq.) in dry NMP (0.5 mL) is added. The reaction mixture is stirred at rt and monitored by LC-MS. Upon reaction completion, a 2M solution of dimethylamine in THF (10 eq.) is added and the reaction mixture is stirred 2 h at rt. It is concentrated under reduced pressure and purification of the residue gives the desired product.

Procedure Z (Carbamate Formation Via Alcohol CDI-Activation and Resin Treatment):

To a solution of CDI (2.0 eq.) in dry DCM (0.5 mL), under inert atmosphere (N$_2$), are added DIPEA (2.0 eq.) and the required alcohol (2.1 eq.). The reaction mixture is stirred at rt for 3 h and a solution of the amine (0.1 mmol; 1.0 eq.) and DIPEA (1.0 eq.) in dry DMF (0.5 mL) is added. The reaction mixture is stirred at rt and monitored by LC-MS. Upon reaction completion, the reaction mixture is either treated with silica gel-supported sulfonic acid (5.0 eq.; Silicycle SiliaBond® Tosic Acid; SCX; R60530B; 0.8 mmol/g), shaken 1 h at rt and filtered, or loaded on a corresponding cartridge. In both cases, the resin is washed with DCM, 1:1 DCM/MeOH and MeOH, and the product eventually released from the resin with a 7M solution of ammonia in MeOH. The solution of crude product is concentrated under reduced pressure and purification of the residue gives the desired product.

Procedure AA (Carbamate Formation Via Alcohol CDI-Activation):

To a solution of CDI (2.0 eq.) in dry DCM (0.5 mL), under inert atmosphere (N$_2$), are added DIPEA (2.0 eq.) and the required alcohol (2.05 eq.). The reaction mixture is stirred at rt for 3 h and a solution of the amine (0.1 mmol; 1.0 eq.) and DIPEA (1.0 eq.) in dry DMF (0.5 mL) is added. The reaction mixture is stirred at rt and monitored by LC-MS. Upon reaction completion, the reaction mixture is treated with 1N NaOH (0.3 mL), stirred at rt for 1 h and diluted with DCM and water. The two layers are separated and the org. layer is washed with an aq. sat. solution of NH$_4$Cl, water and brine, dried over MgSO$_4$, filtered and concentrated under reduced pressure. Purification of the residue gives the desired product.

Procedure AB (Tert-Butyldimethylsilyl Deprotection):

To a stirred solution of protected alcohol (0.1 mmol; 1.0 eq.) in THF (1.0 mL) and water (0.1 mL) is added TFA (20 eq.) at 0° C. The reaction mixture is stirred at rt and monitored by LC-MS. Upon reaction completion, the reaction mixture is concentrated under reduced pressure, diluted in DCM and washed with an aq. sat. solution of NaHCO$_3$. The layers are separated and the aq. layer is extracted with 9:1 DCM/MeOH. The org. layers are combined and washed with brine, dried over MgSO$_4$, filtered and concentrated under reduced pressure. Purification of the residue gives the desired product.

Procedure AC (Preparation of Boronic Esters):

A mixture of PCy$_3$ (0.2 eq.) and Pd$_2$(dba)$_3$ (0.05 eq.) in dry dioxane (15 mL), under inert atmosphere (N$_2$), is stirred at rt for 30 min. The required aromatic halide (1 mmol; 1.0 eq.), bis(pinacolato)diboron (1.5 eq.) and potassium acetate (2.0 eq.) are added. The reaction mixture is purged with N$_2$ for 5 min, stirred at 90° C. and monitored by LC-MS. Upon reaction completion, the reaction mixture is concentrated under reduced pressure. Purification of the residue gives the desired product.

Procedure AD (Suzuki Coupling with Pd(PPh$_3$)$_4$):

To the aromatic boronic ester (0.1 mmol; 1.0 eq.), the required bromide (2.0 eq.) and Pd(PPh$_3$)$_4$ (0.05 eq.) in a glass vial, under inert atmosphere (N$_2$), are added dry dioxane (1.5 mL) and an aq. 1N K$_2$CO$_3$ solution (0.2 mL; 2.0 eq.). The reaction mixture is purged with N$_2$ for 5 min, stirred at 90° C. and monitored by LC-MS. Upon reaction completion, the reaction mixture is either treated with silica gel-supported sulfonic acid (5.0 eq.; Silicycle SiliaBond® Tosic Acid; SCX; R60530B; 0.8 mmol/g), shaken 1 h at rt and filtered, or loaded on a corresponding cartridge. In both cases, the resin is washed with DCM, 1:1 DCM/MeOH and MeOH, and the product eventually released from the resin with a 7M solution of ammonia in MeOH. The solution of crude product is concentrated under reduced pressure and purification of the residue gives the desired product.

Procedure AE (Chloride Formation Using Thionyl Chloride in DCM):

To a solution of the alcohol (10 mmol; 1.0 eq.) in DCM (50 mL) is added thionyl chloride (12 mmol; 1.2 eq.) at 0° C. under inert atmosphere (N$_2$). The reaction mixture is stirred at rt and monitored by LC-MS. Upon reaction completion, sat. NaHCO$_3$ aq. is added, the layers separated and the org. layer washed with brine, dried over MgSO$_4$, filtered and concentrated under reduced pressure. Purification of the residue gives the desired product.

Procedure AF (Boc Deprotection with TFA):

To a solution of the protected amine (0.1 mmol; 1.0 eq.) in dry DCM (1.0 mL) is added TFA (40 eq.). The reaction mixture is stirred at rt and monitored by LC-MS. Upon complete reaction, the reaction mixture is either directly concentrated under reduced pressure, or loaded first on a cartridge containing silica gel-supported sulfonic acid (5.0 eq.; Silicycle SiliaBond® Tosic Acid; SCX; R60530B; 0.8 mmol/g). In the latter case, the resin is washed with DCM, 1:1 DCM/MeOH and MeOH, and the product eventually released from the resin with a 7M solution of ammonia in MeOH. The solution of crude product is concentrated under reduced pressure. Purification of the residue gives the desired product.

Procedure AG (Vinylation):

To a mixture of the aromatic bromide (1 mmol, 1.0 eq.), vinylboronic anhydride pyridine complex (0.7 eq) and Pd(PPh$_3$)$_4$ (0.15 eq.), under inert atmosphere (N$_2$), are added dry dioxane (7.0 mL) and an aq. 1N K$_2$CO$_3$ solution (3.0 eq.). The reaction mixture is purged with N$_2$ for 5 min, stirred at 90° C. and monitored by LC-MS. Upon reaction completion, the reaction mixture is diluted with DCM and a sat. aq. NaHCO$_3$ solution. The layers are separated and the aq. layer is extracted with 9:1 DCM/MeOH (3×). The combined org. layers are washed with a sat. aq. NaHCO$_3$ solution, water and brine, dried over MgSO$_4$, filtered and concentrated under reduced pressure. Purification of the residue gives the desired product.

Procedure AH (Diol Formation):

A solution of the required vinyl derivative (1 mmol, 1.0 eq.), 4-methylmorpholine N-oxide (1.7 eq.) and potassium osmate(VI) dihydrate (0.005 eq.) in acetone (8.0 mL), under inert atmosphere (N$_2$) is vigorously stirred at rt and monitored by LC-MS. Upon reaction completion, the reaction mixture is concentrated under reduced pressure. The residue is taken in water and extracted with 9:1 DCM/MeOH (3×). The combined org. layers are dried over Na₂SO₄ and concentrated under reduced pressure. Purification of the residue gives the desired product.

Procedure AI (Aldehyde Formation):

To a solution of the diol (1 mmol, 1.0 eq.) in acetone (10 mL) and water (5 mL) is added sodium periodate (2.0 eq.). The reaction mixture is stirred at rt and monitored by LC-MS. Upon reaction completion, the reaction mixture is concentrated under reduced pressure. Purification of the residue gives the desired product.

Procedure AJ (Suzuki Coupling with Tricyclohexylphosphine):

To the aromatic halide (1.0 mmol; 1.0 eq.), the required boronic acid (1.5 eq.), Pd₂(dba)₃ (0.05 eq.) and PCy₃ (0.12 eq.) in a glass vial, under inert atmosphere (N₂), are added degassed dioxane (3.3 mL) and a degassed aq. 1N K₃PO₄ solution (1.7 mL; 1.7 eq.) at rt. The reaction mixture is stirred at 90° C. and monitored by LC-MS. Upon reaction completion, the reaction mixture is either directly concentrated to give the crude product, or diluted with 9:1 DCM/MeOH and a sat. aq. NaHCO₃ solution. The layers are separated and the aq. layer is extracted with 9:1 DCM/MeOH (3×). The combined org. layers are washed with a sat. aq. NaHCO₃ solution, water and brine, dried over MgSO₄, filtered and concentrated under reduced pressure. In both cases, the purification of the residue gives the desired product.

Procedure AK (Amide Formation Using T3P):

To a solution of the amine (0.1 mmol; 1.0 eq.), the required acid (1.5 eq.) and DIPEA (3.0 eq.) in dry DMF (0.5 mL), under inert atmosphere (N₂), is added dropwise a 50 wt % solution of T3P in EA (1.2 eq.). The reaction mixture is stirred at rt and monitored by LC-MS. Upon reaction completion, the reaction mixture is concentrated under reduced pressure and purification of the residue gives the desired product.

Procedure AL (Suzuki Coupling with Tricyclohexylphosphine and SCX Treatment):

To the aromatic halide (0.1 mmol; 1.0 eq.), the required boronic acid (1.65 eq.), Pd₂(dba)₃ (0.10 eq.) and PCy₃ (0.24 eq.) in a glass vial, under inert atmosphere (N₂), are added degassed dioxane (0.8 mL) and a degassed aq. 1N K₃PO₄ solution (0.25 mL; 2.5 eq.) at rt. The reaction mixture is stirred at 90° C. and monitored by LC-MS. Upon reaction completion, the reaction mixture is concentrated under reduced pressure, the residue diluted in 1:1:1 DCM/MeOH/NMP and either treated with silica gel-supported sulfonic acid (5.0 eq.; Silicycle SiliaBond® Tosic Acid; SCX; R60530B; 0.8 mmol/g), shaken 1 h at rt and filtered, or loaded on a corresponding cartridge. In both cases, the resin is washed with DCM, 1:1 DCM/MeOH and MeOH and the product is eventually released from the resin with a 7M ammonia solution in MeOH. The solution of crude product is concentrated under reduced pressure and purification of the residue gives the desired product.

Procedure AM (Suzuki Coupling with Tricyclohexylphosphine and SCX Treatment):

To Pd₂(dba)₃ (0.05 eq.) and PCy₃ (0.12 eq.) in a glass vial, under inert atmosphere (N₂), is added degassed dioxane (0.6 mL) at rt. The mixture is stirred at 90° C. for 5 min. To the aromatic boronic ester (0.1 mmol; 1.0 eq.) and the required aromatic halide (2.0 eq.) in a glass vial, under inert atmosphere (N₂), are added the solution of catalyst prepared above and a degassed aq. 1N K₃PO₄ solution (0.15 mL; 1.5 eq.). The reaction mixture is stirred at 90° C. and monitored by LC-MS. Upon reaction completion, the reaction mixture is either treated with silica gel-supported sulfonic acid (5.0 eq.; Silicycle SiliaBond® Tosic Acid; SCX; R60530B; 0.8 mmol/g), shaken 1 h at rt and filtered, or loaded on a corresponding cartridge. In both cases, the resin is washed with DCM, 1:1 DCM/MeOH and MeOH and the product is eventually released from the resin with a 7M ammonia solution in MeOH. The solution of crude product is concentrated under reduced pressure and purification of the residue gives the desired product.

Procedure AN (Suzuki Coupling with Tricyclohexylphosphine):

To the aromatic boronic ester (1.0 mmol; 1.0 eq.), the required aromatic halide (1.5 eq.), Pd₂(dba)₃ (0.05 eq.) and PCy₃ (0.12 eq.) in a glass vial, under inert atmosphere (N₂), are added degassed dioxane (3.3 mL) and a degassed aq. 1N K₃PO₄ solution (1.7 mL; 1.7 eq.) at rt. The reaction mixture is stirred at 90° C. and monitored by LC-MS. Upon reaction completion, the reaction mixture is either directly concentrated to give the crude product, or diluted with 9:1 DCM/MeOH and a sat. aq. NaHCO₃ solution. The layers are separated and the aq. layer is extracted with 9:1 DCM/MeOH (3×). The combined org. layers are washed with a sat. aq. NaHCO₃ solution, water and brine, dried over MgSO₄, filtered and concentrated under reduced pressure. In both cases, the purification of the residue gives the desired product.

Procedure AO (Amide Formation Using T3P):

To a solution of the carboxylic acid (0.1 mmol; 1.0 eq.), the required amine (3.0 eq.) and DIPEA (3.0 eq.) in dry DMF (1.0 mL), under inert atmosphere (N₂), is added dropwise a 50 wt % solution of T3P in EA (3.0 eq.). The reaction mixture is stirred at rt and monitored by LC-MS. Upon reaction completion, the reaction mixture is concentrated under reduced pressure and purification of the residue gives the desired product.

Preparation of Synthetic Intermediates

Preparation A:
1-[8-(aminomethyl)isoquinolin-3-yl]-3-ethyl-urea

A.1. N-(2-bromo-benzyl)-2,2-diethoxy-acetamidine

Starting from 2-bromobenzylamine (20.00 g; commercial) and 2,2-diethoxy-ethanimidic acid methyl ester (24.46 g; 85% pure) and proceeding in analogy to Procedure A, the title compound was obtained as a yellow oil (39.31 g).

MS (ESI, m/z): 315.2 and 317.2 [M+H⁺ of the two main isotopes].

A.2. 8-bromo-isoquinolin-3-yl-amine

Starting from intermediate A.1 (39.31 g) and proceeding in analogy to Procedure B, the title compound was obtained, without additional purification, as a yellow solid (19.66 g; 82% yield over 2 steps).

¹H NMR (d6-DMSO) δ: 8.92 (s, 1H); 7.53 (d, J=8.3 Hz, 1H); 7.41-7.37 (m, 1H); 7.33-7.26 (m, 1H); 6.61 (s, 1H); 6.18 (br. s, 2H).

MS (ESI, m/z): 223.2 and 225.2 [M+H⁺ of the two main isotopes].

A.3. 1-(8-bromo-isoquinolin-3-yl)-3-ethyl-urea

Starting from intermediate A.2 (17.18 g) and ethyl isocyanate (15.99 mL) and proceeding in analogy to Procedure C, a first batch of product was obtained (15.0 g). The mother liquors were concentrated under reduced pressure and the precipitate that appeared was filtered to give a second batch of product (3.30 g). The title compound was obtained, after combining the two batches, as a yellow solid (18.30 g; 81% yield).

¹H NMR (d6-DMSO) δ: 9.19 (s, 1H); 9.14 (m, 1H); 8.09 (s, 1H); 7.81 (d, J=8.4 Hz, 1H); 7.69 (dd, J=7.4, 0.9 Hz, 1H); 7.51 (dd, J=8.4, 7.4 Hz, 1H); 6.94 (t, J=5.4 Hz, 1H); 3.22-3.11 (m, 2H); 1.08 (t, J=7.2 Hz, 3H).
MS (ESI, m/z): 294.2 and 296.2 [M+H⁺ of the two main isotopes].

A.4. Methyl 3-(3-ethyl-ureido)-isoquinoline-8-carboxylate

Starting from intermediate A.3 (10.30 g), and proceeding in analogy to Procedure D, the title compound was obtained, after purification by CC (Hept/EA 50:50 to 0:100), as a brown solid (8.40 g; 87% yield).
¹H NMR (d6-DMSO) δ: 9.78 (s, 1H); 9.18 (s, 1H); 8.14 (s, 1H); 8.08-7.96 (m, 2H); 7.76-7.67 (m, 1H); 7.01 (t, J=5.2 Hz, 1H); 3.96 (s, 3H); 3.24-3.12 (m, 2H); 1.10 (t, J=7.2 Hz, 3H).

A. 5. 1-ethyl-3-(8-hydroxymethyl-isoquinolin-3-yl)-urea

Starting from intermediate A.4 (8.47 g), and proceeding in analogy to Procedure E, the title compound was obtained, after trituration of the residue in THF, as a pale yellow solid (6.2 g; 81% yield).
¹H NMR (d6-DMSO) δ: 9.23 (s, 1H); 9.05 (s, 1H); 8.00 (s, 1H); 7.69-7.64 (m, 1H); 7.61-7.55 (m, 1H); 7.42-7.38 (m, 1H); 7.13 (t, J=5.2 Hz, 1H); 5.39 (t, J=5.5 Hz, 1H); 5.00 (d, J=5.5 Hz, 2H); 3.24-3.15 (m, 2H); 1.11 (t, J=7.2 Hz, 3H).
MS (ESI, m/z): 246.3 [M+H⁺].

A.6. 1-[8-(aminomethyl)isoquinolin-3-yl]-3-ethyl-urea

Starting from intermediate A.5 (1.96 g), and proceeding in analogy to Procedure F, the title compound was obtained, after purification by CC (DCM/MeOH +1% NH₄OH 100:0 to 96:4), as a white solid (995 mg; 51% yield).
¹H NMR (d6-DMSO) δ: 9.25 (s, 1H); 9.00 (s, 1H); 7.95 (d, J=0.5 Hz, 1H); 7.63-7.57 (m, 1H); 7.57-7.50 (m, 1H); 7.38 (dd, J=6.7, 1.2 Hz, 1H); 7.13 (t, J=5.4 Hz, 1H); 4.21 (s, 2H); 3.21-3.11 (m, 2H); 1.88 (br. s, 2H); 1.08 (t, J=7.2 Hz, 3H).
MS (ESI, m/z): 245.2 [M+H⁺].

Preparation B: 1-[8-(aminomethyl)-5-chloro-isoquinolin-3-yl]-3-ethyl-urea

B.1. (2-bromo-5-chloro-phenyl)-methanol

Starting from 2-bromo-5-chlorobenzoic acid (158.0 g; commercial) and proceeding in analogy to Procedure I, the title compound was obtained, without additional purification, as a white solid (146.0 g; 98% yield).
¹H NMR (d6-DMSO) δ: 7.58 (d, J=8.5 Hz, 1H); 7.52-7.49 (d, J=2.8 Hz, 1H); 7.26 (dd, J=8.5, 2.8 Hz, 1H); 5.56 (t, J=5.7 Hz, 1H); 4.47 (d, J=5.7 Hz, 2H).

B.2. 2-bromo-5-chlorobenzyl methanesulfonate

Starting from intermediate B.1 (145.95 g) and proceeding in analogy to Procedure J, the title compound was obtained, without additional purification, as a white solid (193.0 g; 98% yield).
¹H NMR (d6-DMSO) δ: 7.72 (d, J=8.5 Hz, 1H); 7.67 (d, J=2.6 Hz, 1H); 7.44 (dd, J=8.5, 2.6 Hz, 1H); 5.27 (s, 2H); 3.29 (s, 3H).

B.3. 2-(2-bromo-5-chloro-benzyl)-isoindole-1,3-dione

Starting from intermediate B.2 (192.93 g) and proceeding in analogy to Procedure K, the title compound was obtained, without additional purification, as a white solid (220.0 g; 97% yield).
¹H NMR (d6-DMSO) δ: 7.93-7.80 (m, 4H); 7.67 (d, J=8.5 Hz, 1H); 7.38 (d, J=2.5 Hz, 1H); 7.31 (dd, J=8.5, 2.5 Hz, 1H); 4.76 (s, 2H).

B. 4. 2-bromo-5-chloro-benzylamine

Starting from intermediate B.3 (219.83 g) and proceeding in analogy to Procedure L, the title compound was obtained, without additional purification, as a yellow oil (84.10 g; 61% yield).
¹H NMR (d6-DMSO) δ: 7.60 (d, J=2.7 Hz, 1H); 7.55 (d, J=8.4 Hz, 1H); 7.21 (dd, J=8.4, 2.7 Hz, 1H); 3.70 (s, 2H); 1.96 (br. s, 2H).

B.5. N-(2-bromo-5-chloro-benzyl)-2,2-diethoxy-acetamidine

Starting from intermediate B.4 (84.01 g) and 2,2-diethoxy-ethanimidic acid methyl ester (88.12 g; 75% pure) and proceeding in analogy to Procedure A, the title compound was obtained as a yellow oil (129.10 g; 97% yield).
MS (ESI, m/z): 348.7 and 350.8 [M+H⁺ of the two main isotopes].

B.6. 8-bromo-5-chloro-isoquinolin-3-ylamine

Starting from intermediate B.5 (114.69 g) and proceeding in analogy to Procedure B, the title compound was obtained, without additional purification, as a brown solid (75.0 g; 88% yield).
¹H NMR (d6-DMSO) δ: 8.97 (s, 1H); 7.52 (d, J=7.9 Hz, 1H); 7.37 (d, J=7.9 Hz, 1H); 6.82 (s, 1H); 6.57 (s, 2H).
MS (ESI, m/z): 256.9 and 259.0 [M+H⁺ of the two main isotopes].

B.7. 1-(8-bromo-5-chloro-isoquinolin-3-yl)-3-ethyl-urea

Starting from intermediate B.6 (39.9 g) and proceeding in analogy to Procedure M, the title compound was obtained, without additional purification, as a yellow solid (40.5 g; 80% yield).
¹H NMR (d6-DMSO) δ: 9.38 (s, 1H); 9.18 (s, 1H); 8.42 (s, 1H); 7.70 (q, J=8.0 Hz, 2H); 6.92 (t, J=5.5 Hz, 1H); 3.22-3.12 (m, 2H); 1.08 (t, J=7.2 Hz, 3H).
MS (ESI, m/z): 328.1 and 330.2 [M+H⁺ of the two main isotopes].

B.8. 5-chloro-3-(3-ethyl-ureido)-isoquinoline-8-carboxylic acid methyl ester Starting from intermediate B.7 (9.99 g) and proceeding in analogy to Procedure D, the title compound was obtained, after trituration of the residue in MeOH, as a yellow solid (5.93 g; 63% yield).
¹H NMR (d6-DMSO) δ: 9.80 (d, J=0.9 Hz, 1H); 9.32 (s, 1H); 8.48 (d, J=0.9 Hz, 1H); 7.92 (s, 2H); 6.94 (t, J=5.5 Hz, 1H); 3.94 (s, 3H); 3.23-3.12 (m, 2H); 1.08 (t, J=7.2 Hz, 3H).
MS (ESI, m/z): 308.0 [M+H⁺].

B.9. 1-(5-chloro-8-hydroxymethyl-isoquinolin-3-yl)-3-ethyl-urea

Starting from intermediate B.8 (4.0 g), and proceeding in analogy to Procedure E, the title compound was obtained, after quenching the reaction mixture with THF followed by THF wash of the solid and concentration of the mother liquor under reduced pressure, as a pale yellow solid (2.59 g; 71% yield).

$^1$H NMR (d6-DMSO) δ: 9.25 (s, 1H); 9.21 (s, 1H); 8.36 (s, 1H); 7.76 (d, J=7.7 Hz, 1H); 7.36 (d, J=7.5 Hz, 1H); 7.00 (t, J=4.8 Hz, 1H); 5.45 (t, J=5.2 Hz, 1H); 4.98 (d, J=5.2 Hz, 2H); 3.23-3.11 (m, 2H); 1.08 (t, J=7.2 Hz, 3H).

MS (ESI, m/z): 280.1 [M+H$^+$].

B.10. 1-[8-(aminomethyl)-5-chloro-isoquinolin-3-yl]-3-ethyl-urea

Starting from intermediate B.9 (2.26 g), and proceeding in analogy to Procedure F, the title compound was obtained, after purification by CC (DCM/MeOH +1% NH$_4$OH 100:0 to 90:10), as a yellow solid (1.63 g; 70% yield).

$^1$H NMR (d6-DMSO) δ: 9.30 (d, J=0.8 Hz, 1H); 9.18 (s, 1H); 8.33 (d, J=0.7 Hz, 1H); 7.73 (d, J=7.7 Hz, 1H); 7.37 (d, J=7.7 Hz, 1H); 7.03 (t, J=5.6 Hz, 1H); 4.20 (s, 2H); 3.22-3.12 (m, 2H); 1.92 (br. s, 2H); 1.08 (t, J=7.2 Hz, 3H).

MS (ESI, m/z): 279.0 [M+H$^+$].

Preparation C: 1-[8-(aminomethyl)-5-(pyridin-4-yl)-isoquinolin-3-yl]-3-ethyl-urea Starting from the compound of Preparation B (603 mg) and pyridine-4-boronic acid, and proceeding in analogy to Procedure N, the title compound was obtained, after purification by CC (DCM/MeOH +1% NH$_4$OH 100:0 to 90:10), as a yellow solid (530 mg; 72% yield).

$^1$H NMR (d6-DMSO) δ: 9.34 (d, J=0.8 Hz, 1H); 9.01 (s, 1H); 8.72-8.68 (m, 2H); 8.05 (d, J=0.7 Hz, 1H); 7.57-7.53 (m, 1H); 7.51-7.46 (m, 3H); 7.09 (t, J=5.5 Hz, 1H); 4.27 (s, 2H); 3.16-3.05 (m, 2H); 1.96 (br. s, 2H); 1.04 (t, J=7.2 Hz, 3H).

MS (ESI, m/z): 322.1 [M+H$^+$].

Preparation D: 1-[(8-aminomethyl)-5-fluoroisoquinolin-3-yl]-3-ethylurea

D.1. N-(2-bromo-5-fluoro-benzyl)-2,2-diethoxy-acetamidine

Starting from 2-bromo-5-fluorobenzylamine (5.30 g) and proceeding in analogy to Procedure A, the title compound was obtained as an orange oil (14.65 g).

MS (ESI, m/z): 333.2 and 335.1 [M+H$^+$ of the two main isotopes].

D.2. 8-bromo-5-fluoro-isoquinolin-3-ylamine

Starting from intermediate D.1 (14.65 g) and proceeding in analogy to Procedure B, however using 35 eq. of conc. H$_2$SO$_4$, performing the reaction at rt and doing an extraction with 9:1 DCM-MeOH after NaOH treatment, the title compound was obtained, after purification by CC (Hept/EA 100:0 to 30:70), as a yellow solid (3.62 g; 58% yield over 2 steps).

$^1$H NMR (d6-DMSO) δ: 8.95-8.92 (m, 1H); 7.34 (dd, J=8.2, 4.7 Hz, 1H); 7.21 (dd, J=10.8, 8.2 Hz, 1H); 6.67 (d, J=0.6 Hz, 1H); 6.47 (br. s, 2H).

MS (ESI, m/z): 241.3 and 243.2 [M+H$^+$ of the two main isotopes].

D.3. 1-(8-Bromo-5-fluoro-isoquinolin-3-yl)-3-ethyl-urea

Starting from intermediate D.2 (2.0 g) and proceeding in analogy to Procedure C, however adding more ethyl isocyanate (2.0 eq.) after 24 h and 48 h, the title compound was obtained, as a white solid (1.39 g; 54% yield).

$^1$H NMR (d6-DMSO) δ: 9.36 (s, 1H); 9.16 (d, J=1.3 Hz, 1H); 8.22 (s, 1H); 7.67 (dd, J=4.7 Hz, J=8.2 Hz, 1H); 7.43 (dd, J=8.2 Hz, J=10.4 Hz, 1H); 6.97-6.85 (m, 1H); 3.17 (m, 2H); 1.08 (t, J=7.2 Hz, 3H).

MS (ESI, m/z): 312.4 and 314.3 [M+H$^+$ of the two main isotopes].

D.4. 1-Ethyl-3-(5-fluoro-8-vinyl-isoquinolin-3-yl)-urea

Starting from intermediate D.3 (1.33 g) and proceeding in analogy to Procedure AG, however adding more vinylboronic anhydride pyridine complex (0.7 eq) and Pd(PPh$_3$)$_4$ (0.15 eq.) after 18 h, the title compound was obtained, after purification by CC (DCM/MeOH 100:0 to 90:10), as a yellow solid (0.93 g; 84% yield).

$^1$H NMR (d6-DMSO) δ: 9.35 (s, 1H); 9.20 (s, 1H); 8.17 (s, 1H); 7.69-7.40 (m, 3H); 7.02-6.90 (m, 1H); 5.89 (dd, J=1.1 Hz, J=17.1 Hz, 1H); 5.56-5.46 (m, 1H); 3.22-3.10 (m, 2H); 1.08 (t, J=7.2 Hz, 3H).

MS (ESI, m/z): 260.2 [M+H].

D.5. 1-[8-(1,2-Dihydroxy-ethyl)-5-fluoro-isoquinolin-3-yl]-3-ethyl-urea

Starting from intermediate D.4 (0.92 g) and proceeding in analogy to Procedure AH, however adding more 4-methylmorpholine N-oxide (0.5 eq.) and potassium osmate(VI) dihydrate (0.005 eq.) after 18 h and after 63 h, the title compound was obtained, after purification by CC (DCM/MeOH 100:0 to 90:10), as a white solid (0.27 g; 26% yield).

$^1$H NMR (d6-DMSO) δ: 9.38 (s, 1H); 9.15 (s, 1H); 8.14 (s, 1H); 7.42 (d, J=1.2 Hz, 1H); 7.40 (d, J=1.2 Hz, 1H); 7.00 (t, J=5.3 Hz, 1H); 5.55 (d, J=4.3 Hz, 1H); 5.31-5.22 (m, 1H); 4.80 (m, 1H); 3.60 (t, J=5.8 Hz, 2H); 3.17 (m, 2H); 1.08 (t, J=7.2 Hz, 3H).

MS (ESI, m/z): 294.0 [M+H].

D.6. 1-Ethyl-3-(5-fluoro-8-formyl-isoquinolin-3-yl)-urea

Starting from intermediate D.5 (0.27 g) and proceeding in analogy to Procedure AI, a first batch of the product was obtained by filtering the precipitate formed during the reaction (0.18 g). The mother liquor was then extracted with 9:1 DCM/MeOH (2×) and the combined org. layers were dried over MgSO$_4$ and concentrated under reduced pressure to give a second batch of product (0.04 g). The title compound was obtained, after combining the two batches, as an orange solid (0.22 g; 91% yield).

$^1$H NMR (d6-DMSO) δ: 10.27 (s, 1H); 10.10 (s, 1H); 9.36 (s, 1H); 8.28 (s, 1H); 8.10 (dd, J=5.4 Hz, J=7.9 Hz, 1H); 7.70 (dd, J=7.9 Hz, J=10.2 Hz, 1H); 7.01-6.86 (m, 1H); 3.25-3.08 (m, 2H); 1.08 (t, J=7.2 Hz, 3H).

MS (ESI, m/z): 262.2 [M+H].

D.7. 1-Ethyl-3-(5-fluoro-8-hydroxymethyl-isoquinolin-3-yl)-urea

Starting from intermediate D.6 (0.21 g) and proceeding in analogy to Procedure E, however using 1 eq. of LiAlH$_4$ only and performing the extraction with 9:1 DCM-MeOH instead, the title compound was obtained crude and used without further purification, as a beige solid (0.22 g; quantitative yield).

$^1$H NMR (d6-DMSO) δ: 9.25 (s, 1H); 9.19 (s, 1H); 8.15 (s, 1H); 7.44-7.27 (m, 2H); 7.05-6.95 (m, 1H); 5.39 (t, J=5.6 Hz, 1H); 4.93 (d, J=5.4 Hz, 2H); 3.22-3.09 (m, 2 H), 1.08 (t, J=7.2 Hz, 3H).

MS (ESI, m/z): 264.2 [M+H].

D.8. 1-[(8-aminomethyl)-5-fluoroisoquinolin-3-yl]-3-ethylurea

Starting from intermediate D.7 (0.15 g) and proceeding in analogy to Procedure F, however adding more DPPA (1.2 eq.) and DBU (1.2 eq.) after 4 h and 18 h, and adding more PPh$_3$ (1.25 eq.) and water (0.5 mL) after 3 h for the second part of the transformation, the title compound was obtained, after two purifications by CC (DCM/MeOH +1% NH$_4$OH 100:0 to 90:10), as a beige solid (0.15 g; quantitative yield).

MS (ESI, m/z): 263.2 [M+H].

Preparation E: 1-[8-(aminomethyl)-5-(2-methyl-pyridin-4-yl)-isoquinolin-3-yl]-3-ethyl-urea Starting from the compound of Preparation B (500 mg) and 2-methylpyridine-4-boronic acid, and proceeding in analogy to Procedure AJ, the title compound was obtained, after purification by CC (DCM/MeOH +1% NH$_4$OH 100:0 to 90:10), as a yellow solid (478 mg; 80% yield).

$^1$H NMR (d6-DMSO) δ: 9.33 (d, J=0.5 Hz, 1H); 9.02 (s, 1H); 8.55 (d, J=5.1 Hz, 1H); 8.00 (s, 1H); 7.55-7.45 (m, 2H); 7.33 (s, 1H); 7.26 (dd, J=5.1, 1.4 Hz, 1H); 7.18 (t, J=5.4 Hz, 1H); 4.26 (s, 2H); 3.17-3.06 (m, 2H); 2.55 (s, 3H); 1.95 (br s, 2H); 1.04 (t, J=7.2 Hz, 3H).

MS (ESI, m/z): 336.1 [M+H$^+$].

PREPARATION OF THE EXAMPLE COMPOUNDS

Example 1 but-3-ynoic acid [3-(3-ethyl-ureido)-isoquinolin-8-ylmethyl]-amide

Starting from the compound of Preparation A and 3-butynoic acid and proceeding in analogy to Procedure G, the title compound was obtained, after purification by prep-HPLC (basic conditions), as a white solid (31% yield).

$^1$H NMR (d6-DMSO) δ: 9.18 (s, 1H); 9.01 (s, 1H); 8.47 (t, J=5.7 Hz, 1H); 8.00 (s, 1H); 7.70-7.64 (m, 1H); 7.55 (dd, J=8.3, 6.9 Hz, 1H); 7.28 (d, J=6.4 Hz, 1H); 7.09 (t, J=5.4 Hz, 1H); 5.79 (t, J=6.6 Hz, 1H); 5.31 (d, J=6.6 Hz, 2H); 4.79 (d, J=5.7 Hz, 2H); 3.21-3.11 (m, 2H); 1.08 (t, J=7.2 Hz, 3H).

LC-MS(01): MS (ESI, m/z): 311.2 [M+H$^+$]; t$_R$=0.58 min.

Example 2

N-[3-(3-ethyl-ureido)-isoquinolin-8-ylmethyl]-isonicotinamide

Starting from the compound of Preparation A and isonicotinic acid and proceeding in analogy to Procedure H, the title compound was obtained, after purification by prep-HPLC (basic conditions), as an amorphous solid (55% yield).

LC-MS(01): MS (ESI, m/z): 350.2 [M+H$^+$]; t$_R$=0.53 min.

Example 3

N-[3-(3-ethyl-ureido)-isoquinolin-8-ylmethyl]-acetamide

Starting from the compound of Preparation A and acetic acid and proceeding in analogy to Procedure H, the title compound was obtained, after washing the reaction mixture precipitate with 1:1:1 DCM/MeOH/MeCN, as an amorphous solid (51% yield).

LC-MS(01): MS (ESI, m/z): 287.2 [M+H$^+$]; t$_R$=0.50 min.

Example 4

N-[3-(3-ethyl-ureido)-isoquinolin-8-ylmethyl]-benzamide

Starting from the compound of Preparation A and benzoic acid and proceeding in analogy to Procedure H, the title compound was obtained, after washing the reaction mixture precipitate with 1:1:1 DCM/MeOH/MeCN, as an amorphous solid (81% yield).

LC-MS(01): MS (ESI, m/z): 349.2 [M+H$^+$]; t$_R$=0.71 min.

Example 5

2-cyano-N-[3-(3-ethyl-ureido)-isoquinolin-8-ylmethyl]-acetamide

Starting from the compound of Preparation A and cyanoacetic acid and proceeding in analogy to Procedure H, the title compound was obtained, after purification by prep-HPLC (basic conditions), as an amorphous solid (56% yield).

LC-MS(01): MS (ESI, m/z): 312.2 [M+H$^+$]; t$_R$=0.53 min.

Example 6 cyclohexanecarboxylic acid [3-(3-ethyl-ureido)-isoquinolin-8-ylmethyl]-amide Starting from the compound of Preparation A and cyclohexanecarboxylic acid and proceeding in analogy to Procedure H, the title compound was obtained, after washing the reaction mixture precipitate with 1:1:1 DCM/MeOH/MeCN, as an amorphous solid (40% yield).

LC-MS(01): MS (ESI, m/z): 355.3 [M+H$^+$]; t$_R$=0.77 min.

Example 7

2-cyclopropyl-N-[3-(3-ethyl-ureido)-isoquinolin-8-ylmethyl]-acetamide

Starting from the compound of Preparation A and cyclopropylacetic acid and proceeding in analogy to Procedure H, the title compound was obtained, after purification by prep-HPLC (basic conditions), as an amorphous solid (41% yield).

LC-MS(01): MS (ESI, m/z): 327.3 [M+H$^+$]; t$_R$=0.63 min.

Example 8

2-acetylamino-N-[3-(3-ethyl-ureido)-isoquinolin-8-ylmethyl]-acetamide

Starting from the compound of Preparation A and N-acetylglycine and proceeding in analogy to Procedure H, the title compound was obtained, after purification by prep-HPLC (basic conditions), as an amorphous solid (6% yield).
LC-MS(01): MS (ESI, m/z): 344.2 [M+H$^+$]; t$_R$=0.46 min.

Example 9 propynoic acid [3-(3-ethyl-ureido)-isoquinolin-8-ylmethyl]-amide

Starting from the compound of Preparation A and propiolic acid and proceeding in analogy to Procedure H, the title compound was obtained, after purification by prep-HPLC (basic conditions), as an amorphous solid (43% yield).
LC-MS(01): MS (ESI, m/z): 297.2 [M+H$^+$]; t$_R$=0.57 min.

Example 10

N-[3-(3-ethyl-ureido)-isoquinolin-8-ylmethyl]-nicotinamide

Starting from the compound of Preparation A and nicotinic acid and proceeding in analogy to Procedure H, the title compound was obtained, after purification by prep-HPLC (basic conditions), as an amorphous solid (14% yield).
LC-MS(01): MS (ESI, m/z): 350.2 [M+H$^+$]; t$_R$=0.54 min.

Example 11 pyridine-2-carboxylic acid [3-(3-ethyl-ureido)-isoquinolin-8-ylmethyl]-amide

Starting from the compound of Preparation A and 2-picolinic acid and proceeding in analogy to Procedure H, the title compound was obtained, after washing the reaction mixture precipitate with 1:1:1 DCM/MeOH/MeCN, as an amorphous solid (46% yield).
LC-MS(01): MS (ESI, m/z): 350.2 [M+H$^+$]; t$_R$=0.69 min.

Example 12

N-[3-(3-ethyl-ureido)-isoquinolin-8-ylmethyl]-2-phenyl-acetamide

Starting from the compound of Preparation A and phenylacetic acid and proceeding in analogy to Procedure H, the title compound was obtained, after purification by prep-HPLC (basic conditions), as an amorphous solid (18% yield).
LC-MS(01): MS (ESI, m/z): 363.3 [M+H$^+$]; t$_R$=0.72 min.

Example 13 cyclopropanecarboxylic acid [3-(3-ethyl-ureido)-isoquinolin-8-ylmethyl]-amide

Starting from the compound of Preparation A and cyclopropanecarboxylic acid and proceeding in analogy to Procedure H, the title compound was obtained, after washing the reaction mixture precipitate with 1:1:1 DCM/MeOH/MeCN, as an amorphous solid (52% yield).
LC-MS(01): MS (ESI, m/z): 313.2 [M+H$^+$]; t$_R$=0.59 min.

Example 14

N-[3-(3-ethyl-ureido)-isoquinolin-8-ylmethyl]-2,2-dimethyl-propionamide

Starting from the compound of Preparation A and trimethylacetic acid and proceeding in analogy to Procedure H, the title compound was obtained, after purification by prep-HPLC (basic conditions), as an amorphous solid (18% yield).
LC-MS(01): MS (ESI, m/z): 329.3 [M+H$^+$]; t$_R$=0.69 min.

Example 15

N-[3-(3-ethyl-ureido)-isoquinolin-8-ylmethyl]-2-methoxy-acetamide

Starting from the compound of Preparation A and methoxyacetic acid and proceeding in analogy to Procedure H, the title compound was obtained, after purification by prep-HPLC (basic conditions), as an amorphous solid (64% yield).
LC-MS(01): MS (ESI, m/z): 317.2 [M+H$^+$]; t$_R$=0.55 min.

Example 16

1H-imidazole-2-carboxylic acid [3-(3-ethyl-ureido)-isoquinolin-8-ylmethyl]-amide Starting from the compound of Preparation A and 1H-imidazole-2-carboxylic acid and proceeding in analogy to Procedure H, the title compound was obtained, after washing the reaction mixture precipitate with 1:1:1 DCM/MeOH/MeCN, as an amorphous solid (57% yield).
LC-MS(01): MS (ESI, m/z): 339.2 [M+H$^+$]; t$_R$=0.52 min.

Example 17 pent-4-ynoic acid [3-(3-ethyl-ureido)-isoquinolin-8-ylmethyl]-amide

Starting from the compound of Preparation A and 4-pentynoic acid and proceeding in analogy to Procedure H, the title compound was obtained, after purification by prep-HPLC (basic conditions), as an amorphous solid (51% yield).
LC-MS(01): MS (ESI, m/z): 325.2 [M+H$^+$]; t$_R$=0.59 min.

Example 18

N-[3-(3-ethyl-ureido)-isoquinolin-8-ylmethyl]-isobutyramide

Starting from the compound of Preparation A and isobutyric acid and proceeding in analogy to Procedure H, the title compound was obtained, after purification by prep-HPLC (basic conditions), as an amorphous solid (55% yield).
LC-MS(01): MS (ESI, m/z): 315.2 [M+H$^+$]; t$_R$=0.62 min.

Example 19

2-dimethylamino-N-[3-(3-ethyl-ureido)-isoquinolin-8-ylmethyl]-acetamide

Starting from the compound of Preparation A and N,N-dimethylglycine and proceeding in analogy to Procedure H, the title compound was obtained, after purification by prep-HPLC (basic conditions), as an amorphous solid (52% yield).
LC-MS(01): MS (ESI, m/z): 330.3 [M+H$^+$]; t$_R$=0.44 min.

Example 20

2H-[1,2,3]triazole-4-carboxylic acid [3-(3-ethyl-ureido)-isoquinolin-8-ylmethyl]-amide Starting from the compound of Preparation A and 3H-[1,2,3]triazole-4-carboxylic acid and proceeding in analogy to Procedure H, the title compound was obtained, after purification by prep-HPLC (basic conditions), as an amorphous solid (10% yield).
LC-MS(01): MS (ESI, m/z): 340.2 [M+H$^+$]; $t_R$=0.53 min.

Example 21

N-[3-(3-ethyl-ureido)-isoquinolin-8-ylmethyl]-succinamide

Starting from the compound of Preparation A and succinamic acid and proceeding in analogy to Procedure H, the title compound was obtained, after washing the reaction mixture precipitate with 1:1:1 DCM/MeOH/MeCN, as an amorphous solid (46% yield).
LC-MS(01): MS (ESI, m/z): 344.2 [M+H$^+$]; $t_R$=0.46 min.

Example 22

3-methyl-3H-imidazole-4-carboxylic acid [3-(3-ethyl-ureido)-isoquinolin-8-ylmethyl]-amide Starting from the compound of Preparation A and 1-methyl-1H-pyrazole-5-carboxylic acid and proceeding in analogy to Procedure H, the title compound was obtained, after purification by prep-HPLC (basic conditions), as an amorphous solid (54% yield).
LC-MS(01): MS (ESI, m/z): 353.2 [M+H$^+$]; $t_R$=0.48 min.

Example 23

N-[3-(3-ethyl-ureido)-5-pyridin-4-yl-isoquinolin-8-ylmethyl]-nicotinamide

Starting from the compound of Preparation C and nicotinic acid (2.6 eq.) and proceeding in analogy to Procedure G, however using DIPEA (2.8 eq.), the title compound was obtained, after purification by CC (DCM/MeOH +1% NH$_4$OH 100:0 to 95:5) followed by prep-HPLC (basic conditions), as a yellow solid (56% yield).
$^1$H NMR (d6-DMSO) δ: 9.40 (s, 1H); 9.34 (t, J=5.4 Hz, 1H); 9.06 (d, J=1.8 Hz, 1H); 9.04 (s, 1H); 8.74-8.68 (m, 3H); 8.24 (dt, J=7.6, 1.7 Hz, 1H); 8.09 (s, 1H); 7.61-7.56 (m, 1H); 7.54-7.43 (m, 4H); 7.04 (d, J=0.6 Hz, 1H); 5.05 (d, J=5.4 Hz, 2H); 3.17-3.04 (m, 2H); 1.03 (t, J=7.2 Hz, 3H).
LC-MS(01): MS (ESI, m/z): 427.3 [M+H$^+$]; $t_R$=0.47 min.

Example 24

[3-(3-ethyl-ureido)-isoquinolin-8-ylmethyl]-carbamic acid ethyl ester hydrochloride Starting from the compound of Preparation A and ethanol and proceeding in analogy to Procedure O, the title compound was obtained, after purification by prep-HPLC (acidic conditions) and HCl treatment, as an amorphous solid (29% yield).
LC-MS(01): MS (ESI, m/z): 317.2 [M+H$^+$]; $t_R$=0.67 min.

Example 25

[3-(3-ethyl-ureido)-isoquinolin-8-ylmethyl]-carbamic acid pyridin-4-ylmethyl ester hydrochloride Starting from the compound of Preparation A and 4-(hydroxymethyl)pyridine and proceeding in analogy to Procedure O, however adding 4-(hydroxymethyl)pyridine (2.0 eq.) again after 22 h, the title compound was obtained, after purification by prep-HPLC (acidic conditions) and HCl treatment, as an amorphous solid (41% yield).
LC-MS(01): MS (ESI, m/z): 380.2 [M+H$^+$]; $t_R$=0.50 min.

Example 26

[3-(3-ethyl-ureido)-isoquinolin-8-ylmethyl]-carbamic acid pyrimidin-5-ylmethyl ester hydrochloride Starting from the compound of Preparation A and 5-(hydroxymethyl)pyrimidine and proceeding in analogy to Procedure O, however adding 5-(hydroxymethyl)pyrimidine (2.0 eq.) again after 22 h, the title compound was obtained, after purification by prep-HPLC (acidic conditions) and HCl treatment, as an amorphous solid (34% yield).
LC-MS(01): MS (ESI, m/z): 381.2 [M+H$^+$]; $t_R$=0.58 min.

Example 27

[3-(3-ethyl-ureido)-isoquinolin-8-ylmethyl]-carbamic acid 2-fluoro-ethyl ester hydrochloride Starting from the compound of Preparation A and 2-fluoroethanol and proceeding in analogy to Procedure O, however adding 2-fluoroethanol (2.0 eq.) again after 22 h, the title compound was obtained, after purification by prep-HPLC (acidic conditions) and HCl treatment, as an amorphous solid (28% yield).
LC-MS(01): MS (ESI, m/z): 335.2 [M+H$^+$]; $t_R$=0.63 min.

Example 28

[3-(3-ethyl-ureido)-isoquinolin-8-ylmethyl]-carbamic acid cyclopropylmethyl ester hydrochloride Starting from the compound of Preparation A and cyclopropanemethanol and proceeding in analogy to Procedure O, however adding cyclopropanemethanol (2.0 eq.) again after 22 h, the title compound was obtained, after purification by prep-HPLC (acidic conditions) and HCl treatment, as an amorphous solid (27% yield).
LC-MS(01): MS (ESI, m/z): 343.3 [M+H$^+$]; $t_R$=0.75 min.

Example 29

[3-(3-ethyl-ureido)-isoquinolin-8-ylmethyl]-carbamic acid pyrimidin-4-ylmethyl ester hydrochloride Starting from the compound of Preparation A and 4-(hydroxymethyl)pyrimidine and proceeding in analogy to Procedure O, however adding 4-(hydroxymethyl)pyrimidine (2.0 eq.) again after 22 h, the title compound was obtained, after purification by prep-HPLC (acidic conditions) and HCl treatment, as an amorphous solid (29% yield).
LC-MS(01): MS (ESI, m/z): 381.3 [M+H$^+$]; $t_R$=0.58 min.

Example 30

[3-(3-ethyl-ureido)-isoquinolin-8-ylmethyl]-carbamic acid isopropyl ester hydrochloride Starting from the compound of Preparation A and 2-propanol and proceeding in analogy to Procedure O, however adding 2-propanol (2.0 eq.) again after 22 h, the title compound was obtained, after purification by prep-HPLC (acidic conditions) and HCl treatment, as an amorphous solid (24% yield).
LC-MS(01): MS (ESI, m/z): 331.3 [M+H$^+$]; $t_R$=0.74 min.

Example 31

[3-(3-ethyl-ureido)-isoquinolin-8-ylmethyl]-carbamic acid prop-2-ynyl ester hydrochloride Starting from the compound of Preparation A and propargyl alcohol and proceeding in analogy to Procedure O, however adding propargyl alcohol (2.0 eq.) again after 22 h, the title compound was obtained, after purification by prep-HPLC (acidic conditions) and HCl treatment, as an amorphous solid (23% yield).
LC-MS(01): MS (ESI, m/z): 327.2 [M+H$^+$]; $t_R$=0.66 min.

Example 32

[3-(3-ethyl-ureido)-isoquinolin-8-ylmethyl]-carbamic acid 2-cyano-ethyl ester hydrochloride Starting from the compound of Preparation A and 3-hydroxypropionitrile and proceeding in analogy to Procedure O, however adding 3-hydroxypropionitrile (2.0 eq.) again after 22 h, the title compound was obtained, after purification by prep-HPLC (acidic conditions) and HCl treatment, as an amorphous solid (28% yield).
LC-MS(01): MS (ESI, m/z): 342.2 [M+H$^+$]; $t_R$=0.60 min.

Example 33

[3-(3-ethyl-ureido)-isoquinolin-8-ylmethyl]-carbamic acid pyridin-3-ylmethyl ester hydrochloride Starting from the compound of Preparation A and 3-(hydroxymethyl)pyridine and proceeding in analogy to Procedure O, however adding 3-(hydroxymethyl)pyridine (2.0 eq.) again after 22 h, the title compound was obtained, after purification by prep-HPLC (acidic conditions) and HCl treatment, as an amorphous solid (40% yield).
LC-MS(01): MS (ESI, m/z): 380.2 [M+H$^+$]; $t_R$=0.51 min.

Example 34

[3-(3-ethyl-ureido)-isoquinolin-8-ylmethyl]-carbamic acid pyridin-2-ylmethyl ester hydrochloride Starting from the compound of Preparation A and 2-(hydroxymethyl)pyridine and proceeding in analogy to Procedure O, however adding 2-(hydroxymethyl)pyridine (2.0 eq.) again after 22 h, the title compound was obtained, after purification by prep-HPLC (acidic conditions) and HCl treatment, as an amorphous solid (26% yield).
LC-MS(01): MS (ESI, m/z): 380.2 [M+H$^+$]; $t_R$=0.57 min.

Example 35

[3-(3-ethyl-ureido)-isoquinolin-8-ylmethyl]-carbamic acid (1-methyl-1H-pyrazol-3-yl)methyl ester hydrochloride Starting from the compound of Preparation A and (1-methyl-1H-pyrazol-3-yl)methanol and proceeding in analogy to Procedure O, however adding (1-methyl-1H-pyrazol-3-yl)methanol (2.0 eq.) again after 22 h, the title compound was obtained, after purification by prep-HPLC (acidic conditions) and HCl treatment, as an amorphous solid (40% yield).
LC-MS(01): MS (ESI, m/z): 383.3 [M+H$^+$]; $t_R$=0.63 min.

Example 36

[3-(3-ethyl-ureido)-isoquinolin-8-ylmethyl]-carbamic acid benzyl ester hydrochloride Starting from the compound of Preparation A and benzyl alcohol and proceeding in analogy to Procedure O, however adding benzyl alcohol (2.0 eq.) again after 22 h, the title compound was obtained, after purification by prep-HPLC (acidic conditions) and HCl treatment, as an amorphous solid (35% yield).
LC-MS(01): MS (ESI, m/z): 379.3 [M+H$^+$]; $t_R$=0.83 min.

Example 37

[3-(3-ethyl-ureido)-isoquinolin-8-ylmethyl]-carbamic acid 2-methoxy-ethyl ester hydrochloride Starting from the compound of Preparation A and 2-methoxyethanol and proceeding in analogy to Procedure O, however adding 2-methoxyethanol (2.0 eq.) again after 22 h, the title compound was obtained, after purification by prep-HPLC (acidic conditions) and HCl treatment, as an amorphous solid (34% yield).
LC-MS(01): MS (ESI, m/z): 347.2 [M+H$^+$]; $t_R$=0.61 min.

Example 38

[3-(3-ethyl-ureido)-isoquinolin-8-ylmethyl]-carbamic acid 3-methyl-3H-imidazol-4-ylmethyl ester hydrochloride Starting from the compound of Preparation A and (1-methyl-1H-imidazol-5-yl)methanol and proceeding in analogy to Procedure O, however adding (1-methyl-1H-imidazol-5-yl)methanol (2.0 eq.) again after 22 h, the title compound was obtained, after purification by prep-HPLC (acidic conditions) and HCl treatment, as an amorphous solid (39% yield).
LC-MS(01): MS (ESI, m/z): 383.2 [M+H$^+$]; $t_R$=0.48 min.

Example 39

[3-(3-ethyl-ureido)-isoquinolin-8-ylmethyl]-carbamic acid 1H-pyrazol-4-ylmethyl ester hydrochloride

39.1 (1H-pyrazol-4-yl)-methanol

Starting from ethyl pyrazole-4-carboxylate (10.0 g) and proceeding in analogy to Procedure E, the title compound was obtained, without additional purification, as a white solid (5.2 g; 76% yield).
$^1$H NMR (d6-DMSO) δ: 12.60 (s, 1H); 7.50 (s, 2H); 4.77 (br. s, 1H); 4.38 (br. s, 2H).

39.2. [3-(3-ethyl-ureido)-isoquinolin-8-ylmethyl]-carbamic acid 1H-pyrazol-4-ylmethyl ester hydrochloride Starting from the compound of Preparation A and intermediate 39.1 and proceeding in analogy to Procedure O, however adding intermediate 39.1 (2.0 eq.) again after 22 h, the title compound was obtained, after purification by prep-HPLC (acidic conditions) and HCl treatment, as an amorphous solid (46% yield).
LC-MS(01): MS (ESI, m/z): 369.2 [M+H$^+$]; $t_R$=0.59 min.

Example 40

[3-(3-ethyl-ureido)-isoquinolin-8-ylmethyl]-carbamic acid but-3-ynyl ester hydrochloride Starting from the compound of Preparation A and 3-butyn-1-ol and proceeding in analogy to Procedure O, however adding 3-butyn-1-ol (2.0 eq.) again after 22 h, the title compound was obtained, after purification by prep-HPLC (acidic conditions) and HCl treatment, as an amorphous solid (33% yield).

LC-MS(01): MS (ESI, m/z): 341.2 [M+H$^+$]; t$_R$=0.69 min.

Example 41

[3-(3-ethyl-ureido)-5-pyridin-4-yl-isoquinolin-8-ylmethyl]-carbamic acid prop-2-ynyl ester Starting from the compound of Preparation C and propargyl chloroformate and proceeding in analogy to Procedure P, however adding more propargyl chloroformate (1.2 eq.) after 20 h, the title compound was obtained, after purification by CC (DCM/MeOH +1% NH$_4$OH 100:0 to 95:5) followed by prep-HPLC (basic conditions), as a yellow solid (23% yield).

$^1$H NMR (d6-DMSO) δ: 9.30 (s, 1H); 9.04 (s, 1H); 8.73-8.69 (m, 2H); 8.11-8.05 (m, 2H); 7.57 (d, J=7.3 Hz, 1H); 7.51-7.46 (m, 2H); 7.36 (d, J=7.3 Hz, 1H); 7.03 (t, J=5.4 Hz, 1H); 4.75 (d, J=5.9 Hz, 2H); 4.65 (d, J=2.4 Hz, 2H); 3.47 (t, J=2.4 Hz, 1H); 3.16-3.05 (m, 2H); 1.04 (t, J=7.2 Hz, 3H).

LC-MS(01): MS (ESI, m/z): 404.2 [M+H$^+$]; t$_R$=0.56 min.

Example 42

[3-(3-ethyl-ureido)-5-pyridin-4-yl-isoquinolin-8-ylmethyl]-carbamic acid pyridin-3-ylmethyl ester

42.1. [5-chloro-3-(3-ethyl-ureido)-isoquinolin-8-ylmethyl]-carbamic acid pyridin-3-ylmethyl ester Starting from the compound of Preparation B and 3-(hydroxymethyl)pyridine and proceeding in analogy to Procedure O, the title compound was obtained, after purification by prep-HPLC (basic conditions), as a white solid (19% yield).

MS (ESI, m/z): 414.14 [M+H$^+$].

42.2. [3-(3-ethyl-ureido)-5-pyridin-4-yl-isoquinolin-8-ylmethyl]-carbamic acid pyridin-3-ylmethyl ester Starting from intermediate 42.1 and pyridine-4-boronic acid and proceeding in analogy to Procedure Q, the title compound was obtained, after purification by CC (DCM/MeOH +1% NH$_4$OH 100:0 to 90:10), as a yellow solid (33% yield).

$^1$H NMR (d6-DMSO) δ: 9.31 (s, 1H); 9.05 (s, 1H); 8.74-8.69 (m, 2H); 8.60-8.57 (m, 1H); 8.53-8.49 (m, 1H); 8.08 (s, 1H); 8.04 (d, J=5.8 Hz, 1H); 7.80-7.73 (m, 1H); 7.56 (d, J=7.3 Hz, 1H); 7.50-7.45 (m, 2H); 7.42-7.33 (m, 2H); 7.05 (t, J=5.1 Hz, 1H); 5.10 (s, 2H); 4.76 (d, J=5.8 Hz, 2H); 3.16-3.05 (m, 2H); 1.04 (t, J=7.2 Hz, 3H).

LC-MS(01): MS (ESI, m/z): 457.3 [M+H$^+$]; t$_R$=0.45 min.

Example 43

1-ethyl-3-{8-[(3-ethyl-ureido)-methyl]isoquinolin-3-yl}-urea

Starting from the compound of Preparation A and ethyl isocyanate (1.0 eq.) and proceeding in analogy to Procedure C, using however DMF as solvent and rt as temperature, the title compound was obtained, without additional purification, as a white solid (46% yield).

$^1$H NMR (d6-DMSO) δ: 9.21 (s, 1H); 9.01 (s, 1H); 7.98 (s, 1H); 7.67-7.61 (m, 1H); 7.57-7.50 (m, 1H); 7.26 (dd, J=6.7, 0.4 Hz, 1H); 7.09 (t, J=5.3 Hz, 1H); 6.36 (t, J=5.9 Hz, 1H); 5.84 (t, J=5.6 Hz, 1H); 4.68 (d, J=5.8 Hz, 2H); 3.22-3.11 (m, 2H); 3.08-2.97 (m, 2H); 1.08 (t, J=7.2 Hz, 3H); 0.98 (t, J=7.1 Hz, 3H).

LC-MS(01): MS (ESI, m/z): 316.2 [M+H$^+$]; t$_R$=0.53 min.

Example 44

[3-(3-ethyl-ureido)-isoquinolin-8-ylmethyl]-methyl-carbamic acid prop-2-ynyl ester

44.1. 1-(8-(chloromethyl)-isoquinolin-3-yl)-3-ethylurea

Starting from intermediate A.5 (500 mg) and proceeding in analogy to Procedure R, the title compound was obtained, after purification by CC (DCM/MeOH +1% NH$_4$OH 100:0 to 97:3), as a white solid (538 mg; 100% yield).

$^1$H NMR (d6-DMSO) δ: 9.28 (s, 1H); 9.09 (s, 1H); 8.05 (s, 1H); 7.77 (d, J=8.4 Hz, 1H); 7.60-7.53 (m, 1H); 7.51-7.45 (m, 1H); 7.04 (t, J=5.5 Hz, 1H); 5.29 (s, 2H); 3.24-3.10 (m, 2H); 1.08 (t, J=7.2 Hz, 3H).

MS (ESI, m/z): 264.2 [M+H$^+$].

44.2. 1-ethyl-3-(8-methylaminomethyl-isoquinolin-3-yl)-urea

Starting from intermediate 44.1 (68 mg) and a 2.0M solution of methylamine in THF and proceeding in analogy to Procedure S, the title compound was obtained, after purification by prep-HPLC (basic conditions), as a white solid (32 mg; 49% yield).

$^1$H NMR (d6-DMSO) δ: 9.29 (s, 1H); 9.00 (s, 1H); 7.94 (s, 1H); 7.67-7.57 (m, 1H); 7.57-7.46 (m, 1H); 7.36-7.27 (m, 1H); 7.20-7.08 (m, 1H); 4.08 (s, 2H); 3.24-3.09 (m, 2H); 2.33 (s, 3H); 2.21-2.05 (m, 1H); 1.08 (t, J=7.2 Hz, 3H).

MS (ESI, m/z): 259.3 [M+H$^+$].

44.3. [3-(3-ethyl-ureido)-isoquinolin-8-ylmethyl]-methyl-carbamic acid prop-2-ynyl ester Starting from intermediate 44.2 and propargyl chloroformate and proceeding in analogy to Procedure P, the title compound was obtained, after purification by CC (DCM/MeOH 100:0 to 95:5), as a white solid (71% yield).

$^1$H NMR (d6-DMSO) δ: 9.18 (s, 1H); 9.09-8.97 (m, 1H); 8.02 (s, 1H); 7.69 (dd, J=0.6 Hz, J=8.6 Hz, 1H); 7.57 (dd, J=7.0 Hz, J=8.3 Hz, 1H); 7.26-7.13 (m, 1H); 7.09-6.99 (m, 1H); 5.04-4.90 (m, 2H); 4.73 (s, 2H); 3.49 (s, 1H); 3.23-3.09 (m, 2H); 2.83 (s, 3H); 1.08 (t, J=7.2 Hz, 3H).

MS (ESI, m/z): 341.2 [M+H$^+$].

Example 45

N-[3-(3-ethyl-ureido)-5-pyridin-4-yl-isoquinolin-8-ylmethyl]-malonamic acid

Starting from the compound of Preparation C and mono-tert-butyl malonate and proceeding in analogy to Procedure T, the title compound was obtained, after purification by prep-HPLC (basic conditions), as an amorphous solid (37% yield).

LC-MS(02): MS (ESI, m/z): 408.3 [M+H$^+$]; t$_R$=0.42 min.

Example 46

N-[3-(3-ethyl-ureido)-5-pyridin-4-yl-isoquinolin-8-ylmethyl]-succinamic acid tert-butyl ester Starting from the compound of Preparation C and mono-tert-butyl succinate and proceeding in analogy to Procedure T, the title compound was obtained, after purification by prep-HPLC (basic conditions), as an amorphous solid (66% yield).

LC-MS(02): MS (ESI, m/z): 478.5 [M+H$^+$]; $t_R$=0.66 min.

Example 47

({[3-(3-ethyl-ureido)-5-pyridin-4-yl-isoquinolin-8-ylmethyl]-carbamoyl}-methyl)-carbamic acid tert-butyl ester Starting from the compound of Preparation C and N-(tert-butoxycarbonyl)glycine and proceeding in analogy to Procedure T, the title compound was obtained, after purification by prep-HPLC (basic conditions), as an amorphous solid (58% yield).

LC-MS(02): MS (ESI, m/z): 479.4 [M+H$^+$]; $t_R$=0.59 min.

Example 48

({[3-(3-ethyl-ureido)-5-pyridin-4-yl-isoquinolin-8-ylmethyl]-carbamoyl}-methyl)-methyl-carbamic acid tert-butyl ester Starting from the compound of Preparation C and Boc-sarcosine and proceeding in analogy to Procedure T, the title compound was obtained, after purification by prep-HPLC (basic conditions), as an amorphous solid (48% yield).

LC-MS(02): MS (ESI, m/z): 493.5 [M+H$^+$]; $t_R$=0.64 min.

Example 49

(2-{[3-(3-ethyl-ureido)-5-pyridin-4-yl-isoquinolin-8-ylmethyl]-carbamoyl}-ethyl)-carbamic acid tert-butyl ester Starting from the compound of Preparation C and N-(tert-butoxycarbonyl)-L-alanine and proceeding in analogy to Procedure T, the title compound was obtained, after purification by prep-HPLC (basic conditions), as an amorphous solid (57% yield).

LC-MS(02): MS (ESI, m/z): 493.4 [M+H$^+$]; $t_R$=0.62 min.

Example 50

2-amino-N-[3-(3-ethyl-ureido)-5-pyridin-4-yl-isoquinolin-8-ylmethyl]-acetamide hydrochloride Starting from the compound of Example 47 and proceeding in analogy to Procedure X, the title compound was obtained, without additional purification, as an amorphous solid (89% yield).

LC-MS(01): MS (ESI, m/z): 379.3 [M+H$^+$]; $t_R$=0.35 min.

Example 51

3-amino-N-[3-(3-ethyl-ureido)-5-pyridin-4-yl-isoquinolin-8-ylmethyl]-propionamide hydrochloride Starting from the compound of Example 49 and proceeding in analogy to Procedure X, the title compound was obtained, without additional purification, as an amorphous solid (95% yield).

LC-MS(01): MS (ESI, m/z): 393.3 [M+H$^+$]; $t_R$=0.36 min.

Example 52

N-[3-(3-ethyl-ureido)-5-pyridin-4-yl-isoquinolin-8-ylmethyl]-malonamide

Starting from the compound of Example 45 and a 0.5M solution of ammonia in dioxane and proceeding in analogy to Procedure U, the title compound was obtained, after purification by prep-HPLC (basic conditions), as an amorphous solid (29% yield).

LC-MS(02): MS (ESI, m/z): 407.2 [M+H$^+$]; $t_R$=0.42 min.

Example 53

N-[3-(3-ethyl-ureido)-5-pyridin-4-yl-isoquinolin-8-ylmethyl]-N'-methyl-malonamide Starting from the compound of Example 45 and a 2.0M solution of methylamine in THF and proceeding in analogy to Procedure U, the title compound was obtained, after purification by prep-HPLC (basic conditions), as an amorphous solid (30% yield).

LC-MS(02): MS (ESI, m/z): 421.3 [M+H$^+$]; $t_R$=0.43 min.

Example 54

N-[3-(3-ethyl-ureido)-5-pyridin-4-yl-isoquinolin-8-ylmethyl]-succinamide 54.1. N-[3-(3-ethyl-ureido)-5-pyridin-4-yl-isoquinolin-8-ylmethyl]-succinamic acid Starting from the compound of Example 46, and proceeding in analogy to Procedure V, the title compound was obtained, without additional purification, as an amorphous solid (quantitative yield).

MS (ESI, m/z): 421.9 [M+H$^+$].

54.2. N-[3-(3-ethyl-ureido)-5-pyridin-4-yl-isoquinolin-8-ylmethyl]-succinamide

Starting from intermediate 54.1 and a 0.5M solution of ammonia in dioxane and proceeding in analogy to Procedure U, the title compound was obtained, after purification by prep-HPLC (basic conditions), as an amorphous solid (20% yield).

LC-MS(02): MS (ESI, m/z): 421.1 [M+H$^+$]; $t_R$=0.44 min.

Example 55

N-[3-(3-ethyl-ureido)-5-pyridin-4-yl-isoquinolin-8-ylmethyl]-N'-methyl-succinamide Starting from intermediate 54.1 and a 2.0M solution of methylamine in THF and proceeding in analogy to Procedure U, the title compound was obtained, after purification by prep-HPLC (basic conditions), as an amorphous solid (20% yield).
LC-MS(02): MS (ESI, m/z): 435.3 [M+H$^+$]; $t_R$=0.43 min.

Example 56

(3-{[3-(3-ethyl-ureido)-5-pyridin-4-yl-isoquinolin-8-ylmethyl]-carbamoyl}-propyl)-carbamic acid tert-butyl ester Starting from the compound of Preparation C and 4-(tert-butoxycarbonylamino)butyric acid and proceeding in analogy to Procedure W, the title compound was obtained, after purification by prep-HPLC (basic conditions), as an amorphous solid (56% yield).
LC-MS(02): MS (ESI, m/z): 507.4 [M+H$^+$]; $t_R$=0.64 min.

Example 57

2-cyclopropyl-N-[3-(3-ethyl-ureido)-5-pyridin-4-yl-isoquinolin-8-ylmethyl]-acetamide Starting from the compound of Preparation C and cyclopropylacetic acid and proceeding in analogy to Procedure W, the title compound was obtained, after purification by prep-HPLC (basic conditions), as an amorphous solid (47% yield).
LC-MS(02): MS (ESI, m/z): 404.3 [M+H$^+$]; $t_R$=0.55 min.

Example 58

(2-{[3-(3-ethyl-ureido)-5-pyridin-4-yl-isoquinolin-8-ylmethyl]-carbamoyl}-ethyl)-methyl-carbamic acid tert-butyl ester Starting from the compound of Preparation C and 3-[(tert-butoxycarbonyl)(methyl)amino]propanoic acid and proceeding in analogy to Procedure W, the title compound was obtained, after purification by prep-HPLC (basic conditions), as an amorphous solid (56% yield).
LC-MS(02): MS (ESI, m/z): 507.5 [M+H$^+$]; $t_R$=0.67 min.

Example 59

N-[3-(3-ethyl-ureido)-5-pyridin-4-yl-isoquinolin-8-ylmethyl]-propionamide

Starting from the compound of Preparation C and propionic acid and proceeding in analogy to Procedure W, the title compound was obtained, after purification by prep-HPLC (basic conditions), as an amorphous solid (59% yield).
LC-MS(02): MS (ESI, m/z): 378.3 [M+H$^+$]; $t_R$=0.48 min.

Example 60

N-[3-(3-ethyl-ureido)-5-pyridin-4-yl-isoquinolin-8-ylmethyl]-2-(1H-imidazol-4-yl)-acetamide Starting from the compound of Preparation C and 4-imidazole acetic acid hydrochloride and proceeding in analogy to Procedure W, the title compound was obtained, after purification by prep-HPLC (basic conditions), as an amorphous solid (49% yield).
LC-MS(01): MS (ESI, m/z): 430.2 [M+H$^+$]; $t_R$=0.37 min.

Example 61

N-[3-(3-ethyl-ureido)-5-pyridin-4-yl-isoquinolin-8-ylmethyl]-2-hydroxy-acetamide Starting from the compound of Preparation C and acetoxy-acetic acid and proceeding in analogy to Procedure W, the title compound was obtained, after purification by prep-HPLC (basic conditions), as an amorphous solid (19% yield).
LC-MS(02): MS (ESI, m/z): 380.2 [M+H$^+$]; $t_R$=0.41 min.

Example 62

(3-{[3-(3-ethyl-ureido)-5-pyridin-4-yl-isoquinolin-8-ylmethyl]-carbamoyl}propyl)-methyl-carbamic acid tert-butyl ester Starting from the compound of Preparation C and 4-[(tert-butoxycarbonyl)(methyl)amino]butanoic acid and proceeding in analogy to Procedure W, the title compound was obtained, after purification by prep-HPLC (basic conditions), as an amorphous solid (53% yield).
LC-MS(02): MS (ESI, m/z): 521.4 [M+H$^+$]; $t_R$=0.71 min.

Example 63

N-[3-(3-ethyl-ureido)-5-pyridin-4-yl-isoquinolin-8-ylmethyl]-3-methoxy-propionamide Starting from the compound of Preparation C and 3-methoxypropionic acid and proceeding in analogy to Procedure W, the title compound was obtained, after purification by prep-HPLC (basic conditions), as an amorphous solid (61% yield).
LC-MS(02): MS (ESI, m/z): 408.3 [M+H$^+$]; $t_R$=0.47 min.

Example 64

N-[3-(3-ethyl-ureido)-5-pyridin-4-yl-isoquinolin-8-ylmethyl]-acetamide

Starting from the compound of Preparation C and acetic acid and proceeding in analogy to Procedure W, the title compound was obtained, after purification by prep-HPLC (basic conditions), as an amorphous solid (48% yield).
LC-MS(02): MS (ESI, m/z): 364.2 [M+H$^+$]; $t_R$=0.44 min.

Example 65 cyclopropanecarboxylic acid [3-(3-ethyl-ureido)-5-pyridin-4-yl-isoquinolin-8-ylmethyl]-amide Starting from the compound of Preparation C and cyclopropanecarboxylic acid and proceeding in analogy to Procedure W, the title compound was obtained, after purification by prep-HPLC (basic conditions), as an amorphous solid (44% yield).
LC-MS(02): MS (ESI, m/z): 390.3 [M+H$^+$]; $t_R$=0.52 min.

Example 66

N-[3-(3-ethyl-ureido)-5-pyridin-4-yl-isoquinolin-8-ylmethyl]-3-methyl-butyramide Starting from the compound of Preparation C and isovaleric acid and proceeding in analogy to Procedure W, the title compound was obtained, after purification by prep-HPLC (basic conditions), as an amorphous solid (26% yield).
LC-MS(02): MS (ESI, m/z): 406.3 [M+H$^+$]; $t_R$=0.60 min.

Example 67

N-[3-(3-ethyl-ureido)-5-pyridin-4-yl-isoquinolin-8-ylmethyl]-isobutyramide

Starting from the compound of Preparation C and isobutyric acid and proceeding in analogy to Procedure W, the title compound was obtained, after purification by prep-HPLC (basic conditions), as an amorphous solid (20% yield).
LC-MS(02): MS (ESI, m/z): 392.3 [M+H$^+$]; $t_R$=0.54 min.

Example 68

N-[3-(3-ethyl-ureido)-5-pyridin-4-yl-isoquinolin-8-ylmethyl]-3-hydroxy-propionamide Starting from the compound of Preparation C and 3-hydroxypropionic acid and proceeding in analogy to Procedure W, the title compound was obtained, after purification by prep-HPLC (basic conditions), as an amorphous solid (19% yield).
LC-MS(02): MS (ESI, m/z): 394.3 [M+H$^+$]; $t_R$=0.41 min.

Example 69 pent-4-ynoic acid [3-(3-ethyl-ureido)-5-pyridin-4-yl-isoquinolin-8-ylmethyl]-amide Starting from the compound of Preparation C and 4-pentynoic acid and proceeding in analogy to Procedure W, the title compound was obtained, after purification by prep-HPLC (basic conditions), as an amorphous solid (48% yield).
LC-MS(02): MS (ESI, m/z): 402.3 [M+H$^+$]; $t_R$=0.51 min.

Example 70

N-[3-(3-ethyl-ureido)-5-pyridin-4-yl-isoquinolin-8-ylmethyl]-2-pyrazol-1-yl-acetamide Starting from the compound of Preparation C and 2-(1H-pyrazol-1-yl)acetic acid and proceeding in analogy to Procedure W, the title compound was obtained, after purification by prep-HPLC (basic conditions), as an amorphous solid (5% yield).
LC-MS(02): MS (ESI, m/z): 430.3 [M+H$^+$]; $t_R$=0.49 min.

Example 71

3H-imidazole-4-carboxylic acid [3-(3-ethyl-ureido)-5-pyridin-4-yl-isoquinolin-8-ylmethyl]-amide Starting from the compound of Preparation C and 4-imidazolecarboxylic acid and proceeding in analogy to Procedure W, the title compound was obtained, after purification by prep-HPLC (basic conditions), as an amorphous solid (9% yield).
LC-MS(02): MS (ESI, m/z): 416.2 [M+H$^+$]; $t_R$=0.42 min.

Example 72

1H-pyrazole-3-carboxylic acid [3-(3-ethyl-ureido)-5-pyridin-4-yl-isoquinolin-8-ylmethyl]-amide Starting from the compound of Preparation C and 1H-pyrazole-3-carboxylic acid and proceeding in analogy to Procedure W, the title compound was obtained, after purification by prep-HPLC (basic conditions), as an amorphous solid (16% yield).
LC-MS(02): MS (ESI, m/z): 416.3 [M+H$^+$]; $t_R$=0.47 min.

Example 73

1H-pyrazole-4-carboxylic acid [3-(3-ethyl-ureido)-5-pyridin-4-yl-isoquinolin-8-ylmethyl]-amide Starting from the compound of Preparation C and 4-pyrazolecarboxylic acid and proceeding in analogy to Procedure W, the title compound was obtained, after purification by prep-HPLC (basic conditions), as an amorphous solid (40% yield).
LC-MS(02): MS (ESI, m/z): 416.3 [M+H$^+$]; $t_R$=0.45 min.

Example 74

1H-imidazole-2-carboxylic acid [3-(3-ethyl-ureido)-5-pyridin-4-yl-isoquinolin-8-ylmethyl]-amide Starting from the compound of Preparation C and 1H-imidazole-2-carboxylic acid and proceeding in analogy to Procedure W, the title compound was obtained, after purification by prep-HPLC (basic conditions), as an amorphous solid (7% yield).
LC-MS(01): MS (ESI, m/z): 416.3 [M+H$^+$]; $t_R$=0.43 min.

Example 75 propynoic acid [3-(3-ethyl-ureido)-5-pyridin-4-yl-isoquinolin-8-ylmethyl]-amide

Starting from the compound of Preparation C and propiolic acid and proceeding in analogy to Procedure W, the title compound was obtained, after purification by CC (DCM/MeOH 100:0 to 90:10), as a yellow solid (70% yield).
$^1$H NMR (d6-DMSO) δ: 9.47-9.34 (m, 1H); 9.27 (s, 1H); 9.04 (s, 1H); 8.76-8.66 (m, 2H); 8.08 (s, 1H); 7.63-7.53 (m, 1H); 7.48 (dd, J=1.7 Hz, J=3.6 Hz, 2H); 7.40-7.30 (m, 1H); 7.11-6.95 (m, 1H); 4.90-4.76 (m, 2H); 4.18 (s, 1H); 3.20-3.01 (m, 2H); 1.03 (t, J=7.2 Hz, 3H).
LC-MS(02): MS (ESI, m/z): 374.2 [M+H$^+$]; $t_R$=0.49 min.

Example 76

[3-(3-ethyl-ureido)-5-pyridin-4-yl-isoquinolin-8-ylmethyl]-carbamic acid tert-butyl ester To a solution of di-tert-butyl dicarbonate (22 mg; 1.1 eq.) in dry dioxane (1.5 mL), under inert atmosphere (N$_2$), was added at 0° C. the compound of Preparation C (30 mg; 1.0 eq.). The reaction mixture was stirred overnight at rt. It was then concentrated under reduced pressure and the title compound was obtained, after purification by CC (DCM/MeOH 100:0 to 95:5), as a beige yellow solid (33 mg; 83% yield).
$^1$H NMR (d6-DMSO) δ: 9.31 (s, 1H); 9.05 (s, 1H); 8.73-8.68 (m, 2H); 8.08 (s, 1H); 7.62-7.51 (m, 2H); 7.51-7.44 (m, 2H); 7.34 (d, J=7.3 Hz, 1H); 7.05-6.95 (m, 1H); 4.67 (d, J=5.9 Hz, 2H); 3.18-3.03 (m, 2H); 1.39 (s, 9H); 1.03 (t, J=7.2 Hz, 3H).
LC-MS(02): MS (ESI, m/z): 422.3 [M+H$^+$]; $t_R$=0.72 min.

Example 77

[3-(3-ethyl-ureido)-5-pyridin-4-yl-isoquinolin-8-ylmethyl]-carbamic acid isopropyl ester Starting from the compound of Preparation C and 2-propanol and proceeding in analogy to Procedure Y, however adding an additional portion of activated alcohol (2.0 eq.) after 18 h, the title compound was obtained, after purification by prep-HPLC (acidic conditions), as an amorphous solid (27% yield).

LC-MS(02): MS (ESI, m/z): 408.3 [M+H$^+$]; $t_R$=0.65 min.

Example 78

[3-(3-ethyl-ureido)-5-pyridin-4-yl-isoquinolin-8-ylmethyl]-carbamic acid 2-dimethylamino-ethyl ester Starting from the compound of Preparation C and 2-dimethylaminoethanol and proceeding in analogy to Procedure Y, the title compound was obtained, after purification by prep-HPLC (acidic conditions), as an amorphous solid (50% yield).

LC-MS(01): MS (ESI, m/z): 437.4 [M+H$^+$]; $t_R$=0.39 min.

Example 79

[3-(3-ethyl-ureido)-5-pyridin-4-yl-isoquinolin-8-ylmethyl]-carbamic acid methyl ester Starting from the compound of Preparation C and methanol and proceeding in analogy to Procedure Y, the title compound was obtained, after purification by prep-HPLC (acidic conditions), as an amorphous solid (43% yield).

LC-MS(02): MS (ESI, m/z): 380.3 [M+H$^+$]; $t_R$=0.52 min.

Example 80

[3-(3-ethyl-ureido)-5-pyridin-4-yl-isoquinolin-8-ylmethyl]-carbamic acid 2-pyrrolidin-1-yl-ethyl ester Starting from the compound of Preparation C and 1-(2-hydroxyethyl)pyrrolidine and proceeding in analogy to Procedure Y, the title compound was obtained, after purification by prep-HPLC (acidic conditions), as an amorphous solid (71% yield).

LC-MS(01): MS (ESI, m/z): 463.4 [M+H$^+$]; $t_R$=0.41 min.

Example 81

[3-(3-ethyl-ureido)-5-pyridin-4-yl-isoquinolin-8-ylmethyl]-carbamic acid 2-tert-butoxycarbonylamino-ethyl ester Starting from the compound of Preparation C and N-Boc-2-aminoethanol and proceeding in analogy to Procedure Y, the title compound was obtained, after purification by prep-HPLC (basic conditions), as an amorphous solid (44% yield).

LC-MS(02): MS (ESI, m/z): 509.4 [M+H$^+$]; $t_R$=0.67 min.

Example 82 tert-butyl (2-((((3-(3-ethylureido)-5-(pyridin-4-yl)isoquinolin-8-yl)methyl)carbamoyl)oxy)ethyl)(methyl)carbamate Starting from the compound of Preparation C and tert-butyl N-(2-hydroxyethyl)-N-methylcarbamate and proceeding in analogy to Procedure Y, the title compound was obtained, after purification by prep-HPLC (basic conditions), as an amorphous solid (49% yield).

LC-MS(02): MS (ESI, m/z): 523.5 [M+H$^+$]; $t_R$=0.74 min.

Example 83 tert-butyl 4-(2-((((3-(3-ethylureido)-5-(pyridin-4-yl)isoquinolin-8-yl)methyl)carbamoyl)oxy)ethyl)piperazine-1-carboxylate Starting from the compound of Preparation C and 1-Boc-4-(2-hydroxyethyl)piperazine and proceeding in analogy to Procedure Y, the title compound was obtained, after purification by prep-HPLC (basic conditions), as an amorphous solid (56% yield).

LC-MS(01): MS (ESI, m/z): 578.4 [M+H$^+$]; $t_R$=0.52 min.

Example 84

[3-(3-ethyl-ureido)-5-pyridin-4-yl-isoquinolin-8-ylmethyl]-carbamic acid cyclopropylmethyl ester hydrochloride Starting from the compound of Preparation C and (hydroxymethyl)cyclopropane and proceeding in analogy to Procedure Y, the title compound was obtained, after purification by prep-HPLC (acidic conditions) and HCl treatment, as an amorphous solid (37% yield).

LC-MS(02): MS (ESI, m/z): 420.3 [M+H$^+$]; $t_R$=0.67 min.

Example 85

[3-(3-ethyl-ureido)-5-pyridin-4-yl-isoquinolin-8-ylmethyl]-carbamic acid 3-(2-oxo-pyrrolidin-1-yl)-propyl ester hydrochloride Starting from the compound of Preparation C and 1-(3-hydroxypropyl)-2-pyrrolidone and proceeding in analogy to Procedure Y, the title compound was obtained, after purification by prep-HPLC (acidic conditions) and HCl treatment, as an amorphous solid (55% yield).

LC-MS(02): MS (ESI, m/z): 491.4 [M+H$^+$]; $t_R$=0.54 min.

Example 86

(1-methyl-1H-imidazol-2-yl)methyl[(3-(3-ethylureido)-5-(pyridin-4-yl)isoquinolin-8-yl)methyl]carbamate hydrochloride Starting from the compound of Preparation C and (1-methyl-1H-imidazol-2-yl)methanol and proceeding in analogy to Procedure Y, the title compound was obtained, after purification by prep-HPLC (acidic conditions) and HCl treatment, as an amorphous solid (64% yield).

LC-MS(01): MS (ESI, m/z): 460.3 [M+H$^+$]; $t_R$=0.40 min.

Example 87

(S)-[3-(3-ethyl-ureido)-5-pyridin-4-yl-isoquinolin-8-ylmethyl]-carbamic acid 5-oxo-pyrrolidin-2-ylmethyl ester hydrochloride Starting from the compound of Preparation C and (S)-(+)-5-(hydroxymethyl)-2-pyrrolidinone and proceeding in analogy to Procedure Y, the title compound was obtained, after purification by prep-HPLC (acidic conditions) and HCl treatment, as an amorphous solid (48% yield).
LC-MS(02): MS (ESI, m/z): 463.4 [M+H$^+$]; $t_R$=0.48 min.

Example 88

[3-(3-ethyl-ureido)-5-pyridin-4-yl-isoquinolin-8-ylmethyl]-carbamic acid 3-methyl-3H-imidazol-4-ylmethyl ester hydrochloride Starting from the compound of Preparation C and (1-methyl-1H-imidazol-5-yl)methanol and proceeding in analogy to Procedure Y, the title compound was obtained, after purification by prep-HPLC (acidic conditions) and HCl treatment, as an amorphous solid (61% yield).
LC-MS(01): MS (ESI, m/z): 460.3 [M+H$^+$]; $t_R$=0.40 min.

Example 89

[3-(3-ethyl-ureido)-5-pyridin-4-yl-isoquinolin-8-ylmethyl]-carbamic acid 3-dimethylamino-propyl ester hydrochloride Starting from the compound of Preparation C and 3-dimethylamino-1-propanol and proceeding in analogy to Procedure Y, the title compound was obtained, after purification by prep-HPLC (acidic conditions) and HCl treatment, as an amorphous solid (73% yield).
LC-MS(01): MS (ESI, m/z): 451.2 [M+H$^+$]; $t_R$=0.40 min.

Example 90

N-[3-(3-ethyl-ureido)-5-pyridin-4-yl-isoquinolin-8-ylmethyl]-4-hydroxy-butyramide

90.1. Lithium 4-hydroxybutanoate

To a solution of γ-butyrolactone (170 mg) in MeOH (0.5 mL) were added water (0.2 mL) and lithium hydroxide monohydrate (83 mg). The reaction mixture was stirred at rt for 16 h and concentrated under reduced pressure. The title compound was obtained, without additional purification, as a white solid (243 mg; quantitative yield).

90.2. N-[3-(3-ethyl-ureido)-5-pyridin-4-yl-isoquinolin-8-ylmethyl]-4-hydroxy-butyramide Starting from the compound of Preparation C and crude intermediate 90.1 (1.5 eq.) and proceeding in analogy to Procedure W, the title compound was obtained, after purification by prep-HPLC (basic conditions), as an amorphous solid (40% yield).
$^1$H NMR (d6-DMSO): 9.26 (s, 1H); 9.05 (s, 1H); 8.71 (d, J=5.8 Hz, 2H); 8.48-8.38 (m, 1H); 8.08 (s, 1H); 7.59-7.52 (m, 1H); 7.48 (d, J=5.8 Hz, 2H); 7.36 (d, J=7.2 Hz, 1H); 7.11-6.98 (m, 1H); 4.79 (d, J=4.6 Hz, 2H); 4.47-4.36 (m, 1H); 3.43-3.30 (m, 2H); 3.17-3.02 (m, 2H); 2.19 (t, J=7.3 Hz, 2H); 1.57-1.75 (m, 2H); 1.03 (t, J=7.2 Hz, 3H).
LC-MS(02): MS (ESI, m/z):408.3 [M+H$^+$]; $t_R$=0.41 min.

Example 91

[3-(3-ethyl-ureido)-5-pyridin-4-yl-isoquinolin-8-ylmethyl]-carbamic acid 2-morpholin-4-yl-ethyl ester hydrochloride Starting from the compound of Preparation C and 4-(2-hydroxyethyl)morpholine and proceeding in analogy to Procedure Y, the title compound was obtained, after purification by prep-HPLC (acidic conditions) and HCl treatment, as an amorphous solid (75% yield).
LC-MS(01): MS (ESI, m/z): 479.4 [M+H$^+$]; $t_R$=0.40 min.

Example 92

[3-(3-ethyl-ureido)-5-pyridin-4-yl-isoquinolin-8-ylmethyl]-carbamic acid 3-piperidin-1-yl-propyl ester hydrochloride Starting from the compound of Preparation C and 1-piperidinepropanol and proceeding in analogy to Procedure Y, the title compound was obtained, after purification by prep-HPLC (acidic conditions) and HCl treatment, as an amorphous solid (51% yield).
LC-MS(01): MS (ESI, m/z): 491.4 [M+H$^+$]; $t_R$=0.44 min.

Example 93

[3-(3-ethyl-ureido)-5-pyridin-4-yl-isoquinolin-8-ylmethyl]-carbamic acid 2-(2-oxo-imidazolidin-1-yl)-ethyl ester hydrochloride Starting from the compound of Preparation C and 1-(2-hydroxyethyl)-2-imidazolidinone and proceeding in analogy to Procedure Y, the title compound was obtained, after purification by prep-HPLC (acidic conditions) and HCl treatment, as an amorphous solid (51% yield).
LC-MS(02): MS (ESI, m/z): 478.4 [M+H$^+$]; $t_R$=0.49 min.

Example 94

[3-(3-ethyl-ureido)-5-pyridin-4-yl-isoquinolin-8-ylmethyl]-carbamic acid 3-methoxy-propyl ester hydrochloride Starting from the compound of Preparation C and 3-methoxy-1-propanol and proceeding in analogy to Procedure Y, the title compound was obtained, after purification by prep-HPLC (acidic conditions) and HCl treatment, as an amorphous solid (41% yield).
LC-MS(02): MS (ESI, m/z): 438.3 [M+H$^+$]; $t_R$=0.58 min.

Example 95

N-[3-(3-ethyl-ureido)-5-pyridin-4-yl-isoquinolin-8-ylmethyl]-4-methoxy-butyramide Starting from the compound of Preparation C and 4-methoxybutanoic acid (1.5 eq.) and proceeding in analogy to Procedure W, the title compound was obtained, after purification by prep-HPLC (basic conditions), as an amorphous solid (67% yield).
$^1$H NMR (d6-DMSO): 9.26 (s, 1H); 9.03 (s, 1H); 8.74-8.67 (m, 2H); 8.49-8.40 (m, 1H); 8.08 (s, 1H); 7.56 (d, J=7.3 Hz, 1H); 7.50-7.44 (m, 2H); 7.37 (d, J=7.3 Hz, 1H); 7.07-6.96 (m, 1H); 4.79 (d, J=5.6 Hz, 2H); 3.31-3.24 (m, 2H); 3.17 (s, 3H); 3.14-3.04 (m, 2H); 2.19 (t, J=7.2 Hz, 2H); 1.81-1.66 (m, 2H); 1.03 (t, J=7.2 Hz, 3H).
LC-MS(02): MS (ESI, m/z): 422.3 [M+H$^+$]; t$_R$=0.49 min.

Example 96

[3-(3-ethyl-ureido)-5-pyridin-4-yl-isoquinolin-8-ylmethyl]-carbamic acid carbamoylmethyl ester hydrochloride Starting from the compound of Preparation C and 2-hydroxyacetamide and proceeding in analogy to Procedure Y, the title compound was obtained, after purification by prep-HPLC (acidic conditions) and HCl treatment, as an amorphous solid (57% yield).
LC-MS(02): MS (ESI, m/z): 423.3 [M+H$^+$]; t$_R$=0.43 min.

Example 97

[3-(3-ethyl-ureido)-5-pyridin-4-yl-isoquinolin-8-ylmethyl]-carbamic acid 2-(2,5-dioxo-pyrrolidin-1-yl)-ethyl ester hydrochloride Starting from the compound of Preparation C and N-(2-hydroxyethyl)succinimide and proceeding in analogy to Procedure Y, the title compound was obtained, after purification by prep-HPLC (acidic conditions) and HCl treatment, as an amorphous solid (58% yield).
LC-MS(02): MS (ESI, m/z): 491.4 [M+H$^+$]; t$_R$=0.51 min.

Example 98

[3-(3-ethyl-ureido)-5-pyridin-4-yl-isoquinolin-8-ylmethyl]-carbamic acid 2-piperidin-1-yl-ethyl ester hydrochloride Starting from the compound of Preparation C and 1-(2-hydroxyethyl)piperidine and proceeding in analogy to Procedure Y, the title compound was obtained, after purification by prep-HPLC (acidic conditions) and HCl treatment, as an amorphous solid (77% yield).
LC-MS(01): MS (ESI, m/z): 477.4 [M+H$^+$]; t$_R$=0.42 min.

Example 99

[3-(3-ethyl-ureido)-5-pyridin-4-yl-isoquinolin-8-ylmethyl]-carbamic acid isobutyl ester hydrochloride Starting from the compound of Preparation C and 2-methyl-1-propanol and proceeding in analogy to Procedure Y, the title compound was obtained, after purification by prep-HPLC (acidic conditions) and HCl treatment, as an amorphous solid (24% yield).
LC-MS(02): MS (ESI, m/z): 422.3 [M+H$^+$]; t$_R$=0.72 min.

Example 100

[3-(3-ethyl-ureido)-5-pyridin-4-yl-isoquinolin-8-ylmethyl]-carbamic acid (R)-2-piperidin-3-yl-ethyl ester hydrochloride 100.1. (R)-tert-butyl 3-(2-((((3-(3-ethylureido)-5-(pyridin-4-yl)isoquinolin-8-yl)methyl)carbamoyl)oxy)ethyl)piperidine-1-carboxylate hydrochloride Starting from the compound of Preparation C and (R)-1-N-Boc-piperidine-3-ethanol and proceeding in analogy to Procedure Y, the title compound was obtained, after purification by prep-HPLC (acidic conditions) and HCl treatment, as an amorphous solid (18% yield).
MS (ESI, m/z): 577.4 [M+H$^+$].

100.2. [3-(3-ethyl-ureido)-5-pyridin-4-yl-isoquinolin-8-ylmethyl]-carbamic acid (R)-2-piperidin-3-yl-ethyl ester hydrochloride Starting from intermediate 100.1 and proceeding in analogy to Procedure X, the title compound was obtained, without additional purification, as an amorphous solid (97% yield).
LC-MS(01): MS (ESI, m/z): 477.4 [M+H$^+$]; t$_R$=0.44 min.

Example 101 trans-[3-(3-ethyl-ureido)-5-pyridin-4-yl-isoquinolin-8-ylmethyl]-carbamic acid 4-(aminomethyl)-(cyclohexylmethyl) ester hydrochloride 101.1. trans-[3-(3-ethyl-ureido)-5-pyridin-4-yl-isoquinolin-8-ylmethyl]-carbamic acid 4-(tert-butoxycarbonylamino-methyl)-cyclohexylmethyl ester hydrochloride Starting from the compound of Preparation C and tert-butyl(trans-4-hydroxymethylcyclohexylmethyl)carbamate and proceeding in analogy to Procedure Y, the title compound was obtained, after purification by prep-HPLC (acidic conditions) and HCl treatment, as an amorphous solid (34% yield).
MS (ESI, m/z): 591.4 [M+H$^+$].

101.2. trans-[3-(3-ethyl-ureido)-5-pyridin-4-yl-isoquinolin-8-ylmethyl]-carbamic acid 4-(aminomethyl)-(cyclohexylmethyl)ester hydrochloride Starting from intermediate 101.1 and proceeding in analogy to Procedure X, the title compound was obtained, without additional purification, as an amorphous solid (98% yield).
LC-MS(01): MS (ESI, m/z): 491.4 [M+H$^+$]; t$_R$=0.48 min.

Example 102

(R)-[3-(3-ethyl-ureido)-5-pyridin-4-yl-isoquinolin-8-ylmethyl]-carbamic acid 3,4-dihydroxy-butyl ester hydrochloride 102.1. (R)-[3-(3-ethyl-ureido)-5-pyridin-4-yl-isoquinolin-8-ylmethyl]-carbamic acid 2-(2,2-dimethyl-[1,3]dioxolan-4-yl)-ethyl ester hydrochloride Starting from the compound of Preparation C and (4R)-4-(2-hydroxyethyl)-2,2-dimethyl-1,3-dioxolane and proceeding in analogy to Procedure Y, the title compound was obtained, after purification by prep-HPLC (acidic conditions) and HCl treatment, as an amorphous solid (56% yield).
MS (ESI, m/z): 494.4 [M+H$^+$].

102.2. (R)-[3-(3-ethyl-ureido)-5-pyridin-4-yl-isoquinolin-8-ylmethyl]-carbamic acid 3,4-dihydroxy-butyl ester hydrochloride To the intermediate 102.1 is added 2M aq. HCl (2.2 eq.). The mixture is stirred at rt for 10 min and concentrated under reduced pressure. The title compound was obtained, without additional purification, as an amorphous solid (66% yield).

LC-MS(02): MS (ESI, m/z): 454.4 [M+H$^+$]; $t_R$=0.45 min.

Example 103

(±)-[3-(3-ethyl-ureido)-5-pyridin-4-yl-isoquinolin-8-ylmethyl]-carbamic acid 2,3-dihydroxy-propyl ester hydrochloride

103.1. (±)-[3-(3-ethyl-ureido)-5-pyridin-4-yl-isoquinolin-8-ylmethyl]-carbamic acid 2,2-dimethyl-[1,3]dioxolan-4-ylmethyl ester hydrochloride Starting from the compound of Preparation C and (+/−)-2,2-dimethyl-1,3-dioxolane-4-methanol and proceeding in analogy to Procedure Y, the title compound was obtained, after purification by prep-HPLC (acidic conditions) and HCl treatment, as an amorphous solid (32% yield).

MS (ESI, m/z): 480.4 [M+H$^+$].

103.2. (±)-[3-(3-ethyl-ureido)-5-pyridin-4-yl-isoquinolin-8-ylmethyl]-carbamic acid 2,3-dihydroxy-propyl ester hydrochloride To the intermediate 103.1 is added 2M aq. HCl (2.7 eq.). The mixture is stirred at rt for 10 min and concentrated under reduced pressure. The title compound was obtained, without additional purification, as an amorphous solid (25% yield).

LC-MS(02): MS (ESI, m/z): 440.3 [M+H$^+$]; $t_R$=0.43 min.

Example 104

3-((((3-(3-ethylureido)-5-(pyridin-4-yl)isoquinolin-8-yl)methyl)carbamoyl)oxy)propanoic acid

104.1. tert-butyl 3-((((3-(3-ethylureido)-5-(pyridin-4-yl)isoquinolin-8-yl)methyl)carbamoyl)oxy)propanoate Starting from the compound of Preparation C and tert-butyl 3-hydroxypropionate and proceeding in analogy to Procedure Z, the title compound was obtained, after purification by CC (DCM/MeOH 100:0 to 90:10) and trituration in diethylether, as a white solid (71% yield).

$^1$H NMR (d6-DMSO) δ: 9.31 (s, 1H); 9.04 (s, 1H); 8.75-8.66 (m, 2H); 8.07 (s, 1H); 7.95-7.83 (m, 1H); 7.55 (d, J=7.4 Hz, 1H); 7.50-7.43 (m, 2H); 7.35 (d, J=7.4 Hz, 1H); 7.10-6.98 (m, 1H); 4.26-4.65 (m, 2H); 4.20-4.08 (m, 2H); 3.31-3.22 (m, 2H); 3.18-3.01 (m, 2H); 1.35 (s, 9H); 1.03 (t, J=7.1 Hz, 3H).

MS (ESI, m/z): 494.4 [M+H$^+$].

104.2. 3-((((3-(3-ethylureido)-5-(pyridin-4-yl)isoquinolin-8-yl)methyl)carbamoyl)oxy)propanoic acid Starting from intermediate 104.1 and proceeding in analogy to Procedure V, however adding first triethylsilane (1.1 eq.) and then TFA (30 eq.), the title compound was obtained, after purification by prep-HPLC (basic conditions), as a yellow solid (64% yield).

$^1$H NMR (d6-DMSO) δ: 9.30 (s, 1H); 9.07 (s, 1H); 8.74-8.66 (m, 2H); 8.07 (s, 1H); 7.91-7.82 (m, 1H); 7.55 (d, J=7.3 Hz, 1H); 7.51-7.44 (m, 2H); 7.35 (d, J=7.3 Hz, 1H); 7.13-7.02 (m, 1H); 4.77-4.65 (m, 2H); 4.14 (t, J=6.4 Hz, 2H); 3.16-3.03 (m, 2H); 2.48-2.41 (m, 2H); 1.03 (t, J=7.2 Hz, 3H).

LC-MS(02): MS (ESI, m/z): 438.3 [M+H$^+$]; $t_R$=0.48 min.

Example 105 methyl 3-((((3-(3-ethylureido)-5-(pyridin-4-yl)isoquinolin-8-yl)methyl)carbamoyl)oxy)propanoate hydrochloride Starting from intermediate 104.1 and proceeding in analogy to Procedure V, however adding 4M HCl in dioxane (2.0 eq.), diluting with MeOH (excess) and stirring 2 h at rt after reaction mixture concentration, the title compound was obtained, after purification by prep-HPLC (acidic conditions and HCl treatment), as an amorphous solid (95% yield).

LC-MS(02): MS (ESI, m/z): 452.3 [M+H$^+$]; $t_R$=0.56 min.

Example 106

[3-(3-ethyl-ureido)-5-pyridin-4-yl-isoquinolin-8-ylmethyl]-carbamic acid 4-hydroxy-but-2-ynyl ester Starting from the compound of Preparation C and 2-butyn-1,4-diol and proceeding in analogy to Procedure Z, however using 6.0 eq. of CDI, 6.0 eq. of DIPEA and 3.0 eq. of 2-butyn-1,4-diol for alcohol activation, using NMP instead of DMF and adding 1M NaOH (5.0 eq.) instead of dimethylamine, the title compound was obtained, after purification by CC (DCM/MeOH 100:0 to 90:10) as a yellow solid (61% yield).

$^1$H NMR (d6-DMSO) δ: 9.30 (s, 1H); 9.04 (s, 1H); 8.74-8.67 (m, 2H); 8.14-7.99 (m, 2H); 7.57 (d, J=7.3 Hz, 1H); 7.51-7.44 (m, 2H); 7.36 (d, J=7.3 Hz, 1H); 7.08-6.99 (m, 1H); 5.19 (t, J=6.0 Hz, 1H); 4.75 (d, J=5.4 Hz, 2H); 4.69 (t, J=1.8 Hz, 2H); 4.12-4.03 (m, 2H); 3.17-3.03 (m, 2H); 1.03 (t, J=7.2 Hz, 3H).

LC-MS(02): MS (ESI, m/z): 434.3 [M+H$^+$]; $t_R$=0.51 min.

Example 107

[3-(3-ethyl-ureido)-5-pyridin-4-yl-isoquinolin-8-ylmethyl]-carbamic acid 2-hydroxy-ethyl ester

107.1. 2-(tert-butyl-dimethyl-silanyloxy)-ethanol

To a stirred solution of ethylene glycol (2.44 mL; 6.0 eq.) in dry THF (35 mL), under inert atmosphere (N$_2$), were added imidazole (497 mg; 1.0 eq.) and a solution of tert-butyldimethylsilyl chloride (1.10 g; 1.0 eq.) in dry THF (35 mL). The reaction mixture was stirred at rt over the weekend. Water was added and THF was removed under vacuum. The residual aq. layer was extracted with EA (3×) and the combined org. layers were washed with water, dried over MgSO$_4$, filtered and concentrated under reduced pressure. The title compound was obtained, after purification by CC (Hept/EA 100:0 to 60:40), as a colorless liquid (258 mg; 20% yield).

$^1$H NMR (d6-DMSO) δ: 4.47 (t, J=5.6 Hz, 1H); 3.59-3.52 (m, 2H); 3.43-3.35 (m, 2H); 0.85 (s, 9H); 0.02 (s, 6H).

107.2. [3-(3-ethyl-ureido)-5-pyridin-4-yl-isoquinolin-8-ylmethyl]-carbamic acid 2-(tert-butyl-dimethyl-silanyloxy)-ethyl ester Starting from the compound of Preparation C and intermediate 107.1 and proceeding in analogy to Procedure Z, the title compound was obtained, after purification by CC (DCM/MeOH 100:0 to 98:2), as a yellow solid (87% yield).

¹H NMR (d6-DMSO) δ: 9.32 (s, 1H); 9.03 (s, 1H); 8.74-8.68 (m, 2H); 8.06 (s, 1H); 7.93-7.82 (m, 1H); 7.55 (d, J=7.3 Hz, 1H); 7.50-7.43 (m, 2H); 7.36 (d, J=7.3 Hz, 1H); 7.12-7.01 (m, 1H); 4.72 (d, J=6.0 Hz, 2H); 4.05-3.97 (m, 2H); 3.77-3.67 (m, 2H); 3.18-3.03 (m, 2H); 1.03 (t, J=7.2 Hz, 3H); 0.81 (s, 9H); 0.00 (s, 6H).
MS (ESI, m/z): 524.3 [M+H$^+$].

107.3. [3-(3-ethyl-ureido)-5-pyridin-4-yl-isoquinolin-8-ylmethyl]-carbamic acid 2-hydroxy-ethyl ester Starting from intermediate 107.2 and proceeding in analogy to Procedure AB, the title compound was obtained, after purification by CC (DCM/MeOH 100:0 to 90:10) followed by prep-HPLC (basic conditions), as a white solid (58% yield).
¹H NMR (d6-DMSO) δ: 9.32 (s, 1H); 9.04 (s, 1H); 8.74-8.67 (m, 2H); 8.07 (s, 1H); 7.91-7.79 (m, 1H); 7.56 (d, J=7.3 Hz, 1H); 7.51-7.45 (m, 2H); 7.37 (d, J=7.4 Hz, 1H); 7.07-6.99 (m, 1H); 4.77-4.66 (m, 3H); 3.99 (t, J=5.0 Hz, 2H); 3.53 (q, J=5.3 Hz, 2H); 3.17-3.04 (m, 2H); 1.03 (t, J=7.2 Hz, 3H).
LC-MS(02): MS (ESI, m/z): 410.3 [M+H$^+$]; $t_R$=0.45 min.

Example 108

(±)-[3-(3-ethyl-ureido)-5-pyridin-4-yl-isoquinolin-8-ylmethyl]-carbamic acid 1-methyl-prop-2-ynyl ester Starting from the compound of Preparation C and 3-butyn-2-ol and proceeding in analogy to Procedure Z, however using 3.0 eq. of CDI and 4.0 eq. of DIPEA for activating 3-butyn-2-ol (3.0 eq.), and using NMP instead of DMF, the title compound was obtained, after purification by prep-HPLC (basic conditions), as an amorphous solid (10% yield).
LC-MS(02): MS (ESI, m/z): 418.3 [M+H$^+$]; $t_R$=0.64 min.

Example 109

[3-(3-ethyl-ureido)-5-pyridin-4-yl-isoquinolin-8-ylmethyl]-carbamic acid 4-amino-but-2-ynyl ester Starting from the compound of Example 106 and proceeding in analogy to Procedure F, the title compound was obtained, after purification by CC (DCM/MeOH +1% NH$_4$OH 100:0 to 90:10), as a yellow solid (35% yield).
¹H NMR (d6-DMSO) δ: 9.30 (s, 1H); 9.03 (s, 1H); 8.76-8.66 (m, 2H); 8.08 (s, 1H); 8.07-7.98 (m, 1H); 7.57 (d, J=7.3 Hz, 1H); 7.52-7.44 (m, 2H); 7.36 (d, J=7.4 Hz, 1H); 7.10-6.99 (m, 1H); 4.74 (d, J=5.9 Hz, 2H); 4.66 (t, J=1.9 Hz, 2H); 3.34-3.24 (m, 2H); 3.17-3.03 (m, 2H); 1.03 (t, J=7.2 Hz, 3H).
LC-MS(01): MS (ESI, m/z): 433.2 [M+H$^+$]; $t_R$=0.40 min.

Example 110

[3-(3-ethyl-ureido)-5-pyridin-4-yl-isoquinolin-8-ylmethyl]-carbamic acid 3-morpholin-4-yl-propyl ester Starting from the compound of Preparation C and 4-(3-hydroxypropyl)morpholine and proceeding in analogy to Procedure Z, however adding an additional portion of activated alcohol (2.0 eq.) after 4 days, the title compound was obtained, after purification by prep-HPLC (basic conditions), as a yellow solid (67% yield).
¹H NMR (d6-DMSO) δ: 9.31 (s, 1H); 9.03 (s, 1H); 8.74-8.67 (m, 2H); 8.07 (s, 1H); 7.89-7.75 (m, 1H); 7.56 (d, J=7.3 Hz, 1H); 7.51-7.44 (m, 2H); 7.35 (d, J=7.3 Hz, 1H); 7.09-6.98 (m, 1H); 4.72 (d, J=6.0 Hz, 2H); 4.00 (t, J=6.6 Hz, 2H); 3.59-3.46 (m, 4H); 3.17-3.03 (m, 2H); 2.38-2.21 (m, 6H); 1.79-1.59 (m, 2H); 1.03 (t, J=7.2 Hz, 3H).
LC-MS(01): MS (ESI, m/z): 493.4 [M+H$^+$]; $t_R$=0.41 min.

Example 111

[5-chloro-3-(3-ethyl-ureido)-isoquinolin-8-ylmethyl]-carbamic acid 2-methoxy-ethyl ester Starting from the compound of Preparation B and 2-methoxyethanol and proceeding in analogy to Procedure Y, however using DMF instead of NMP, the title compound was obtained, after purification by CC (DCM/MeOH 100:0 to 95:5), as a beige solid (81% yield).
¹H NMR (d6-DMSO) δ: 9.28 (d, J=0.7 Hz, 1H); 9.21 (s, 1H); 8.38 (d, J=0.5 Hz, 1H); 7.95-7.84 (m, 1H); 7.76 (d, J=7.7 Hz, 1H); 7.23 (d, J=7.7 Hz, 1H); 7.04-6.95 (m, 1H); 4.66 (d, J=6.0 Hz, 2H); 4.11-4.03 (m, 2H); 3.51-3.43 (m, 2H); 3.22 (s, 3H); 3.20-3.11 (m, 2H); 1.08 (t, J=7.2 Hz, 3H).
LC-MS(02): MS (ESI, m/z): 381.2 [M+H$^+$]; $t_R$=0.77 min.

Example 112

[5-chloro-3-(3-ethyl-ureido)-isoquinolin-8-ylmethyl]-carbamic acid prop-2-ynyl ester Starting from the compound of Preparation B and propargyl chloroformate and proceeding in analogy to Procedure P, however filtering the precipitate formed at the end of the reaction, the title compound was obtained, after purification by CC (DCM/MeOH 100:0 to 95:5), as a light yellow solid (47% yield).
¹H NMR (d6-DMSO) δ: 9.28 (d, J=0.7 Hz, 1H); 9.22 (s, 1H); 8.39 (d, J=0.7 Hz, 1H); 8.09-7.98 (m, 1H); 7.77 (d, J=7.7 Hz, 1H); 7.25 (d, J=7.7 Hz, 1H); 6.99 (t, J=5.7 Hz, 1H); 4.70 (d, J=5.9 Hz, 2H); 4.64 (d, J=2.5 Hz, 2H); 3.46 (t, J=2.4 Hz, 1H); 3.24-3.11 (m, 2H); 1.09 (t, J=7.2 Hz, 3H).
LC-MS(02): MS (ESI, m/z): 361.2 [M+H$^+$]; $t_R$=0.82 min.

Example 113

[5-chloro-3-(3-ethyl-ureido)-isoquinolin-8-ylmethyl]-carbamic acid tert-butyl ester To a stirred solution of di-tert-butyl dicarbonate (1.1 eq.) in anhydrous dioxane (6.0 mL) was added the compound of Preparation B (1 mmol; 1.0 eq.) at 0° C. The reaction mixture was stirred at rt for 2 h and concentrated under reduced pressure. The title compound was obtained, after purification by CC (DCM/MeOH 100:0 to 98:2), as a beige solid (84% yield).
¹H NMR (d6-DMSO) δ: 9.27 (s, 1H); 9.22 (s, 1H); 8.37 (d, J=0.7 Hz, 1H); 7.76 (d, J=7.6 Hz, 1H); 7.57-7.45 (m, 1H); 7.22 (d, J=7.7 Hz, 1H); 6.96 (t, J=5.5 Hz, 1H); 4.60 (d, J=5.7 Hz, 2H); 3.24-3.10 (m, 2H); 1.37 (s, 9H); 1.08 (t, J=7.2 Hz, 3H).
LC-MS(02): MS (ESI, m/z): 379.2 [M+H$^+$]; $t_R$=0.97 min.

Example 114

[3-(3-ethyl-ureido)-5-pyridin-4-yl-isoquinolin-8-ylmethyl]-carbamic acid 2-methoxy-ethyl ester Starting from the compound of Example 111 and pyridine-4-boronic acid and proceeding in analogy to Procedure N, the title compound was obtained, after purification by CC (DCM/MeOH 100:0 to 90:10), as a yellow solid (83% yield).

$^1$H NMR (d6-DMSO) δ: 9.31 (d, J=0.7 Hz, 1H); 9.04 (s, 1H); 8.75-8.67 (m, 2H); 8.07 (d, J=0.4 Hz, 1H); 8.00-7.87 (m, 1H); 7.56 (d, J=7.3 Hz, 1H); 7.51-7.45 (m, 2H); 7.36 (d, J=7.3 Hz, 1H); 7.08-6.98 (m, 1H); 4.72 (d, J=5.9 Hz, 2H); 4.14-4.04 (m, 2H); 3.54-3.42 (m, 2H); 3.23 (s, 3H); 3.17-3.03 (m, 2H); 1.03 (t, J=7.2 Hz, 3H).

LC-MS(02): MS (ESI, m/z): 424.3 [M+H$^+$]; $t_R$=0.54 min.

Example 115

[5-(2-amino-pyridin-4-yl)-3-(3-ethyl-ureido)-isoquinolin-8-ylmethyl]-carbamic acid 2-methoxy-ethyl ester Starting from the compound of Example 111 and 2-aminopyridine-4-boronic acid pinacol ester and proceeding in analogy to Procedure N, the title compound was obtained, after purification by CC (DCM/MeOH 100:0 to 90:10), as a yellow solid (85% yield).

$^1$H NMR (d6-DMSO) δ: 9.27 (d, J=0.5 Hz, 1H); 9.02 (s, 1H); 8.08 (s, 1H); 7.99 (dd, J=0.4 Hz, J=5.2 Hz, 1H); 7.95-7.86 (m, 1H); 7.49-7.42 (m, 1H); 7.31 (d, J=7.3 Hz, 1H); 7.13-7.03 (m, 1H); 6.53 (dd, J=1.4 Hz, J=5.2 Hz, 1H); 6.48-6.45 (m, 1H); 6.08-6.00 (m, 2H); 4.70 (d, J=5.8 Hz, 2H); 4.13-4.05 (m, 2H); 3.53-3.43 (m, 2H); 3.23 (s, 3H); 3.18-3.04 (m, 2H); 1.04 (t, J=7.2 Hz, 3H).

LC-MS(01): MS (ESI, m/z): 439.3 [M+H$^+$]; $t_R$=0.52 min.

Example 116

[5-(2,6-dimethyl-pyridin-4-yl)-3-(3-ethyl-ureido)-isoquinolin-8-ylmethyl]-carbamic acid 2-methoxy-ethyl ester Starting from the compound of Example 111 and 2,6-dimethylpyridine-4-boronic acid pinacol ester and proceeding in analogy to Procedure N, the title compound was obtained, after purification by CC (DCM/MeOH 100:0 to 90:10) followed by prep-HPLC (basic conditions), as a white solid (37% yield).

$^1$H NMR (d6-DMSO) δ: 9.29 (s, 1H); 9.05 (s, 1H); 7.98 (s, 1H); 7.97-7.86 (m, 1H); 7.51 (d, J=7.4 Hz, 1H); 7.37-7.28 (m, 1H); 7.27-7.14 (m, 1H); 7.11 (s, 2H); 4.78-4.65 (m, 2H); 4.16-4.01 (m, 2H); 3.54-3.41 (m, 2H); 3.23 (s, 3H); 3.19-3.04 (m, 2H); 2.49 (s, 6H); 1.04 (t, J=7.2 Hz, 3H).

LC-MS(02): MS (ESI, m/z): 452.4 [M+H$^+$]; $t_R$=0.54 min.

Example 117

[3-(3-ethyl-ureido)-5-(2-methoxy-pyridin-4-yl)-isoquinolin-8-ylmethyl]-carbamic acid 2-methoxy-ethyl ester Starting from the compound of Example 111 and 2-methoxypyridine-4-ylboronic acid and proceeding in analogy to Procedure N, the title compound was obtained, after purification by CC (DCM/MeOH 100:0 to 90:10), as a white solid (76% yield).

$^1$H NMR (d6-DMSO) δ: 9.30 (d, J=0.5 Hz, 1H); 9.03 (s, 1H); 8.28 (dd, J=0.5 Hz, J=5.3 Hz, 1H); 8.06 (s, 1H); 7.98-7.87 (m, 1H); 7.58-7.50 (m, 1H); 7.33 (d, J=7.3 Hz, 1H); 7.11-7.01 (m, 2H); 6.86 (d, J=0.6 Hz, 1H); 4.71 (d, J=6.1 Hz, 2H); 4.12-4.04 (m, 2H); 3.92 (s, 3H); 3.53-3.42 (m, 2H); 3.23 (s, 3H); 3.18-3.03 (m, 2H); 1.04 (t, J=7.2 Hz, 3H).

LC-MS(02): MS (ESI, m/z): 454.0 [M+H$^+$]; $t_R$=0.80 min.

Example 118

[3-(3-ethyl-ureido)-5-(2-fluoro-pyridin-4-yl)-isoquinolin-8-ylmethyl]-carbamic acid 2-methoxy-ethyl ester Starting from the compound of Example 111 and 2-fluoropyridine-4-boronic acid and proceeding in analogy to Procedure Q, the title compound was obtained, after purification by CC (DCM/MeOH 100:0 to 90:10) followed by prep-HPLC (basic conditions), as a yellow solid (42% yield).

$^1$H NMR (d6-DMSO) δ: 9.32 (s, 1H); 9.06 (s, 1H); 8.38 (d, J=5.2 Hz, 1H); 8.05 (s, 1H); 8.00-7.88 (m, 1H); 7.62 (d, J=7.3 Hz, 1H); 7.50-7.42 (m, 1H); 7.36 (d, J=7.3 Hz, 1H); 7.31 (s, 1H); 7.14-7.02 (m, 1H); 4.80-4.67 (m, 2H); 4.14-4.04 (m, 2H); 3.53-3.43 (m, 2H); 3.23 (s, 3H); 3.18-3.04 (m, 2H); 1.04 (t, J=7.2 Hz, 3H).

LC-MS(02): MS (ESI, m/z): 442.3 [M+H$^+$]; $t_R$=0.78 min.

Example 119

[3-(3-ethyl-ureido)-5-(2-methyl-pyridin-4-yl)-isoquinolin-8-ylmethyl]-carbamic acid 2-methoxy-ethyl ester Starting from the compound of Example 111 and 2-methylpyridine-4-boronic acid and proceeding in analogy to Procedure Q, the title compound was obtained, after purification by CC (DCM/MeOH 100:0 to 90:10), as a beige yellow solid (74% yield).

$^1$H NMR (d6-DMSO) δ: 9.30 (s, 1H); 9.04 (s, 1H); 8.55 (d, J=5.0 Hz, 1H); 8.03 (s, 1H); 7.99-7.86 (m, 1H); 7.54 (d, J=7.3 Hz, 1H); 7.38-7.31 (m, 2H); 7.29-7.21 (m, 1H); 7.16-7.04 (m, 1H); 4.72 (d, J=5.9 Hz, 2H); 4.12-4.04 (m, 2H); 3.52-3.43 (m, 2H); 3.23 (s, 3H); 3.18-3.04 (m, 2H); 2.54 (s, 3H); 1.04 (t, J=7.2 Hz, 3H).

LC-MS(02): MS (ESI, m/z): 438.3 [M+H$^+$]; $t_R$=0.53 min.

Example 120

[5-(2-cyano-pyridin-4-yl)-3-(3-ethyl-ureido)-isoquinolin-8-ylmethyl]-carbamic acid 2-methoxy-ethyl ester 120.1. [3-(3-ethyl-ureido)-5-(4,4,5,5-tetramethyl-[1,3,2]dioxaborolan-2-yl)-isoquinolin-8-ylmethyl]-carbamic acid 2-methoxy-ethyl ester Starting from the compound of Example 111 (1 g), and proceeding in analogy to Procedure AC, however adding again after 21 h a solution of PCy$_3$ (0.1 eq.), Pd$_2$(dba)$_3$ (0.05 eq.) and bis(pinacolato)diboron (0.5 eq.) in dry dioxane (4.0 mL), the title compound was obtained, after purification by CC (DCM/MeOH 100:0 to 97:3), as a white solid (673 mg; 49% yield).

$^1$H NMR (d6-DMSO) δ: 9.22 (d, J=0.7 Hz, 1H); 9.14 (s, 1H); 8.56 (d, J=0.6 Hz, 1H); 7.92 (d, J=7.0 Hz, 1H); 7.90-7.82 (m, 1H); 7.59-7.49 (m, 1H); 7.25 (d, J=7.1 Hz, 1H); 4.68 (d, J=6.0 Hz, 2H); 4.11-4.02 (m, 2H); 3.51-3.43 (m, 2H); 3.27-3.12 (m, 5H); 1.35 (s, 12H); 1.10 (t, J=7.2 Hz, 3H).

MS (ESI, m/z): 473.4 [M+H$^+$].

120.2. [5-(2-cyano-pyridin-4-yl)-3-(3-ethyl-ureido)-isoquinolin-8-ylmethyl]-carbamic acid 2-methoxy-ethyl ester Starting from intermediate 120.1 and 4-chloro-2-pyridinecarbonitrile and proceeding in analogy to Procedure N, however using 1.4 eq. of chloride and 1.0 eq. of boronic ester, the title compound was obtained, after purification by CC (DCM/MeOH 100:0 to 90:10), as a yellow solid (64% yield).

$^1$H NMR (d6-DMSO) δ: 9.34 (d, J=0.3 Hz, 1H); 9.09 (s, 1H); 8.89 (dd, J=0.4 Hz, J=5.1 Hz, 1H); 8.20 (d, J=0.9 Hz, 1H); 8.01-7.91 (m, 2H); 7.86 (dd, J=1.7 Hz, J=5.1 Hz, 1H); 7.65 (d, J=7.3 Hz, 1H); 7.38 (d, J=7.4 Hz, 1H); 7.22-7.09 (m, 1H); 4.74 (d, J=6.1 Hz, 2H); 4.14-4.03 (m, 2H); 3.53-3.42 (m, 2H); 3.24 (s, 3H); 3.19-3.05 (m, 2H); 1.04 (t, J=7.2 Hz, 3H).

LC-MS(02): MS (ESI, m/z): 449.3 [M+H$^+$]; $t_R$=0.76 min.

Example 121

[3-(3-ethyl-ureido)-5-(3-methyl-pyridin-4-yl)-isoquinolin-8-ylmethyl]-carbamic acid 2-methoxy-ethyl ester Starting from intermediate 120.1 and 4-bromo-3-methylpyridine and proceeding in analogy to Procedure AD, however using 1.2 eq. of bromide, the title compound was obtained, after purification by CC (DCM/MeOH 100:0 to 90:10), as a white solid (42% yield).

$^1$H NMR (d6-DMSO) δ: 9.30 (s, 1H); 8.98 (s, 1H); 8.59 (s, 1H); 8.50 (d, J=4.6 Hz, 1H); 8.00-7.85 (m, 1H); 7.55 (s, 1H); 7.59-7.40 (m, 1H); 7.39-7.30 (m, 1H); 7.24-7.15 (m, 1H); 7.05-6.93 (m, 1H); 4.80-4.68 (m, 2H); 4.17-4.04 (m, 2H); 3.56-3.41 (m, 2H); 3.24 (s, 3H); 3.16-2.99 (m, 2H); 1.98 (s, 3H); 1.01 (t, J=7.1 Hz, 3H).

LC-MS(02): MS (ESI, m/z): 438.4 [M+H$^+$]; $t_R$=0.55 min.

Example 122

[3-(3-ethyl-ureido)-5-(2-hydroxymethyl-pyridin-4-yl)-isoquinolin-8-ylmethyl]-carbamic acid 2-methoxy-ethyl ester Starting from intermediate 120.1 and (4-bromopyridin-2-yl)methanol and proceeding in analogy to Procedure AD, the title compound was obtained, after purification by CC (DCM/MeOH 100:0 to 90:10), as a yellow solid (54% yield).

$^1$H NMR (d6-DMSO) δ: 9.31 (d, J=0.6 Hz, 1H); 9.04 (s, 1H); 8.65-8.55 (m, 1H); 8.02 (s, 1H); 7.98-7.87 (m, 1H); 7.58-7.53 (m, 1H); 7.50 (d, J=0.8 Hz, 1H); 7.41-7.28 (m, 2H); 7.16-7.04 (m, 1H); 5.41 (t, J=5.9 Hz, 1H); 4.73 (d, J=5.9 Hz, 2H); 4.65 (d, J=5.7 Hz, 2H); 4.13-4.04 (m, 2H); 3.54-3.43 (m, 2H); 3.24 (s, 3H); 3.17-3.03 (m, 2H); 1.04 (t, J=7.2 Hz, 3H).

LC-MS(02): MS (ESI, m/z): 454.4 [M+H$^+$]; $t_R$=0.54 min.

Example 123

{3-(3-ethyl-ureido)-5-[(2-morpholin-4-ylmethyl)-pyridin-4-yl]-isoquinolin-8-ylmethyl}-carbamic acid 2-methoxy-ethyl ester 123.1. (4-bromo-pyridin-2-yl)-methanol To a suspension of 4-bromopyridine-2-carboxylic acid (1.00 g; 5 mmol; 1.0 eq.) in dry toluene (7.0 mL), under inert atmosphere (N$_2$), were added TEA (1.5 eq.) and methyl chloroformate (1.5 eq.). The reaction mixture was stirred at rt for 16 h, then the triethylamine hydrochloride was filtered off and the filtrate was concentrated under reduced pressure. The mixed anhydride obtained was dissolved in THF (7.5 mL) and added dropwise to a 1M suspension of LiAlH$_4$ in THF (0.5 eq.) at −78° C. The reaction mixture was stirred at −78° C. for 1 h, and water (0.2 mL) was carefully added followed by 4M NaOH (0.2 mL) and water (0.6 mL). The reaction mixture was stirred overnight at rt and concentrated under reduced pressure. The title compound was then obtained, after purification by CC (Hept/EA 100:0 to 50:50), as a yellow oil (44% yield).

$^1$H NMR (d6-DMSO) δ: 8.35 (d, J=5.3 Hz, 1H); 7.66-7.60 (m, 1H); 7.53-7.47 (m, 1H); 5.51 (t, J=5.9 Hz, 1H); 4.54 (d, J=5.9 Hz, 2H).

MS (ESI, m/z): 188.1 [M+H$^+$].

123.2. 4-bromo-2-(chloromethyl)pyridine

Starting from intermediate 123.1 and proceeding in analogy to Procedure AE, the title compound was obtained, without additional purification, as a yellow oil (83% yield).

$^1$H NMR (d6-DMSO) δ: 8.44 (d, J=5.2 Hz, 1H); 7.83 (s, 1H); 7.68-7.59 (m, 1H); 4.75 (s, 2H).

MS (ESI, m/z): 208.1 [M+H$^+$].

123.3. 4-(4-bromo-pyridin-2-ylmethyl)-morpholine

Starting from intermediate 123.2 and morpholine (4.0 eq) and proceeding in analogy to Procedure S, the title compound was obtained, after purification by CC (Hept/EA 100:0 to 50:50), as a yellow oil (70% yield).

$^1$H NMR (d6-DMSO) δ: 8.37 (d, J=5.2 Hz, 1H); 7.65 (d, J=1.7 Hz, 1H); 7.53 (dd, J=2.0 Hz, J=5.3 Hz, 1H); 3.61-3.51 (m, 6H); 2.4-2.34 (m, 4H).

MS (ESI, m/z): 259.0 [M+H$^+$].

123.4. {3-(3-ethyl-ureido)-5-[(2-morpholin-4-ylmethyl)-pyridin-4-yl]-isoquinolin-8-ylmethyl}-carbamic acid 2-methoxy-ethyl ester Starting from intermediate 120.1 and intermediate 123.3 and proceeding in analogy to Procedure AD, the title compound was obtained, after purification by prep-HPLC (basic conditions) followed by CC (DCM/MeOH 100:0 to 90:10), as a white solid (58% yield).

$^1$H NMR (d6-DMSO) δ: 9.31 (s, 1H); 9.01 (s, 1H); 8.63 (d, J=5.1 Hz, 1H); 8.08 (s, 1H); 8.01-7.85 (m, 1H); 7.55 (d, J=7.3 Hz, 1H); 7.50 (s, 1H); 7.41-7.29 (m, 2H); 6.98-6.83 (m, 1H); 4.72 (d, J=5.9 Hz, 2H); 4.14-4.03 (m, 2H); 3.66 (s, 2H); 3.59-3.50 (m, 4H); 3.52-3.43 (m, 2H); 3.23 (s, 3H); 3.14-3.00 (m, 2H); 2.52-2.44 (m, 4H); 1.02 (t, J=7.2 Hz, 3H).

LC-MS(01): MS (ESI, m/z): 523.4 [M+H$^+$]; $t_R$=0.56 min.

Example 124

[3-(3-ethyl-ureido)-5-pyridazin-4-yl-isoquinolin-8-ylmethyl]-carbamic acid tert-butyl ester 124.1. [3-(3-ethyl-ureido)-5-(4,4,5,5-tetramethyl-[1,3,2]dioxaborolan-2-yl)-isoquinolin-8-ylmethyl]-carbamic acid tert-butyl ester Starting from the compound of Example 113 and proceeding in analogy to Procedure AC, the title compound was obtained, after purification by CC (DCM/MeOH 100:0 to 98:2), as a beige solid (93% yield).

$^1$H NMR (d6-DMSO) δ: 9.22 (s, 1H); 9.14 (s, 1H); 8.56 (s, 1H); 7.92 (d, J=7.0 Hz, 1H); 7.58-7.42 (m, 2H); 7.24 (d, J=7.0 Hz, 1H); 4.68-4.54 (m, 2H); 3.25-3.12 (m, 2H); 1.37 (s, 9H); 1.34 (s, 12H); 1.09 (t, J=7.2 Hz, 3H).

MS (ESI, m/z): 471.5 [M+H$^+$].

124.2. [3-(3-ethyl-ureido)-5-pyridazin-4-yl-isoquinolin-8-ylmethyl]-carbamic acid tert-butyl ester Starting from intermediate 124.1 and 4-bromopyridazine hydrobromide and proceeding in analogy to Procedure AD, the title compound was obtained, after purification by CC (DCM/MeOH 100:0 to 90:10), as a yellow solid (53% yield).
$^1$H NMR (d6-DMSO) δ: 9.41-9.36 (m, 2H); 9.34 (s, 1H); 9.10 (s, 1H); 8.04 (s, 1H); 7.84 (dd, J=2.6 Hz, J=5.1 Hz, 1H); 7.68 (d, J=7.3 Hz, 1H); 7.63-7.53 (m, 1H); 7.37 (d, J=7.4 Hz, 1H); 7.06-6.96 (m, 1H); 4.69 (d, J=6.0 Hz, 2H); 3.18-3.04 (m, 2H); 1.39 (s, 9H); 1.03 (t, J=7.2 Hz, 3H).
LC-MS(02): MS (ESI, m/z): 423.3 [M+H$^+$]; $t_R$=0.80 min.

Example 125

[3-(3-ethyl-ureido)-5-pyridin-3-yl-isoquinolin-8-ylmethyl]-carbamic acid prop-2-ynyl ester hydrochloride 125.1. 1-(8-(aminomethyl)-5-(pyridin-3-yl)isoquinolin-3-yl)-3-ethylurea Starting from the compound of Preparation B and 3-pyridinylboronic acid and proceeding in analogy to Procedure N, the title compound was obtained, without additional purification, as an amorphous solid (quantitative yield).
MS (ESI, m/z): 322.3 [M+H$^+$].

125.2. [3-(3-ethyl-ureido)-5-pyridin-3-yl-isoquinolin-8-ylmethyl]-carbamic acid prop-2-ynyl ester hydrochloride Starting from intermediate 125.1 and propargyl alcohol and proceeding in analogy to Procedure Y, the title compound was obtained, after purification by prep-HPLC (acidic conditions) and HCl treatment, as an amorphous solid (53% yield).
LC-MS(02): MS (ESI, m/z): 404.3 [M+H$^+$]; $t_R$=0.63 min.

Example 126

[3-(3-ethyl-ureido)-5-(3-methyl-pyridin-4-yl)-isoquinolin-8-ylmethyl]-carbamic acid prop-2-ynyl ester 126.1. [3-(3-ethyl-ureido)-5-(3-methyl-pyridin-4-yl)-isoquinolin-8-ylmethyl]-carbamic acid tert-butyl ester Starting from intermediate 124.1 and 4-bromo-3-methylpyridine and proceeding in analogy to Procedure AD, the title compound was obtained, after purification by CC (DCM/MeOH 100:0 to 90:10), as a beige solid (43% yield).
$^1$H NMR (d6-DMSO) δ: 9.30 (s, 1H); 9.00 (s, 1H); 8.59 (s, 1H); 8.50 (d, J=4.8 Hz, 1H); 7.60-7.50 (m, 2H); 7.48-7.40 (m, 1H); 7.36-7.28 (m, 1H); 7.19 (d, J=4.9 Hz, 1H); 7.01-6.91 (m, 1H); 4.73-4.63 (m, 2H); 3.14-3.01 (m, 2H); 1.98 (s, 3H); 1.40 (s, 9H); 1.01 (t, J=7.2 Hz, 3H).
MS (ESI, m/z): 436.2 [M+H$^+$].

126.2. 1-(8-(aminotnethyl)-5-(3-methylpyridin-4-yl) isoquinolin-3-yl)-3-ethylurea Starting from intermediate 126.1 and proceeding in analogy to Procedure AF, the title compound was obtained, without additional purification, as an amorphous solid (quantitative yield).
$^1$H NMR (d6-DMSO) δ: 9.34 (s, 1H); 8.96 (s, 1H); 8.57 (d, J=5.4 Hz, 2H); 8.50 (d, J=4.9 Hz, 1H); 7.54-7.50 (m, 1H); 7.46-7.39 (m, 1H); 7.33-7.25 (m, 1H); 7.19 (d, J=4.9 Hz, 1H); 6.95-6.87 (m, 1H); 4.30 (s, 1H); 3.89-3.74 (m, 2H); 3.14-3.00 (m, 2H); 1.98 (s, 3H); 1.01 (t, J=7.2 Hz, 3H).
MS (ESI, m/z): 336.2 [M+H$^+$].

126.3. [3-(3-ethyl-ureido)-5-(3-methyl-pyridin-4-yl)-isoquinolin-8-ylmethyl]-carbamic acid prop-2-ynyl ester Starting from intermediate 126.2 and propargyl chloroformate and proceeding in analogy to Procedure P, the title compound was obtained, after purification by prep-HPLC (basic conditions), as a white solid (17% yield).
$^1$H NMR (d6-DMSO) δ: 9.29 (d, J=0.5 Hz, 1H); 8.99 (s, 1H); 8.59 (s, 1H); 8.54-8.46 (m, 1H); 8.14-8.00 (m, 1H); 7.56 (s, 1H); 7.49-7.40 (m, 1H); 7.39-7.30 (m, 1H); 7.19 (d, J=4.3 Hz, 1H); 7.05-6.94 (m, 1H); 4.82-4.71 (m, 2H); 4.66 (d, J=2.0 Hz, 2H); 3.56-3.40 (m, 1H); 3.16-2.99 (m, 2H); 1.98 (s, 3H); 1.01 (t, J=7.1 Hz, 3H).
LC-MS(02): MS (ESI, m/z): 418.3 [M+H$^+$]; $t_R$=0.59 min.

Example 127

[3-(3-ethyl-ureido)-5-pyridazin-4-yl-isoquinolin-8-ylmethyl]-carbamic acid prop-2-ynyl ester 127.1. 1-[8-(aminomethyl)-5-pyridazin-4-yl-isoquinolin-3-yl]-3-ethyl-urea Starting from the compound of Example 124 and proceeding in analogy to Procedure AF, the title compound was obtained, after purification by CC (DCM/MeOH +1% NH$_4$OH 100:0 to 80:20), as a yellow solid (88% yield).
$^1$H NMR (d6-DMSO) δ: 9.41-9.35 (m, 2H); 9.32 (s, 1H); 9.08 (d, J=6.9 Hz, 1H); 8.05-8.00 (m, 1H); 7.87-7.81 (m, 1H); 7.72-7.63 (m, 1H); 7.57-7.49 (m, 1H); 7.17-6.99 (m, 1H); 4.91 (s, 1H); 4.36 (s, 1H); 3.18-3.04 (m, 2H); 2.00 (s, 2H); 1.04 (t, J=7.3 Hz, 3H).
MS (ESI, m/z): 323.3 [M+H$^+$].

127.2. [3-(3-ethyl-ureido)-5-pyridazin-4-yl-isoquinolin-8-ylmethyl]-carbamic acid prop-2-ynyl ester Starting from intermediate 127.1 and propargyl chloroformate and proceeding in analogy to Procedure P, however adding more propargyl chloroformate (1.2 eq.) after 5 h, the title compound was obtained, after purification by CC (DCM/MeOH 100:0 to 90:10), as a beige solid (23% yield).
$^1$H NMR (d6-DMSO) δ: 9.41-9.35 (m, 2H); 9.33 (s, 1H); 9.09 (s, 1H); 8.14-8.05 (m, 1H); 8.04 (s, 1H); 7.84 (dd, J=2.5 Hz, J=5.2 Hz, 1H); 7.68 (d, J=7.3 Hz, 1H); 7.39 (d, J=7.4 Hz, 1H); 7.09-6.99 (m, 1H); 4.76 (d, J=5.9 Hz, 2H); 4.65 (d, J=2.4 Hz, 2H); 3.47 (t, J=2.4 Hz, 1H); 3.17-3.04 (m, 2H); 1.04 (t, J=7.2 Hz, 3H).
LC-MS(02): MS (ESI, m/z): 405.3 [M+H$^+$]; $t_R$=0.66 min.

Example 128

[5-(2-cyano-pyridin-4-yl)-3-(3-ethyl-ureido)-isoquinolin-8-ylmethyl]-carbamic acid prop-2-ynyl ester 128.1. Tert-butyl((5-(2-cyanopyridin-4-yl)-3-(3-ethylureido)isoquinolin-8-yl)methyl)carbamate Starting from intermediate 124.1 and 4-chloro-2-pyridinecarbonitrile and proceeding in analogy to Procedure Q, however using 1.0 eq. of boronic ester and 1.2 eq. of chloride, the title compound was obtained, after purification by CC (DCM/MeOH 100:0 to 90:10), as a yellow solid (88% yield).

¹H NMR (d6-DMSO) δ: 9.33 (s, 1H); 9.10 (s, 1H); 8.89 (dd, J=0.7 Hz, J=5.1 Hz, 1H); 8.20 (dd, J=0.7 Hz, J=1.6 Hz, 1H); 7.99 (s, 1H); 7.86 (dd, J=1.7 Hz, J=5.1 Hz, 1H); 7.65 (d, J=7.3 Hz, 1H); 7.62-7.54 (m, 1H); 7.36 (d, J=7.3 Hz, 1H); 7.18-7.08 (m, 1H); 4.68 (d, J=6.0 Hz, 2H); 3.18-3.05 (m, 2H); 1.39 (s, 9H); 1.04 (t, J=7.3 Hz, 3H).

MS (ESI, m/z): 447.2 [M+H⁺].

128.2. 1-[8-(aminomethyl)-5-(2-cyanopyridin-4-yl)isoquinolin-3-yl]-3-ethylurea Starting from intermediate 128.1 and proceeding in analogy to Procedure AF, the title compound was obtained, without additional purification, as an amorphous solid (quantitative yield).

MS (ESI, m/z): 347.2 [M+H⁺].

128.3. [5-(2-cyano-pyridin-4-yl)-3-(3-ethyl-ureido)-isoquinolin-8-ylmethyl]-carbamic acid prop-2-ynyl ester Starting from intermediate 128.2 and propargyl chloroformate (2.0 eq.) and proceeding in analogy to Procedure P, the title compound was obtained, after purification by CC (DCM/MeOH 100:0 to 90:10) followed by prep-HPLC (basic conditions), as a beige solid (12% yield).

¹H NMR (d6-DMSO) δ: 9.33 (s, 1H); 9.10 (s, 1H); 8.89 (dd, J=0.7 Hz, J=5.0 Hz, 1H); 8.24-8.17 (m, 1H); 8.15-8.05 (m, 1H); 7.98 (s, 1H); 7.86 (dd, J=1.7 Hz, J=5.1 Hz, 1H); 7.66 (d, J=7.2 Hz, 1H); 7.38 (d, J=7.4 Hz, 1H); 7.22-7.07 (m, 1H); 4.76 (d, J=5.8 Hz, 2H); 4.65 (d, J=2.4 Hz, 2H); 3.51-3.44 (m, 1H); 3.19-3.05 (m, 2H); 1.04 (t, J=7.2 Hz, 3H).

LC-MS(02): MS (ESI, m/z): 429.3 [M+H⁺]; $t_R$=0.81 min.

Example 129 propynoic acid [3-(3-ethyl-ureido)-5-pyridazin-4-yl-isoquinolin-8-ylmethyl]-amide Starting from intermediate 127.1 and propiolic acid and proceeding in analogy to Procedure W, the title compound was obtained, after purification by CC (DCM/MeOH 100:0 to 90:10), as a yellow solid (46% yield).

¹H NMR (d6-DMSO) δ: 9.47-9.35 (m, 3H); 9.30 (d, J=0.7 Hz, 1H); 9.09 (s, 1H); 8.05 (d, J=0.6 Hz, 1H); 7.84 (dd, J=2.5 Hz, J=5.2 Hz, 1H); 7.69 (d, J=7.3 Hz, 1H); 7.39 (d, J=7.3 Hz, 1H); 7.09-6.98 (m, 1H); 4.86 (d, J=5.8 Hz, 2H); 4.19 (s, 1H); 3.18-3.04 (m, 2H); 1.04 (t, J=7.2 Hz, 3H).

LC-MS(02): MS (ESI, m/z): 375.2 [M+H⁺]; $t_R$=0.57 min.

Example 130

3-cyclopropyl-N-[3-(3-ethyl-ureido)-5-pyridin-4-yl-isoquinolin-8-ylmethyl]-propionamide Starting from the compound of Preparation C and 3-cyclopropylpropanoic acid (1.5 eq.) and proceeding in analogy to Procedure W, the title compound was obtained, after purification by CC (DCM/MeOH 100:0 to 90:10), as a yellow solid (76% yield).

¹H NMR (d6-DMSO): 9.26 (d, J=0.7 Hz, 1H); 9.03 (s, 1H); 8.74-8.67 (m, 2H), 8.48-8.38 (m, 1H), 8.07 (d, J=0.5 Hz, 1H); 7.56 (d, J=7.3 Hz, 1H); 7.50-7.44 (m, 2H); 7.37 (d, J=7.3 Hz, 1H); 7.08-6.97 (m, 1H); 4.79 (d, J=5.7 Hz, 2H); 3.16-3.04 (m, 2H); 2.27-2.17 (m, 2H); 1.48-1.37 (m, 2H); 1.03 (t, J=7.2 Hz, 3H); 0.71-0.59 (m, 1H); 0.37-0.28 (m, 2H); 0.04 to −0.03 (m, 2H).

LC-MS(02): MS (ESI, m/z): 418.3 [M+H⁺]; $t_R$=0.60 min.

Example 131

[5-(6-amino-pyridin-3-yl)-3-(3-ethyl-ureido)-isoquinolin-8-ylmethyl]-carbamic acid prop-2-ynyl ester hydrochloride

131.1. 1-(8-(aminomethyl)-5-(6-aminopyridin-3-yl)isoquinolin-3-yl)-3-ethylurea Starting from the compound of Preparation B and 2-aminopyridine-5-boronic acid pinacol ester (1.1 eq.) and proceeding in analogy to Procedure N, however adding acetic acid (1.5 eq.) before the SCX treatment, the title compound was obtained, without additional purification, as an amorphous solid.

MS (ESI, m/z): 337.3 [M+H⁺].

131.2. [5-(6-amino-pyridin-3-yl)-3-(3-ethyl-ureido)-isoquinolin-8-ylmethyl]-carbamic acid prop-2-ynyl ester hydrochloride Starting from intermediate 131.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (44% yield).

LC-MS(01): MS (ESI, m/z): 419.3 [M+H⁺]; $t_R$=0.55 min.

Example 132

{5-[3-(acetylamino-methyl)-phenyl]-3-(3-ethyl-ureido)-isoquinolin-8-ylmethyl}-carbamic acid prop-2-ynyl ester hydrochloride

132.1. N-(3-(8-(aminomethyl)-3-(3-ethylureido)isoquinolin-5-yl)benzyl)acetamide Starting from the compound of Preparation B and 3-acetamidomethylphenylboronic acid (1.1 eq.) and proceeding in analogy to Procedure N, however adding acetic acid (1.5 eq.) before the SCX treatment, the title compound was obtained, without additional purification, as an amorphous solid.

MS (ESI, m/z): 392.3 [M+H⁺].

132.2. {5-[3-(acetylamino-methyl)-phenyl]-3-(3-ethyl-ureido)-isoquinolin-8-ylmethyl}-carbamic acid prop-2-ynyl ester hydrochloride Starting from intermediate 132.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (56% yield).

LC-MS(02): MS (ESI, m/z): 474.4 [M+H⁺]; $t_R$=0.79 min.

Example 133

[3-(3-ethyl-ureido)-5-(3-hydroxy-phenyl)-isoquinolin-8-ylmethyl]-carbamic acid prop-2-ynyl ester hydrochloride

133.1. 1-(8-(aminotnethyl)-5-(3-hydroxyphenyl)isoquinolin-3-yl)-3-ethylurea Starting from the compound of Preparation B and 3-hydroxyphenylboronic acid (1.1 eq.) and proceeding in analogy to Procedure N, however adding acetic acid (1.5 eq.) before the SCX treatment, the title compound was obtained, without additional purification, as an amorphous solid.
MS (ESI, m/z): 337.3 [M+H$^+$].

133.2. [3-(3-ethyl-ureido)-5-(3-hydroxy-phenyl)-isoquinolin-8-ylmethyl]-carbamic acid prop-2-ynyl ester hydrochloride Starting from intermediate 133.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (41% yield).
LC-MS(02): MS (ESI, m/z): 419.3 [M+H$^+$]; $t_R$=0.81 min.

Example 134 prop-2-yn-1-yl((5-(3-((dimethylamino)methyl)phenyl)-3-(3-ethylureido)isoquinolin-8-yl)methyl)carbamate hydrochloride

134.1. 1-(8-(aminomethyl)-5-(3-((dimethylamino)methyl)phenyl)isoquinolin-3-yl)-3-ethylurea Starting from the compound of Preparation B and 3-[(N,N-dimethylamino)methyl]benzeneboronic acid pinacol ester hydrochloride (1.1 eq.) and proceeding in analogy to Procedure N, however adding acetic acid (1.5 eq.) before the SCX treatment, the title compound was obtained, without additional purification, as an amorphous solid.
MS (ESI, m/z): 378.3 [M+H$^+$].

134.2. Prop-2-yn-1-yl((5-(3-((dimethylamino)methyl)phenyl)-3-(3-ethylureido)isoquinolin-8-yl)methyl)carbamate hydrochloride Starting from intermediate 134.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (54% yield).
LC-MS(01): MS (ESI, m/z): 460.4 [M+H$^+$]; $t_R$=0.63 min.

Example 135

{3-[3-(3-ethyl-ureido)-8-(prop-2-ynyloxycarbonylamino-methyl)-isoquinolin-5-yl]-phenyl}-acetic acid hydrochloride

135.1. 2-(3-(8-(aminomethyl)-3-(3-ethylureido)isoquinolin-5-yl)phenyl)acetic acid Starting from the compound of Preparation B and phenylacetic acid-3-boronic acid pinacol ester (1.1 eq.) and proceeding in analogy to Procedure N, however adding acetic acid (1.5 eq.) before the SCX treatment, the title compound was obtained, without additional purification, as an amorphous solid.
MS (ESI, m/z): 379.3 [M+H$^+$].

135.2. {3-[3-(3-ethyl-ureido)-8-(prop-2-ynyloxycarbonylamino-methyl)-isoquinolin-5-yl]-phenyl}-acetic acid hydrochloride Starting from intermediate 135.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (28% yield).
LC-MS(02): MS (ESI, m/z): 461.3 [M+H$^+$]; $t_R$=0.81 min.

Example 136

[5-(3-carbamoyl-phenyl)-3-(3-ethyl-ureido)-isoquinolin-8-ylmethyl]-carbamic acid prop-2-ynyl ester hydrochloride

136.1. 3-(8-(aminotnethyl)-3-(3-ethylureido)isoquinolin-5-yl)benzamide

Starting from the compound of Preparation B and 3-aminocarbonylphenylboronic acid (1.1 eq.) and proceeding in analogy to Procedure N, however adding acetic acid (1.5 eq.) before the SCX treatment, the title compound was obtained, without additional purification, as an amorphous solid.
MS (ESI, m/z): 364.3 [M+H$^+$].

136.2. [5-(3-carbamoyl-phenyl)-3-(3-ethyl-ureido)-isoquinolin-8-ylmethyl]-carbamic acid prop-2-ynyl ester hydrochloride Starting from intermediate 136.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (32% yield).
LC-MS(02): MS (ESI, m/z): 446.3 [M+H$^+$]; $t_R$=0.74 min.

Example 137

4-[3-(3-ethyl-ureido)-8-(prop-2-ynyloxycarbonylamino-methyl)-isoquinolin-5-yl]-benzoic acid hydrochloride

137.1. 4-(8-(aminotnethyl)-3-(3-ethylureido)isoquinolin-5-yl)benzoic acid

Starting from the compound of Preparation B and 4-carboxyphenylboronic acid (1.1 eq.) and proceeding in analogy to Procedure N, however adding acetic acid (1.5 eq.) before the SCX treatment, the title compound was obtained, without additional purification, as an amorphous solid.
MS (ESI, m/z): 365.2 [M+H$^+$].

137.2. 4-[3-(3-ethyl-ureido)-8-(prop-2-ynyloxycarbonylamino-methyl)-isoquinolin-5-yl]-benzoic acid hydrochloride Starting from intermediate 137.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (11% yield).

LC-MS(02): MS (ESI, m/z): 447.3 [M+H$^+$]; $t_R$=0.79 min.

Example 138

[3-(3-ethyl-ureido)-5-(4-hydroxy-phenyl)-isoquinolin-8-ylmethyl]-carbamic acid prop-2-ynyl ester hydrochloride 138.1. 1-(8-(aminotnethyl)-5-(4-hydroxyphenyl)isoquinolin-3-yl)-3-ethylurea Starting from the compound of Preparation B and 4-hydroxyphenylboronic acid (1.1 eq.) and proceeding in analogy to Procedure N, however adding acetic acid (1.5 eq.) before the SCX treatment, the title compound was obtained, without additional purification, as an amorphous solid.

MS (ESI, m/z): 337.3 [M+H$^+$].

138.2. [3-(3-ethyl-ureido)-5-(4-hydroxy-phenyl)-isoquinolin-8-ylmethyl]-carbamic acid prop-2-ynyl ester hydrochloride Starting from intermediate 138.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (41% yield).

LC-MS(02): MS (ESI, m/z): 419.3 [M+H$^+$]; $t_R$=0.79 min.

Example 139

[3-(3-ethyl-ureido)-5-(2-hydroxy-phenyl)-isoquinolin-8-ylmethyl]-carbamic acid prop-2-ynyl ester hydrochloride 139.1. 1-(8-(aminomethyl)-5-(2-hydroxyphenyl)isoquinolin-3-yl)-3-ethylurea Starting from the compound of Preparation B and 2-hydroxyphenylboronic acid (1.1 eq.) and proceeding in analogy to Procedure N, however adding acetic acid (1.5 eq.) before the SCX treatment, the title compound was obtained, without additional purification, as an amorphous solid.

MS (ESI, m/z): 337.2 [M+H$^+$].

139.2. [3-(3-ethyl-ureido)-5-(2-hydroxy-phenyl)-isoquinolin-8-ylmethyl]-carbamic acid prop-2-ynyl ester hydrochloride Starting from intermediate 139.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (29% yield).

LC-MS(02): MS (ESI, m/z): 419.3 [M+H$^+$]; $t_R$=0.83 min.

Example 140

[3-(3-ethyl-ureido)-5-pyrimidin-5-yl-isoquinolin-8-ylmethyl]-carbamic acid prop-2-ynyl ester hydrochloride 140.1. 1-(8-(aminomethyl)-5-(pyrimidin-5-yl)isoquinolin-3-yl)-3-ethylurea Starting from the compound of Preparation B and pyrimidin-4-ylboronic acid (1.1 eq.) and proceeding in analogy to Procedure N, however adding acetic acid (1.5 eq.) before the SCX treatment, the title compound was obtained, without additional purification, as an amorphous solid.

MS (ESI, m/z): 323.3 [M+H$^+$].

140.2. [3-(3-ethyl-ureido)-5-pyrimidin-5-yl-isoquinolin-8-ylmethyl]-carbamic acid prop-2-ynyl ester hydrochloride Starting from intermediate 140.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (47% yield).

LC-MS(02): MS (ESI, m/z): 405.3 [M+H$^+$]; $t_R$=0.69 min.

Example 141

[5-(4-carbamoyl-phenyl)-3-(3-ethyl-ureido)-isoquinolin-8-ylmethyl]-carbamic acid prop-2-ynyl ester hydrochloride 141.1. 4-(8-(aminotnethyl)-3-(3-ethylureido)isoquinolin-5-yl)benzamide Starting from the compound of Preparation B and 4-aminocarbonylphenylboronic acid (1.1 eq.) and proceeding in analogy to Procedure N, however adding acetic acid (1.5 eq.) before the SCX treatment, the title compound was obtained, without additional purification, as an amorphous solid.

MS (ESI, m/z): 364.3 [M+H$^+$].

141.2. [5-(4-carbamoyl-phenyl)-3-(3-ethyl-ureido)-isoquinolin-8-ylmethyl]-carbamic acid prop-2-ynyl ester hydrochloride Starting from intermediate 141.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (10% yield).

LC-MS(02): MS (ESI, m/z): 446.3 [M+H$^+$]; $t_R$=0.72 min.

Example 142

[3-(3-ethyl-ureido)-5-(6-hydroxymethyl-pyridin-3-yl)-isoquinolin-8-ylmethyl]-carbamic acid prop-2-ynyl ester hydrochloride 142.1. 1-(8-(aminomethyl)-5-(6-(hydroxymethyl)pyridin-3-yl)isoquinolin-3-yl)-3-ethylurea Starting from the compound of Preparation B and 6-(hydroxymethyl)pyridine-3-boronic acid (1.1 eq.) and proceeding in analogy to Procedure N, however adding acetic acid (1.5 eq.) before the SCX treatment, the title compound was obtained, without additional purification, as an amorphous solid.
MS (ESI, m/z): 352.3 [M+H$^+$].

142.2. [3-(3-ethyl-ureido)-5-(6-hydroxymethyl-pyridin-3-yl)-isoquinolin-8-ylmethyl]-carbamic acid prop-2-ynyl ester hydrochloride Starting from intermediate 142.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (21% yield).
LC-MS(02): MS (ESI, m/z): 434.3 [M+H$^+$]; $t_R$=0.61 min.

Example 143

[3-(3-ethyl-ureido)-5-(4-hydroxymethyl-phenyl)-isoquinolin-8-ylmethyl]-carbamic acid prop-2-ynyl ester hydrochloride 143.1. 1-(8-(aminomethyl)-5-(4-(hydroxymethyl)phenyl)isoquinolin-3-yl)-3-ethylurea Starting from the compound of Preparation B and 4-hydroxymethylphenylboronic acid (1.1 eq.) and proceeding in analogy to Procedure N, however adding acetic acid (1.5 eq.) before the SCX treatment, the title compound was obtained, without additional purification, as an amorphous solid.
MS (ESI, m/z): 351.3 [M+H$^+$].

143.2. [3-(3-ethyl-ureido)-5-(4-hydroxymethyl-phenyl)-isoquinolin-8-ylmethyl]-carbamic acid prop-2-ynyl ester hydrochloride Starting from intermediate 143.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (31% yield).
LC-MS(02): MS (ESI, m/z): 433.3 [M+H$^+$]; $t_R$=0.78 min.

Example 144

[5-(2-amino-pyridin-4-yl)-3-(3-ethyl-ureido)-isoquinolin-8-ylmethyl]-carbamic acid prop-2-ynyl ester hydrochloride 144.1. 1-(8-(aminomethyl)-5-(2-aminopyridin-4-yl)isoquinolin-3-yl)-3-ethylurea Starting from the compound of Preparation B and 2-aminopyridine-4-boronic acid pinacol ester (1.1 eq.) and proceeding in analogy to Procedure N, however adding acetic acid (1.5 eq.) before the SCX treatment, the title compound was obtained, without additional purification, as an amorphous solid.
MS (ESI, m/z): 337.3 [M+H$^+$].

144.2. [5-(2-amino-pyridin-4-yl)-3-(3-ethyl-ureido)-isoquinolin-8-ylmethyl]-carbamic acid prop-2-ynyl ester hydrochloride Starting from intermediate 144.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (39% yield).
LC-MS(01): MS (ESI, m/z): 419.3 [M+H$^+$]; $t_R$=0.56 min.

Example 145 prop-2-yn-1-yl((5-(4-(aminomethyl)phenyl)-3-(3-ethylureido)isoquinolin-8-yl)methyl)carbamate hydrochloride 145.1. Tert-butyl 4-(8-(aminomethyl)-3-(3-ethylureido)isoquinolin-5-yl)benzylcarbamate Starting from the compound of Preparation B and 4-(N-Boc-aminomethyl)phenylboronic acid (1.1 eq.) and proceeding in analogy to Procedure N, however adding acetic acid (1.5 eq.) before the SCX treatment, the title compound was obtained, without additional purification, as an amorphous solid.
MS (ESI, m/z): 450.4 [M+H$^+$].

145.2. {4-[3-(3-ethyl-ureido)-8-(prop-2-ynyloxycarbonylamino-methyl)-isoquinolin-5-yl]-benzyl}-carbamic acid tert-butyl ester hydrochloride Starting from intermediate 145.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (42% yield).
MS (ESI, m/z): 532.4 [M+H$^+$].

145.3. Prop-2-yn-1-yl((5-(4-(aminomethyl)phenyl)-3-(3-ethylureido)isoquinolin-8-yl)methyl)carbamate hydrochloride Starting from intermediate 145.2 and proceeding in analogy to Procedure Y, the title compound was obtained, without additional purification, as an amorphous solid (91% yield).
LC-MS(01): MS (ESI, m/z): 432.3 [M+H$^+$]; $t_R$=0.59 min.

Example 146 prop-2-yn-1-yl((5-(3-(aminomethyl)phenyl)-3-(3-ethylureido)isoquinolin-8-yl)methyl)carbamate hydrochloride 146.1. Tert-butyl 3-(8-(aminomethyl)-3-(3-ethylureido)isoquinolin-5-yl)benzylcarbamate Starting from the compound of Preparation B and 3-(N-Boc-aminomethyl)phenylboronic acid (1.1 eq.) and proceeding in analogy to Procedure N, however adding acetic acid (1.5 eq.) before the SCX treatment, the title compound was obtained, without additional purification, as an amorphous solid.
MS (ESI, m/z): 450.4 [M+H$^+$].

146.2. {3-[3-(3-ethyl-ureido)-8-(prop-2-ynyloxycarbonylamino-methyl)-isoquinolin-5-yl]-benzyl}-carbamic acid tert-butyl ester hydrochloride Starting from intermediate 146.1 and propargyl alcohol and proceeding in analogy to Procedure Y, however without adding 2M dimethylamine in THF at the end of the reaction, the title compound was obtained, after purification by prep-HPLC (acidic conditions) and HCl treatment, as an amorphous solid (40% yield).
MS (ESI, m/z): 532.4 [M+H$^+$].

146.3. Prop-2-yn-1-yl((5-(3-(aminomethyl)phenyl)-3-(3-ethylureido)isoquinolin-8-yl)methyl)carbamate hydrochloride Starting from intermediate 146.2 and proceeding in analogy to Procedure Y, the title compound was obtained, without additional purification, as an amorphous solid (91% yield).
LC-MS(01): MS (ESI, m/z): 432.1 [M+H$^+$]; $t_R$=0.61 min.

Example 147

N-[3-(3-ethyl-ureido)-5-pyridin-4-yl-isoquinolin-8-ylmethyl]-4-morpholin-4-yl-butyramide 147.1. 4-morpholin-4-yl-butyric acid ethyl ester A solution of ethyl 4-bromobutyrate (681 mg) in MeCN (5.0 mL) was treated with morpholine (0.61 mL) at rt. The reaction mixture was heated to 80° C. for 3 h and cooled down to rt. It was concentrated under reduced pressure, diluted with EA and the org. layer was washed with water and brine, dried over MgSO$_4$, filtered and concentrated under reduced pressure. The title compound was obtained, without additional purification, as a yellow oil (643 mg; 96% yield).
$^1$H NMR (d6-DMSO): 4.03 (q, J=7.1 Hz, 2H); 3.56-3.45 (m, 4H); 2.35-2.16 (m, 8H); 1.65 (quint, J=7.1 Hz, 2H); 1.16 (t, J=7.1 Hz, 3 H).

147.2. 4-morpholin-4-yl-butyric acid

A suspension of intermediate 147.1 (202 mg) in 1M NaOH (1.0 mL) was heated to 100° C. for 16 h, cooled down to rt, acidified to pH 4 with 2M HCl (1.0 mL) and concentrated under reduced pressure. The residue was suspended in EtOH (2.0 mL), filtered and the title compound was obtained, after concentration of the mother liquor under reduced pressure, as a white solid (67% yield).
$^1$H NMR (d6-DMSO): 4.04-3.62 (m, 4H); 3.55-3.09 (m, 4H); 3.14-2.91 (m, 2H); 2.32 (t, J=7.3 Hz, 2H); 2.01-1.80 (m, 2H).

147.3. N-[3-(3-ethyl-ureido)-S-pyridin-4-yl-isoquinolin-8-ylmethyl]-4-morpholin-4-yl-butyramide Starting from the compound of Preparation C and intermediate 147.2 (3.0 eq.) and proceeding in analogy to Procedure W, the title compound was obtained, after purification by prep-HPLC (basic conditions), as an amorphous solid (59% yield).
$^1$H NMR (d6-DMSO): 9.26 (s, 1H); 9.02 (s, 1H); 8.76-8.65 (m, 2H); 8.47-8.35 (m, 1H); 8.07 (s, 1H); 7.56 (d, J=7.3 Hz, 1H); 7.51-7.43 (m, 2H); 7.37 (d, J=7.3 Hz, 1H); 7.11-6.98 (m, 1H); 4.79 (d, J=5.6 Hz, 2H); 3.55-3.44 (m, 4H); 3.17-3.03 (m, 2H); 2.30-2.22 (m, 4H); 2.22-2.12 (m, 4H); 1.73-1.59 (m, 2H); 1.03 (t, J=7.2 Hz, 3H).
LC-MS(01): MS (ESI, m/z): 477.4 [M+H$^+$]; $t_R$=0.38 min.

Example 148

[5-chloro-3-(3-ethyl-ureido)-isoquinolin-8-ylmethyl]-carbamic acid 3-morpholin-4-yl-propyl ester Starting from the compound of Preparation B and 4-(3-hydroxypropyl)morpholine and proceeding in analogy to Procedure AA, the title compound was obtained, after purification by CC (DCM/MeOH +1% NH$_4$OH 100:0 to 97:3), as a yellow solid (80% yield).
$^1$H NMR (d6-DMSO) δ: 9.28 (d, J=0.5 Hz, 1H); 9.20 (s, 1H); 8.37 (d, J=0.6 Hz, 1H); 7.82-7.72 (m, 1H); 7.76 (d, J=7.7 Hz, 1H); 7.23 (d, J=7.7 Hz, 1H); 7.04-6.93 (m, 1H); 4.65 (d, J=5.9 Hz, 2H); 4.05-3.92 (m, 2H); 3.59-3.45 (m, 4H); 3.24-3.09 (m, 2H); 2.37-2.19 (m, 6H); 1.77-1.60 (m, 2H); 1.08 (t, J=7.2 Hz, 3H).
LC-MS(01): MS (ESI, m/z): 450.3 [M+H$^+$]; $t_R$=0.57 min.

Example 149

[3-(3-ethyl-ureido)-5-fluoro-isoquinolin-8-ylmethyl]-carbamic acid 3-morpholin-4-yl-propyl ester Starting from the compound of Preparation D and 4-(3-hydroxypropyl)morpholine and proceeding in analogy to Procedure AA, the title compound was obtained, after purification by CC (DCM/MeOH +1% NH$_4$OH 100:0 to 97:3), as a yellow solid (85% yield).
$^1$H NMR (d6-DMSO) δ: 9.27 (s, 1H); 9.18 (s, 1H); 8.16 (s, 1H); 7.80-7.69 (m, 1H); 7.45-7.35 (m, 1H); 7.25-7.17 (m, 1H); 6.98 (t, J=5.5 Hz, 1H); 4.62 (d, J=6.0 Hz, 2H); 3.98 (t, J=6.5 Hz, 2H); 3.57-3.46 (m, 4H); 3.22-3.10 (m, 2H); 2.34-2.21 (m, 6H); 1.75-1.60 (m, 2H); 1.08 (t, J=7.2 Hz, 3H).
LC-MS(01): MS (ESI, m/z): 434.3 [M+H$^+$]; $t_R$=0.53 min.

Example 150

[3-(3-ethyl-ureido)-5-fluoro-isoquinolin-8-ylmethyl]-carbamic acid prop-2-ynyl ester Starting from the compound of Preparation D and propargyl alcohol and proceeding in analogy to Procedure AA, the title compound was obtained, after purification by CC (DCM/MeOH +1% NH$_4$OH 100:0 to 97:3), as a yellow solid (41% yield).
$^1$H NMR (d6-DMSO) δ: 9.26 (s, 1H); 9.19 (s, 1H); 8.17 (s, 1H); 8.05-7.95 (m, 1H); 7.45-7.35 (m, 1H); 7.23 (dd, J=5.1 Hz, J=7.8 Hz, 1H); 7.03-6.92 (m, 1H); 4.65 (d, J=6.0 Hz, 2H); 4.63 (d, J=2.5 Hz, 2H); 3.45 (t, J=2.4 Hz, 1H); 3.22-3.10 (m, 2H); 1.08 (t, J=7.2 Hz, 3H).
LC-MS(02): MS (ESI, m/z): 345.2 [M+H$^+$]; $t_R$=0.76 min.

Example 151

[3-(3-ethyl-ureido)-5-fluoro-isoquinolin-8-ylmethyl]-carbamic acid 2-methoxy-ethyl ester Starting from the compound of Preparation D and 2-methoxyethanol and proceeding in analogy to Procedure AA, the title compound was obtained, after purification by CC (DCM/MeOH +1% NH$_4$OH 100:0 to 97:3), as a yellow solid (59% yield).
$^1$H NMR (d6-DMSO) δ: 9.26 (s, 1H); 9.18 (s, 1H); 8.17 (s, 1H); 7.91-7.81 (m, 1H); 7.46-7.34 (m, 1H); 7.27-7.17 (m, 1H); 7.02-6.93 (m, 1H); 4.63 (d, J=5.9 Hz, 2H); 4.11-4.02 (m, 2H); 3.51-3.41 (m, 2H); 3.22 (s, 3H); 3.21-3.10 (m, 2H); 1.08 (t, J=7.2 Hz, 3H).
LC-MS(02): MS (ESI, m/z): 365.2 [M+H$^+$]; $t_R$=0.71 min.

Example 152

[3-(3-ethyl-ureido)-5-pyridin-4-yl-isoquinolin-8-ylmethyl]-carbamic acid 2-(3H-[1,2,3]triazol-4-yl)-ethyl ester Starting from the compound of Preparation C and 2-(1H-[1,2,3]triazol-4-yl)-ethanol and proceeding in analogy to Procedure AA, the title compound was obtained, after purification by CC (DCM/MeOH +1% NH$_4$OH 100:0 to 90:10), as a pale yellow solid (70% yield).

$^1$H NMR (d6-DMSO) δ: 9.30 (s, 1H); 9.04 (s, 1H); 8.73-8.69 (m, 2H); 8.07 (s, 1H); 8.07 (s, 1H); 7.88 (t, J=6.2 Hz, 1H); 7.65-7.58 (m, 1H); 7.56 (d, J=7.3 Hz, 1H); 7.50-7.46 (m, 2H); 7.33 (d, J=7.3 Hz, 1H); 7.04 (t, J=5.3 Hz, 1H); 4.72 (d, J=5.7 Hz, 2H); 4.23 (t, J=6.6 Hz, 2H); 3.16-3.04 (m, 2H); 2.95 (t, J=6.7 Hz, 2H); 1.03 (t, J=7.2 Hz, 3H).

LC-MS(02): MS (ESI, m/z): 461.3 [M+H$^+$]; t$_R$=0.52 min.

Example 153

N-[3-(3-ethyl-ureido)-5-(2-methyl-pyridin-4-yl)-isoquinolin-8-ylmethyl]-acetamide Starting from the compound of Preparation E and acetic acid and proceeding in analogy to Procedure AK, the title compound was obtained, after purification by CC (DCM/MeOH 100:0 to 90:10), as a pale yellow solid (69% yield).

$^1$H NMR (d6-DMSO) δ: 9.26 (d, J=0.6 Hz, 1H); 9.02 (s, 1H); 8.56 (dd, J=5.0, 0.6 Hz, 1H); 8.45 (t, J=5.8 Hz, 1H); 8.03 (s, 1H); 7.55-7.52 (m, 1H); 7.36 (d, J=7.3 Hz, 1H); 7.33 (br s, 1H); 7.26 (dd, J=5.2, 1.2 Hz, 1H); 7.12 (t, J=5.3 Hz, 1H); 4.77 (d, J=5.7 Hz, 2H); 3.16-3.05 (m, 2H); 2.54 (s, 3H); 1.88 (s, 3H); 1.03 (t, J=7.2 Hz, 3H).

LC-MS(02): MS (ESI, m/z): 378.3 [M+H$^+$]; t$_R$=0.46 min.

Example 154 cyclopropanecarboxylic acid [3-(3-ethyl-ureido)-5-(2-methyl-pyridin-4-yl)-isoquinolin-8-ylmethyl]-amide Starting from the compound of Preparation E and cyclopropanecarboxylic acid and proceeding in analogy to Procedure AK, the title compound was obtained, after purification by CC (DCM/MeOH 100:0 to 90:10), as a colourless solid (59% yield).

$^1$H NMR (d6-DMSO) δ: 9.25 (d, J=0.7 Hz, 1H); 9.04 (s, 1H); 8.67 (t, J=5.7 Hz, 1H); 8.56 (d, J=5.0 Hz, 1H); 8.04 (s, 1H); 7.58-7.52 (m, 1H); 7.37 (d, J=7.3 Hz, 1H); 7.33 (br. s, 1H); 7.26 (dd, J=5.1, 1.3 Hz, 1H); 7.09 (t, J=5.4 Hz, 1H); 4.81 (d, J=5.7 Hz, 2H); 3.16-3.05 (m, 2H); 2.55 (s, 3H); 1.67-1.56 (m, 1H); 1.04 (t, J=7.2 Hz, 3H); 0.76-0.62 (m, 4H).

LC-MS(02): MS (ESI, m/z): 404.3 [M+H$^+$]; t$_R$=0.54 min.

Example 155 propynoic acid [3-(3-ethyl-ureido)-5-(2-methyl-pyridin-4-yl)-isoquinolin-8-ylmethyl]-amide Starting from the compound of Preparation E and propiolic acid and proceeding in analogy to Procedure AK, the title compound was obtained, after purification by CC (DCM/MeOH 100:0 to 90:10), as a pale orange solid (64% yield).

$^1$H NMR (d6-DMSO) δ: 9.40 (t, J=5.8 Hz, 1H); 9.26 (d, J=0.7 Hz, 1H); 9.05 (s, 1H); 8.56 (dd, J=5.1, 0.4 Hz, 1H); 8.04 (d, J=0.7 Hz, 1H); 7.55 (d, J=7.3 Hz, 1H); 7.36-7.32 (m, 2H); 7.26 (dd, J=5.3, 1.2 Hz, 1H); 7.12 (t, J=5.6 Hz, 1H); 4.83 (d, J=5.9 Hz, 2H); 4.18 (s, 1H); 3.16-3.05 (m, 2H); 2.55 (s, 3H); 1.04 (t, J=7.2 Hz, 3H).

LC-MS(02): MS (ESI, m/z): 388.3 [M+H$^+$]; t$_R$=0.51 min.

Example 156

1H-imidazole-2-carboxylic acid [3-(3-ethyl-ureido)-5-(2-methyl-pyridin-4-yl)-isoquinolin-8-ylmethyl]-amide Starting from the compound of Preparation E and 1H-imidazole-2-carboxylic acid and proceeding in analogy to Procedure AK, the title compound was obtained, after purification by CC (DCM/MeOH 100:0 to 90:10), as a yellow solid (62% yield).

LC-MS(02): MS (ESI, m/z): 430.3 [M+H$^+$]; t$_R$=0.48 min.

Example 157

N-[3-(3-ethyl-ureido)-5-(2-methyl-pyridin-4-yl)-isoquinolin-8-ylmethyl]-3-methoxy-propionamide Starting from the compound of Preparation E and 3-methoxypropionic acid and proceeding in analogy to Procedure AK, the title compound was obtained, after purification by two CCs (DCM/MeOH 100:0 to 90:10), as a yellow solid (67% yield).

$^1$H NMR (d6-DMSO) δ: 9.25 (d, J=0.4 Hz, 1H); 9.03 (s, 1H); 8.56 (d, J=5.0 Hz, 1H); 8.48 (t, J=5.8 Hz, 1H); 8.03 (s, 1H); 7.56-7.52 (m, 1H); 7.37 (d, J=7.3 Hz, 1H); 7.33 (br. s, 1H); 7.26 (dd, J=5.1, 1.2 Hz, 1H); 7.13 (t, J=5.3 Hz, 1H); 4.80 (d, J=5.7 Hz, 2H); 3.56 (t, J=6.3 Hz, 2H); 3.21 (s, 3H); 3.17-3.06 (m, 2H); 2.55 (s, 3H); 2.39 (t, J=6.2 Hz, 2H); 1.04 (t, J=7.2 Hz, 3H).

LC-MS(02): MS (ESI, m/z): 422.3 [M+H$^+$]; t$_R$=0.49 min.

Example 158

[3-(3-ethyl-ureido)-5-(2-methyl-pyridin-4-yl)-isoquinolin-8-ylmethyl]-carbamic acid prop-2-ynyl ester Starting from the compound of Preparation E and propargyl chloroformate and proceeding in analogy to Procedure P, the title compound was obtained, after purification by CC (DCM/MeOH 100:0 to 95:5) and prep-HPLC (basic conditions), as a beige solid (31% yield).

$^1$H NMR (d6-DMSO) δ: 9.29 (s, 1H); 9.06 (s, 1H); 8.56 (d, J=5.0 Hz, 1H); 8.09 (t, J=5.6 Hz, 1H); 8.04 (s, 1H); 7.55 (d, J=7.3 Hz, 1H); 7.38-7.32 (m, 2H); 7.26 (d, J=5.3 Hz, 1H); 7.10 (t, J=5.3 Hz, 1H); 4.78-4.71 (m, 2H); 4.65 (d, J=2.4 Hz, 2H); 3.48 (t, J=2.4 Hz, 1H); 3.16-3.05 (m, 2H); 2.54 (s, 3H); 1.04 (t, J=7.2 Hz, 3H).

LC-MS(02): MS (ESI, m/z): 418.3 [M+H$^+$]; t$_R$=0.59 min.

Example 159

[5-chloro-3-(3-ethyl-ureido)-isoquinolin-8-ylmethyl]-carbamic acid methyl ester

Starting from the compound of Preparation B and methyl chloroformate (1.5 eq.) and proceeding in analogy to Procedure P, however using TEA (1.1 eq.) and filtering the precipitate formed at the end of the reaction, the title compound was obtained, after purification by CC (DCM/MeOH +1% NH$_4$OH 100:0 to 96:4), as a colourless solid (60% yield).

$^1$H NMR (d6-DMSO) δ: 9.27 (s, 1H); 9.22 (s, 1H); 8.37 (s, 1H); 7.81 (t, J=6.2 Hz, 1H); 7.76 (d, J=7.6 Hz, 1H); 7.23 (d,

J=7.7 Hz, 1H); 6.99 (t, J=5.0 Hz, 1H); 4.67 (d, J=5.9 Hz, 2H); 3.54 (s, 3H); 3.23-3.11 (m, 2H); 1.08 (t, J=7.2 Hz, 3H).
LC-MS(02): MS (ESI, m/z): 337.2 [M+H$^+$]; t$_R$=0.78 min.

Example 160

[5-(2-cyclopropyl-pyridin-4-yl)-3-(3-ethyl-ureido)-isoquinolin-8-ylmethyl]-carbamic acid methyl ester Starting from the compound of Example 159 and 2-cyclopropylpyridine-4-boronic acid pinacol ester and proceeding in analogy to Procedure AJ, the title compound was obtained, after purification by two CCs (DCM/MeOH +1% NH$_4$OH 100:0 to 97:3), as a yellow solid (60% yield).
$^1$H NMR (d6-DMSO) δ: 9.30 (s, 1H); 9.04 (s, 1H); 8.50 (d, J=5.1 Hz, 1H); 8.04 (s, 1H); 7.84 (t, J=5.9 Hz, 1H); 7.55 (d, J=7.4 Hz, 1H); 7.37-7.32 (m, 2H); 7.19 (dd, J=5.0, 1.4 Hz, 1H); 7.11 (t, J=5.3 Hz, 1H); 4.72 (d, J=5.9 Hz, 2H); 3.56 (s, 3H); 3.17-3.05 (m, 2H); 2.21-2.11 (m, 1H); 1.04 (t, J=7.2 Hz, 3H); 1.03-0.94 (m, 4H).
LC-MS(02): MS (ESI, m/z): 420.3 [M+H$^+$]; t$_R$=0.63 min.

Example 161

[3-(3-ethyl-ureido)-5-(2-fluoro-pyridin-4-yl)-isoquinolin-8-ylmethyl]-carbamic acid methyl ester Starting from the compound of Example 159 and 2-fluoropyridine-4-boronic acid and proceeding in analogy to Procedure AJ, the title compound was obtained, after purification by two CCs (DCM/MeOH +1% NH$_4$OH 100:0 to 97:3), as a yellow solid (46% yield).
$^1$H NMR (d6-DMSO) δ: 9.32 (s, 1H); 9.06 (s, 1H); 8.38 (d, J=5.2 Hz, 1H); 8.05 (d, J=0.4 Hz, 1H); 7.86 (t, J=5.9 Hz, 1H); 7.62 (d, J=7.3 Hz, 1H); 7.47-7.44 (m, 1H); 7.37 (d, J=7.3 Hz, 1H); 7.31 (br s, 1H); 7.08 (t, J=5.6 Hz, 1H); 4.74 (d, J=5.9 Hz, 2H); 3.56 (s, 3H); 3.17-3.06 (m, 2H); 1.04 (t, J=7.2 Hz, 3H).
LC-MS(02): MS (ESI, m/z): 398.3 [M+H$^+$]; t$_R$=0.79 min.

Example 162

[3-(3-ethyl-ureido)-5-(2-methoxy-pyridin-4-yl)-isoquinolin-8-ylmethyl]-carbamic acid methyl ester Starting from the compound of Example 159 and 2-methoxypyridine-4-ylboronic acid and proceeding in analogy to Procedure AJ, the title compound was obtained, after purification by CC (DCM/MeOH +1% NH$_4$OH 100:0 to 97:3), as a yellow solid (60% yield).
$^1$H NMR (d6-DMSO) δ: 9.29 (s, 1H); 9.03 (s, 1H); 8.28 (d, J=5.3 Hz, 1H); 8.06 (s, 1H); 7.84 (t, J=5.0 Hz, 1H); 7.54 (d, J=7.3 Hz, 1H); 7.34 (d, J=7.3 Hz, 1H); 7.07 (t, J=5.6 Hz, 1H); 7.06 (dd, J=5.2, 1.4 Hz, 1H); 6.87 (d, J=0.4 Hz, 1H); 4.72 (d, J=5.9 Hz, 2H); 3.92 (s, 3H); 3.56 (s, 3H); 3.17-3.06 (m, 2H); 1.04 (t, J=7.2 Hz, 3H).
LC-MS(02): MS (ESI, m/z): 410.3 [M+H$^+$]; t$_R$=0.81 min.

Example 163

[5-(2-amino-pyridin-4-yl)-3-(3-ethyl-ureido)-isoquinolin-8-ylmethyl]-carbamic acid methyl ester Starting from the compound of Example 159 and 2-aminopyridine-4-boronic acid pinacol ester and proceeding in analogy to Procedure AJ, the title compound was obtained, after purification by CC (DCM/MeOH +1% NH$_4$OH 100:0 to 97:3), as a colourless solid (43% yield).
$^1$H NMR (d6-DMSO) δ: 9.27 (s, 1H); 9.01 (s, 1H); 8.09 (s, 1H); 7.99 (d, J=4.9 Hz, 1H); 7.82 (t, J=6.4 Hz, 1H); 7.50-7.43 (m, 1H); 7.31 (d, J=7.3 Hz, 1H); 7.09 (t, J=5.6 Hz, 1H); 6.52 (d, J=5.0 Hz, 1H); 6.46 (s, 1H); 6.01 (br. s, 2H); 4.71 (d, J=5.7 Hz, 2H); 3.56 (s, 3H); 3.17-3.06 (m, 2H); 1.04 (t, J=7.1 Hz, 3H).
LC-MS(02): MS (ESI, m/z): 395.3 [M+H$^+$]; t$_R$=0.55 min.

Example 164

[5-(2,6-dimethyl-pyridin-4-yl)-3-(3-ethyl-ureido)-isoquinolin-8-ylmethyl]-carbamic acid methyl ester Starting from the compound of Example 159 and 2,6-dimethylpyridine-4-boronic acid pinacol ester and proceeding in analogy to Procedure AJ, the title compound was obtained, after purification by CC (DCM/MeOH +1% NH$_4$OH 100:0 to 97:3), as a colourless solid (86% yield).
$^1$H NMR (d6-DMSO) δ: 9.29 (s, 1H); 9.04 (s, 1H); 7.98 (s, 1H); 7.83 (t, J=5.6 Hz, 1H); 7.52 (d, J=7.2 Hz, 1H); 7.33 (d, J=7.2 Hz, 1H); 7.21 (t, J=5.6 Hz, 1H); 7.11 (s, 2H); 4.72 (d, J=5.7 Hz, 2H); 3.56 (s, 3H); 3.18-3.06 (m, 2H); 2.48 (s, 6H, below DMSO signal); 1.05 (t, J=7.2 Hz, 3H).
LC-MS(02): MS (ESI, m/z): 408.3 [M+H$^+$]; t$_R$=0.55 min.

Example 165

[3-(3-ethyl-ureido)-5-(2-trifluoromethyl-pyridin-4-yl)-isoquinolin-8-ylmethyl]-carbamic acid methyl ester Starting from the compound of Example 159 and 2-(trifluoromethyl)pyridine-4-boronic acid and proceeding in analogy to Procedure AL, the title compound was obtained, after purification by prep-HPLC (basic conditions), as an amorphous solid (40% yield).
LC-MS(02): MS (ESI, m/z): 448.3 [M+H$^+$]; t$_R$=0.89 min.

Example 166

[5-(2-ethoxy-pyridin-4-yl)-3-(3-ethyl-ureido)-isoquinolin-8-ylmethyl]-carbamic acid methyl ester Starting from the compound of Example 159 and 2-ethoxy-pyridine-4-boronic acid and proceeding in analogy to Procedure AL, the title compound was obtained, after purification by prep-HPLC (basic conditions), as an amorphous solid (64% yield).
LC-MS(02): MS (ESI, m/z): 424.3 [M+H$^+$]; t$_R$=0.88 min.

Example 167

[5-(2-tert-butoxy-pyridin-4-yl)-3-(3-ethyl-ureido)-isoquinolin-8-ylmethyl]-carbamic acid methyl ester Starting from the compound of Example 159 and 2-(tert-butoxy)pyridine-4-boronic acid pinacol ester and proceeding in analogy to Procedure AL, the title compound was obtained, after purification by prep-HPLC (basic conditions), as an amorphous solid (25% yield).
LC-MS(02): MS (ESI, m/z): 452.3 [M+H$^+$]; t$_R$=1.01 min.

Example 168

[3-(3-ethyl-ureido)-5-(2-hydroxy-pyridin-4-yl)-isoquinolin-8-ylmethyl]-carbamic acid methyl ester Starting from the compound of Example 159 and 2-(hydroxy)pyridine-4-boronic acid pinacol ester and proceeding

Example 169

[3-(3-ethyl-ureido)-5-(2-morpholin-4-yl-pyridin-4-yl)-isoquinolin-8-ylmethyl]-carbamic acid methyl ester Starting from the compound of Example 159 and 2-morpholinopyridine-4-boronic acid pinacol ester and proceeding in analogy to Procedure AL, the title compound was obtained, after purification by prep-HPLC (basic conditions), as an amorphous solid (25% yield).
LC-MS(02): MS (ESI, m/z): 465.4 [M+H$^+$]; $t_R$=0.60 min.

Example 170

[5-(2-ethyl-pyridin-4-yl)-3-(3-ethyl-ureido)-isoquinolin-8-ylmethyl]-carbamic acid methyl ester Starting from the compound of Example 159 and 2-ethylpyridine-4-boronic acid and proceeding in analogy to Procedure AL, the title compound was obtained, after purification by prep-HPLC (basic conditions), as an amorphous solid (67% yield).
LC-MS(02): MS (ESI, m/z): 408.3 [M+H$^+$]; $t_R$=0.58 min.

Example 171

[3-(3-ethyl-ureido)-5-(2-pyrrolidin-1-yl-pyridin-4-yl)-isoquinolin-8-ylmethyl]-carbamic acid methyl ester Starting from the compound of Example 159 and 2-(pyrrolidino)pyridine-4-boronic acid pinacol ester and proceeding in analogy to Procedure AL, the title compound was obtained, after purification by prep-HPLC (basic conditions), as an amorphous solid (23% yield).
LC-MS(02): MS (ESI, m/z): 449.3 [M+H$^+$]; $t_R$=0.64 min.

Example 172

[5-(2,6-difluoro-pyridin-4-yl)-3-(3-ethyl-ureido)-isoquinolin-8-ylmethyl]-carbamic acid methyl ester Starting from the compound of Example 159 and 2,6-difluoropyridine-4-boronic acid and proceeding in analogy to Procedure AL, the title compound was obtained, after purification by prep-HPLC (basic conditions), as an amorphous solid (51% yield).
LC-MS(02): MS (ESI, m/z): 416.3 [M+H$^+$]; $t_R$=0.88 min.

Example 173

[3-(3-ethyl-ureido)-5-(2-isopropoxy-pyridin-4-yl)-isoquinolin-8-ylmethyl]-carbamic acid methyl ester Starting from the compound of Example 159 and 2-(isopropoxy)pyridine-4-boronic acid pinacol ester and proceeding in analogy to Procedure AL, the title compound was obtained, after purification by prep-HPLC (basic conditions), as an amorphous solid (49% yield).
LC-MS(02): MS (ESI, m/z): 438.3 [M+H$^+$]; $t_R$=0.94 min.

Example 174

[3-(3-ethyl-ureido)-5-(3,4,5,6-tetrahydro-2H-[1,2']bipyridinyl-4'-yl)-isoquinolin-8-ylmethyl]-carbamic acid methyl ester Starting from the compound of Example 159 and 2-piperidinopyridine-4-boronic acid and proceeding in analogy to Procedure AL, the title compound was obtained, after purification by prep-HPLC (basic conditions), as an amorphous solid (42% yield).
LC-MS(02): MS (ESI, m/z): 463.4 [M+H$^+$]; $t_R$=0.68 min.

Example 175

[3-(3-ethyl-ureido)-5-(2-methyl-pyridin-4-yl)-isoquinolin-8-ylmethyl]-carbamic acid methyl ester Starting from the compound of Example 159 and 2-methylpyridine-4-boronic acid and proceeding in analogy to Procedure AJ, the title compound was obtained, after purification by CC (DCM/MeOH +1% NH$_4$OH 100:0 to 95:5), as a yellow solid (79% yield).
$^1$H NMR (d6-DMSO) δ: 9.30 (s, 1H); 9.04 (s, 1H); 8.56 (d, J=5.0 Hz, 1H); 8.03 (s, 1H); 7.84 (t, J=5.9 Hz, 1H); 7.54 (d, J=7.3 Hz, 1H); 7.38-7.32 (m, 2H); 7.26 (dd, J=5.1, 1.3 Hz, 1H); 7.11 (t, J=5.9 Hz, 1H); 4.73 (d, J=5.9 Hz, 2H); 3.56 (s, 3H); 3.17-3.05 (m, 2H); 2.55 (s, 3H); 1.04 (t, J=7.2 Hz, 3H).
LC-MS(02): MS (ESI, m/z): 394.3 [M+H$^+$]; $t_R$=0.53 min.

Example 176

[3-(3-ethyl-ureido)-5-(2-methyl-pyridin-4-yl)-isoquinolin-8-ylmethyl]-carbamic acid tert-butyl ester Starting from the compound of Example 113 and 2-methylpyridine-4-boronic acid and proceeding in analogy to Procedure AJ, the title compound was obtained, after purification by CC (DCM/MeOH +1% NH$_4$OH 100:0 to 97:3), as a yellow solid (88% yield).
$^1$H NMR (d6-DMSO) δ: 9.29 (s, 1H); 9.05 (s, 1H); 8.55 (d, J=5.1 Hz, 1H); 8.03 (s, 1H); 7.59-7.50 (m, 2H); 7.36-7.29 (m, 2H); 7.28-7.23 (m, 1H); 7.08 (t, J=5.6 Hz, 1H); 4.66 (d, J=5.6 Hz, 2H); 3.16-3.05 (m, 2H); 2.54 (s, 3H); 1.38 (s, 9H); 1.03 (t, J=7.2 Hz, 3H).
LC-MS(02): MS (ESI, m/z): 436.4 [M+H$^+$]; $t_R$=0.71 min.

Example 177

[5-[2-(2-carbamoyl-ethyl)-pyridin-4-yl]-3-(3-ethyl-ureido)-isoquinolin-8-ylmethyl]-carbamic acid 2-methoxy-ethyl ester

177.1. 2-(4-bromo-pyridin-2-ylmethyl)-malonic acid dimethyl ester

To a solution of dimethyl malonate (3.83 g) in dry THF (10 mL) at 0° C. was added NaH (463 mg) and the reaction mixture was stirred at rt for 30 min. A solution of 4-bromo-2-chloromethyl-pyridine (1.99 g) in dry THF (10 mL) was added and the reaction mixture stirred at rt for 15 h. It was then diluted with DCM, treated with a sat. aq. NH$_4$Cl solution and the org. layers were washed with water and brine, dried over MgSO$_4$, filtered and concentrated under reduced pressure. The title compound was obtained, after purification by CC (Hept/EA 100:0 to 50:50), as a yellow oil (1.65 g; 57% yield).

$^1$H NMR (d6-DMSO) δ: 8.32 (d, J=5.4 Hz, 1H); 7.63 (d, J=2.0 Hz, 1H); 7.49 (dd, J=5.4, 2.0 Hz, 1H); 4.08 (t, J=7.7 Hz, 1H); 3.62 (s, 6H); 3.26 (d, J=7.7 Hz, 2H).

MS (ESI, m/z): 302.0 and 304.0 [M+H$^+$ of the two main isotopes].

177.2. 3-(4-bromo-pyridin-2-yl)-propionic acid methyl ester

To a solution of intermediate 177.1 (1.14 g) in DMSO (12 mL) was added anhydrous LiCl (322 mg) followed by water (0.068 mL; 1.0 eq.). The reaction mixture was stirred at 100° C. for 2 days. The reaction mixture was concentrated under reduced pressure and the title compound was obtained, after purification by two CCs (Hept/EA 100:0 to 80:20), as a yellow oil (386 mg; 42% yield).

$^1$H NMR (d6-DMSO) δ: 8.33 (d, J=5.3 Hz, 1H); 7.58 (d, J=1.8 Hz, 1H); 7.46 (dd, J=5.3, 1.8 Hz, 1H); 3.55 (s, 3H); 2.98 (t, J=7.2 Hz, 2H); 2.74 (t, J=7.2 Hz, 2H).

MS (ESI, m/z): 244.0 and 246.0 [M+H$^+$ of the two main isotopes].

177.3. 3-(4-bromo-pyridin-2-yl)-propionamide

To intermediate 177.2 (100 mg) was added a 30% ammonium hydroxide aq. solution (0.5 mL). The reaction mixture was stirred at 60° C. for 1 h. The reaction mixture was concentrated under reduced pressure and the title compound was obtained, after purification by CC (EA), as a colourless solid (53 mg; 57% yield).

$^1$H NMR (d6-DMSO) δ: 8.34 (d, J=5.3 Hz, 1H); 7.53 (d, J=1.5 Hz, 1H); 7.46 (dd, J=5.3, 1.5 Hz, 1H); 7.27 (br s, 1H); 6.73 (br s, 1H); 2.92 (t, J=7.5 Hz, 2H); 2.46 (t, J=7.5 Hz, 2H).

177.4. [5-[2-(2-carbamoyl-ethyl)-pyridin-4-yl]-3-(3-ethyl-ureido)-isoquinolin-8-ylmethyl]-carbamic acid 2-methoxy-ethyl ester Starting from intermediate 120.1 and intermediate 177.3 and proceeding in analogy to Procedure AJ, the title compound was obtained, after purification by CC (DCM/MeOH +1% NH$_4$OH 100:0 to 95:5), as a yellow solid (47% yield).

$^1$H NMR (d6-DMSO) δ: 9.31 (s, 1H); 9.05 (s, 1H); 8.59 (d, J=4.9 Hz, 1H); 8.08 (s, 1H); 7.93 (t, J=5.9 Hz, 1H); 7.56 (d, J=7.3 Hz, 1H); 7.39-7.26 (m, 4H); 7.12 (t, J=5.0 Hz, 1H); 6.74 (br s, 1H); 4.73 (d, J=5.9 Hz, 2H); 4.13-4.06 (m, 2H); 3.52-3.45 (m, 2H); 3.24 (s, 3H); 3.17-3.06 (m, 2H); 3.06-2.98 (m, 2H); 2.60-2.52 (m, 2H); 1.04 (t, J=7.2 Hz, 3H).

LC-MS(02): MS (ESI, m/z): 495.3 [M+H$^+$]; t$_R$=0.54 min.

Example 178

(4-{3-(3-ethyl-ureido)-8-[(2-methoxy-ethoxycarbonylamino)-methyl]-isoquinolin-5-yl}-pyridin-2-yl)-acetic acid tert-butyl ester

178.1. (2-(tert-butoxy)-2-oxoethyl)zinc(II) bromide

To a solution of zinc dust (809 mg) in dry THF (10 mL) at rt was added 1,2-dibromoethane (0.10 mL; 0.2 eq.). The reaction mixture was stirred at 70° C. for 1 min and cooled down to rt. This procedure was repeated 3 times. Chlorotrimethylsilane (0.06 mL; 0.08 eq.) was added and the resulting suspension was stirred at rt for 15 min. It was then heated to 65° C. and a few drops of tert-butyl bromoacetate were added. A solution of tert-butyl bromoacetate (1.99 g) in dry THF (2.0 mL) was then added at such a rate that reflux was maintained. Upon completion of the addition, the reaction mixture was refluxed for an additional 20 min and allowed to cool down to rt. The zinc was allowed to settle and the supernatant was used further.

178.2. (4-chloro-pyridin-2-yl)-acetic acid tert-butyl ester

To a solution of 2-bromo-4-chloro-pyridine (203 mg) in dry THF (2 mL) at rt was added the solution obtained at step 178.1 (2.0 mL; 1.0 eq.) and Pd(PPh$_3$)$_4$ (120 mg). The reaction mixture was stirred at 70° C. for 2 h. The reaction mixture was cooled down to rt and treated with a sat. aq. NH$_4$Cl solution. It was extracted with EA (3×) and the org. layers were washed with water and brine, dried over MgSO$_4$, filtered and concentrated under reduced pressure. The title compound was obtained, after purification by CC (Hept/EA 100:0 to 50:50), as a yellow oil (59 mg; 26% yield).

$^1$H NMR (d6-DMSO) δ: 8.46 (d, J=5.3 Hz, 1H); 7.48 (d, J=1.7 Hz, 1H); 7.42 (dd, J=5.3, 1.7 Hz, 1H); 3.75 (s, 2H); 1.38 (s, 9H).

MS (ESI, m/z): 227.6 [M+H$^+$].

178.3. (4-{3-(3-ethyl-ureido)-8-[(2-methoxy-ethoxycarbonylamino)-methyl]-isoquinolin-5-yl}-pyridin-2-yl)-acetic acid tert-butyl ester Starting from intermediate 120.1 and intermediate 178.2 and proceeding in analogy to Procedure AJ, the title compound was obtained, after purification by CC (DCM/MeOH +1% NH$_4$OH 100:0 to 95:5), as a yellow solid (32% yield).

$^1$H NMR (d6-DMSO) δ: 9.31 (s, 1H); 9.03 (s, 1H); 8.61 (d, J=5.0 Hz, 1H); 8.03 (s, 1H); 7.93 (t, J=5.9 Hz, 1H); 7.57-7.51 (m, 1H); 7.42-7.33 (m, 3H); 7.08 (t, J=5.3 Hz, 1H); 4.73 (d, J=5.8 Hz, 2H); 4.12-4.06 (m, 2H); 3.81 (s, 2H); 3.51-3.42 (m, 2H); 3.24 (s, 3H); 3.16-3.05 (m, 2H); 1.39 (s, 9H); 1.04 (t, J=7.2 Hz, 3H).

LC-MS(02): MS (ESI, m/z): 538.4 [M+H$^+$]; t$_R$=0.85 min.

Example 179

[5-(2-carbamoyl-pyridin-4-yl)-3-(3-ethyl-ureido)-isoquinolin-8-ylmethyl]-carbamic acid 2-methoxy-ethyl ester Starting from intermediate 120.1 and 4-bromo-2-pyridinecarboxamide and proceeding in analogy to Procedure AD, however skipping the work-up and concentrating the reaction mixture upon reaction completion, the title compound was obtained, after purification by CC (DCM/MeOH 100:0 to 90:10), as a colourless solid (87% yield).

$^1$H NMR (d6-DMSO) δ: 9.32 (d, J=0.5 Hz, 1H); 9.06 (s, 1H); 8.76 (dd, J=5.0, 0.7 Hz, 1H); 8.21 (d, J=2.4 Hz, 1H); 8.05 (dd, J=1.7, 0.7 Hz, 1H); 7.98 (s, 1H); 7.94 (t, J=5.6 Hz, 1H); 7.75-7.71 (m, 1H); 7.68 (dd, J=5.0, 1.8 Hz, 1H); 7.61 (d, J=7.3 Hz, 1H); 7.37 (d, J=7.4 Hz, 1H); 7.09 (t, J=5.0 Hz, 1H); 4.74 (d, J=5.9 Hz, 2H); 4.12-4.05 (m, 2H); 3.48 (t, J=4.6 Hz, 2H); 3.23 (s, 3H); 3.15-3.04 (m, 2H); 1.03 (t, J=7.2 Hz, 3H).

LC-MS(02): MS (ESI, m/z): 467.3 [M+H$^+$]; t$_R$=0.69 min.

Example 180

[3-(3-ethyl-ureido)-5-(2-methyl-pyridin-4-yl)-isoquinolin-8-ylmethyl]-methyl-carbamic acid methyl ester

180.1. 1-[5-chloro-8-(chloromethyl)-isoquinolin-3-yl]-3-ethyl-urea

Starting from intermediate B.9 and proceeding in analogy to Procedure R, the title compound was obtained, after purification by CC (DCM/MeOH 100:0 to 95:5), as a yellow solid (99% yield).

$^1$H NMR (d6-DMSO) δ: 9.33 (s, 1H); 9.29 (s, 1H); 8.42 (s, 1H); 7.79 (d, J=7.6 Hz, 1H); 7.48 (d, J=7.6 Hz, 1H); 6.97 (t, J=5.3 Hz, 1H); 5.30 (s, 2H); 3.24-3.12 (m, 2H); 1.08 (t, J=7.2 Hz, 3H).

MS (ESI, m/z): 297.9 [M+H$^+$].

180.2. 1-[5-chloro-8-(methylaminomethyl)-isoquinolin-3-yl]-3-ethyl-urea

Starting from intermediate 180.1 and a 2.0M solution of methylamine in THF and proceeding in analogy to Procedure S, however adding another portion of amine after 15 h, the title compound was obtained, after purification by CC (DCM/MeOH +1% NH$_4$OH 100:0 to 90:10), as a beige solid (47% yield).

$^1$H NMR (d6-DMSO) δ: 9.35 (s, 1H); 9.18 (s, 1H); 8.32 (s, 1H); 7.72 (d, J=7.6 Hz, 1H); 7.32 (d, J=7.6 Hz, 1H); 7.03 (t, J=5.0 Hz, 1H); 4.09 (s, 2H); 3.21-3.11 (m, 2H); 2.32 (s, 3H); 2.21 (br. s, 1H); 1.08 (t, J=7.1 Hz, 3H).

MS (ESI, m/z): 293.0 [M+H$^+$].

180.3. [5-chloro-3-(3-ethyl-ureido)-isoquinolin-8-ylmethyl]-methyl-carbamic acid methyl ester Starting from intermediate 180.2 and methyl chloroformate (1.5 eq.) and proceeding in analogy to Procedure P, however adding more TEA (1.2 eq.) and methyl chloroformate (1.5 eq.) after 20 h, the title compound was obtained, after purification by CC (DCM/MeOH 100:0 to 95:5), as a beige solid (62% yield).

MS (ESI, m/z): 351.0 [M+H$^+$].

180.4. [3-(3-ethyl-ureido)-5-(2-methyl-pyridin-4-yl)-isoquinolin-8-ylmethyl]-methyl-carbamic acid methyl ester Starting from intermediate 180.3 and 2-methylpyridine-4-boronic acid and proceeding in analogy to Procedure AJ, the title compound was obtained, after purification by CC (DCM/MeOH +1% NH$_4$OH 100:0 to 95:5), as a yellow solid (51% yield).

$^1$H NMR (d6-DMSO) δ: 9.26 (s, 1H); 9.05 (s, 1H); 8.56 (d, J=5.1 Hz, 1H); 8.06 (s, 1H); 7.56 (d, J=7.2 Hz, 1H); 7.35 (s, 1H); 7.30-7.25 (m, 2H); 7.11-7.02 (m, 1H); 5.02 (s, 2H); 3.66 (s, 3H); 3.16-3.05 (m, 2H); 2.87 (s, 3H); 2.54 (s, 3H); 1.03 (t, J=7.2 Hz, 3H).

LC-MS(02): MS (ESI, m/z): 408.3 [M+H$^+$]; $t_R$=0.61 min.

Example 181

[3-(3-ethyl-ureido)-5-(2-methyl-pyridin-4-yl)-isoquinolin-8-ylmethyl]-methyl-carbamic acid 2-methoxy-ethyl ester

181.1. [5-chloro-3-(3-ethyl-ureido)-isoquinolin-8-ylmethyl]-methyl-carbamic acid 2-methoxy-ethyl ester Starting from intermediate 180.2 and 2-methoxyethanol and proceeding in analogy to Procedure AA, however adding another portion of activated alcohol after 3 days and after 4 days, the title compound was obtained, after purification by CC (DCM/MeOH 100:0 to 95:5), as a yellow solid (99% yield; 70% purity).

MS (ESI, m/z): 395.1 [M+H$^+$].

181.2. [3-(3-ethyl-ureido)-5-(2-methyl-pyridin-4-yl)-isoquinolin-8-ylmethyl]-methyl-carbamic acid 2-methoxy-ethyl ester Starting from intermediate 181.1 and 2-methylpyridine-4-boronic acid and proceeding in analogy to Procedure AJ, however adding again boronic acid (1.5 eq.), Pd$_2$dba$_3$ (0.05 eq.) and PCy$_3$ (0.12 eq.) after 2 h, the title compound was obtained, after purification by CC (DCM/MeOH +1% NH$_4$OH 100:0 to 95:5), as a yellow solid (35% yield).

$^1$H NMR (d6-DMSO) δ: 9.28 (s, 1H); 9.06 (s, 1H); 8.56 (d, J=5.2 Hz, 1H); 8.06 (s, 1H); 7.57 (d, J=7.3 Hz, 1H); 7.35 (s, 1H); 7.32-7.22 (m, 2H); 7.13-7.05 (m, 1H); 5.09-4.96 (m, 2H); 4.23-4.15 (m, 2H); 3.58-3.46 (m, 2H); 3.30 (s, 3H); 3.16-3.04 (m, 2H); 2.86 (s, 3H); 2.55 (s, 3H); 1.03 (t, J=7.2 Hz, 3H).

LC-MS(02): MS (ESI, m/z): 452.3 [M+H$^+$]; $t_R$=0.62 min.

Example 182

[3-(3-ethyl-ureido)-5-pyridin-4-yl-isoquinolin-8-ylmethyl]-carbamic acid 2-carbamoyl-ethyl ester Starting from the compound of Example 104 and a 0.5M solution of ammonia in dioxane and proceeding in analogy to Procedure U, the title compound was obtained, after purification by CC (DCM/MeOH 100:0 to 90:10), as a yellow solid (71% yield).

LC-MS(02): MS (ESI, m/z): 437.3 [M+H$^+$]; $t_R$=0.46 min.

Example 183

3H-[1,2,3]triazole-4-carboxylic acid [3-(3-ethyl-ureido)-isoquinolin-8-ylmethyl]-amide Starting from the compound of Preparation A and 3H-[1,2,3]triazole-4-carboxylic acid and proceeding in analogy to Procedure AK, the title compound was obtained, after purification by CC (DCM/MeOH +1% NH$_4$OH 100:0 to 90:10), as a colourless solid (74% yield).

LC-MS(02): MS (ESI, m/z): 340.3 [M+H$^+$]; $t_R$=0.55 min.

Example 184

[3-(3-ethyl-ureido)-5-(3-fluoro-pyridin-4-yl)-isoquinolin-8-ylmethyl]-carbamic acid methyl ester hydrochloride 184.1. [3-(3-ethyl-ureido)-5-(4,4,5,5-tetramethyl-[1,3,2]dioxaborolan-2-yl)-isoquinolin-8-ylmethyl]-carbamic acid methyl ester Starting from the compound of Example 159 and proceeding in analogy to Procedure AC, however adding another portion of all reagents after 2 h, the title compound was obtained, after purification by CC (DCM/MeOH 100:0 to 95:5), as a yellow solid (56% yield).

$^1$H NMR (d6-DMSO) δ: 9.22 (s, 1H); 9.14 (s, 1H); 8.57 (d, J=0.5 Hz, 1H); 7.93 (d, J=7.0 Hz, 1H); 7.78 (t, J=5.9 Hz, 1H); 7.54 (t, J=5.3 Hz, 1H); 7.26 (d, J=7.1 Hz, 1H); 4.69 (d, J=5.9 Hz, 2H); 3.54 (s, 3H); 3.25-3.13 (m, 2H); 1.35 (s, 12H); 1.10 (t, J=7.2 Hz, 3H).

MS (ESI, m/z): 429.2 [M+H$^+$].

184.2. [3-(3-ethyl-ureido)-5-(3-fluoro-pyridin-4-yl)-isoquinolin-8-ylmethyl]-carbamic acid methyl ester hydrochloride Starting from intermediate 184.1 and 4-bromo-3-fluoropyridine and proceeding in analogy to Procedure AM, the title compound was obtained, after purification by prep-HPLC (acidic conditions) and HCl treatment, as an amorphous solid (50% yield).

LC-MS(02): MS (ESI, m/z): 398.3 [M+H$^+$]; $t_R$=0.69 min.

Example 185

[3-(3-ethyl-ureido)-5-(3-methyl-pyridin-4-yl)-isoquinolin-8-ylmethyl]-carbamic acid methyl ester hydrochloride Starting from intermediate 184.1 and 4-bromo-3-methylpyridine and proceeding in analogy to Procedure AM, the title compound was obtained, after purification by prep-HPLC (acidic conditions) and HCl treatment, as an amorphous solid (38% yield).

LC-MS(02): MS (ESI, m/z): 394.3 [M+H$^+$]; $t_R$=0.51 min.

Example 186

[3-(3-ethyl-ureido)-5-(2-fluoro-5-methyl-pyridin-4-yl)-isoquinolin-8-ylmethyl]-carbamic acid methyl ester hydrochloride Starting from intermediate 184.1 and 2-fluoro-4-iodo-5-picoline and proceeding in analogy to Procedure AM, the title compound was obtained, after purification by prep-HPLC (acidic conditions) and HCl treatment, as an amorphous solid (42% yield).

LC-MS(02): MS (ESI, m/z): 412.3 [M+H$^+$]; $t_R$=0.78 min.

Example 187

[3-(3-ethyl-ureido)-5-(2-fluoro-3-methyl-pyridin-4-yl)-isoquinolin-8-ylmethyl]-carbamic acid methyl ester hydrochloride Starting from intermediate 184.1 and 2-fluoro-4-iodo-3-picoline and proceeding in analogy to Procedure AM, the title compound was obtained, after purification by prep-HPLC (acidic conditions) and HCl treatment, as an amorphous solid (72% yield).

LC-MS(02): MS (ESI, m/z): 412.3 [M+H$^+$]; $t_R$=0.79 min.

Example 188

[3-(3-ethyl-ureido)-5-(5-fluoro-2-methyl-pyridin-4-yl)-isoquinolin-8-ylmethyl]-carbamic acid methyl ester hydrochloride Starting from intermediate 184.1 and 4-chloro-5-fluoro-2-picoline and proceeding in analogy to Procedure AM, the title compound was obtained, after purification by prep-HPLC (acidic conditions) and HCl treatment, as an amorphous solid (32% yield).

LC-MS(02): MS (ESI, m/z): 412.3 [M+H$^+$]; $t_R$=0.71 min.

Example 189

[5-(2,3-dimethyl-pyridin-4-yl)-3-(3-ethyl-ureido)-isoquinolin-8-ylmethyl]-carbamic acid methyl ester hydrochloride Starting from intermediate 184.1 and 4-bromo-2,3-dimethylpyridine and proceeding in analogy to Procedure AM, the title compound was obtained, after purification by prep-HPLC (acidic conditions) and HCl treatment, as an amorphous solid (69% yield).

LC-MS(02): MS (ESI, m/z): 408.3 [M+H$^+$]; $t_R$=0.50 min.

Example 190

[5-(2,5-dimethyl-pyridin-4-yl)-3-(3-ethyl-ureido)-isoquinolin-8-ylmethyl]-carbamic acid methyl ester hydrochloride Starting from intermediate 184.1 and 4-bromo-2,5-dimethylpyridine and proceeding in analogy to Procedure AM, the title compound was obtained, after purification by prep-HPLC (acidic conditions) and HCl treatment, as an amorphous solid (67% yield).

LC-MS(02): MS (ESI, m/z): 408.3 [M+H$^+$]; $t_R$=0.51 min.

Example 191

[5-(2,5-difluoro-pyridin-4-yl)-3-(3-ethyl-ureido)-isoquinolin-8-ylmethyl]-carbamic acid methyl ester hydrochloride Starting from intermediate 184.1 and 2,5-difluoro-4-iodopyridine and proceeding in analogy to Procedure AM, the title compound was obtained, after purification by prep-HPLC (acidic conditions) and HCl treatment, as an amorphous solid (63% yield).

LC-MS(02): MS (ESI, m/z): 416.3 [M+H$^+$]; $t_R$=0.78 min.

Example 192

{3-(3-ethyl-ureido)-5-[2-(3-hydroxy-propyl)-pyridin-4-yl]-isoquinolin-8-ylmethyl}-carbamic acid methyl ester 192.1. 3-(4-bromo-pyridin-2-yl)propan-1-ol To a 1M solution of LiAlH$_4$ (2.0 eq.) in THF at −78° C. was added dropwise a solution of intermediate 177.2 (100 mg) in dry THF (1.5 mL). The reaction mixture was stirred at −78° C. for 1 h and water (30 μL) was carefully added, followed by a 4N aq. NaOH solution (30 μL) and water (90 μL). After stirring at rt for 1 h, 9:1 DCM/MeOH was added and the suspension filtered over Celite. The title compound was obtained, after concentrating the filtrate, as a yellow solid (108 mg; crude product).

MS (ESI, m/z): 216.1 and 218.1 [M+H$^+$ of the two main isotopes].

192.2. {3-(3-ethyl-ureido)-5-[2-(3-hydroxy-propyl)-pyridin-4-yl]-isoquinolin-8-ylmethyl}-carbamic acid methyl ester Starting from intermediate 184.1 and intermediate 192.1 (2.1 eq.) and proceeding in analogy to Procedure AN, the title compound was obtained, after purification by two CCs (DCM/MeOH 100:0 to 90:10), as a beige solid (44% yield).
LC-MS(02): MS (ESI, m/z): 438.4 [M+H$^+$]; $t_R$=0.49 min.

Example 193

[3-(3-ethyl-ureido)-5-(2-(methylcarbamoyl-methyl)-pyridin-4-yl)-isoquinolin-8-ylmethyl]-carbamic acid methyl ester 193.1. 2-(4-chloro-pyridin-2-yl)acetic acid To intermediate 178.2 (500 mg) was added TFA (15.0 eq.) at rt. The reaction mixture was stirred at rt for 2 h and concentrated under reduced pressure. The title compound was obtained, after co-evaporating once the crude product with toluene, as a yellow oil (634 mg; crude product).
MS (ESI, m/z): 172.1 [M+H$^+$].

193.2. 2-(4-chloro-pyridin-2-yl)-N-methyl-acetamide

Starting from intermediate 193.1 and a 2.0M solution of methylamine in THF and proceeding in analogy to Procedure AO, the title compound was obtained, after purification by CC (DCM/MeOH 100:0 to 90:10), as a yellow oil (44% yield).
MS (ESI, m/z): 185.2 [M+H$^+$].

193.3. [3-(3-ethyl-ureido)-5-(2-(methylcarbamoyl-methyl)-pyridin-4-yl)-isoquinolin-8-ylmethyl]-carbamic acid methyl ester Starting from intermediate 184.1 and intermediate 193.2 (1.6 eq.) and proceeding in analogy to Procedure AN, the title compound was obtained, after purification by two CCs (DCM/MeOH 100:0 to 90:10), as a colourless solid (47% yield).
LC-MS(02): MS (ESI, m/z): 451.3 [M+H$^+$]; $t_R$=0.54 min.

Example 194

[5-[2-(dimethylcarbamoyl-methyl)-pyridin-4-yl]-3-(3-ethyl-ureido)-isoquinolin-8-ylmethyl]-carbamic acid methyl ester 194.1. 2-(4-chloro-pyridin-2-yl)-N,N-dimethyl-acetamide Starting from intermediate 193.1 and a 2.0M solution of dimethylamine in THF and proceeding in analogy to Procedure AO, the title compound was obtained, after purification by CC (DCM/MeOH 100:0 to 90:10), as a yellow oil (62% yield).
MS (ESI, m/z): 199.2 [M+H$^+$].

194.2. [5-[2-(dimethylcarbamoyl-methyl)-pyridin-4-yl]-3-(3-ethyl-ureido)-isoquinolin-8-ylmethyl]-carbamic acid methyl ester Starting from intermediate 184.1 and intermediate 194.1 (2.2 eq.) and proceeding in analogy to Procedure AN, the title compound was obtained, after purification by CC (DCM/MeOH 100:0 to 90:10), as a yellow solid (61% yield).
$^1$H NMR (d6-DMSO) δ: 9.30 (s, 1H); 9.03 (s, 1H); 8.62-8.57 (m, 1H); 8.06 (s, 1H); 7.84 (t, J=5.9 Hz, 1H); 7.54 (d, J=7.3 Hz, 1H); 7.39-7.31 (m, 3H); 7.07 (t, J=5.6 Hz, 1H); 4.73 (d, J=5.9 Hz, 2H); 3.93 (s, 2H); 3.56 (s, 3H); 3.17-3.05 (m, 2H); 3.07 (s, 3H); 2.83 (s, 3H); 1.04 (t, J=7.2 Hz, 3H).
LC-MS(02): MS (ESI, m/z): 465.3 [M+H$^+$]; $t_R$=0.56 min.

Example 195

{3-(3-ethyl-ureido)-5-[2-(2-methylcarbamoyl-ethyl)-pyridin-4-yl]-isoquinolin-8-ylmethyl}-carbamic acid methyl ester 195.1. 3-(4-bromo-pyridin-2-yl)-propionic acid To a suspension of intermediate 177.2 (100 mg) in dioxane (1.0 mL) and water (0.1 mL) was added a 8N aq. NaOH solution (1.8 eq.). The reaction mixture was stirred at 65° C. for 2 h and cooled down to rt. A 1N aq. HCl solution was added until pH=4 and the mixture was concentrated under reduced pressure. The title compound was obtained, after filtration over a plug of silica gel, as a colourless solid (85 mg; crude product).
MS (ESI, m/z): 230.1 and 232.2 [M+H$^+$ of the two main isotopes].

195.2. 3-(4-bromo-pyridin-2-yl)-N-methyl-propionamide

Starting from intermediate 195.1 and a 2.0M solution of methylamine in THF and proceeding in analogy to Procedure AO, the title compound was obtained, after purification by CC (DCM/MeOH 100:0 to 90:10), as a yellow oil (81% yield).
MS (ESI, m/z): 243.1 and 245.2 [M+H$^+$ of the two main isotopes].

195.3. {3-(3-ethyl-ureido)-5-[2-(2-methylcarbamoyl-ethyl)-ethyl)-4-yl]-isoquinolin-8-ylmethyl}-carbamic acid methyl ester Starting from intermediate 184.1 and intermediate 195.2 (1.3 eq.) and proceeding in analogy to Procedure AN, the title compound was obtained, after purification by two CCs (DCM/MeOH 100:0 to 90:10), as a beige solid (85% yield).
LC-MS(02): MS (ESI, m/z): 465.4 [M+H$^+$]; $t_R$=0.51 min.

Example 196

[5-[2-(2-dimethylcarbamoyl-ethyl)-pyridin-4-yl]-3-(3-ethyl-ureido)-isoquinolin-8-ylmethyl]-carbamic acid methyl ester 196.1. 3-(4-bromo-pyridin-2-yl)-N,N-dimethyl-propionamide Starting from intermediate 195.1 and a 2.0M solution of dimethylamine in THF and proceeding in analogy to Procedure AO, the title compound was obtained, after purification by two CCs (DCM/MeOH 100:0 to 90:10), as a yellow oil (63% yield).

MS (ESI, m/z): 257.1 and 259.1 [M+H$^+$ of the two main isotopes].

196.2. [5-[2-(2-dimethylcarbamoyl-ethyl)-pyridin-4-yl]-3-(3-ethyl-ureido)-isoquinolin-8-ylmethyl]-carbamic acid methyl ester Starting from intermediate 184.1 and intermediate 196.1 and proceeding in analogy to Procedure AN, the title compound was obtained, after purification by CC (DCM/MeOH 100:0 to 90:10), as a yellow solid (75% yield).

LC-MS(02): MS (ESI, m/z): 479.4 [M+H$^+$]; $t_R$=0.54 min.

Example 197

[5-(2-cyano-pyridin-4-yl)-3-(3-ethyl-ureido)-isoquinolin-8-ylmethyl]-carbamic acid methyl ester Starting from intermediate 184.1 and 4-chloropicolinonitrile (2.0 eq.) and proceeding in analogy to Procedure AN, the title compound was obtained, after purification by CC (DCM/MeOH 100:0 to 95:5), as a yellow solid (56% yield).

$^1$H NMR (d6-DMSO) δ: 9.33 (s, 1H); 9.09 (s, 1H); 8.89 (dd, J=5.0, 0.8 Hz, 1H); 8.20 (dd, J=1.7, 0.8 Hz, 1H); 7.98 (s, 1H); 7.86 (dd, J=5.0, 1.7 Hz, 2H); 7.65 (d, J=7.4 Hz, 1H); 7.38 (d, J=7.4 Hz, 1H); 7.15 (t, J=6.2 Hz, 1H); 4.74 (d, J=6.2 Hz, 2H); 3.56 (s, 3H); 3.17-3.07 (m, 2H); 1.04 (t, J=7.2 Hz, 3H).

LC-MS(02): MS (ESI, m/z): 405.3 [M+H$^+$]; $t_R$=0.73 min.

Pharmacological Properties of the Invention Compounds
In Vitro Assays

Experimental Methods

Minimal inhibitory concentrations (MICs; mg/l) were determined in cation-adjusted MuellerHinton Broth (supplemented with 3% (v/v) lysed horse blood for testing *Streptococcus pneumoniae*) by a microdilution method following the description given in "Methods for Dilution Antimicrobial Susceptibility Tests for Bacteria that Grow Aerobically", Approved standard, 7$^{th}$ ed., a Clinical and Laboratory Standards Institute (CLSI) Document M7-A7, Wayne, Pa., USA, 2006.

Results

All Example compounds were tested against several Gram positive and Gram negative bacteria.

Typical antibacterial test results are given in the table hereafter (MIC in mg/l).

| Example No. | MIC for S. pneumoniae ATCC 49619 | Example No. | MIC for S. pneumoniae ATCC 49619 | Example No. | MIC for S. pneumoniae ATCC 49619 |
|---|---|---|---|---|---|
| 1 | 2 | 2 | 2 | 3 | 4 |
| 4 | 2 | 5 | 4 | 6 | 4 |
| 7 | 2 | 8 | 8 | 9 | 2 |
| 10 | 4 | 11 | 2 | 12 | 1 |
| 13 | 2 | 14 | 4 | 15 | 4 |
| 16 | 4 | 17 | 8 | 18 | 4 |
| 19 | 8 | 20 | 1 | 21 | 8 |
| 22 | 4 | 23 | 1 | 24 | 4 |
| 25 | 2 | 26 | 4 | 27 | 4 |
| 28 | 4 | 29 | 4 | 30 | 4 |
| 31 | 2 | 32 | 4 | 33 | 4 |
| 34 | 4 | 35 | 4 | 36 | 4 |
| 37 | 4 | 38 | 8 | 39 | 2 |
| 40 | 4 | 41 | 0.25 | 42 | 0.5 |
| 43 | 4 | 44 | 8 | 45 | 8 |
| 46 | 2 | 47 | 1 | 48 | 2 |
| 49 | 0.5 | 50 | 4 | 51 | 8 |
| 52 | 2 | 53 | 4 | 54 | 4 |
| 55 | 8 | 56 | 1 | 57 | 0.5 |
| 58 | 2 | 59 | 0.5 | 60 | 8 |
| 61 | 4 | 62 | 1 | 63 | 1 |
| 64 | 0.5 | 65 | 0.25 | 66 | 0.25 |
| 67 | 0.5 | 68 | 4 | 69 | 0.25 |
| 70 | 0.5 | 71 | 2 | 72 | 0.5 |
| 73 | 2 | 74 | 0.25 | 75 | 0.25 |
| 76 | 0.25 | 77 | 0.5 | 78 | 4 |
| 79 | 0.25 | 80 | 8 | 81 | 0.5 |
| 82 | 2 | 83 | 1 | 84 | 0.5 |
| 85 | 1 | 86 | 0.5 | 87 | 0.25 |
| 88 | 2 | 89 | 8 | 90 | 2 |
| 91 | 1 | 92 | 4 | 93 | 8 |
| 94 | 0.5 | 95 | 0.5 | 96 | 2 |
| 97 | 2 | 98 | 4 | 99 | 0.5 |
| 100 | 8 | 101 | 2 | 102 | 1 |
| 103 | 4 | 104 | 8 | 105 | 4 |
| 106 | 0.25 | 107 | 1 | 108 | 0.25 |
| 109 | 2 | 110 | 2 | 111 | 0.5 |
| 112 | 0.5 | 113 | 1 | 114 | 0.5 |
| 115 | 2 | 116 | 1 | 117 | 1 |
| 118 | 0.5 | 119 | 0.5 | 120 | 1 |
| 121 | 1 | 122 | 4 | 123 | 8 |
| 124 | 0.5 | 125 | 1 | 126 | 1 |
| 127 | 8 | 128 | 1 | 129 | 0.5 |
| 130 | 0.5 | 131 | 0.5 | 132 | 4 |
| 133 | 0.5 | 134 | 4 | 135 | 4 |
| 136 | 2 | 137 | 0.25 | 138 | 0.5 |
| 139 | 1 | 140 | 1 | 141 | 0.25 |
| 142 | 1 | 143 | 0.5 | 144 | 0.5 |
| 145 | 8 | 146 | 2 | 147 | 4 |
| 148 | 4 | 149 | 4 | 150 | 1 |
| 151 | 2 | 152 | 1 | 153 | 1 |
| 154 | 0.5 | 155 | 0.5 | 156 | 0.5 |
| 157 | 1 | 158 | 0.5 | 159 | 1 |
| 160 | 2 | 161 | 0.5 | 162 | 1 |
| 163 | 0.5 | 164 | 1 | 165 | 4 |
| 166 | 2 | 167 | 4 | 168 | 8 |
| 169 | 4 | 170 | 1 | 171 | 4 |
| 172 | 1 | 173 | 4 | 174 | 4 |
| 175 | 0.5 | 176 | 1 | 177 | 8 |
| 178 | 2 | 179 | 8 | 180 | 8 |
| 181 | 8 | 182 | 2 | 183 | 1 |
| 184 | 1 | 185 | 2 | 186 | 2 |
| 187 | 4 | 188 | 2 | 189 | 8 |
| 190 | 4 | 191 | 2 | 192 | 2 |
| 193 | 8 | 194 | 4 | 195 | 4 |
| 196 | 4 | 197 | 2 | | |

The invention claimed is:
1. A compound of formula I

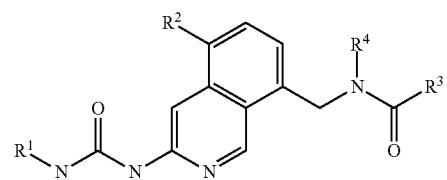

wherein
R$^1$ is (C$_1$-C$_3$)alkyl, (C$_2$-C$_3$)haloalkyl or cyclopropyl;
R$^2$ is H, halogen, pyridazin-4-yl, pyrimidin-5-yl or a group having the formula (A1), (A2) or (A3) shown hereafter

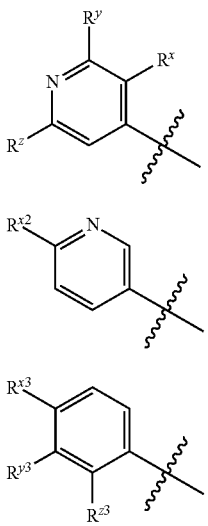

wherein $R^x$ is H and each of $R^y$ and $R^z$ is independently H or methyl, or each of $R^x$ and $R^z$ is H and $R^y$ is halogen, cyano, $(C_2-C_4)$alkyl, $(C_1-C_4)$alkoxy, amino, hydroxy, hydroxy-$(C_1-C_3)$alkyl, trifluoromethyl, carbamoyl, carbamoyl-$(C_1-C_2)$alkyl, (methylcarbamoyl)-$(C_1-C_2)$alkyl, (dimethylcarbamoyl)-$(C_1-C_2)$alkyl, tert-butoxycarbonylmethyl, cyclopropyl, pyrrolidin-1-yl, piperidin-1-yl, morpholin-1-yl or 1-morpholinomethyl, or $R^x$ is H and each of $R^y$ and $R^z$ is independently halogen, or $R^x$ is methyl, $R^y$ is methyl or halogen and $R^z$ is H, or $R^x$ is methyl or halogen, $R^y$ is H and $R^z$ is methyl or halogen, or $R^x$ is methyl or halogen and each of $R^y$ and $R^z$ is H;

$R^{x2}$ is H, amino or hydroxymethyl;

$R^{x3}$ is hydroxy, carboxy, carbamoyl, hydroxymethyl or aminomethyl, $R^{y3}$ is H and $R^{z3}$ is H or each of $R^{x3}$ and $R^{z3}$ is H and $R^{y3}$ is hydroxy, acetamidomethyl, (dimethylamino)methyl, carboxymethyl, carbamoyl or aminoethyl, or each of $R^{x3}$ and $R^{y3}$ is H and $R^{z3}$ is hydroxy;

$R^3$ is $(C_1-C_4)$alkyl, $(C_2-C_4)$alkynyl, amino-$(C_1-C_3)$alkyl, carbamoyl-$(C_1-C_3)$alkyl, (methylcarbamoyl)-$(C_1-C_3)$alkyl, $(C_1-C_4)$alkoxy, $(C_1-C_4)$haloalkoxy, $(C_3-C_4)$alkynyloxy, (4-hydroxybut-2-yn-1-yl)oxy, (4-aminobut-2-yn-1-yl)oxy, dimethylamino-$(C_2-C_3)$alkoxy, carbamoyl-$(C_1-C_3)$alkoxy, $(C_1-C_3)$alkylamino, $(C_3-C_6)$cycloalkyl, $(C_3-C_6)$cycloalkyl-$(C_1-C_4)$alkyl, $(C_3-C_6)$cycloalkyl-$(C_1-C_4)$alkoxy, hydroxy-$(C_1-C_3)$alkyl, hydroxy-$(C_2-C_3)$alkoxy, $(C_1-C_3)$alkoxy-$(C_1-C_3)$alkyl, $(C_1-C_3)$alkoxy-$(C_1-C_3)$alkoxy, carboxy-$(C_1-C_3)$alkyl, carboxy-$(C_1-C_3)$alkoxy, $(C_1-C_2)$alkoxycarbonyl-$(C_1-C_3)$alkoxy, aryl, $(C_5-C_6)$heteroaryl, benzyl, benzyloxy, 2-cyanoethoxy, 2,3-dihydroxypropoxy, 3,4-dihydroxybutoxy, —$CH_2R^a$, —$CH_2CH_2R^b$, —$(CH_2)_n$—C(O)O—$R^d$, —$(CH_2)_n$—N($R^c$)C(O)O—$R^d$, —O—$(CH_2)_n$—N($R^c$)C(O)O—$R^d$, —$(CH_2)_n$—$R^e$ or —O—$(CH_2)_n$—$R^e$;

n is 1, 2 or 3;

$R^a$ is cyano, acetylamino, N,N-dimethylamino; and $R^b$ is cyano or carbamoyl;

$R^c$ is H or methyl;

$R^d$ is $(C_1-C_4)$alkyl;

$R^e$ is pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl or $(C_5-C_6)$heteroaryl;

$R^4$ is H or methyl;

or a salt thereof.

2. The compound according to claim 1, wherein each of $R^x$ and $R^z$ is H and $R^y$ is methoxy, or hydroxymethyl;

or a salt thereof.

3. The compound according to claim 1, having the formula $I_{P1}$

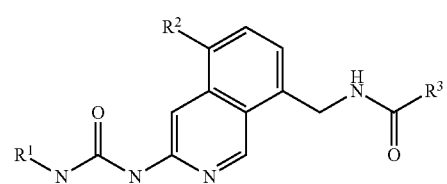

wherein $R^1$ is $(C_1-C_3)$alkyl, $(C_2-C_3)$haloalkyl or cyclopropyl;

$R^2$ is H or a group of the formula

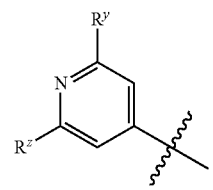

wherein either each of $R^y$ and $R^x$ is independently hydrogen or methyl, or $R^z$ is hydrogen and $R^y$ is halogen, methoxy or amino;

$R^3$ is $(C_1-C_4)$alkyl, $(C_2-C_4)$alkynyl, $(C_1-C_4)$alkoxy, $(C_1-C_4)$haloalkoxy, linear $(C_3-C_4)$alkynyloxy, $(C_1-C_3)$alkylamino, $(C_3-C_6)$cycloalkyl, $(C_3-C_6)$cycloalkyl-$(C_1-C_4)$alkyl, aryl, $(C_5-C_6)$heteroaryl, $((C_5-C_6)$heteroaryl)methoxy, benzyl, benzyloxy, methoxymethyl, 2-methoxyethoxy, 2-cyanoethoxy, —$CH_2R^a$ or —$CH_2CH_2R^b$;

or a salt thereof.

4. The compound according to claim 1, having the formula $I_{CE}$

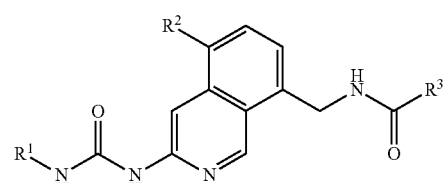

wherein $R^1$ is $(C_1-C_3)$alkyl;

$R^2$ is H, halogen, pyridazin-4-yl, pyrimidin-5-yl or a group having the formula (A1), (A2) or (A3) shown hereafter

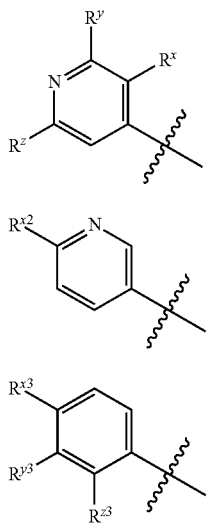

wherein R$^x$ is H and either each of R$^y$ and R$^z$ is independently H or methyl, or R$^z$ is H and R$^y$ is halogen, cyano, ethyl, (C$_1$-C$_4$)alkoxy, hydroxy, amino, hydroxymethyl, trifluoromethyl, carbamoyl, carbamoyl-(C$_1$-C$_2$)alkyl, tert-butoxycarbonylmethyl, cyclopropyl, pyrrolidin-1-yl, piperidin-1-yl, morpholin-1-yl or 1-morpholinomethyl, or R$^x$ is H and each of R$^y$ and R$^z$ is independently halogen, or R$^x$ is methyl and each of R$^y$ and R$^z$ is H;

R$^3$ is (C$_1$-C$_4$)alkyl, (C$_2$-C$_4$)alkynyl, amino-(C$_1$-C$_3$)alkyl, carbamoyl-(C$_1$-C$_3$)alkyl, (methylcarbamoyl)-(C$_1$-C$_3$)alkyl, (C$_1$-C$_4$)alkoxy, (C$_1$-C$_4$)haloalkoxy, (C$_3$-C$_4$)alkynyloxy, (4-hydroxybut-2-yn-1-yl)oxy, (4-aminobut-2-yn-1-yl)oxy, dimethylamino-(C$_2$-C$_3$)alkoxy, carbamoyl-(C$_1$-C$_3$)alkoxy, (C$_1$-C$_3$)alkylamino, (C$_3$-C$_6$)cycloalkyl, (C$_3$-C$_6$)cycloalkylmethyl, hydroxy-(C$_1$-C$_3$)alkyl, hydroxy-(C$_1$-C$_3$)alkoxy, (C$_1$-C$_3$)alkoxy-(C$_1$-C$_3$)alkyl, (C$_1$-C$_3$)alkoxy-(C$_1$-C$_3$)alkoxy, carboxy-(C$_1$-C$_3$)alkyl, carboxy-(C$_1$-C$_3$)alkoxy, (C$_1$-C$_2$)alkoxycarbonyl-(C$_1$-C$_3$)alkoxy, phenyl, benzyl, benzyloxy, 2-cyanoethoxy, 2,3-dihydroxypropoxy, 3,4-dihydroxybutoxy, —CH$_2$R$^a$, —(CH$_2$)$_n$—C(O)O—R$^d$, —(CH$_2$)$_n$—N(R$^c$)C(O)O—R$^d$, —O—(CH$_2$)$_n$—N(R$^c$)C(O)O—R$^d$, —(CH$_2$)$_n$—R$^e$ or —O—(CH$_2$)$_n$—R$^e$, or R$^3$ is a five- or six-membered heteroaryl group which has one to three ring heteroatoms, each of which is nitrogen, whereby said heteroaryl group can be substituted once with methyl, or also R$^3$ is a (heteroaryl)methoxy group wherein the heteroaryl is a five- or six-membered heteroaryl group which has one to three ring heteroatoms, each of which is nitrogen, whereby said heteroaryl group can be substituted once with methyl;

n is 1, 2 or 3;

R$^e$ is pyrrolidin-1-yl, piperidin-1-yl, piperidin-3-yl, morpholin-1-yl, 2-oxopyrrolidin-1-yl, 5-oxopyrrolidin-2-yl, 2,5-dioxopyrrolidin-1-yl, 2-oxoimidazolidin-1-yl, 4-(tert-butoxycarbonyl)piperazin-1-yl, 4-(aminomethyl)cyclohexyl, or R$^e$ is a five- or six-membered heteroaryl group which has one to three ring heteroatoms, each of which is nitrogen, whereby said heteroaryl group can be substituted once with methyl;

or a salt thereof.

5. The compound according to claim 1, wherein R$^1$ is (C$_1$-C$_3$)alkyl;

or a salt thereof.

6. The compound according to claim 5, wherein R$^1$ is ethyl;

or a salt thereof.

7. The compound according to claim 1, wherein R$^2$ is H;

or a salt thereof.

8. The compound according to claim 7, wherein R$^1$ is (C$_1$-C$_3$)alkyl and R$^3$ is (C$_2$-C$_4$)alkynyl, linear (C$_3$-C$_4$)alkynyloxy, (C$_3$-C$_6$)cycloalkyl, (C$_3$-C$_6$)cycloalkyl-(C$_1$-C$_4$)alkyl, aryl, (C$_5$-C$_6$)heteroaryl, ((C$_5$-C$_6$)heteroaryl)methoxy or benzyl;

or a salt thereof.

9. The compound according to claim 1, wherein R$^2$ is a group wherein either each of R$^y$ and R$^z$ is independently hydrogen or methyl, or R$^z$ is hydrogen and R$^y$ is halogen, methoxy or amino;

or a salt thereof.

10. The compound according to claim 9, wherein R$^2$ is pyridin-4-yl;

or a salt thereof.

11. The compound according to claim 9, wherein R$^3$ is alkynyloxy, (C$_5$-C$_6$)heteroaryl or ((C$_5$-C$_6$)heteroaryl)methoxy;

or a salt thereof.

12. The compound according to claim 1, wherein the compound is:

but-3-ynoic acid [3-(3-ethyl-ureido)-isoquinolin-8-ylmethyl]-amide;

N-[3-(3-ethyl-ureido)-isoquinolin-8-ylmethyl]-isonicotinamide;

N-[3-(3-ethyl-ureido)-isoquinolin-8-ylmethyl]-acetamide;

N-[3-(3-ethyl-ureido)-isoquinolin-8-ylmethyl]-benzamide;

2-cyano-N-[3-(3-ethyl-ureido)-isoquinolin-8-ylmethyl]-acetamide;

cyclohexanecarboxylic acid [3-(3-ethyl-ureido)-isoquinolin-8-ylmethyl]-amide;

2-cyclopropyl-N-[3-(3-ethyl-ureido)-isoquinolin-8-ylmethyl]-acetamide;

2-acetylamino-N-[3-(3-ethyl-ureido)-isoquinolin-8-ylmethyl]-acetamide;

propynoic acid [3-(3-ethyl-ureido)-isoquinolin-8-ylmethyl]-amide;

N-[3-(3-ethyl-ureido)-isoquinolin-8-ylmethyl]-nicotinamide;

pyridine-2-carboxylic acid [3-(3-ethyl-ureido)-isoquinolin-8-ylmethyl]-amide;

N-[3-(3-ethyl-ureido)-isoquinolin-8-ylmethyl]-2-phenyl-acetamide;

cyclopropanecarboxylic acid [3-(3-ethyl-ureido)-isoquinolin-8-ylmethyl]-amide;

N-[3-(3-ethyl-ureido)-isoquinolin-8-ylmethyl]-2,2-dimethyl-propionamide;

N-[3-(3-ethyl-ureido)-isoquinolin-8-ylmethyl]-2-methoxy-acetamide;

1H-imidazole-2-carboxylic acid [3-(3-ethyl-ureido)-isoquinolin-8-ylmethyl]-amide;
pent-4-ynoic acid [3-(3-ethyl-ureido)-isoquinolin-8-ylmethyl]-amide;
N-[3-(3-ethyl-ureido)-isoquinolin-8-ylmethyl]-isobutyramide;
2-dimethylamino-N-[3-(3-ethyl-ureido)-isoquinolin-8-ylmethyl]-acetamide;
2H-[1,2,3]triazole-4-carboxylic acid [3-(3-ethyl-ureido)-isoquinolin-8-ylmethyl]-amide;
N-[3-(3-ethyl-ureido)-isoquinolin-8-ylmethyl]-succinamide;
3-methyl-3H-imidazole-4-carboxylic acid [3-(3-ethyl-ureido)-isoquinolin-8-ylmethyl]-amide;
N-[3-(3-ethyl-ureido)-5-pyridin-4-yl-isoquinolin-8-ylmethyl]-nicotinamide;
[3-(3-ethyl-ureido)-isoquinolin-8-ylmethyl]-carbamic acid ethyl ester;
[3-(3-ethyl-ureido)-isoquinolin-8-ylmethyl]-carbamic acid pyridin-4-ylmethyl ester;
[3-(3-ethyl-ureido)-isoquinolin-8-ylmethyl]-carbamic acid pyrimidin-5-ylmethyl ester;
[3-(3-ethyl-ureido)-isoquinolin-8-ylmethyl]-carbamic acid 2-fluoro-ethyl ester;
[3-(3-ethyl-ureido)-isoquinolin-8-ylmethyl]-carbamic acid cyclopropylmethyl ester;
[3-(3-ethyl-ureido)-isoquinolin-8-ylmethyl]-carbamic acid pyrimidin-4-ylmethyl ester;
[3-(3-ethyl-ureido)-isoquinolin-8-ylmethyl]-carbamic acid isopropyl ester;
[3-(3-ethyl-ureido)-isoquinolin-8-ylmethyl]-carbamic acid prop-2-ynyl ester;
[3-(3-ethyl-ureido)-isoquinolin-8-ylmethyl]-carbamic acid 2-cyano-ethyl ester;
[3-(3-ethyl-ureido)-isoquinolin-8-ylmethyl]-carbamic acid pyridin-3-ylmethyl ester;
[3-(3-ethyl-ureido)-isoquinolin-8-ylmethyl]-carbamic acid pyridin-2-ylmethyl ester;
[3-(3-ethyl-ureido)-isoquinolin-8-ylmethyl]-carbamic acid (1-methyl-1H-pyrazol-3-yl)methyl ester;
[3-(3-ethyl-ureido)-isoquinolin-8-ylmethyl]-carbamic acid benzyl ester;
[3-(3-ethyl-ureido)-isoquinolin-8-ylmethyl]-carbamic acid 2-methoxy-ethyl ester;
[3-(3-ethyl-ureido)-isoquinolin-8-ylmethyl]-carbamic acid 3-methyl-3H-imidazol-4-ylmethyl ester;
[3-(3-ethyl-ureido)-isoquinolin-8-ylmethyl]-carbamic acid 1H-pyrazol-4-ylmethyl ester;
[3-(3-ethyl-ureido)-isoquinolin-8-ylmethyl]-carbamic acid but-3-ynyl ester;
[3-(3-ethyl-ureido)-5-pyridin-4-yl-isoquinolin-8-ylmethyl]-carbamic acid prop-2-ynyl ester;
[3-(3-ethyl-ureido)-5-pyridin-4-yl-isoquinolin-8-ylmethyl]-carbamic acid pyridin-3-ylmethyl ester;
1-ethyl-3-{8-[(3-ethyl-ureido)-methyl]isoquinolin-3-yl}-urea;
[3-(3-ethyl-ureido)-isoquinolin-8-ylmethyl]-methyl-carbamic acid prop-2-ynyl ester;
N-[3-(3-ethyl-ureido)-5-pyridin-4-yl-isoquinolin-8-ylmethyl]-malonamic acid;
N-[3-(3-ethyl-ureido)-5-pyridin-4-yl-isoquinolin-8-ylmethyl]-succinamic acid tert-butyl ester;
({[3-(3-ethyl-ureido)-5-pyridin-4-yl-isoquinolin-8-ylmethyl]-carbamoyl}-methyl)-carbamic acid tert-butyl ester;
({[3-(3-ethyl-ureido)-5-pyridin-4-yl-isoquinolin-8-ylmethyl]-carbamoyl}-methyl)-methyl-carbamic acid tert-butyl ester;
(2-{[3-(3-ethyl-ureido)-5-pyridin-4-yl-isoquinolin-8-ylmethyl]-carbamoyl}-ethyl)-carbamic acid tert-butyl ester;
2-amino-N-[3-(3-ethyl-ureido)-5-pyridin-4-yl-isoquinolin-8-ylmethyl]-acetamide;
3-amino-N-[3-(3-ethyl-ureido)-5-pyridin-4-yl-isoquinolin-8-ylmethyl]-propionamide;
N-[3-(3-ethyl-ureido)-5-pyridin-4-yl-isoquinolin-8-ylmethyl]-malonamide;
N-[3-(3-ethyl-ureido)-5-pyridin-4-yl-isoquinolin-8-ylmethyl]-N'-methyl-malonamide;
N-[3-(3-ethyl-ureido)-5-pyridin-4-yl-isoquinolin-8-ylmethyl]-succinamide;
N-[3-(3-ethyl-ureido)-5-pyridin-4-yl-isoquinolin-8-ylmethyl]-N'-methyl-succinamide;
(3-{[3-(3-ethyl-ureido)-5-pyridin-4-yl-isoquinolin-8-ylmethyl]-carbamoyl}-propyl)-carbamic acid tert-butyl ester;
2-cyclopropyl-N-[3-(3-ethyl-ureido)-5-pyridin-4-yl-isoquinolin-8-ylmethyl]-acetamide;
(2-{[3-(3-ethyl-ureido)-5-pyridin-4-yl-isoquinolin-8-ylmethyl]-carbamoyl}-ethyl)-methyl-carbamic acid tert-butyl ester;
N-[3-(3-ethyl-ureido)-5-pyridin-4-yl-isoquinolin-8-ylmethyl]-propionamide;
N-[3-(3-ethyl-ureido)-5-pyridin-4-yl-isoquinolin-8-ylmethyl]-2-(1H-imidazol-4-yl)-acetamide;
N-[3-(3-ethyl-ureido)-5-pyridin-4-yl-isoquinolin-8-ylmethyl]-2-hydroxy-acetamide;
(3-{[3-(3-ethyl-ureido)-5-pyridin-4-yl-isoquinolin-8-ylmethyl]-carbamoyl}-propyl)-methyl-carbamic acid tert-butyl ester;
N-[3-(3-ethyl-ureido)-5-pyridin-4-yl-isoquinolin-8-ylmethyl]-3-methoxy-propionamide;
N-[3-(3-ethyl-ureido)-5-pyridin-4-yl-isoquinolin-8-ylmethyl]-acetamide;
cyclopropanecarboxylic acid [3-(3-ethyl-ureido)-5-pyridin-4-yl-isoquinolin-8-ylmethyl]-amide;
N-[3-(3-ethyl-ureido)-5-pyridin-4-yl-isoquinolin-8-ylmethyl]-3-methyl-butyramide;
N-[3-(3-ethyl-ureido)-5-pyridin-4-yl-isoquinolin-8-ylmethyl]-isobutyramide;
N-[3-(3-ethyl-ureido)-5-pyridin-4-yl-isoquinolin-8-ylmethyl]-3-hydroxy-propionamide;
pent-4-ynoic acid [3-(3-ethyl-ureido)-5-pyridin-4-yl-isoquinolin-8-ylmethyl]-amide;
N-[3-(3-ethyl-ureido)-5-pyridin-4-yl-isoquinolin-8-ylmethyl]-2-pyrazol-1-yl-acetamide;
3H-imidazole-4-carboxylic acid [3-(3-ethyl-ureido)-5-pyridin-4-yl-isoquinolin-8-ylmethyl]-amide;
1H-pyrazole-3-carboxylic acid [3-(3-ethyl-ureido)-5-pyridin-4-yl-isoquinolin-8-ylmethyl]-amide;
1H-pyrazole-4-carboxylic acid [3-(3-ethyl-ureido)-5-pyridin-4-yl-isoquinolin-8-ylmethyl]-amide;
1H-imidazole-2-carboxylic acid [3-(3-ethyl-ureido)-5-pyridin-4-yl-isoquinolin-8-ylmethyl]-amide;
propynoic acid [3-(3-ethyl-ureido)-5-pyridin-4-yl-isoquinolin-8-ylmethyl]-amide;
[3-(3-ethyl-ureido)-5-pyridin-4-yl-isoquinolin-8-ylmethyl]-carbamic acid tert-butyl ester;
[3-(3-ethyl-ureido)-5-pyridin-4-yl-isoquinolin-8-ylmethyl]-carbamic acid isopropyl ester;
[3-(3-ethyl-ureido)-5-pyridin-4-yl-isoquinolin-8-ylmethyl]-carbamic acid 2-dimethylamino-ethyl ester;

[3-(3-ethyl-ureido)-5-pyridin-4-yl-isoquinolin-8-ylmethyl]-carbamic acid methyl ester;
[3-(3-ethyl-ureido)-5-pyridin-4-yl-isoquinolin-8-ylmethyl]-carbamic acid 2-pyrrolidin-1-yl-ethyl ester;
[3-(3-ethyl-ureido)-5-pyridin-4-yl-isoquinolin-8-ylmethyl]-carbamic acid 2-tert-butoxycarbonylamino-ethyl ester;
tert-butyl(2-((((3-(3-ethylureido)-5-(pyridin-4-yl)isoquinolin-8-yl)methyl)carbamoyl)oxy)ethyl)(methyl)carbamate;
tert-butyl 4-(2-((((3-(3-ethylureido)-5-(pyridin-4-yl)isoquinolin-8-yl)methyl)carbamoyl)oxy)ethyl)piperazine-1-carboxylate;
[3-(3-ethyl-ureido)-5-pyridin-4-yl-isoquinolin-8-ylmethyl]-carbamic acid cyclopropylmethyl ester;
[3-(3-ethyl-ureido)-5-pyridin-4-yl-isoquinolin-8-ylmethyl]-carbamic acid 3-(2-oxo-pyrrolidin-1-yl)-propyl ester;
(1-methyl-1H-imidazol-2-yl)methyl[(3-(3-ethylureido)-5-(pyridin-4-yl)isoquinolin-8-yl)methyl]carbamate;
(S)-[3-(3-ethyl-ureido)-5-pyridin-4-yl-isoquinolin-8-ylmethyl]-carbamic acid 5-oxo-pyrrolidin-2-ylmethyl ester;
[3-(3-ethyl-ureido)-5-pyridin-4-yl-isoquinolin-8-ylmethyl]-carbamic acid 3-methyl-3H-imidazol-4-ylmethyl ester;
[3-(3-ethyl-ureido)-5-pyridin-4-yl-isoquinolin-8-ylmethyl]-carbamic acid 3-dimethylamino-propyl ester;
N-[3-(3-ethyl-ureido)-5-pyridin-4-yl-isoquinolin-8-ylmethyl]-4-hydroxy-butyramide;
[3-(3-ethyl-ureido)-5-pyridin-4-yl-isoquinolin-8-ylmethyl]-carbamic acid 2-morpholin-4-yl-ethyl ester;
[3-(3-ethyl-ureido)-5-pyridin-4-yl-isoquinolin-8-ylmethyl]-carbamic acid 3-piperidin-1-yl-propyl ester;
[3-(3-ethyl-ureido)-5-pyridin-4-yl-isoquinolin-8-ylmethyl]-carbamic acid 2-(2-oxo-imidazolidin-1-yl)-ethyl ester;
[3-(3-ethyl-ureido)-5-pyridin-4-yl-isoquinolin-8-ylmethyl]-carbamic acid 3-methoxy-propyl ester;
N-[3-(3-ethyl-ureido)-5-pyridin-4-yl-isoquinolin-8-ylmethyl]-4-methoxy-butyramide;
[3-(3-ethyl-ureido)-5-pyridin-4-yl-isoquinolin-8-ylmethyl]-carbamic acid carbamoylmethyl ester;
[3-(3-ethyl-ureido)-5-pyridin-4-yl-isoquinolin-8-ylmethyl]-carbamic acid 2-(2,5-dioxo-pyrrolidin-1-yl)-ethyl ester;
[3-(3-ethyl-ureido)-5-pyridin-4-yl-isoquinolin-8-ylmethyl]-carbamic acid 2-piperidin-1-yl-ethyl ester;
[3-(3-ethyl-ureido)-5-pyridin-4-yl-isoquinolin-8-ylmethyl]-carbamic acid isobutyl ester;
[3-(3-ethyl-ureido)-5-pyridin-4-yl-isoquinolin-8-ylmethyl]-carbamic acid (R)-2-piperidin-3-yl-ethyl ester;
trans-[3-(3-ethyl-ureido)-5-pyridin-4-yl-isoquinolin-8-ylmethyl]-carbamic acid 4-(aminomethyl)-(cyclohexylmethyl) ester;
(R)-[3-(3-ethyl-ureido)-5-pyridin-4-yl-isoquinolin-8-ylmethyl]-carbamic acid 3,4-dihydroxy-butyl ester;
[3-(3-ethyl-ureido)-5-pyridin-4-yl-isoquinolin-8-ylmethyl]-carbamic acid 2,3-dihydroxy-propyl ester;
3-((((3-(3-ethylureido)-5-(pyridin-4-yl)isoquinolin-8-yl)methyl)carbamoyl)oxy)propanoic acid;
methyl 3-((((3-(3-ethylureido)-5-(pyridin-4-yl)isoquinolin-8-yl)methyl)carbamoyl)oxy)propanoate;
[3-(3-ethyl-ureido)-5-pyridin-4-yl-isoquinolin-8-ylmethyl]-carbamic acid 4-hydroxy-but-2-ynyl ester;
[3-(3-ethyl-ureido)-5-pyridin-4-yl-isoquinolin-8-ylmethyl]-carbamic acid 2-hydroxy-ethyl ester;
[3-(3-ethyl-ureido)-5-pyridin-4-yl-isoquinolin-8-ylmethyl]-carbamic acid 1-methyl-prop-2-ynyl ester;
[3-(3-ethyl-ureido)-5-pyridin-4-yl-isoquinolin-8-ylmethyl]-carbamic acid 4-amino-but-2-ynyl ester;
[3-(3-ethyl-ureido)-5-pyridin-4-yl-isoquinolin-8-ylmethyl]-carbamic acid 3-morpholin-4-yl-propyl ester;
[5-chloro-3-(3-ethyl-ureido)-isoquinolin-8-ylmethyl]-carbamic acid 2-methoxy-ethyl ester;
[5-chloro-3-(3-ethyl-ureido)-isoquinolin-8-ylmethyl]-carbamic acid prop-2-ynyl ester;
[5-chloro-3-(3-ethyl-ureido)-isoquinolin-8-ylmethyl]-carbamic acid tert-butyl ester;
[3-(3-ethyl-ureido)-5-pyridin-4-yl-isoquinolin-8-ylmethyl]-carbamic acid 2-methoxy-ethyl ester;
[5-(2-amino-pyridin-4-yl)-3-(3-ethyl-ureido)-isoquinolin-8-ylmethyl]-carbamic acid 2-methoxy-ethyl ester;
[5-(2,6-dimethyl-pyridin-4-yl)-3-(3-ethyl-ureido)-isoquinolin-8-ylmethyl]-carbamic acid 2-methoxy-ethyl ester;
[3-(3-ethyl-ureido)-5-(2-methoxy-pyridin-4-yl)-isoquinolin-8-ylmethyl]-carbamic acid 2-methoxy-ethyl ester;
[3-(3-ethyl-ureido)-5-(2-fluoro-pyridin-4-yl)-isoquinolin-8-ylmethyl]-carbamic acid 2-methoxy-ethyl ester;
[3-(3-ethyl-ureido)-5-(2-methyl-pyridin-4-yl)-isoquinolin-8-ylmethyl]-carbamic acid 2-methoxy-ethyl ester;
[5-(2-cyano-pyridin-4-yl)-3-(3-ethyl-ureido)-isoquinolin-8-ylmethyl]-carbamic acid 2-methoxy-ethyl ester;
[3-(3-ethyl-ureido)-5-(3-methyl-pyridin-4-yl)-isoquinolin-8-ylmethyl]-carbamic acid 2-methoxy-ethyl ester;
[3-(3-ethyl-ureido)-5-(2-hydroxymethyl-pyridin-4-yl)-isoquinolin-8-ylmethyl]-carbamic acid 2-methoxy-ethyl ester;
{3-(3-ethyl-ureido)-5-[(2-morpholin-4-ylmethyl)-pyridin-4-yl]-isoquinolin-8-ylmethyl}-carbamic acid 2-methoxy-ethyl ester;
[3-(3-ethyl-ureido)-5-pyridazin-4-yl-isoquinolin-8-ylmethyl]-carbamic acid tert-butyl ester;
[3-(3-ethyl-ureido)-5-pyridin-3-yl-isoquinolin-8-ylmethyl]-carbamic acid prop-2-ynyl ester;
[3-(3-ethyl-ureido)-5-(3-methyl-pyridin-4-yl)-isoquinolin-8-ylmethyl]-carbamic acid prop-2-ynyl ester;
[3-(3-ethyl-ureido)-5-pyridazin-4-yl-isoquinolin-8-ylmethyl]-carbamic acid prop-2-ynyl ester;
[5-(2-cyano-pyridin-4-yl)-3-(3-ethyl-ureido)-isoquinolin-8-ylmethyl]-carbamic acid prop-2-ynyl ester;
propynoic acid [3-(3-ethyl-ureido)-5-pyridazin-4-yl-isoquinolin-8-ylmethyl]-amide;
3-cyclopropyl-N-[3-(3-ethyl-ureido)-5-pyridin-4-yl-isoquinolin-8-ylmethyl]-propionamide;
[5-(6-amino-pyridin-3-yl)-3-(3-ethyl-ureido)-isoquinolin-8-ylmethyl]-carbamic acid prop-2-ynyl ester;
{5-[3-(acetylamino-methyl)-phenyl]-3-(3-ethyl-ureido)-isoquinolin-8-ylmethyl}-carbamic acid prop-2-ynyl ester;
[3-(3-ethyl-ureido)-5-(3-hydroxy-phenyl)-isoquinolin-8-ylmethyl]-carbamic acid prop-2-ynyl ester;
prop-2-yn-1-yl((5-(3-((dimethylamino)methyl)phenyl)-3-(3-ethylureido)isoquinolin-8-yl)methyl)carbamate;
{3-[3-(3-ethyl-ureido)-8-(prop-2-ynyloxycarbonylamino-methyl)-isoquinolin-5-yl]-phenyl}-acetic acid;
[5-(3-carbamoyl-phenyl)-3-(3-ethyl-ureido)-isoquinolin-8-ylmethyl]-carbamic acid prop-2-ynyl ester;
4-[3-(3-ethyl-ureido)-8-(prop-2-ynyloxycarbonylamino-methyl)-isoquinolin-5-yl]-benzoic acid;
[3-(3-ethyl-ureido)-5-(4-hydroxy-phenyl)-isoquinolin-8-ylmethyl]-carbamic acid prop-2-ynyl ester;

[3-(3-ethyl-ureido)-5-(2-hydroxy-phenyl)-isoquinolin-8-ylmethyl]-carbamic acid prop-2-ynyl ester;
[3-(3-ethyl-ureido)-5-pyrimidin-5-yl-isoquinolin-8-ylmethyl]-carbamic acid prop-2-ynyl ester;
[5-(4-carbamoyl-phenyl)-3-(3-ethyl-ureido)-isoquinolin-8-ylmethyl]-carbamic acid prop-2-ynyl ester;
[3-(3-ethyl-ureido)-5-(6-hydroxymethyl-pyridin-3-yl)-isoquinolin-8-ylmethyl]-carbamic acid prop-2-ynyl ester;
[3-(3-ethyl-ureido)-5-(4-hydroxymethyl-phenyl)-isoquinolin-8-ylmethyl]-carbamic acid prop-2-ynyl ester;
[5-(2-amino-pyridin-4-yl)-3-(3-ethyl-ureido)-isoquinolin-8-ylmethyl]-carbamic acid prop-2-ynyl ester;
prop-2-yn-1-yl((5-(4-(aminomethyl)phenyl)-3-(3-ethylureido)isoquinolin-8-yl)methyl)carbamate;
prop-2-yn-1-yl((5-(3-(aminomethyl)phenyl)-3-(3-ethylureido)isoquinolin-8-yl)methyl)carbamate;
N-[3-(3-ethyl-ureido)-5-pyridin-4-yl-isoquinolin-8-ylmethyl]-4-morpholin-4-yl-butyramide;
[5-chloro-3-(3-ethyl-ureido)-isoquinolin-8-ylmethyl]-carbamic acid 3-morpholin-4-yl-propyl ester;
[3-(3-ethyl-ureido)-5-fluoro-isoquinolin-8-ylmethyl]-carbamic acid 3-morpholin-4-yl-propyl ester;
[3-(3-ethyl-ureido)-5-fluoro-isoquinolin-8-ylmethyl]-carbamic acid prop-2-ynyl ester;
[3-(3-ethyl-ureido)-5-fluoro-isoquinolin-8-ylmethyl]-carbamic acid 2-methoxy-ethyl ester;
[3-(3-ethyl-ureido)-5-pyridin-4-yl-isoquinolin-8-ylmethyl]-carbamic acid 2-(3H-[1,2,3]triazol-4-yl)-ethyl ester;
N-[3-(3-ethyl-ureido)-5-(2-methyl-pyridin-4-yl)-isoquinolin-8-ylmethyl]-acetamide;
cyclopropanecarboxylic acid [3-(3-ethyl-ureido)-5-(2-methyl-pyridin-4-yl)-isoquinolin-8-ylmethyl]-amide;
propynoic acid [3-(3-ethyl-ureido)-5-(2-methyl-pyridin-4-yl)-isoquinolin-8-ylmethyl]-amide;
1H-imidazole-2-carboxylic acid [3-(3-ethyl-ureido)-5-(2-methyl-pyridin-4-yl)-isoquinolin-8-ylmethyl]-amide;
N-[3-(3-ethyl-ureido)-5-(2-methyl-pyridin-4-yl)-isoquinolin-8-ylmethyl]-3-methoxy-propionamide;
[3-(3-ethyl-ureido)-5-(2-methyl-pyridin-4-yl)-isoquinolin-8-ylmethyl]-carbamic acid prop-2-ynyl ester;
[5-chloro-3-(3-ethyl-ureido)-isoquinolin-8-ylmethyl]-carbamic acid methyl ester;
[5-(2-cyclopropyl-pyridin-4-yl)-3-(3-ethyl-ureido)-isoquinolin-8-ylmethyl]-carbamic acid methyl ester;
[3-(3-ethyl-ureido)-5-(2-fluoro-pyridin-4-yl)-isoquinolin-8-ylmethyl]-carbamic acid methyl ester;
[3-(3-ethyl-ureido)-5-(2-methoxy-pyridin-4-yl)-isoquinolin-8-ylmethyl]-carbamic acid methyl ester;
[5-(2-amino-pyridin-4-yl)-3-(3-ethyl-ureido)-isoquinolin-8-ylmethyl]-carbamic acid methyl ester;
[5-(2,6-dimethyl-pyridin-4-yl)-3-(3-ethyl-ureido)-isoquinolin-8-ylmethyl]-carbamic acid methyl ester;
[3-(3-ethyl-ureido)-5-(2-trifluoromethyl-pyridin-4-yl)-isoquinolin-8-ylmethyl]-carbamic acid methyl ester;
[5-(2-ethoxy-pyridin-4-yl)-3-(3-ethyl-ureido)-isoquinolin-8-ylmethyl]-carbamic acid methyl ester;
[5-(2-tert-butoxy-pyridin-4-yl)-3-(3-ethyl-ureido)-isoquinolin-8-ylmethyl]-carbamic acid methyl ester;
[3-(3-ethyl-ureido)-5-(2-hydroxy-pyridin-4-yl)-isoquinolin-8-ylmethyl]-carbamic acid methyl ester;
[3-(3-ethyl-ureido)-5-(2-morpholin-4-yl-pyridin-4-yl)-isoquinolin-8-ylmethyl]-carbamic acid methyl ester;
[5-(2-ethyl-pyridin-4-yl)-3-(3-ethyl-ureido)-isoquinolin-8-ylmethyl]-carbamic acid methyl ester;
[3-(3-ethyl-ureido)-5-(2-pyrrolidin-1-yl-pyridin-4-yl)-isoquinolin-8-ylmethyl]-carbamic acid methyl ester;
[5-(2,6-difluoro-pyridin-4-yl)-3-(3-ethyl-ureido)-isoquinolin-8-ylmethyl]-carbamic acid methyl ester;
[3-(3-ethyl-ureido)-5-(2-isopropoxy-pyridin-4-yl)-isoquinolin-8-ylmethyl]-carbamic acid methyl ester;
[3-(3-ethyl-ureido)-5-(3,4,5,6-tetrahydro-2H-[1,2']bipyridinyl-4'-yl)-isoquinolin-8-ylmethyl]-carbamic acid methyl ester;
[3-(3-ethyl-ureido)-5-(2-methyl-pyridin-4-yl)-isoquinolin-8-ylmethyl]-carbamic acid methyl ester;
[3-(3-ethyl-ureido)-5-(2-methyl-pyridin-4-yl)-isoquinolin-8-ylmethyl]-carbamic acid tert-butyl ester;
[5-[2-(2-carbamoyl-ethyl)-pyridin-4-yl]-3-(3-ethyl-ureido)-isoquinolin-8-ylmethyl]-carbamic acid 2-methoxy-ethyl ester;
(4-{3-(3-ethyl-ureido)-8-[(2-methoxy-ethoxycarbonylamino)-methyl]-isoquinolin-5-yl}-pyridin-2-yl)-acetic acid tert-butyl ester;
[5-(2-carbamoyl-pyridin-4-yl)-3-(3-ethyl-ureido)-isoquinolin-8-ylmethyl]-carbamic acid 2-methoxy-ethyl ester;
[3-(3-ethyl-ureido)-5-(2-methyl-pyridin-4-yl)-isoquinolin-8-ylmethyl]-methyl-carbamic acid methyl ester;
[3-(3-ethyl-ureido)-5-(2-methyl-pyridin-4-yl)-isoquinolin-8-ylmethyl]-methyl-carbamic acid 2-methoxy-ethyl ester;
[3-(3-ethyl-ureido)-5-pyridin-4-yl-isoquinolin-8-ylmethyl]-carbamic acid 2-carbamoyl-ethyl ester;
3H-[1,2,3]triazole-4-carboxylic acid [3-(3-ethyl-ureido)-isoquinolin-8-ylmethyl]-amide;
[3-(3-ethyl-ureido)-5-(3-fluoro-pyridin-4-yl)-isoquinolin-8-ylmethyl]-carbamic acid methyl ester;
[3-(3-ethyl-ureido)-5-(3-methyl-pyridin-4-yl)-isoquinolin-8-ylmethyl]-carbamic acid methyl ester;
[3-(3-ethyl-ureido)-5-(2-fluoro-5-methyl-pyridin-4-yl)-isoquinolin-8-ylmethyl]-carbamic acid methyl ester;
[3-(3-ethyl-ureido)-5-(2-fluoro-3-methyl-pyridin-4-yl)-isoquinolin-8-ylmethyl]-carbamic acid methyl ester;
[3-(3-ethyl-ureido)-5-(5-fluoro-2-methyl-pyridin-4-yl)-isoquinolin-8-ylmethyl]-carbamic acid methyl ester;
[5-(2,3-dimethyl-pyridin-4-yl)-3-(3-ethyl-ureido)-isoquinolin-8-ylmethyl]-carbamic acid methyl ester;
[5-(2,5-dimethyl-pyridin-4-yl)-3-(3-ethyl-ureido)-isoquinolin-8-ylmethyl]-carbamic acid methyl ester;
[5-(2,5-difluoro-pyridin-4-yl)-3-(3-ethyl-ureido)-isoquinolin-8-ylmethyl]-carbamic acid methyl ester;
{3-(3-ethyl-ureido)-5-[2-(3-hydroxy-propyl)-pyridin-4-yl]-isoquinolin-8-ylmethyl}-carbamic acid methyl ester;
[3-(3-ethyl-ureido)-5-(2-(methylcarbamoyl-methyl)-pyridin-4-yl)-isoquinolin-8-ylmethyl]-carbamic acid methyl ester;
[5-[2-(dimethylcarbamoyl-methyl)-pyridin-4-yl]-3-(3-ethyl-ureido)-isoquinolin-8-ylmethyl]-carbamic acid methyl ester;
{3-(3-ethyl-ureido)-5-[2-(2-methylcarbamoyl-ethyl)-pyridin-4-yl]-isoquinolin-8-ylmethyl}-carbamic acid methyl ester;
[5-[2-(2-dimethylcarbamoyl-ethyl)-pyridin-4-yl]-3-(3-ethyl-ureido)-isoquinolin-8-ylmethyl]-carbamic acid methyl ester; or
[5-(2-cyano-pyridin-4-yl)-3-(3-ethyl-ureido)-isoquinolin-8-ylmethyl]-carbamic acid methyl ester;
or a salt thereof.

13. A medicament comprising the compound according to claim 1, or a pharmaceutically acceptable salt thereof.

14. A pharmaceutical composition comprising, as an active principle, the compound according to claim 1, or a pharmaceutically acceptable salt thereof, and at least one therapeutically inert excipient.

15. A method of treating or preventing a bacterial infection comprising administering an amount to a patient in need thereof the compound according to claim 1, wherein the administered amount is effective to treat or prevent a bacterial infection.

16. A method for treating or preventing a bacterial infection comprising administering an amount to a patient in need thereof the compound according to claim 14, wherein the administered amount is effective to treat or prevent a bacterial infection.

* * * * *